US007427488B2

(12) United States Patent
Nichols et al.

(10) Patent No.: US 7,427,488 B2
(45) Date of Patent: Sep. 23, 2008

(54) PURIFIED AND ISOLATED PLATELET CALCIUM CHANNEL NUCLEIC ACIDS AND POLYPEPTIDES AND THERAPEUTIC AND SCREENING METHODS USING SAME

(75) Inventors: Timothy C. Nichols, Chapel Hill, NC (US); Nadia Malouf, Durham, NC (US); Elizabeth Merricks, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 424 days.

(21) Appl. No.: 10/726,216

(22) Filed: Dec. 2, 2003

(65) Prior Publication Data
US 2004/0146851 A1    Jul. 29, 2004

Related U.S. Application Data

(63) Continuation-in-part of application No. 10/029,413, filed on Dec. 20, 2001, now Pat. No. 7,041,475.

(60) Provisional application No. 60/258,169, filed on Dec. 22, 2000.

(51) Int. Cl.
G01N 33/53    (2006.01)
G01N 33/567   (2006.01)
C12N 15/00    (2006.01)
C12N 5/00     (2006.01)
C07H 21/04    (2006.01)

(52) U.S. Cl. ............... 435/7.2; 435/7.21; 435/320.1; 435/325; 536/23.5

(58) Field of Classification Search .................. None
See application file for complete search history.

(56) References Cited

U.S. PATENT DOCUMENTS

| 5,429,921 | A | 7/1995 | Harpold et al. ............... 435/4 |
| 5,686,241 | A | 11/1997 | Ellis et al. .................... 435/56 |
| 2002/0165353 | A1 | 11/2002 | Malouf et al. | |

OTHER PUBLICATIONS

MacKenzie et al., Journal of Biological Chemistry, 271(6):2879-81, 1996.*
Sage, Experimental Physiology, 82:807-23, 1997.*
Sun et al., Journal of Biological Chemistry, 273(19):11544-47, 1998.*
Jin et al., PNAS, 95:8070-8074, Jul. 1998.*
Kunapuli et al., TiPS, 19:391-394, Oct. 1998.*
Hogan, et al. *Human dihydroxypyridine-sensitive L-type calcium channel alpha-1 subunit (CACNL1A3) mRNA*, Database accession No. L33798 XP002224388 (Abstract) (Dec. 16, 1994).
Hogan et al., The Structure of the Gene Encoding the Human Skeletal Muscle $\alpha_1$ Subunit of the Dihydropyridine-Sensitive L-type Calcium Channel (CACNLaA3), *Genomics* 31:392-394 (1996).
Hogan et al., Cloning of the human skeletal muscle alpha-1 subunit of dihydroxypyridine-sensitive L-type calcium channel, *Genomics* 24, No. 3:608-609 (Dec. 1, 1994).
Chaudhari et al., *Mus musculus dihydropyridine sensitive skeletal muscle calcium channel mRNA*, Database accession No. L06234 XP002224389 (Abstract) (Nov. 17, 1992).
Chaudhari, A Single Nucleotide Delection in the Skeletal Muscle-specific Calcium Channel Transcript of Muscular Dysgenesis (mdg) Mice, *J. of Biological Chemistry* 287, No. 36:25636-25639 (1992).
Tang et al., *Molecular Localization Studies of the Dihydropyridine (DHP) Binding Site in the Cardiac L-type Voltage Dependent $Ca^{2+}$ Channel (L-VDCC) $\alpha_1$ Subunit Reveal Motif IV S3 to IV S6 as Essential*, XP000604115 (Abstract) (1993).
Kunzelmann-Marche et al. Regulation of Phosphatidylserine Transbilayer Redistribution by Store-operated Ca2+ Entry *The Journal of Biological Chemistry*, vol. 276, No. 7, (2001), pp. 5134-5139.
Zhou et al. Normal hemostasis but defective hematopoietic response to growth factors in mice deficient in phospholipids scramblase1 *Blood*, vol. 99, No. 11, (2002), pp. 4030-4038.

* cited by examiner

*Primary Examiner*—Marianne P Allen
(74) *Attorney, Agent, or Firm*—Jenkins, Wilson, Taylor & Hunt, P.A.

(57) ABSTRACT

Isolated and purified platelet voltage dependent calcium channel (VDCC) $\alpha_1$ subunit polypeptides, and nucleic acid molecules encoding the same. Recombinant host cells, recombinant nucleic acids, and recombinant proteins are also disclosed, along with methods of producing each. Isolated and purified antibodies to platelet VDCC $\alpha_1$ subunit polypeptides, and methods of producing the same, are also disclosed. Platelet VDCC $\alpha_1$ subunit polypeptides have biological activity in calcium transport. Thus, therapeutic and diagnostic methods involving this activity are also disclosed.

9 Claims, 20 Drawing Sheets

>ref|XM_001910.1| Homo sapiens calcium channel, voltage-dependent, L type,
alpha 1S subunit (CACNA1S), mRNA, Length = 6615

Score = 79.8 bits (40), Expect = 1e-12
Identities = 46/48 (95%)
Strand = Plus / Plus

```
Query:    1 ctgattgtcatcggcagcatcattgacgtcatcctcagtgagatcgac   48
            |||||||||||||||||||||||||| ||||||| |||||||||||||
Sbjct: 3938 ctgattgtcattggcagcatcattgatgtcatcatcagtgagatcgac 3985
```

Score = 622 bits (314), Expect = e-176
Identities = 462/510 (90%), Gaps = 1/510 (0%)
Strand = Plus / Plus

```
Query:   49 gaccccgacgagagtgcccgcatctccagcgccttctccgccgttccgggtcatgagg   108
            ||||| || ||||||||||||||||||||||||||||||||||||  ||||||||||
Sbjct: 4043 gacccagatgagagtgcccgcatctccagcgccttctccgccgttccgttccgtcatgagg 4102

Query:  109 ttgatcaagctgctgagccgcgagggcgtgcgcacgctgctccggacttcatcaag   168
            |||||||||||||||||||||||| |||||| ||| |||| |||||| |||||||
Sbjct: 4103 ctgatcaagctgctgagccgcgagccggggcagagagagtgcgaaccctgtggacgttcatcaag 4162

Query:  169 tccttccaggccctgccctacgtggctctgctcatcgtcatcttcttcatctatgct   228
            |||||||||||||||||||||| ||| |||| ||||||| |||||||||||| |||
Sbjct: 4163 tccttccaggccctaccctacgtggctctgctcatcgtcatcttcttcatctacgct 4222
```

FIG. 3B

```
Query:  229  gtcatcggcatgcagatgtttgggaagatcgccatggtggacggaacccagataaaccgg  288
             ||||||||||||||||||||||||||||||||||||||||||||||||||||||||||||
Sbjct: 4223  gtcatcggcatgcagatgtttgggaagatcgccttggtggatggacccaaataaaccgg  4282

Query:  289  aacaacaatttccagaccttccctcaggtctgtgctcttcaggtgcgccacgggt  348
             ||||||||||||||||||||||||||||||||||||||||||||||||||||||
Sbjct: 4283  aacaacaactccagaccttcccacaagctgtgctcttcaggtgtgtgcaacaggt  4342

Query:  349  gaggcgtggcaggagatcctgctgcaggtacgggcagctgtgcgaccccgagtca  408
             ||||||||||||||||||||||||||||||||||||||||||||||||||||||
Sbjct: 4343  gaggcctggcaggagatcctactggcctgcagctatggaagctgtgaccccagagtcg  4402

Query:  409  gactacctccctggggaggagtataccctgcggcaccgacttcgcctactacttcatc  468
             |||||||||||||||||||||||||||||||||||||||||||||||||||||||||
Sbjct: 4403  gactatgccccaggggaggagtacacatggcaccaacttttgcatactacttcatc  4462

Query:  469  agcttctacatgctctgtgcctcctgatcatcaacctctttgtggctgtgatcatggac  528
             |||||||||||||||||||||||||||||||||||||||||||||||||||||||||
Sbjct: 4463  agcttctacatgctctgtgcctcctggtcatcaacctcctcttgtgctgtcatcatggac  4522

Query:  529  aatttgactacctcaccc-ggactggtcc   557
             ||||||||||||||||||  ||||||||||
Sbjct: 4523  aatttgactacctcacccgggactggtcc  4552
```

FIG. 3C

>ref|NM_000069.1| Homo sapiens calcium channel, voltage-dependent, L type, alpha 1S, subunit (CACNA1S), mRNA, Length = 6160

Score = 79.8 bits (40), Expect = 1e-12
Identities = 46/48 (95%)
Strand = Plus / Plus

```
Query: 1     ctgattgtcatcggcagcatcattgacgtcatcctcagtgagatcgac    48
             |||||||||||| ||||||||||| ||||||||||||||||||||||||
Sbjct: 3787  ctgattgtcattggcagcatcattgatgtcatcctcagtgagatcgac    3834
```

Score = 622 bits (314), Expect = e-176
Identities = 462/510 (90%), Gaps = 1/510 (0%)
Strand = Plus / Plus

```
Query: 49    gaccccgacgagagtgcccgcatctccagcgcctctccgcctgttc-ggtcatgagg    108
             ||||| || |||||||||||||||||||||||| ||||||||||||  |||||||||
Sbjct: 3892  gacccagatgagagtgcccgcatctccagcgcctctccgcctgttccggtcatgagg    3951

Query: 109   ttgatcaagctgctgagccgcgaggggcgtgcgcacgtgctccggacttcatcaag     168
             ||||||||||||||||||||||| ||||| ||| ||||||||  ||||||||||||
Sbjct: 3952  ctgatcaagctgctgagccgggagcggcgagaggagtgcgaacctcctgtgacgttcatcaag     4011

Query: 169   tccttccaggccctgcctcacgtggctctctgctcatgtctcttcatctatgct     228
             |||||||||||||||| ||||||| ||||||||||||  |||||| |||| |||
Sbjct: 4012  tccttccaggccctaccctcacgtggctcatgctctgctgtctcttcatctacgct     4071
```

FIG. 3D

```
Query:  229  gtcatcggcatgcagatgtttgggaagatcgccatggtgtggacggaacccagataaaccgg  288
             ||||||||||||||||||||||||||||||||||||||||||||||||||||||||||||||
Sbjct: 4072  gtcatcggcatgcagatgtttgggaagatcgccatggtgtggaccccaaataaaccgg    4131

Query:  289  aacaacaatttccagaccttccctcaggctgctgctgctcttcaggtgcgccacgggt     348
             ||||||||||||||||||||||||||||||||||||||||||||||||||||||||||
Sbjct: 4132  aacaacaacttccagaccttcccacaagctgctactgctgctcttcaggtgtgcaacaggt  4191

Query:  349  gaggcgtgtggcaggagagatcctgctgcctgcaggtacgggccagcagtgtgcgaccccgagtca     408
             |||||||||||||||||||||||||||||||||||||||||||||||||||||||||||||||||
Sbjct: 4192  gaggcctggcgcaggagagatcctgctgcctatggccagctatgtggtgtgaccagagtcg  4251

Query:  409  gactacctcccctgggggaggagtatacctgccggcaccgacttcgcctactactacttcatc     468
             ||||||||||||| |||||||||||||||||||||||||||||||||||||||||||||||||
Sbjct: 4252  gactatgccccaggggggaggagtacacacatgtggcaccaacttggcaccatcattcatc    4311

Query:  469  agcttctacatgctctgtgcctctttgtggctgtgatcatggac     528
             ||||||||||||||||||||||||||||||||||||||||||||
Sbjct: 4312  agcttctacatgctctgtgcctctttgtggctgtcatcatggac    4371

Query:  529  aatttgactacctcaccc-ggactggtcc     557
             ||||||||||||||||||  ||||||||||
Sbjct: 4372  aatttgactacctcacccgggactggtcc   4401
```

FIG. 3E

```
>gb|L13798.1|HUMCACNLA Human dihydropyridine-sensitive L-type calcium channel
alpha-1 subunit (CACNL1A3) mRNA, complete cds, Length = 6160

Score = 79.8 bits (40), Expect = 1e-12
Identities = 46/48 (95%)
Strand = Plus / Plus Query:    1 ctgattgtcatcggcagcatcattgacgtcatcctcagtgagatcgac 48
            |||||||||||||||||||||||||| |||||||||||||||||||||
Sbjct: 3787 ctgattgtcattggcagcatcattgatgtcatcctcagtgagatcgac 3834

Score = 622 bits (314), Expect = e-176
Identities = 462/510 (90%), Gaps = 1/510 (0%)
Strand = Plus / Plus Query:   49 gaccccgacgagagtgccccgcatctccagcgcctttctccgcgttccgggtcatgagg 108
            ||||||| ||||||||||||||||||||||||||||||||||||||| |||||||||||
Sbjct: 3892 gacccagatgagagtgccccgcatctccagcgcctttctccgcgttccgtgtcatgagg 3951

Query:  109 ttgatcaagctgctgagccgcgagggcgtgcgcacgctgctccggaccttcatcaag 168
            |||||||||||||||||||||||||  |||  ||||||||||||||||||||||||
Sbjct: 3952 ctgatcaagctgctgagccgcgagccgaaccctgtggacgttcatcaag 4011
```

```
Query:  169  tccttccaggccctgccctacgtggctctgctcatgtctcttcatctatgct  228
             ||||||||||||||||||||||||||||||||||||||||||||||||||||
Sbjct:  4012 tccttccaggccctaccctacgtggctctgctcatgtctcttcatctacgct  4071

Query:  229  gtcatcggcatgcagatgtttgggaagatcgccatggtggacggaacccagataaaccgg  288
             ||||||||||||||||||||||||||||||||||||||||||||||||||||||||||||
Sbjct:  4072 gtcatcggcatgcagatgtttgggaagatcgccatggtggaccccaaataaaccgg  4131

Query:  289  aacaacaattcccagacccttcctgctgtgctcttcaggctgcgccacgggt  348
             ||||||||||||||||||||||||||||||||||||||||||||||||||||
Sbjct:  4132 aacaacaacttccagacccttcccacaagctgtgctcttcaggtgcaacaggt  4191

Query:  349  gaggcgtggcaggagagatcctgctgctggcctgcaggtacgggcagctgtgcgaccccgagtca  408
             ||||||||||||||||||||||||||||||||||||||||||||||||||||||||||||
Sbjct:  4192 gaggcctggcaggagagatcctgctgctggcctgcagctagggcagctgtgtgaccagagtcg  4251

Query:  409  gactactccctggggaggagtataccgcggcaccgacttcgcctactacttcatc  468
             ||||||||||||||||||||||||||||||||||||||||||||||||||||||
Sbjct:  4252 gactatgcccaggggaggagtagtacaccatgtggcaccaacttgcaccaacttactacttcatc  4311

Query:  469  agctcctacatgctctgtgcctcctgatcatcaacctctttgtggctgtgatcatggac  528
             |||||||||||||||||||||||||||||||||||||||||||||||||||||||||||
Sbjct:  4312 agcttctacatgctctgtgcctcctgtcatcaacctctttgtggctgtcatcatggac  4371

Query:  529  aattttgactacctcaccc-ggactggtcc  557
             ||||||||||||||||||| ||||||||||
Sbjct:  4372 aattttgactacctcacccgggactggtcc  4401
```

>ref|XM_001910.1| Homo sapiens calcium channel, voltage-dependent, L type,
alpha 1S subunit (CACNA1S), mRNA, Length = 6615

Score = 107 bits (54), Expect = 5e-21
Identities = 63/66 (95%)
Strand = Plus / Plus

```
Query: 1     tggaatgtgttcgacttcctgattgtcatcggcagcatcattgacgtcatcctcagtgag   60
             |||||||||||| ||||||||||||||||||||||||||||| |||||||||||||||||
Sbjct: 3920  tggaatgtgtttgacttcctgattgtcatcggcagcatcattgatgtcatcctcagtgag 3979

Query: 61    atcgac  66
             ||||||
Sbjct: 3980  atcgac  3985
```

Score = 507 bits (256), Expect = e-141
Identities = 388/432 (89%)
Strand = Plus / Plus

```
Query: 67    gaccccgacgagagtgccgcgcatctccagcgccttcttccagcgcctgttccgggtcatgagg   126
             |||||| |||||||||||||||||||||||||||||||||||||||||||||||||||||||||
Sbjct: 4043  gaccagatgagagtgccgcgcatctccagcgccttcttccagcgcctgttccgtgtcatgagg  4102

Query: 127   ttgatcaagctgctgagccgcgcgagggcgtgcgcacgcgtctgacttcatcaag   186
             |||||||||||||||||||| |||||||  ||||     |||||| ||||||||
Sbjct: 4103  ctgatcaagctgctgagccgggcgagggcagaaggagtgcgaacccctgtgacgttcatcaag  4162
```

FIG. 4B

```
Query:   187  tccttccaggccctgccctacgtggctctgctcatcgtcatctcttcatctatgct  246
              ||||||||||||||||||||||||||||||||||||||||||||||||||||||||
Sbjct:  4163  tccttccaggccctaccctacgtggctctgctcatcgtcatctcttcatctacgct  4222

Query:   247  gtcatcggcatgcagatgtttgggaagatcgccatggtggacggaacccagataaaaccgg  306
              ||||||||||||||||||||||||||||||||||||||||||||||||||||||||||||
Sbjct:  4223  gtcatcggcatgcagatgtttgggaagatcgccatggtggatgggacccaaataaaaccgg  4282

Query:   307  aacaacaatttccagacccttccctcaggctgctgctcttcagtgtgcgccacgggt  366
              ||||||||||||||||||||||||||||||||||||||||||||||||||||||||
Sbjct:  4283  aacaacaacttccagacccttcccacaagctgctgctcttcagtgtgcgccacgggt  4342

Query:   367  gaggcgtggcaggagatcctgctgccagtacgggcagctgtgcgacccgagtca  426
              ||||||||||||||||||||||||||||||||||||||||||||||||||||
Sbjct:  4343  gaggcctggcaggagatcctgctgccagtacgggcagctgtgcgacccgagtcg  4402

Query:   427  gactacctcccctggggaggagtataccgcctacttcgcggcaccgacttcatc  486
              ||||||||||||||||||||||||||||||||||||||||||||||||||||
Sbjct:  4403  gactatgccccagggaggggagtacacatgtggcaccaacttttgcatactacttcatc  4462

Query:   487  agcttctacatg  498
              ||||||||||||
Sbjct:  4463  agcttctacatg  4474
```

FIG. 5A

>ref|XM_003238.1| Homo sapiens calcium channel, voltage-dependent, L type, alpha 1D subunit (CACNA1D), mRNA, Length = 7362

Score = 89.7 bits (45), Expect = 1e-15
Identities = 45/45 (100%)
Strand = Plus / Plus

```
Query:    1  ctcatcgtaatcggcagcattatagacgtggccctcagcgaagca   45
             |||||||||||||||||||||||||||||||||||||||||||||
Sbjct: 4171  ctcatcgtaatcggcagcattatagacgtggccctcagcgaagca   4215
```

Score = 946 bits (477), Expect = 0.0
Identities = 496/500 (99%), Gaps = 2/500 (0%)
Strand = Plus / Plus

```
Query:   49  aactctgaagagagcaatagaatctccatcaccttttccgtctttttccgagtgatgcga  108
             ||||||||||||||||||||||||||||||||||||||||||||||||||||||||||||
Sbjct: 4264  aactctgaagagagcaatagaatctccatcaccttttccgtctttttccgagtgatgcga  4323

Query:  109  ttggtgaagcttctcagcagcaggggggaagcattgctgtggactttttattaag  168
             ||||||||||||||||||||||||||||||||||||||||||||||||||||||||||||
Sbjct: 4324  ttggtgaagcttctcagcagcagggggggaagcattgctgtggactttttattaag  4383

Query:  169  tcctttcaggcgctcccgtatgtggccctcctcatagccatgctgttcttcatctatgcg  228
             ||||||||||||||||||||||||||||||||||||||||||||||||||||||||||||
Sbjct: 4384  tcctttcaggcgctcccgtatgtggccctcctcatagccatgctgttcttcatctatgcg  4443
```

FIG. 5B

```
Query: 229   gtcattggcatgcagatgtttgggaaagttgccatgagagataacaaccagatcaataggg  288
             ||||||||||||||||||||||||||||||||||||||||||||||||||||||||||||
Sbjct: 4444  gtcattggcatgcagatgtttgggaaagttgccatgagagataacaaccagatcaataggg  4503

Query: 289   aacaataacttccagacgtttccccaggcggtgctgtctcttcaggtgtgcaacaggt  348
             ||||||||||||||||||||||||||||||||||||||||||||||||||||||||||||
Sbjct: 4504  aacaataacttccagacgtttccccaggcggtgctgtctcttcaggtgtgcaacaggt  4563

Query: 349   gaggcctggcaggagatcatgctggcctgtctcccaggaagctctgtgaccctgagtca  408
             ||||||||||||||||||||||||||||||||||||||||||||||||||||||||||||
Sbjct: 4564  gaggcctggcaggagatcatgctggcctgtctcccaggaagctctgtgaccctgagtca  4623

Query: 409   gattacaaacctcggggaggagtatacatgtgggagcaacttgccattgtctatttcatc  468
             ||||||||||||||||||||||||||||||||||||||||||||||||||||||||||||
Sbjct: 4624  gattacaaccccggggaggagtatacatgtgggagcaacttgccattgtctatttcatc  4683

Query: 469   agntttacatgctctgtgcatttctga-catcaatctgtttggctgtcatgga  527
             || |||||||||||||||||||||||| |||||||||||||||||| ||||||
Sbjct: 4684  agtttttacatgctctgtgcattctgatcatcaatctgttt-gtggctgtcatcatgga  4742

Query: 528   taatttcgactatctgaccc  547
             ||||||||||||||||||||
Sbjct: 4743  taatttcgactatctgaccc  4762
```

FIG. 5C

>ref|NM_000720.1| Homo sapiens calcium channel, voltage-dependent, L type, alpha 1D subunit (CACNA1D), mRNA, Length = 7193

Score = 87.7 bits (44), Expect = 5e-15
Identities = 44/44 (100%)
Strand = Plus / Plus Query: 1      ctcatcgtaatcggcagcattatagacgtggccctcagcgaagc   44
              ||||||||||||||||||||||||||||||||||||||||||||
Sbjct: 4001   ctcatcgtaatcggcagcattatagacgtggccctcagcgaagc   4044

Score = 946 bits (477), Expect = 0.0
Identities = 496/500 (99%), Gaps = 2/500 (0%)
Strand = Plus / Plus Query: 49     aactctgaagagagagcaatagaatctccatcaccttttccgtcttttccgagtgatgcga   108
              ||||||||||||||||||||||||||||||||||||||||||||||||||||||||||||
Sbjct: 4094   aactctgaagagagagcaatagaatctccatcaccttttccgtcttttccgagtgatgcga   4153

Query: 109    ttggtgaagcttctcagcaggggggaaggcatccggacattgctgtgtggactttattaag   168
              |||||||||||||||||||||| |||||||||||||||||||||||||||||||||||||
Sbjct: 4154   ttggtgaagcttctcagcagggggggaaggcatccggacattgctgtgtggactttattaag   4213

Query: 169    tcctttcaggcgtcccgtatgtggccctcctcatagccatgctgttcttcatctatgcg    228
              |||||||||||||||||||||||||||||||||||||||||||||||||||||||||||
Sbjct: 4214   tcctttcaggcgtcccgtatgtggccctcctcatagccatgctgttcttcatctatgcg    4273

FIG. 5D

```
Query:  229  gtcattggcatgcagatgtgtttgggaaagttgccatgagagataacaaccagatcaatagg  288
             ||||||||||||||||||||||||||||||||||||||||||||||||||||||||||||||
Sbjct: 4274  gtcattggcatgcagatgtgtttgggaaagttgccatgagagataacaaccagatcaatagg  4333

Query:  289  aacaataacttccagacgttccccaggcggtgctgctctcttcaggtgtgcaacaggt  348
             |||||||||||||||||||||||||||||||||||||||||||||||||||||||||
Sbjct: 4334  aacaataacttccagacgttccccaggcggtgctgctctcttcaggtgtgcaacaggt  4393

Query:  349  gaggcctggcaggagatcatgctggcctgtctcccagggaagctctgtgaccctgagtca  408
             ||||||||||||||||||||||||||||||||||||||||||||||||||||||||||||
Sbjct: 4394  gaggcctggcaggagatcatgctggcctgtctcccagggaagctctgtgaccctgagtca  4453

Query:  409  gattacaacctcggggaggagtatacacatgtgggagcaacttgccattgtctattcatc  468
             ||||||||||||||||||||||||||||||||||||||||||||||||||||||||||||
Sbjct: 4454  gattacaaccccggggaggagtatacacatgtgggagcaacttgccattgtctattcatc  4513

Query:  469  agntttttacatgctctgtgcatttctga-catcaatctgtttggtggctgtcatcatgga  527
             || ||||||||||||||||||||||||| ||||||||||||| |||||||||||||||||
Sbjct: 4514  agtttttacatgctctgtgcattctgatcatcaatctgttt-gtggctgtcatcatgga  4572

Query:  528  taatttcgactatctgaccc  547
             ||||||||||||||||||||
Sbjct: 4573  taatttcgactatctgaccc  4592
```

FIG. 5E

>gb|M83566.1|HUMCACH1A Human neuroendocrine/beta-cell-type calcium channel
alpha-1 subunit mRNA, complete cds, Length = 7193

Score = 87.7 bits (44), Expect = 5e-15
Identities = 44/44 (100%)
Strand = Plus / Plus Query: 1      ctcatcgtaatcggcagcattatagacgtggccctcagcgaagc  44
              ||||||||||||||||||||||||||||||||||||||||||||
Sbjct: 4001   ctcatcgtaatcggcagcattatagacgtggccctcagcgaagc  4044

Score = 946 bits (477), Expect = 0.0
Identities = 496/500 (99%), Gaps = 2/500 (0%)
Strand = Plus / Plus Query: 49     aactctgaagagagagcaatagaatctccatcacctttccgtcttttccgagtgatgcga  108
              ||||||||||||||||||||||||||||||||||||||||||||||||||||||||||||
Sbjct: 4094   aactctgaagagagagcaatagaatctccatcacctttccgtcttttccgagtgatgcga  4153

Query: 109    ttggtgaagcttctcagcaggggggaaggcatccggacattgctgtggactttattaag   168
              ||||||||||||||||||||||||||||||||||||||||||||||||||||||||||||
Sbjct: 4154   ttggtgaagcttctcagcaggggggaaggcatccggacattgctgtggactttattaag   4213

```
Query: 169   tcctttcaggcggctcccgtatgtggccctcctcatagccatgctgtcttcatctatgcg   228
             ||||||||||||||||||||||||||||||||||||||||||||||||||||||||||||
Sbjct: 4214  tcctttcaggcggctcccgtatgtggccctcctcatagccatgctgtcttcatctatgcg  4273

Query: 229   gtcattggcatgcagatgtttgggaaagttgccatgagagataacaaccagatcaatagg   288
             ||||||||||||||||||||||||||||||||||||||||||||||||||||||||||||
Sbjct: 4274  gtcattggcatgcagatgtttgggaaagttgccatgagagataacaaccagatcaatagg  4333

Query: 289   aacaataacttccagacgtttccccaggcggtgctgctcttcaggtgtgcaacaggt     348
             ||||||||||||||||||||||||||||||||||||||||||||||||||||||||
Sbjct: 4334  aacaataacttccagacgtttccccaggcggtgctgctcttcaggtgtgcaacaggt    4393

Query: 349   gaggcctggcaggagatcatgctggcctgtctcccagggaagctctgtgaccctgagtca   408
             ||||||||||||||||||||||||||||||||||||||||||||||||||||||||||||
Sbjct: 4394  gaggcctggcaggagatcatgctggcctgtctcccagggaagctctgtgaccctgagtca  4453

Query: 409   gattacaacctcggggaggagtatacatgtgggagcaacttctgccattgtctatttcatc  468
             ||||||||||||||||||||||||||||||||||||||||||||||||||||||||||||
Sbjct: 4454  gattacaaccccggggaggagtatacatgtgggagcaacttctgccattgtctatttcatc  4513

Query: 469   agnttttacatgctctgtgcattctga-catcaatctgtttggtggctgtcatcatgga   527
             || ||||||||||||||||||||||| |||||||||||||||||||||||||||||||
Sbjct: 4514  agttttacatgctctgtgcattctgatcatcaatcatcatcatctgttt-gtggctgtcatcatgga  4572

Query: 528   taatttcgactatctgaccc   547
             ||||||||||||||||||||
Sbjct: 4573  taatttcgactatctgaccc  4592
```

FIG. 5F

SEQUENCE LISTING

```
<160> NUMBER OF SEQ ID NOS: 29

<210> SEQ ID NO 1
<211> LENGTH: 5565
<212> TYPE: DNA
<213> ORGANISM: Homo sapiens
<220> FEATURE:
<221> NAME/KEY: CDS
<222> LOCATION: (1)..(5565)

<400> SEQUENCE: 1 atg gag cca tcc tca ccc cag gat gaa ggc ctg agg aag aaa cag ccc      48
Met Glu Pro Ser Ser Pro Gln Asp Glu Gly Leu Arg Lys Lys Gln Pro
1               5                   10                  15 aag aag cca gtt cct gag att ctg cca agg cca ccc cgg gct ttg ttc      96
```

```
                                            -continued

Lys Lys Pro Val Pro Glu Ile Leu Pro Arg Pro Pro Arg Ala Leu Phe
            20                  25                  30 tgc ctg acc ctg gag aac ccc ctg agg aag gcc tgc atc agc att gta      144
Cys Leu Thr Leu Glu Asn Pro Leu Arg Lys Ala Cys Ile Ser Ile Val
        35                  40                  45 gaa tgg aag ccc ttc gag acg atc atc ttg ctc acc atc ttt gcc aat      192
Glu Trp Lys Pro Phe Glu Thr Ile Ile Leu Leu Thr Ile Phe Ala Asn
    50                  55                  60 tgt gtg gcc ctg gcc gtg tac ctg ccc atg ccg gaa gat gac aac aac      240
Cys Val Ala Leu Ala Val Tyr Leu Pro Met Pro Glu Asp Asp Asn Asn
65                  70                  75                  80 tct ctg aac ctc ggc ctg gag aag ctg gag tat ttc ttc ctc att gtc      288
Ser Leu Asn Leu Gly Leu Glu Lys Leu Glu Tyr Phe Phe Leu Ile Val
                85                  90                  95 ttc tcg att gaa gcc gcc atg aag atc att gcc tac ggc ttc tta ttc      336
Phe Ser Ile Glu Ala Ala Met Lys Ile Ile Ala Tyr Gly Phe Leu Phe
            100                 105                 110 cac cag gac gct tac ctg cgc agt ggc tgg aat gtg ctg gac ttc acc      384
His Gln Asp Ala Tyr Leu Arg Ser Gly Trp Asn Val Leu Asp Phe Thr
        115                 120                 125 att gtc ttc ctg ggg gtc ttc acc gtg att ctg gaa cag gtt aac gtc      432
Ile Val Phe Leu Gly Val Phe Thr Val Ile Leu Glu Gln Val Asn Val
    130                 135                 140 atc caa agc cac aca gcc cca atg agc agc aaa gga gcc ggc ttg gat      480
Ile Gln Ser His Thr Ala Pro Met Ser Ser Lys Gly Ala Gly Leu Asp
145                 150                 155                 160 gtc aag gcc ctc aga gcc ttc cga gtg ctc aga ccc ctc cgg ctg gtg      528
Val Lys Ala Leu Arg Ala Phe Arg Val Leu Arg Pro Leu Arg Leu Val
                165                 170                 175 tcg ggg gtg cct agc ctg cag gtg gtc ctg aac tcc atc ttc aag gcc      576
Ser Gly Val Pro Ser Leu Gln Val Val Leu Asn Ser Ile Phe Lys Ala
            180                 185                 190 atg ctc ccc ctc ttt cac atc gcc ctg ctg gtc ctc ttt atg gtc atc      624
Met Leu Pro Leu Phe His Ile Ala Leu Leu Val Leu Phe Met Val Ile
        195                 200                 205 atc tat gcc atc atc ggg ctg gag ctc ttc aag ggc aag atg cac aag      672
Ile Tyr Ala Ile Ile Gly Leu Glu Leu Phe Lys Gly Lys Met His Lys
    210                 215                 220 acc tgc tac ttc att ggt aca gat atc gtg gcc acg gtg gag aat gaa      720
Thr Cys Tyr Phe Ile Gly Thr Asp Ile Val Ala Thr Val Glu Asn Glu
225                 230                 235                 240 gag cca tcg ccc tgc gcc agg acg ggc tca ggg cgc cgg tgc acc atc      768
Glu Pro Ser Pro Cys Ala Arg Thr Gly Ser Gly Arg Arg Cys Thr Ile
                245                 250                 255 aat ggc agt gag tgc cgg ggc ggc tgc cca ggg ccc aac cat ggc atc      816
Asn Gly Ser Glu Cys Arg Gly Gly Cys Pro Gly Pro Asn His Gly Ile
            260                 265                 270 acc cac ttc gac aac ttc ggc ttc tcc atg ctc acc gtg tac cag tgc      864
Thr His Phe Asp Asn Phe Gly Phe Ser Met Leu Thr Val Tyr Gln Cys
        275                 280                 285 att acc atg gag gga tgg act gac gtc ctt tac tgg gtc aat gat gcc      912
Ile Thr Met Glu Gly Trp Thr Asp Val Leu Tyr Trp Val Asn Asp Ala
    290                 295                 300 atc ggg aat gag tgg ccc tgg atc tat ttt gtc acc ctc att ttg ctg      960
Ile Gly Asn Glu Trp Pro Trp Ile Tyr Phe Val Thr Leu Ile Leu Leu
305                 310                 315                 320 gga tcc ttc ttc atc ctc aac ctg gtg ctg ggt gtc ctg agt ggg gaa      1008
Gly Ser Phe Phe Ile Leu Asn Leu Val Leu Gly Val Leu Ser Gly Glu
                325                 330                 335
```

```
ttc acc aag gag cgg gag aag gcc aag tcc agg gga acc ttc cag aag      1056
Phe Thr Lys Glu Arg Glu Lys Ala Lys Ser Arg Gly Thr Phe Gln Lys
        340                 345                 350 ctc cgg gag aag cag caa cta gat gag gac ctt cgg ggc tac atg agc      1104
Leu Arg Glu Lys Gln Gln Leu Asp Glu Asp Leu Arg Gly Tyr Met Ser
            355                 360                 365 tgg atc acg cag ggc gag gtc atg gat gtt gag gac ttc aga gaa gga      1152
Trp Ile Thr Gln Gly Glu Val Met Asp Val Glu Asp Phe Arg Glu Gly
    370                 375                 380 aaa ctg tct ttg gat gaa ggt ggc tct gac aca gag agc ctg tat gaa      1200
Lys Leu Ser Leu Asp Glu Gly Gly Ser Asp Thr Glu Ser Leu Tyr Glu
385                 390                 395                 400 att gca ggc ttg aac aaa atc atc cag ttc atc cga cat tgg agg cag      1248
Ile Ala Gly Leu Asn Lys Ile Ile Gln Phe Ile Arg His Trp Arg Gln
                405                 410                 415 tgg aac cgc atc ttt cgc tgg aag tgc cat gac atc gtg aag tcc aag      1296
Trp Asn Arg Ile Phe Arg Trp Lys Cys His Asp Ile Val Lys Ser Lys
            420                 425                 430 gtc ttc tat tgg ctg gtg att ctc atc gtt gcc ctc aac acc ctg tct      1344
Val Phe Tyr Trp Leu Val Ile Leu Ile Val Ala Leu Asn Thr Leu Ser
        435                 440                 445 atc gcc tca gag cac cac aac cag ccg cac tgg ctg acc cgt ttg caa      1392
Ile Ala Ser Glu His His Asn Gln Pro His Trp Leu Thr Arg Leu Gln
450                 455                 460 gac att gcc aac cgg gtg ctg ctg tcc ctc ttc acc act gag atg ctg      1440
Asp Ile Ala Asn Arg Val Leu Leu Ser Leu Phe Thr Thr Glu Met Leu
465                 470                 475                 480 atg aag atg tac ggg ctg ggc ctg cgc cag tac ttc atg tct atc ttc      1488
Met Lys Met Tyr Gly Leu Gly Leu Arg Gln Tyr Phe Met Ser Ile Phe
                485                 490                 495 aac cgc ttc gac tgc ttc gtg gtg tgc agc ggt atc ctg gag atc ctg      1536
Asn Arg Phe Asp Cys Phe Val Val Cys Ser Gly Ile Leu Glu Ile Leu
            500                 505                 510 ctg gtg gag tcg ggc gcc atg aca ccc ctg ggc atc tcc gtg ctc cgc      1584
Leu Val Glu Ser Gly Ala Met Thr Pro Leu Gly Ile Ser Val Leu Arg
        515                 520                 525 tgc atc cgc ctc ctg agg atc ttc aag atc acc aaa tat tgg acg tcg      1632
Cys Ile Arg Leu Leu Arg Ile Phe Lys Ile Thr Lys Tyr Trp Thr Ser
530                 535                 540 ctg agc aac ctg gtg gca tcc ctg ctc aac tcc atc cgc tcc atc gcc      1680
Leu Ser Asn Leu Val Ala Ser Leu Leu Asn Ser Ile Arg Ser Ile Ala
545                 550                 555                 560 tcc ctg ctg ctg ctg ctc ttc ctc ttc atc gtc atc ttc gcc ctc ctg      1728
Ser Leu Leu Leu Leu Leu Phe Leu Phe Ile Val Ile Phe Arg Leu Leu
                565                 570                 575 ggc atg cag ctc ttt ggg ggg agg tat gac ttt gaa gac aca gaa gta      1776
Gly Met Gln Leu Phe Gly Gly Arg Tyr Asp Phe Glu Asp Thr Glu Val
            580                 585                 590 cgg cgc agc aac ttt gac aac ttt ccc caa gcc ctc atc agc gtc ttc      1824
Arg Arg Ser Asn Phe Asp Asn Phe Pro Gln Ala Leu Ile Ser Val Phe
        595                 600                 605 cag gta ctg aca ggg gaa gac tgg acc tca atg atg tac aat ggg atc      1872
Gln Val Leu Thr Gly Glu Asp Trp Thr Ser Met Met Tyr Asn Gly Ile
            610                 615                 620 atg gcc tcg agc ggg ccg tcc tac cct ggc atg ctt gtg tgc att tac      1920
Met Ala Ser Ser Gly Pro Ser Tyr Pro Gly Met Leu Val Cys Ile Tyr
625                 630                 635                 640 ttc atc atc ctt ttc gtc tgt ggc aac tac atc ctg ctc aat gtc ttc      1968
Phe Ile Ile Leu Phe Val Cys Gly Asn Tyr Ile Leu Leu Asn Val Phe
                645                 650                 655
```

| | | |
|---|---|---|
| ctg gcc att gcc gtg gac aac ctg gcc gag gcg gag agc ctg act tct<br>Leu Ala Ile Ala Val Asp Asn Leu Ala Glu Ala Glu Ser Leu Thr Ser<br>         660                     665                    670 | 2016 |
| gcc cag aag gcc aag gct gag gag aaa aaa cgc agg aag atg tcc aag<br>Ala Gln Lys Ala Lys Ala Glu Glu Lys Lys Arg Arg Lys Met Ser Lys<br>      675                      680                    685 | 2064 |
| ggt ctc cca gac aag tca gaa gag gag aag tca acg atg gcc aag aag<br>Gly Leu Pro Asp Lys Ser Glu Glu Glu Lys Ser Thr Met Ala Lys Lys<br>690                      695                    700 | 2112 |
| ctg gag cag aaa ccc aag ggt gag ggc atc ccc acc act gcc aag ctg<br>Leu Glu Gln Lys Pro Lys Gly Glu Gly Ile Pro Thr Thr Ala Lys Leu<br>705                      710                    715                    720 | 2160 |
| aaa atc gat gag ttt gaa tct aat gtc aat gag gtg aag gat ccc tac<br>Lys Ile Asp Glu Phe Glu Ser Asn Val Asn Glu Val Lys Asp Pro Tyr<br>                      725                    730                    735 | 2208 |
| ccc tca gcc gac ttc cca ggg gat gac gag gaa gat gag cct gag atc<br>Pro Ser Ala Asp Phe Pro Gly Asp Asp Glu Glu Asp Glu Pro Glu Ile<br>      740                      745                    750 | 2256 |
| ccg ctg agc ccc cga cca cgt ccc ctg gct gag ctg cag ctg aaa gag<br>Pro Leu Ser Pro Arg Pro Arg Pro Leu Ala Glu Leu Gln Leu Lys Glu<br>755                      760                    765 | 2304 |
| aag gcc gtg ccc att cca gaa gcc agc tcc ttc ttc atc ttc agc ccc<br>Lys Ala Val Pro Ile Pro Glu Ala Ser Ser Phe Phe Ile Phe Ser Pro<br>770                      775                    780 | 2352 |
| acc aat aag atc cgt gtc ctg tgt cac cgc atc gtc aat gcc acc tgg<br>Thr Asn Lys Ile Arg Val Leu Cys His Arg Ile Val Asn Ala Thr Trp<br>785                      790                    795                    800 | 2400 |
| ttc acc aac ttc atc ctg ctc ttc atc ctg ctc agc agc gct gca ctg<br>Phe Thr Asn Phe Ile Leu Leu Phe Ile Leu Leu Ser Ser Ala Ala Leu<br>                      805                    810                    815 | 2448 |
| gct gcg gaa gac ccc atc cgg gct gat tcc atg aga aat cag atc ctt<br>Ala Ala Glu Asp Pro Ile Arg Ala Asp Ser Met Arg Asn Gln Ile Leu<br>      820                      825                    830 | 2496 |
| aaa cac ttt gac atc ggg ttc acc tct gtc ttc act gtg gag att gtc<br>Lys His Phe Asp Ile Gly Phe Thr Ser Val Phe Thr Val Glu Ile Val<br>835                      840                    845 | 2544 |
| ctc aag atg acg acc tac gga gcc ttc ctg cac aag ggt tcc ttc tgc<br>Leu Lys Met Thr Thr Tyr Gly Ala Phe Leu His Lys Gly Ser Phe Cys<br>850                      855                    860 | 2592 |
| cgc aat tac ttc aac atg ctg gac ctg ctg gtg gtg gcc gtg tcc ctc<br>Arg Asn Tyr Phe Asn Met Leu Asp Leu Leu Val Val Ala Val Ser Leu<br>865                      870                    875                    880 | 2640 |
| atc tcc atg gga ctt gag tcc agt gcc atc tcc gtg gtg aag atc ctg<br>Ile Ser Met Gly Leu Glu Ser Ser Ala Ile Ser Val Val Lys Ile Leu<br>                      885                    890                    895 | 2688 |
| agg gtg ctg agg gtg ctc cga cca ctc aga gcc atc aac aga gcc aag<br>Arg Val Leu Arg Val Leu Arg Pro Leu Arg Ala Ile Asn Arg Ala Lys<br>      900                      905                    910 | 2736 |
| ggg ttg aag cac gtg gct agg tgc atg ttc gtg gcc atc agc acc atc<br>Gly Leu Lys His Val Ala Arg Cys Met Phe Val Ala Ile Ser Thr Ile<br>915                      920                    925 | 2784 |
| ggg aac atc gtg ctg gtc act acc ctc cta cag ttc atg ttt gcc tgc<br>Gly Asn Ile Val Leu Val Thr Thr Leu Leu Gln Phe Met Phe Ala Cys<br>930                      935                    940 | 2832 |
| atc ggc gtc cag ctc ttc aag ggg aag ttc ttc agg tgc acc gac ttg<br>Ile Gly Val Gln Leu Phe Lys Gly Lys Phe Phe Arg Cys Thr Asp Leu<br>945                      950                    955                    960 | 2880 |
| tcc aag atg aca gag gag gag tgc agg ggc tac tac tac gtg tac aag<br>Ser Lys Met Thr Glu Glu Glu Cys Arg Gly Tyr Tyr Tyr Val Tyr Lys | 2928 |

-continued

|  |  |  |  |  |  |  |  |  |  |  |  |  |  |  |  |
|---|---|---|---|---|---|---|---|---|---|---|---|---|---|---|---|
|  |  | 965 |  |  |  | 970 |  |  |  | 975 |  |  |  |  |  |
| gac | ggg | gac | ccc | atg | cag | ata | gag | ctg | cgt | cac | cgc | gag | tgg | gta | cac | 2976 |
| Asp | Gly | Asp | Pro | Met | Gln | Ile | Glu | Leu | Arg | His | Arg | Glu | Trp | Val | His |
|  |  | 980 |  |  |  |  | 985 |  |  |  |  | 990 |  |  |  | agc gac ttc cac ttc gac aat gtg ctc tca gcc atg atg tcc ctc ttc    3024
Ser Asp Phe His Phe Asp Asn Val Leu Ser Ala Met Met Ser Leu Phe
         995                1000               1005 acg gtc tcc acc ttc gag gga tgg cct cag ctg ctg tac aag gcc        3069
Thr Val Ser Thr Phe Glu Gly Trp Pro Gln Leu Leu Tyr Lys Ala
1010              1015               1020 ata gac tcc aat gcg gag gac gtg ggt ccc atc tac aac aac cgt        3114
Ile Asp Ser Asn Ala Glu Asp Val Gly Pro Ile Tyr Asn Asn Arg
1025              1030               1035 gtg gag atg gcc atc ttc ttc atc atc tac atc atc ctc att gcc        3159
Val Glu Met Ala Ile Phe Phe Ile Ile Tyr Ile Ile Leu Ile Ala
1040              1045               1050 ttc ttc atg atg aac atc ttt gtg ggc ttc gtc att gtc acc ttc        3204
Phe Phe Met Met Asn Ile Phe Val Gly Phe Val Ile Val Thr Phe
1055              1060               1065 cag gag cag gga gag act gag tac aag aac tgt gag ctg gac aag        3249
Gln Glu Gln Gly Glu Thr Glu Tyr Lys Asn Cys Glu Leu Asp Lys
1070              1075               1080 aac cag cgc caa tgt gta cag tat gcc ctg aag gcc cgc cca ctg        3294
Asn Gln Arg Gln Cys Val Gln Tyr Ala Leu Lys Ala Arg Pro Leu
1085              1090               1095 agg tgc tac att ccc aaa aac cca tac cag tac cag gtg tgg tac        3339
Arg Cys Tyr Ile Pro Lys Asn Pro Tyr Gln Tyr Gln Val Trp Tyr
1100              1105               1110 att gtc acc tcc tcc tac ttt gaa tac ctg atg ttt gcc ctc atc        3384
Ile Val Thr Ser Ser Tyr Phe Glu Tyr Leu Met Phe Ala Leu Ile
1115              1120               1125 atg ctc aac acc atc tgc ctc ggc atg cag cac tac aac cag tcg        3429
Met Leu Asn Thr Ile Cys Leu Gly Met Gln His Tyr Asn Gln Ser
1130              1135               1140 gag cag atg aac cac atc tca gac atc ctc aat gtg gcc ttc act        3474
Glu Gln Met Asn His Ile Ser Asp Ile Leu Asn Val Ala Phe Thr
1145              1150               1155 atc atc ttc acc ctg gag atg atc ctc aag ctc atg gcc ttc aag        3519
Ile Ile Phe Thr Leu Glu Met Ile Leu Lys Leu Met Ala Phe Lys
1160              1165               1170 gcc agg ggc tac ttt gga aac ccc tgg aat gtg ttt gac ttc ctg        3564
Ala Arg Gly Tyr Phe Gly Asn Pro Trp Asn Val Phe Asp Phe Leu
1175              1180               1185 att gtc att ggc agc atc att gat gtc atc ctc agt gag atc gac        3609
Ile Val Ile Gly Ser Ile Ile Asp Val Ile Leu Ser Glu Ile Asp
1190              1195               1200 gac cca gat gag agt gcc cgc atc tcc agc gcc ttc ttc cgc ctg        3654
Asp Pro Asp Glu Ser Ala Arg Ile Ser Ser Ala Phe Phe Arg Leu
1205              1210               1215 ttc cgt gtc atg agg ctg atc aag ctg ctg agc cgg gca gaa gga        3699
Phe Arg Val Met Arg Leu Ile Lys Leu Leu Ser Arg Ala Glu Gly
1220              1225               1230 gtg cga acc ctc ctg tgg acg ttc atc aag tcc ttc cag gcc cta        3744
Val Arg Thr Leu Leu Trp Thr Phe Ile Lys Ser Phe Gln Ala Leu
1235              1240               1245 ccc tac gtg gct ctg ctc atc gtc atg ctc ttc ttc atc tac gct        3789
Pro Tyr Val Ala Leu Leu Ile Val Met Leu Phe Phe Ile Tyr Ala
1250              1255               1260 gtc atc ggc atg cag atg ttt ggg aag atc gcc ttg gtg gat ggg        3834

-continued

| | | | | | | | | | | | | |
|---|---|---|---|---|---|---|---|---|---|---|---|---|
| Val | Ile | Gly | Met | Gln | Met | Phe | Gly | Lys | Ile | Ala | Leu | Val | Asp | Gly |
| | 1265 | | | | 1270 | | | | 1275 | | | |

| acc | caa | ata | aac | cgg | aac | aac | aac | ttc | cag | acc | ttc | cca | caa | gct | 3879 |
|---|---|---|---|---|---|---|---|---|---|---|---|---|---|---|---|
| Thr | Gln | Ile | Asn | Arg | Asn | Asn | Asn | Phe | Gln | Thr | Phe | Pro | Gln | Ala | |
| | 1280 | | | | 1285 | | | | 1290 | | | | | | |

| gtg | cta | ctg | ctc | ttc | agg | tgt | gca | aca | ggt | gag | gcc | tgg | cag | gag | 3924 |
|---|---|---|---|---|---|---|---|---|---|---|---|---|---|---|---|
| Val | Leu | Leu | Leu | Phe | Arg | Cys | Ala | Thr | Gly | Glu | Ala | Trp | Gln | Glu | |
| 1295 | | | | | 1300 | | | | | 1305 | | | | | |

| atc | cta | ctg | gcc | tgc | agc | tat | ggg | aag | ctg | tgt | gac | cca | gag | tcg | 3969 |
|---|---|---|---|---|---|---|---|---|---|---|---|---|---|---|---|
| Ile | Leu | Leu | Ala | Cys | Ser | Tyr | Gly | Lys | Leu | Cys | Asp | Pro | Glu | Ser | |
| 1310 | | | | | 1315 | | | | | 1320 | | | | | |

| gac | tat | gcc | cca | ggg | gag | gag | tac | aca | tgt | ggc | acc | aac | ttt | gca | 4014 |
|---|---|---|---|---|---|---|---|---|---|---|---|---|---|---|---|
| Asp | Tyr | Ala | Pro | Gly | Glu | Glu | Tyr | Thr | Cys | Gly | Thr | Asn | Phe | Ala | |
| 1325 | | | | | 1330 | | | | | 1335 | | | | | |

| tac | tac | tac | ttc | atc | agc | ttc | tac | atg | ctc | tgt | gcc | ttc | ctg | gtc | 4059 |
|---|---|---|---|---|---|---|---|---|---|---|---|---|---|---|---|
| Tyr | Tyr | Tyr | Phe | Ile | Ser | Phe | Tyr | Met | Leu | Cys | Ala | Phe | Leu | Val | |
| 1340 | | | | | 1345 | | | | | 1350 | | | | | |

| atc | aac | ctc | ttt | gtg | gct | gtc | atc | atg | gac | aat | ttt | gac | tac | ctc | 4104 |
|---|---|---|---|---|---|---|---|---|---|---|---|---|---|---|---|
| Ile | Asn | Leu | Phe | Val | Ala | Val | Ile | Met | Asp | Asn | Phe | Asp | Tyr | Leu | |
| 1355 | | | | | 1360 | | | | | 1365 | | | | | |

| acc | cgg | gac | tgg | tcc | atc | ctg | ggc | cct | cat | cac | ctg | gat | gag | ttc | 4149 |
|---|---|---|---|---|---|---|---|---|---|---|---|---|---|---|---|
| Thr | Arg | Asp | Trp | Ser | Ile | Leu | Gly | Pro | His | His | Leu | Asp | Glu | Phe | |
| 1370 | | | | | 1375 | | | | | 1380 | | | | | |

| aag | gcc | atc | tgg | gca | gag | tat | gac | cca | gag | gct | aag | ggg | agg | atc | 4194 |
|---|---|---|---|---|---|---|---|---|---|---|---|---|---|---|---|
| Lys | Ala | Ile | Trp | Ala | Glu | Tyr | Asp | Pro | Glu | Ala | Lys | Gly | Arg | Ile | |
| 1385 | | | | | 1390 | | | | | 1395 | | | | | |

| aaa | cac | ctg | gac | gtg | gtg | acc | ctg | ctg | aga | agg | att | cag | ccc | cct | 4239 |
|---|---|---|---|---|---|---|---|---|---|---|---|---|---|---|---|
| Lys | His | Leu | Asp | Val | Val | Thr | Leu | Leu | Arg | Arg | Ile | Gln | Pro | Pro | |
| 1400 | | | | | 1405 | | | | | 1410 | | | | | |

| ctg | ggc | ttt | ggg | aag | ttc | tgc | cca | cat | cgg | gta | gct | tgt | aag | cgg | 4284 |
|---|---|---|---|---|---|---|---|---|---|---|---|---|---|---|---|
| Leu | Gly | Phe | Gly | Lys | Phe | Cys | Pro | His | Arg | Val | Ala | Cys | Lys | Arg | |
| 1415 | | | | | 1420 | | | | | 1425 | | | | | |

| ctg | gtg | ggc | atg | aac | atg | ccc | ctg | aac | agc | gac | ggc | aca | gtc | acc | 4329 |
|---|---|---|---|---|---|---|---|---|---|---|---|---|---|---|---|
| Leu | Val | Gly | Met | Asn | Met | Pro | Leu | Asn | Ser | Asp | Gly | Thr | Val | Thr | |
| 1430 | | | | | 1435 | | | | | 1440 | | | | | |

| ttc | aat | gcc | aca | ctc | ttt | gcc | ctg | gtc | cgc | acg | gca | ctc | aag | atc | 4374 |
|---|---|---|---|---|---|---|---|---|---|---|---|---|---|---|---|
| Phe | Asn | Ala | Thr | Leu | Phe | Ala | Leu | Val | Arg | Thr | Ala | Leu | Lys | Ile | |
| 1445 | | | | | 1450 | | | | | 1455 | | | | | |

| aag | acg | gaa | ggt | aac | ttt | gag | cag | gcc | aac | gag | gag | ctg | agg | gcc | 4419 |
|---|---|---|---|---|---|---|---|---|---|---|---|---|---|---|---|
| Lys | Thr | Glu | Gly | Asn | Phe | Glu | Gln | Ala | Asn | Glu | Glu | Leu | Arg | Ala | |
| 1460 | | | | | 1465 | | | | | 1470 | | | | | |

| atc | atc | aag | aag | atc | tgg | aag | aga | acc | agc | atg | aag | ctc | ttg | gac | 4464 |
|---|---|---|---|---|---|---|---|---|---|---|---|---|---|---|---|
| Ile | Ile | Lys | Lys | Ile | Trp | Lys | Arg | Thr | Ser | Met | Lys | Leu | Leu | Asp | |
| 1475 | | | | | 1480 | | | | | 1485 | | | | | |

| cag | gtc | atc | cct | cca | ata | gga | gat | gat | gag | gtg | aca | gtg | ggg | aag | 4509 |
|---|---|---|---|---|---|---|---|---|---|---|---|---|---|---|---|
| Gln | Val | Ile | Pro | Pro | Ile | Gly | Asp | Asp | Glu | Val | Thr | Val | Gly | Lys | |
| 1490 | | | | | 1495 | | | | | 1500 | | | | | |

| ttc | tac | gcc | aca | ttc | ctc | atc | cag | gag | cac | ttc | cgg | aag | ttc | atg | 4554 |
|---|---|---|---|---|---|---|---|---|---|---|---|---|---|---|---|
| Phe | Tyr | Ala | Thr | Phe | Leu | Ile | Gln | Glu | His | Phe | Arg | Lys | Phe | Met | |
| 1505 | | | | | 1510 | | | | | 1515 | | | | | |

| aaa | cgc | caa | gag | gag | tat | tat | ggc | tat | cgg | ccc | aag | aag | gac | att | 4599 |
|---|---|---|---|---|---|---|---|---|---|---|---|---|---|---|---|
| Lys | Arg | Gln | Glu | Glu | Tyr | Tyr | Gly | Tyr | Arg | Pro | Lys | Lys | Asp | Ile | |
| 1520 | | | | | 1525 | | | | | 1530 | | | | | |

| gta | cag | atc | cag | gca | ggg | ctg | cgg | acc | att | gag | gaa | gag | gca | gcc | 4644 |
|---|---|---|---|---|---|---|---|---|---|---|---|---|---|---|---|
| Val | Gln | Ile | Gln | Ala | Gly | Leu | Arg | Thr | Ile | Glu | Glu | Glu | Ala | Ala | |
| 1535 | | | | | 1540 | | | | | 1545 | | | | | |

| ccc | gag | atc | tgt | cgc | acg | gtc | tca | gga | gac | ctg | gct | gct | gag | gag | 4689 |
|---|---|---|---|---|---|---|---|---|---|---|---|---|---|---|---|
| Pro | Glu | Ile | Cys | Arg | Thr | Val | Ser | Gly | Asp | Leu | Ala | Ala | Glu | Glu | |
| 1550 | | | | | 1555 | | | | | 1560 | | | | | |

-continued

| | |
|---|---|
| gag ctg gag aga gcc atg gtg gag gct gcg atg gag gag ggg ata<br>Glu Leu Glu Arg Ala Met Val Glu Ala Ala Met Glu Glu Gly Ile<br>1565                         1570                       1575 | 4734 |
| ttc cgg agg act gga ggc ctg ttt ggc cag gtg gac aac ttc ctg<br>Phe Arg Arg Thr Gly Gly Leu Phe Gly Gln Val Asp Asn Phe Leu<br>1580                         1585                       1590 | 4779 |
| gaa agg acc aac tcc ctg ccc cct gtc atg gcc aat cag aga ccc<br>Glu Arg Thr Asn Ser Leu Pro Pro Val Met Ala Asn Gln Arg Pro<br>1595                         1600                       1605 | 4824 |
| ctc cag ttt gct gag ata gag atg gaa gag atg gag tca cct gtc<br>Leu Gln Phe Ala Glu Ile Glu Met Glu Glu Met Glu Ser Pro Val<br>1610                         1615                       1620 | 4869 |
| ttc ttg gag gac ttc cca caa gat cca cgc acc aac ccc ctg gct<br>Phe Leu Glu Asp Phe Pro Gln Asp Pro Arg Thr Asn Pro Leu Ala<br>1625                         1630                       1635 | 4914 |
| cgt gcc aat acc aac aat gcc aac gcc aat gtc gcc tat gcg aac<br>Arg Ala Asn Thr Asn Asn Ala Asn Ala Asn Val Ala Tyr Ala Asn<br>1640                         1645                       1650 | 4959 |
| agc aac cat agc aac agc cat gtg ttt tcc agt gtc cac tat gaa<br>Ser Asn His Ser Asn Ser His Val Phe Ser Ser Val His Tyr Glu<br>1655                         1660                       1665 | 5004 |
| agg gag ttc cca gaa gag aca gag acg cct gct acc aga gga cga<br>Arg Glu Phe Pro Glu Glu Thr Glu Thr Pro Ala Thr Arg Gly Arg<br>1670                         1675                       1680 | 5049 |
| gcc ctt ggc caa ccc tgc agg tcc ctg gga ccc cac agc aaa ccc<br>Ala Leu Gly Gln Pro Cys Arg Ser Leu Gly Pro His Ser Lys Pro<br>1685                         1690                       1695 | 5094 |
| tgt gtg gag atg ctg aag gga ctg ctg acc cag agg gca atg ccc<br>Cys Val Glu Met Leu Lys Gly Leu Leu Thr Gln Arg Ala Met Pro<br>1700                         1705                       1710 | 5139 |
| aga ggc cag gca cct cct gcc ccc tgc cag tgc ccc agg gtg gag<br>Arg Gly Gln Ala Pro Pro Ala Pro Cys Gln Cys Pro Arg Val Glu<br>1715                         1720                       1725 | 5184 |
| tcc tcc atg cct gag gac aga aag agc tcc aca cca ggg tct ctt<br>Ser Ser Met Pro Glu Asp Arg Lys Ser Ser Thr Pro Gly Ser Leu<br>1730                         1735                       1740 | 5229 |
| cat gag gag aca ccc cac agc agg agc acc agg gag aat act tcc<br>His Glu Glu Thr Pro His Ser Arg Ser Thr Arg Glu Asn Thr Ser<br>1745                         1750                       1755 | 5274 |
| agg tgc tca gca cca gct aca gcc ctg ctg atc caa aag gct ctg<br>Arg Cys Ser Ala Pro Ala Thr Ala Leu Leu Ile Gln Lys Ala Leu<br>1760                         1765                       1770 | 5319 |
| gtt cga ggg ggc ctg ggc acc ttg gca gct gat gca aac ttc atc<br>Val Arg Gly Gly Leu Gly Thr Leu Ala Ala Asp Ala Asn Phe Ile<br>1775                         1780                       1785 | 5364 |
| atg gca aca ggc cag gcc ctc gga gat gcc tgc caa atg gaa cca<br>Met Ala Thr Gly Gln Ala Leu Gly Asp Ala Cys Gln Met Glu Pro<br>1790                         1795                       1800 | 5409 |
| gag gaa gtg gag atc atg gca aca gag cta ctg aaa gga cga gag<br>Glu Glu Val Glu Ile Met Ala Thr Glu Leu Leu Lys Gly Arg Glu<br>1805                         1810                       1815 | 5454 |
| gcc cca gac ggc atg gcc agc tcc ctg gga tgc ctg aac ctc ggg<br>Ala Pro Asp Gly Met Ala Ser Ser Leu Gly Cys Leu Asn Leu Gly<br>1820                         1825                       1830 | 5499 |
| tcc tcc ctg ggc agc ctc gac caa cac cag ggc tcc cag gag acc<br>Ser Ser Leu Gly Ser Leu Asp Gln His Gln Gly Ser Gln Glu Thr<br>1835                         1840                       1845 | 5544 |
| ctt att cct cca agg ctg tga<br>Leu Ile Pro Pro Arg Leu<br>1850 | 5565 |

```
<210> SEQ ID NO 2
<211> LENGTH: 1854
<212> TYPE: PRT
<213> ORGANISM: Homo sapiens

<400> SEQUENCE: 2

Met Glu Pro Ser Ser Pro Gln Asp Glu Gly Leu Arg Lys Lys Gln Pro
1               5                   10                  15

Lys Lys Pro Val Pro Glu Ile Leu Pro Arg Pro Arg Ala Leu Phe
            20                  25                  30

Cys Leu Thr Leu Glu Asn Pro Leu Arg Lys Ala Cys Ile Ser Ile Val
        35                  40                  45

Glu Trp Lys Pro Phe Glu Thr Ile Ile Leu Leu Thr Ile Phe Ala Asn
    50                  55                  60

Cys Val Ala Leu Ala Val Tyr Leu Pro Met Pro Glu Asp Asp Asn Asn
65                  70                  75                  80

Ser Leu Asn Leu Gly Leu Glu Lys Leu Glu Tyr Phe Phe Leu Ile Val
                85                  90                  95

Phe Ser Ile Glu Ala Ala Met Lys Ile Ile Ala Tyr Gly Phe Leu Phe
            100                 105                 110

His Gln Asp Ala Tyr Leu Arg Ser Gly Trp Asn Val Leu Asp Phe Thr
        115                 120                 125

Ile Val Phe Leu Gly Val Phe Thr Val Ile Leu Glu Gln Val Asn Val
    130                 135                 140

Ile Gln Ser His Thr Ala Pro Met Ser Ser Lys Gly Ala Gly Leu Asp
145                 150                 155                 160

Val Lys Ala Leu Arg Ala Phe Arg Val Leu Arg Pro Leu Arg Leu Val
                165                 170                 175

Ser Gly Val Pro Ser Leu Gln Val Val Leu Asn Ser Ile Phe Lys Ala
            180                 185                 190

Met Leu Pro Leu Phe His Ile Ala Leu Leu Val Leu Phe Met Val Ile
        195                 200                 205

Ile Tyr Ala Ile Ile Gly Leu Glu Leu Phe Lys Gly Lys Met His Lys
    210                 215                 220

Thr Cys Tyr Phe Ile Gly Thr Asp Ile Val Ala Thr Val Glu Asn Glu
225                 230                 235                 240

Glu Pro Ser Pro Cys Ala Arg Thr Gly Ser Gly Arg Arg Cys Thr Ile
                245                 250                 255

Asn Gly Ser Glu Cys Arg Gly Gly Cys Pro Gly Pro Asn His Gly Ile
            260                 265                 270

Thr His Phe Asp Asn Phe Gly Phe Ser Met Leu Thr Val Tyr Gln Cys
        275                 280                 285

Ile Thr Met Glu Gly Trp Thr Asp Val Leu Tyr Trp Val Asn Asp Ala
    290                 295                 300

Ile Gly Asn Glu Trp Pro Trp Ile Tyr Phe Val Thr Leu Ile Leu Leu
305                 310                 315                 320

Gly Ser Phe Phe Ile Leu Asn Leu Val Leu Gly Val Leu Ser Gly Glu
                325                 330                 335

Phe Thr Lys Glu Arg Glu Lys Ala Lys Ser Arg Gly Thr Phe Gln Lys
            340                 345                 350

Leu Arg Glu Lys Gln Gln Leu Asp Glu Asp Leu Arg Gly Tyr Met Ser
        355                 360                 365

Trp Ile Thr Gln Gly Glu Val Met Asp Val Glu Asp Phe Arg Glu Gly
```

-continued

```
            370                 375                 380
Lys Leu Ser Leu Asp Glu Gly Gly Ser Asp Thr Glu Ser Leu Tyr Glu
385                 390                 395                 400

Ile Ala Gly Leu Asn Lys Ile Ile Gln Phe Ile Arg His Trp Arg Gln
                405                 410                 415

Trp Asn Arg Ile Phe Arg Trp Lys Cys His Asp Ile Val Lys Ser Lys
                420                 425                 430

Val Phe Tyr Trp Leu Val Ile Leu Ile Val Ala Leu Asn Thr Leu Ser
            435                 440                 445

Ile Ala Ser Glu His His Asn Gln Pro His Trp Leu Thr Arg Leu Gln
450                 455                 460

Asp Ile Ala Asn Arg Val Leu Leu Ser Leu Phe Thr Thr Glu Met Leu
465                 470                 475                 480

Met Lys Met Tyr Gly Leu Gly Leu Arg Gln Tyr Phe Met Ser Ile Phe
                485                 490                 495

Asn Arg Phe Asp Cys Phe Val Val Cys Ser Gly Ile Leu Glu Ile Leu
                500                 505                 510

Leu Val Glu Ser Gly Ala Met Thr Pro Leu Gly Ile Ser Val Leu Arg
            515                 520                 525

Cys Ile Arg Leu Leu Arg Ile Phe Lys Ile Thr Lys Tyr Trp Thr Ser
530                 535                 540

Leu Ser Asn Leu Val Ala Ser Leu Leu Asn Ser Ile Arg Ser Ile Ala
545                 550                 555                 560

Ser Leu Leu Leu Leu Leu Phe Leu Phe Ile Val Ile Phe Arg Leu Leu
                565                 570                 575

Gly Met Gln Leu Phe Gly Gly Arg Tyr Asp Phe Glu Asp Thr Glu Val
            580                 585                 590

Arg Arg Ser Asn Phe Asp Asn Phe Pro Gln Ala Leu Ile Ser Val Phe
                595                 600                 605

Gln Val Leu Thr Gly Glu Asp Trp Thr Ser Met Met Tyr Asn Gly Ile
            610                 615                 620

Met Ala Ser Ser Gly Pro Ser Tyr Pro Gly Met Leu Val Cys Ile Tyr
625                 630                 635                 640

Phe Ile Ile Leu Phe Val Cys Gly Asn Tyr Ile Leu Leu Asn Val Phe
                645                 650                 655

Leu Ala Ile Ala Val Asp Asn Leu Ala Glu Ala Glu Ser Leu Thr Ser
                660                 665                 670

Ala Gln Lys Ala Lys Ala Glu Glu Lys Arg Arg Lys Met Ser Lys
                675                 680                 685

Gly Leu Pro Asp Lys Ser Glu Glu Lys Ser Thr Met Ala Lys Lys
            690                 695                 700

Leu Glu Gln Lys Pro Lys Gly Glu Gly Ile Pro Thr Thr Ala Lys Leu
705                 710                 715                 720

Lys Ile Asp Glu Phe Glu Ser Asn Val Asn Glu Val Lys Asp Pro Tyr
                725                 730                 735

Pro Ser Ala Asp Phe Pro Gly Asp Asp Glu Glu Asp Glu Pro Glu Ile
                740                 745                 750

Pro Leu Ser Pro Arg Pro Arg Pro Leu Ala Glu Leu Gln Leu Lys Glu
            755                 760                 765

Lys Ala Val Pro Ile Pro Glu Ala Ser Ser Phe Phe Ile Phe Ser Pro
770                 775                 780

Thr Asn Lys Ile Arg Val Leu Cys His Arg Ile Val Asn Ala Thr Trp
785                 790                 795                 800
```

-continued

Phe Thr Asn Phe Ile Leu Leu Phe Ile Leu Leu Ser Ser Ala Ala Leu
        805                 810                 815

Ala Ala Glu Asp Pro Ile Arg Ala Asp Ser Met Arg Asn Gln Ile Leu
        820                 825                 830

Lys His Phe Asp Ile Gly Phe Thr Ser Val Phe Thr Val Glu Ile Val
        835                 840                 845

Leu Lys Met Thr Thr Tyr Gly Ala Phe Leu His Lys Gly Ser Phe Cys
        850                 855                 860

Arg Asn Tyr Phe Asn Met Leu Asp Leu Leu Val Val Ala Val Ser Leu
865                 870                 875                 880

Ile Ser Met Gly Leu Glu Ser Ser Ala Ile Ser Val Val Lys Ile Leu
                885                 890                 895

Arg Val Leu Arg Val Leu Arg Pro Leu Arg Ala Ile Asn Arg Ala Lys
                900                 905                 910

Gly Leu Lys His Val Ala Arg Cys Met Phe Val Ala Ile Ser Thr Ile
                915                 920                 925

Gly Asn Ile Val Leu Val Thr Thr Leu Leu Gln Phe Met Phe Ala Cys
930                 935                 940

Ile Gly Val Gln Leu Phe Lys Gly Lys Phe Phe Arg Cys Thr Asp Leu
945                 950                 955                 960

Ser Lys Met Thr Glu Glu Cys Arg Gly Tyr Tyr Tyr Val Tyr Lys
                965                 970                 975

Asp Gly Asp Pro Met Gln Ile Glu Leu Arg His Arg Glu Trp Val His
                980                 985                 990

Ser Asp Phe His Phe Asp Asn Val Leu Ser Ala Met Met Ser Leu Phe
        995                 1000                1005

Thr Val Ser Thr Phe Glu Gly Trp Pro Gln Leu Leu Tyr Lys Ala
        1010                1015                1020

Ile Asp Ser Asn Ala Glu Asp Val Gly Pro Ile Tyr Asn Asn Arg
        1025                1030                1035

Val Glu Met Ala Ile Phe Phe Ile Ile Tyr Ile Ile Leu Ile Ala
        1040                1045                1050

Phe Phe Met Met Asn Ile Phe Val Gly Phe Val Ile Val Thr Phe
        1055                1060                1065

Gln Glu Gln Gly Glu Thr Glu Tyr Lys Asn Cys Glu Leu Asp Lys
        1070                1075                1080

Asn Gln Arg Gln Cys Val Gln Tyr Ala Leu Lys Ala Arg Pro Leu
        1085                1090                1095

Arg Cys Tyr Ile Pro Lys Asn Pro Tyr Gln Tyr Gln Val Trp Tyr
        1100                1105                1110

Ile Val Thr Ser Ser Tyr Phe Glu Tyr Leu Met Phe Ala Leu Ile
        1115                1120                1125

Met Leu Asn Thr Ile Cys Leu Gly Met Gln His Tyr Asn Gln Ser
        1130                1135                1140

Glu Gln Met Asn His Ile Ser Asp Ile Leu Asn Val Ala Phe Thr
        1145                1150                1155

Ile Ile Phe Thr Leu Glu Met Ile Leu Lys Leu Met Ala Phe Lys
        1160                1165                1170

Ala Arg Gly Tyr Phe Gly Asn Pro Trp Asn Val Phe Asp Phe Leu
        1175                1180                1185

Ile Val Ile Gly Ser Ile Ile Asp Val Ile Leu Ser Glu Ile Asp
        1190                1195                1200

-continued

Asp Pro Asp Glu Ser Ala Arg Ile Ser Ser Ala Phe Phe Arg Leu
1205                1210                1215

Phe Arg Val Met Arg Leu Ile Lys Leu Leu Ser Arg Ala Glu Gly
1220                1225                1230

Val Arg Thr Leu Leu Trp Thr Phe Ile Lys Ser Phe Gln Ala Leu
1235                1240                1245

Pro Tyr Val Ala Leu Leu Ile Val Met Leu Phe Phe Ile Tyr Ala
1250                1255                1260

Val Ile Gly Met Gln Met Phe Gly Lys Ile Ala Leu Val Asp Gly
1265                1270                1275

Thr Gln Ile Asn Arg Asn Asn Phe Gln Thr Phe Pro Gln Ala
1280                1285                1290

Val Leu Leu Leu Phe Arg Cys Ala Thr Gly Glu Ala Trp Gln Glu
1295                1300                1305

Ile Leu Leu Ala Cys Ser Tyr Gly Lys Leu Cys Asp Pro Glu Ser
1310                1315                1320

Asp Tyr Ala Pro Gly Glu Glu Tyr Thr Cys Gly Thr Asn Phe Ala
1325                1330                1335

Tyr Tyr Tyr Phe Ile Ser Phe Tyr Met Leu Cys Ala Phe Leu Val
1340                1345                1350

Ile Asn Leu Phe Val Ala Val Ile Met Asp Asn Phe Asp Tyr Leu
1355                1360                1365

Thr Arg Asp Trp Ser Ile Leu Gly Pro His His Leu Asp Glu Phe
1370                1375                1380

Lys Ala Ile Trp Ala Glu Tyr Asp Pro Glu Ala Lys Gly Arg Ile
1385                1390                1395

Lys His Leu Asp Val Val Thr Leu Leu Arg Arg Ile Gln Pro Pro
1400                1405                1410

Leu Gly Phe Gly Lys Phe Cys Pro His Arg Val Ala Cys Lys Arg
1415                1420                1425

Leu Val Gly Met Asn Met Pro Leu Asn Ser Asp Gly Thr Val Thr
1430                1435                1440

Phe Asn Ala Thr Leu Phe Ala Leu Val Arg Thr Ala Leu Lys Ile
1445                1450                1455

Lys Thr Glu Gly Asn Phe Glu Gln Ala Asn Glu Glu Leu Arg Ala
1460                1465                1470

Ile Ile Lys Lys Ile Trp Lys Arg Thr Ser Met Lys Leu Leu Asp
1475                1480                1485

Gln Val Ile Pro Pro Ile Gly Asp Asp Glu Val Thr Val Gly Lys
1490                1495                1500

Phe Tyr Ala Thr Phe Leu Ile Gln Glu His Phe Arg Lys Phe Met
1505                1510                1515

Lys Arg Gln Glu Glu Tyr Tyr Gly Tyr Arg Pro Lys Lys Asp Ile
1520                1525                1530

Val Gln Ile Gln Ala Gly Leu Arg Thr Ile Glu Glu Glu Ala Ala
1535                1540                1545

Pro Glu Ile Cys Arg Thr Val Ser Gly Asp Leu Ala Ala Glu Glu
1550                1555                1560

Glu Leu Glu Arg Ala Met Val Glu Ala Ala Met Glu Glu Gly Ile
1565                1570                1575

Phe Arg Arg Thr Gly Gly Leu Phe Gly Gln Val Asp Asn Phe Leu
1580                1585                1590

Glu Arg Thr Asn Ser Leu Pro Pro Val Met Ala Asn Gln Arg Pro

```
                    1595                1600                1605

Leu Gln  Phe Ala Glu Ile Glu  Met Glu Glu Met Glu  Ser Pro Val
    1610                1615                1620

Phe Leu  Glu Asp Phe Pro Gln  Asp Pro Arg Thr Asn  Pro Leu Ala
    1625                1630                1635

Arg Ala  Asn Thr Asn Asn Ala  Asn Ala Asn Val Ala  Tyr Ala Asn
    1640                1645                1650

Ser Asn  His Ser Asn Ser His  Val Phe Ser Ser Val  His Tyr Glu
    1655                1660                1665

Arg Glu  Phe Pro Glu Glu Thr  Glu Thr Pro Ala Thr  Arg Gly Arg
    1670                1675                1680

Ala Leu  Gly Gln Pro Cys Arg  Ser Leu Gly Pro His  Ser Lys Pro
    1685                1690                1695

Cys Val  Glu Met Leu Lys Gly  Leu Leu Thr Gln Arg  Ala Met Pro
    1700                1705                1710

Arg Gly  Gln Ala Pro Pro Ala  Pro Cys Gln Cys Pro  Arg Val Glu
    1715                1720                1725

Ser Ser  Met Pro Glu Asp Arg  Lys Ser Ser Thr Pro  Gly Ser Leu
    1730                1735                1740

His Glu  Glu Thr Pro His Ser  Arg Ser Thr Arg Glu  Asn Thr Ser
    1745                1750                1755

Arg Cys  Ser Ala Pro Ala Thr  Ala Leu Leu Ile Gln  Lys Ala Leu
    1760                1765                1770

Val Arg  Gly Gly Leu Gly Thr  Leu Ala Ala Asp Ala  Asn Phe Ile
    1775                1780                1785

Met Ala  Thr Gly Gln Ala Leu  Gly Asp Ala Cys Gln  Met Glu Pro
    1790                1795                1800

Glu Glu  Val Glu Ile Met Ala  Thr Glu Leu Leu Lys  Gly Arg Glu
    1805                1810                1815

Ala Pro  Asp Gly Met Ala Ser  Ser Leu Gly Cys Leu  Asn Leu Gly
    1820                1825                1830

Ser Ser  Leu Gly Ser Leu Asp  Gln His Gln Gly Ser  Gln Glu Thr
    1835                1840                1845

Leu Ile  Pro Pro Arg Leu
    1850

<210> SEQ ID NO 3
<211> LENGTH: 6501
<212> TYPE: DNA
<213> ORGANISM: Homo sapiens
<220> FEATURE:
<221> NAME/KEY: CDS
<222> LOCATION: (1)..(6501)

<400> SEQUENCE: 3 atg atg atg atg atg atg atg aaa aaa atg cag cat caa cgg cag cag      48
Met Met Met Met Met Met Met Lys Lys Met Gln His Gln Arg Gln Gln
1               5                   10                  15 caa gcg gac cac gcg aac gag gca aac tat gca aga ggc acc aga ctt      96
Gln Ala Asp His Ala Asn Glu Ala Asn Tyr Ala Arg Gly Thr Arg Leu
            20                  25                  30 cct ctt tct ggt gaa gga cca act tct cag ccg aat agc tcc aag caa     144
Pro Leu Ser Gly Glu Gly Pro Thr Ser Gln Pro Asn Ser Ser Lys Gln
        35                  40                  45 act gtc ctg tct tgg caa gct gca atc gat gct gct aga cag gcc aag     192
Thr Val Leu Ser Trp Gln Ala Ala Ile Asp Ala Ala Arg Gln Ala Lys
    50                  55                  60
```

-continued

```
gct gcc caa act atg agc acc tct gca ccc cca cct gta gga tct ctc      240
Ala Ala Gln Thr Met Ser Thr Ser Ala Pro Pro Pro Val Gly Ser Leu
 65          70                  75                  80 tcc caa aga aaa cgt cag caa tac gcc aag agc aaa aaa cag ggt aac      288
Ser Gln Arg Lys Arg Gln Gln Tyr Ala Lys Ser Lys Lys Gln Gly Asn
             85                  90                  95 tcg tcc aac agc cga cct gcc cgc gcc ctt ttc tgt tta tca ctc aat      336
Ser Ser Asn Ser Arg Pro Ala Arg Ala Leu Phe Cys Leu Ser Leu Asn
            100                 105                 110 aac ccc atc cga aga gcc tgc att agt ata gtg gaa tgg aaa cca ttt      384
Asn Pro Ile Arg Arg Ala Cys Ile Ser Ile Val Glu Trp Lys Pro Phe
        115                 120                 125 gac ata ttt ata tta ttg gct att ttt gcc aat tgt gtg gcc tta gct      432
Asp Ile Phe Ile Leu Leu Ala Ile Phe Ala Asn Cys Val Ala Leu Ala
        130                 135                 140 att tac atc cca ttc cct gaa gat gat tct aat tca aca aat cat aac      480
Ile Tyr Ile Pro Phe Pro Glu Asp Asp Ser Asn Ser Thr Asn His Asn
145                 150                 155                 160 ttg gaa aaa gta gaa tat gcc ttc ctg att att ttt aca gtc gag aca      528
Leu Glu Lys Val Glu Tyr Ala Phe Leu Ile Ile Phe Thr Val Glu Thr
                165                 170                 175 ttt ttg aag att ata gcg tat gga tta ttg cta cat cct aat gct tat      576
Phe Leu Lys Ile Ile Ala Tyr Gly Leu Leu Leu His Pro Asn Ala Tyr
            180                 185                 190 gtt agg aat gga tgg aat tta ctg gat ttt gtt ata gta ata gta gga      624
Val Arg Asn Gly Trp Asn Leu Leu Asp Phe Val Ile Val Ile Val Gly
        195                 200                 205 ttg ttt agt gta att ttg gaa caa tta acc aaa gaa aca gaa ggc ggg      672
Leu Phe Ser Val Ile Leu Glu Gln Leu Thr Lys Glu Thr Glu Gly Gly
    210                 215                 220 aac cac tca agc ggc aaa tct gga ggc ttt gat gtc aaa gcc ctc cgt      720
Asn His Ser Ser Gly Lys Ser Gly Gly Phe Asp Val Lys Ala Leu Arg
225                 230                 235                 240 gcc ttt cga gtg ttg cga cca ctt cga cta gtg tca ggg gtg ccc agt      768
Ala Phe Arg Val Leu Arg Pro Leu Arg Leu Val Ser Gly Val Pro Ser
                245                 250                 255 tta caa gtt gtc ctg aac tcc att ata aaa gcc atg gtt ccc ctc ctt      816
Leu Gln Val Val Leu Asn Ser Ile Ile Lys Ala Met Val Pro Leu Leu
            260                 265                 270 cac ata gcc ctt ttg gta tta ttt gta atc ata atc tat gct att ata      864
His Ile Ala Leu Leu Val Leu Phe Val Ile Ile Ile Tyr Ala Ile Ile
        275                 280                 285 gga ttg gaa ctt ttt att gga aaa atg cac aaa aca tgt ttt ttt gct      912
Gly Leu Glu Leu Phe Ile Gly Lys Met His Lys Thr Cys Phe Phe Ala
    290                 295                 300 gac tca gat atc gta gct gaa gag gac cca gct cca tgt gcg ttc tca      960
Asp Ser Asp Ile Val Ala Glu Glu Asp Pro Ala Pro Cys Ala Phe Ser
305                 310                 315                 320 ggg aat gga cgc cag tgt act gcc aat ggc acg gaa tgt agg agt ggc     1008
Gly Asn Gly Arg Gln Cys Thr Ala Asn Gly Thr Glu Cys Arg Ser Gly
                325                 330                 335 tgg gtt ggc ccg aac gga ggc atc acc aac ttt gat aac ttt gcc ttt     1056
Trp Val Gly Pro Asn Gly Gly Ile Thr Asn Phe Asp Asn Phe Ala Phe
            340                 345                 350 gcc atg ctt act gtg ttt cag tgc atc acc atg gag ggc tgg aca gac     1104
Ala Met Leu Thr Val Phe Gln Cys Ile Thr Met Glu Gly Trp Thr Asp
        355                 360                 365 gtg ctc tac tgg gta aat gat gcg ata gga tgg gaa tgg cca tgg gtg     1152
Val Leu Tyr Trp Val Asn Asp Ala Ile Gly Trp Glu Trp Pro Trp Val
```

-continued

```
         370                 375                 380
tat ttt gtt agt ctg atc atc ctt ggc tca ttt ttc gtc ctt aac ctg      1200
Tyr Phe Val Ser Leu Ile Ile Leu Gly Ser Phe Phe Val Leu Asn Leu
385                 390                 395                 400 gtt ctt ggt gtc ctt agt gga gaa ttc tca aag gaa aga gag aag gca      1248
Val Leu Gly Val Leu Ser Gly Glu Phe Ser Lys Glu Arg Glu Lys Ala
                405                 410                 415 aaa gca cgg gga gat ttc cag aag ctc cgg gag aag cag cag ctg gag      1296
Lys Ala Arg Gly Asp Phe Gln Lys Leu Arg Glu Lys Gln Gln Leu Glu
            420                 425                 430 gag gat cta aag ggc tac ttg gat tgg atc acc caa gct gag gac atc      1344
Glu Asp Leu Lys Gly Tyr Leu Asp Trp Ile Thr Gln Ala Glu Asp Ile
        435                 440                 445 gat ccg gag aat gag gaa gaa gga gga gag gaa ggc aaa cga aat act      1392
Asp Pro Glu Asn Glu Glu Glu Gly Gly Glu Glu Gly Lys Arg Asn Thr
    450                 455                 460 agc atg ccc acc agc gag act gag tct gtg aac aca gag aac gtc agc      1440
Ser Met Pro Thr Ser Glu Thr Glu Ser Val Asn Thr Glu Asn Val Ser
465                 470                 475                 480 ggt gaa ggc gag aac cga ggc tgc tgt gga agt ctc tgg tgc tgg tgg      1488
Gly Glu Gly Glu Asn Arg Gly Cys Cys Gly Ser Leu Trp Cys Trp Trp
                485                 490                 495 aga cgg aga ggc gcg gcc aag gcg ggg ccc tct ggg tgt cgg cgg tgg      1536
Arg Arg Arg Gly Ala Ala Lys Ala Gly Pro Ser Gly Cys Arg Arg Trp
            500                 505                 510 ggt caa gcc atc tca aaa tcc aaa ctc agc cga cgc tgg cgt cgc tgg      1584
Gly Gln Ala Ile Ser Lys Ser Lys Leu Ser Arg Arg Trp Arg Arg Trp
        515                 520                 525 aac cga ttc aat cgc aga aga tgt agg gcc gcc gtg aag tct gtc acg      1632
Asn Arg Phe Asn Arg Arg Arg Cys Arg Ala Ala Val Lys Ser Val Thr
    530                 535                 540 ttt tac tgg ctg gtt atc gtc ctg gtg ttt ctg aac acc tta acc att      1680
Phe Tyr Trp Leu Val Ile Val Leu Val Phe Leu Asn Thr Leu Thr Ile
545                 550                 555                 560 tcc tct gag cac tac aat cag cca gat tgg ttg aca cag att caa gat      1728
Ser Ser Glu His Tyr Asn Gln Pro Asp Trp Leu Thr Gln Ile Gln Asp
                565                 570                 575 att gcc aac aaa gtc ctc ttg gct ctg ttc acc tgc gag atg ctg gta      1776
Ile Ala Asn Lys Val Leu Leu Ala Leu Phe Thr Cys Glu Met Leu Val
            580                 585                 590 aaa atg tac agc ttg ggc ctc caa gca tat ttc gtc tct ctt ttc aac      1824
Lys Met Tyr Ser Leu Gly Leu Gln Ala Tyr Phe Val Ser Leu Phe Asn
        595                 600                 605 cgg ttt gat tgc ttc gtg gtg tgt ggt gga atc act gag acg atc ctg      1872
Arg Phe Asp Cys Phe Val Val Cys Gly Gly Ile Thr Glu Thr Ile Leu
    610                 615                 620 gtg gaa ctg gaa atc atg tct ccc ctg ggg atc tct gtg ttt cgg tgt      1920
Val Glu Leu Glu Ile Met Ser Pro Leu Gly Ile Ser Val Phe Arg Cys
625                 630                 635                 640 gtg cgc ctc tta aga atc ttc aaa gtg acc agg cac tgg act tcc ctg      1968
Val Arg Leu Leu Arg Ile Phe Lys Val Thr Arg His Trp Thr Ser Leu
                645                 650                 655 agc aac tta gtg gca tcc tta tta aac tcc atg aag tcc atc gct tcg      2016
Ser Asn Leu Val Ala Ser Leu Leu Asn Ser Met Lys Ser Ile Ala Ser
            660                 665                 670 ctg ttg ctt ctg ctt ttt ctc ttc att atc atc ttt tcc ttg ctt ggg      2064
Leu Leu Leu Leu Leu Phe Leu Phe Ile Ile Ile Phe Ser Leu Leu Gly
        675                 680                 685 atg cag ctg ttt ggc ggc aag ttt aat ttt gat gaa acg caa acc aag      2112
```

```
            Met Gln Leu Phe Gly Gly Lys Phe Asn Phe Asp Glu Thr Gln Thr Lys
                690                 695                 700 cgg agc acc ttt gac aat ttc cct caa gca ctt ctc aca gtg ttc cag        2160
Arg Ser Thr Phe Asp Asn Phe Pro Gln Ala Leu Leu Thr Val Phe Gln
705                 710                 715                 720 atc ctg aca ggc gaa gac tgg aat gct gtg atg tac gat ggc atc atg        2208
Ile Leu Thr Gly Glu Asp Trp Asn Ala Val Met Tyr Asp Gly Ile Met
                725                 730                 735 gct tac ggg ggc cca tcc tct tca gga atg atc gtc tgc atc tac ttc        2256
Ala Tyr Gly Gly Pro Ser Ser Ser Gly Met Ile Val Cys Ile Tyr Phe
            740                 745                 750 atc atc ctc ttc att tgt ggt aac tat att cta ctg aat gtc ttc ttg        2304
Ile Ile Leu Phe Ile Cys Gly Asn Tyr Ile Leu Leu Asn Val Phe Leu
        755                 760                 765 gcc atc gct gta gac aat ttg gct gat gct gaa agt ctg aac act gct        2352
Ala Ile Ala Val Asp Asn Leu Ala Asp Ala Glu Ser Leu Asn Thr Ala
    770                 775                 780 cag aaa gaa gaa gcg gaa gaa aag gag agg aaa aag att gcc aga aaa        2400
Gln Lys Glu Glu Ala Glu Glu Lys Glu Arg Lys Lys Ile Ala Arg Lys
785                 790                 795                 800 gag agc cta gaa aat aaa aag aac aac aaa cca gaa gtc aac cag ata        2448
Glu Ser Leu Glu Asn Lys Lys Asn Asn Lys Pro Glu Val Asn Gln Ile
                805                 810                 815 gcc aac agt gac aac aag gtt aca att gat gac tat aga gaa gag gat        2496
Ala Asn Ser Asp Asn Lys Val Thr Ile Asp Asp Tyr Arg Glu Glu Asp
            820                 825                 830 gaa gac aag gac ccc tat ccg cct tgc gat gtg cca gta ggg gaa gag        2544
Glu Asp Lys Asp Pro Tyr Pro Pro Cys Asp Val Pro Val Gly Glu Glu
        835                 840                 845 gaa gag gaa gag gag gag gat gaa cct gag gtt cct gcc gga ccc cgt        2592
Glu Glu Glu Glu Glu Glu Asp Glu Pro Glu Val Pro Ala Gly Pro Arg
    850                 855                 860 cct cga agg atc tcg gag ttg aac atg aag gaa aaa att gcc ccc atc        2640
Pro Arg Arg Ile Ser Glu Leu Asn Met Lys Glu Lys Ile Ala Pro Ile
865                 870                 875                 880 cct gaa ggg agc gct ttc ttc att ctt agc aag acc aac ccg atc cgc        2688
Pro Glu Gly Ser Ala Phe Phe Ile Leu Ser Lys Thr Asn Pro Ile Arg
                885                 890                 895 gta ggc tgc cac aag ctc atc aac cac cac atc ttc acc aac ctc atc        2736
Val Gly Cys His Lys Leu Ile Asn His His Ile Phe Thr Asn Leu Ile
            900                 905                 910 ctt gtc ttc atc atg ctg agc agc gct gcc ctg gcc gca gag gac ccc        2784
Leu Val Phe Ile Met Leu Ser Ser Ala Ala Leu Ala Ala Glu Asp Pro
        915                 920                 925 atc cgc agc cac tcc ttc cgg aac acg ata ctg ggt tac ttt gac tat        2832
Ile Arg Ser His Ser Phe Arg Asn Thr Ile Leu Gly Tyr Phe Asp Tyr
    930                 935                 940 gcc ttc aca gcc atc ttt act gtt gag atc ctg ttg aag atg aca act        2880
Ala Phe Thr Ala Ile Phe Thr Val Glu Ile Leu Leu Lys Met Thr Thr
945                 950                 955                 960 ttt gga gct ttc ctc cac aaa ggg gcc ttc tgc agg aac tac ttc aat        2928
Phe Gly Ala Phe Leu His Lys Gly Ala Phe Cys Arg Asn Tyr Phe Asn
                965                 970                 975 ttg ctg gat atg ctg gtg gtt ggg gtg tct ctg gtg tca ttt ggg att        2976
Leu Leu Asp Met Leu Val Val Gly Val Ser Leu Val Ser Phe Gly Ile
            980                 985                 990 caa tcc agt gcc atc tcc gtt gtg  aag att ctg agg gtc  tta agg gtc    3024
Gln Ser Ser Ala Ile Ser Val Val  Lys Ile Leu Arg Val  Leu Arg Val
        995                 1000                    1005
```

| | | |
|---|---|---|
| ctg cgt ccc ctc agg gcc atc aac aga gca aaa gga ctt aag cac<br>Leu Arg Pro Leu Arg Ala Ile Asn Arg Ala Lys Gly Leu Lys His<br>1010                    1015                  1020 | | 3069 |
| gtg gtc cag tgc gtc ttc gtg gcc atc cgg acc atc ggc aac atc<br>Val Val Gln Cys Val Phe Val Ala Ile Arg Thr Ile Gly Asn Ile<br>1025                    1030                  1035 | | 3114 |
| atg atc gtc act acc ctc ctg cag ttc atg ttt gcc tgt atc ggg<br>Met Ile Val Thr Thr Leu Leu Gln Phe Met Phe Ala Cys Ile Gly<br>1040                    1045                  1050 | | 3159 |
| gtc cag ttg ttc aag ggg aag ttc tat cgc tgt acg gat gaa gcc<br>Val Gln Leu Phe Lys Gly Lys Phe Tyr Arg Cys Thr Asp Glu Ala<br>1055                    1060                  1065 | | 3204 |
| aaa agt aac cct gaa gaa tgc agg gga ctt ttc atc ctc tac aag<br>Lys Ser Asn Pro Glu Glu Cys Arg Gly Leu Phe Ile Leu Tyr Lys<br>1070                    1075                  1080 | | 3249 |
| gat ggg gat gtt gac agt cct gtg gtc cgt gaa cgg atc tgg caa<br>Asp Gly Asp Val Asp Ser Pro Val Val Arg Glu Arg Ile Trp Gln<br>1085                    1090                  1095 | | 3294 |
| aac agt gat ttc aac ttc gac aac gtc ctc tct gct atg atg gcg<br>Asn Ser Asp Phe Asn Phe Asp Asn Val Leu Ser Ala Met Met Ala<br>1100                    1105                  1110 | | 3339 |
| ctc ttc aca gtc tcc acg ttt gag ggc tgg cct gcg ttg ctg tat<br>Leu Phe Thr Val Ser Thr Phe Glu Gly Trp Pro Ala Leu Leu Tyr<br>1115                    1120                  1125 | | 3384 |
| aaa gcc atc gac tcg aat gga gag aac atc ggc cca atc tac aac<br>Lys Ala Ile Asp Ser Asn Gly Glu Asn Ile Gly Pro Ile Tyr Asn<br>1130                    1135                  1140 | | 3429 |
| cac cgc gtg gag atc tcc atc ttc ttc atc atc tac atc atc att<br>His Arg Val Glu Ile Ser Ile Phe Phe Ile Ile Tyr Ile Ile Ile<br>1145                    1150                  1155 | | 3474 |
| gta gct ttc ttc atg atg aac atc ttt gtg ggc ttt gtc atc gtt<br>Val Ala Phe Phe Met Met Asn Ile Phe Val Gly Phe Val Ile Val<br>1160                    1165                  1170 | | 3519 |
| aca ttt cag gaa caa gga gaa aaa gag tat aag aac tgt gag ctg<br>Thr Phe Gln Glu Gln Gly Glu Lys Glu Tyr Lys Asn Cys Glu Leu<br>1175                    1180                  1185 | | 3564 |
| gac aaa aat cag cgt cag tgt gtt gaa tac gcc ttg aaa gca cgt<br>Asp Lys Asn Gln Arg Gln Cys Val Glu Tyr Ala Leu Lys Ala Arg<br>1190                    1195                  1200 | | 3609 |
| ccc ttg cgg aga tac atc ccc aaa aac ccc tac cag tac aag ttc<br>Pro Leu Arg Arg Tyr Ile Pro Lys Asn Pro Tyr Gln Tyr Lys Phe<br>1205                    1210                  1215 | | 3654 |
| tgg tac gtg gtg aac tct tcg cct ttc gaa tac atg atg ttt gtc<br>Trp Tyr Val Val Asn Ser Ser Pro Phe Glu Tyr Met Met Phe Val<br>1220                    1225                  1230 | | 3699 |
| ctc atc atg ctc aac aca ctc tgc ttg gcc atg cag cac tac gag<br>Leu Ile Met Leu Asn Thr Leu Cys Leu Ala Met Gln His Tyr Glu<br>1235                    1240                  1245 | | 3744 |
| cag tcc aag atg ttc aat gat gcc atg gac att ctg aac atg gtc<br>Gln Ser Lys Met Phe Asn Asp Ala Met Asp Ile Leu Asn Met Val<br>1250                    1255                  1260 | | 3789 |
| ttc acc ggg gtg ttc acc gtc gag atg gtt ttg aaa gtc atc gca<br>Phe Thr Gly Val Phe Thr Val Glu Met Val Leu Lys Val Ile Ala<br>1265                    1270                  1275 | | 3834 |
| ttt aag cct aag ggg tat ttt agt gac gcc tgg aac acg ttt gac<br>Phe Lys Pro Lys Gly Tyr Phe Ser Asp Ala Trp Asn Thr Phe Asp<br>1280                    1285                  1290 | | 3879 |
| tcc ctc atc gta atc ggc agc att ata gac gtg gcc ctc agc gaa<br>Ser Leu Ile Val Ile Gly Ser Ile Ile Asp Val Ala Leu Ser Glu<br>1295                    1300                  1305 | | 3924 |

| | | |
|---|---|---|
| gcg gac aac tct gaa gag agc aat aga atc tcc atc acc ttt ttc<br>Ala Asp Asn Ser Glu Glu Ser Asn Arg Ile Ser Ile Thr Phe Phe<br>1310                         1315                    1320 | | 3969 |
| cgt ctt ttc cga gtg atg cga ttg gtg aag ctt ctc agc agg ggg<br>Arg Leu Phe Arg Val Met Arg Leu Val Lys Leu Leu Ser Arg Gly<br>1325                         1330                    1335 | | 4014 |
| gaa ggc atc cgg aca ttg ctg tgg act ttt att aag tcc ttt cag<br>Glu Gly Ile Arg Thr Leu Leu Trp Thr Phe Ile Lys Ser Phe Gln<br>1340                         1345                    1350 | | 4059 |
| gcg ctc ccg tat gtg gcc ctc ctc ata gcc atg ctg ttc ttc atc<br>Ala Leu Pro Tyr Val Ala Leu Leu Ile Ala Met Leu Phe Phe Ile<br>1355                         1360                    1365 | | 4104 |
| tat gcg gtc att ggc atg cag atg ttt ggg aaa gtt gcc atg aga<br>Tyr Ala Val Ile Gly Met Gln Met Phe Gly Lys Val Ala Met Arg<br>1370                         1375                    1380 | | 4149 |
| gat aac aac cag atc aat agg aac aat aac ttc cag acg ttt ccc<br>Asp Asn Asn Gln Ile Asn Arg Asn Asn Asn Phe Gln Thr Phe Pro<br>1385                         1390                    1395 | | 4194 |
| cag gcg gtg ctg ctg ctc ttc agg tgt gca aca ggt gag gcc tgg<br>Gln Ala Val Leu Leu Leu Phe Arg Cys Ala Thr Gly Glu Ala Trp<br>1400                         1405                    1410 | | 4239 |
| cag gag atc atg ctg gcc tgt ctc cca ggg aag ctc tgt gac cct<br>Gln Glu Ile Met Leu Ala Cys Leu Pro Gly Lys Leu Cys Asp Pro<br>1415                         1420                    1425 | | 4284 |
| gag tca gat tac aac ccc ggg gag gag tat aca tgt ggg agc aac<br>Glu Ser Asp Tyr Asn Pro Gly Glu Glu Tyr Thr Cys Gly Ser Asn<br>1430                         1435                    1440 | | 4329 |
| ttt gcc att gtc tat ttc atc agt ttt tac atg ctc tgt gca ttt<br>Phe Ala Ile Val Tyr Phe Ile Ser Phe Tyr Met Leu Cys Ala Phe<br>1445                         1450                    1455 | | 4374 |
| ctg atc atc aat ctg ttt gtg gct gtc atc atg gat aat ttc gac<br>Leu Ile Ile Asn Leu Phe Val Ala Val Ile Met Asp Asn Phe Asp<br>1460                         1465                    1470 | | 4419 |
| tat ctg acc cgg gac tgg tct att ttg ggg cct cac cat tta gat<br>Tyr Leu Thr Arg Asp Trp Ser Ile Leu Gly Pro His His Leu Asp<br>1475                         1480                    1485 | | 4464 |
| gaa ttc aaa aga ata tgg tca gaa tat gac cct gag gca aag gga<br>Glu Phe Lys Arg Ile Trp Ser Glu Tyr Asp Pro Glu Ala Lys Gly<br>1490                         1495                    1500 | | 4509 |
| agg ata aaa cac ctt gat gtg gtc act ctg ctt cga cgc atc cag<br>Arg Ile Lys His Leu Asp Val Val Thr Leu Leu Arg Arg Ile Gln<br>1505                         1510                    1515 | | 4554 |
| cct ccc ctg ggg ttt ggg aag tta tgt cca cac agg gta gcg tgc<br>Pro Pro Leu Gly Phe Gly Lys Leu Cys Pro His Arg Val Ala Cys<br>1520                         1525                    1530 | | 4599 |
| aag aga tta gtt gcc atg aac atg cct ctc aac agt gac ggg aca<br>Lys Arg Leu Val Ala Met Asn Met Pro Leu Asn Ser Asp Gly Thr<br>1535                         1540                    1545 | | 4644 |
| gtc atg ttt aat gca acc ctg ttt gct ttg gtt cga acg gct ctt<br>Val Met Phe Asn Ala Thr Leu Phe Ala Leu Val Arg Thr Ala Leu<br>1550                         1555                    1560 | | 4689 |
| aag atc aag acc gaa ggg aac ctg gag caa gct aat gaa gaa ctt<br>Lys Ile Lys Thr Glu Gly Asn Leu Glu Gln Ala Asn Glu Glu Leu<br>1565                         1570                    1575 | | 4734 |
| cgg gct gtg ata aag aaa att tgg aag aaa acc agc atg aaa tta<br>Arg Ala Val Ile Lys Lys Ile Trp Lys Lys Thr Ser Met Lys Leu<br>1580                         1585                    1590 | | 4779 |
| ctt gac caa gtt gtc cct cca gct ggt gat gat gag gta acc gtg<br>Leu Asp Gln Val Val Pro Pro Ala Gly Asp Asp Glu Val Thr Val | | 4824 |

-continued

|  |  |  |  |  |  |  |  |  |  |  |  |  |  |  |
|---|---|---|---|---|---|---|---|---|---|---|---|---|---|---|
|  |  | 1595 |  |  |  | 1600 |  |  |  | 1605 |  |  |  |  |

```
ggg aag ttc tat gcc act ttc ctg ata cag gac tac ttt agg aaa       4869
Gly Lys Phe Tyr Ala Thr Phe Leu Ile Gln Asp Tyr Phe Arg Lys
1610             1615                 1620 ttc aag aaa cgg aaa gaa caa gga ctg gtg gga aag tac cct gcg       4914
Phe Lys Lys Arg Lys Glu Gln Gly Leu Val Gly Lys Tyr Pro Ala
1625             1630                 1635 aag aac acc aca att gcc cta cag gcg gga tta agg aca ctg cat       4959
Lys Asn Thr Thr Ile Ala Leu Gln Ala Gly Leu Arg Thr Leu His
1640             1645                 1650 gac att ggg cca gaa atc cgg cgt gct ata tcg tgt gat ttg caa       5004
Asp Ile Gly Pro Glu Ile Arg Arg Ala Ile Ser Cys Asp Leu Gln
1655             1660                 1665 gat gac gag cct gag gaa aca aaa cga gaa gaa gaa gat gat gtg       5049
Asp Asp Glu Pro Glu Glu Thr Lys Arg Glu Glu Glu Asp Asp Val
1670             1675                 1680 ttc aaa aga aat ggt gcc ctg ctt gga aac cat gtc aat cat gtt       5094
Phe Lys Arg Asn Gly Ala Leu Leu Gly Asn His Val Asn His Val
1685             1690                 1695 aat agt gat agg aga gat tcc ctt cag cag acc aat acc acc cac       5139
Asn Ser Asp Arg Arg Asp Ser Leu Gln Gln Thr Asn Thr Thr His
1700             1705                 1710 cgt ccc ctg cat gtc caa agg cct tca att cca cct gca agt gat       5184
Arg Pro Leu His Val Gln Arg Pro Ser Ile Pro Pro Ala Ser Asp
1715             1720                 1725 act gag aaa ccg ctg ttt cct cca gca gga aat tcg gtg tgt cat       5229
Thr Glu Lys Pro Leu Phe Pro Pro Ala Gly Asn Ser Val Cys His
1730             1735                 1740 aac cat cat aac cat aat tcc ata gga aag caa gtt ccc acc tca       5274
Asn His His Asn His Asn Ser Ile Gly Lys Gln Val Pro Thr Ser
1745             1750                 1755 aca aat gcc aat ctc aat aat gcc aat atg tcc aaa gct gcc cat       5319
Thr Asn Ala Asn Leu Asn Asn Ala Asn Met Ser Lys Ala Ala His
1760             1765                 1770 gga aag cgg ccc agc att ggg aac ctt gag cat gtg tct gaa aat       5364
Gly Lys Arg Pro Ser Ile Gly Asn Leu Glu His Val Ser Glu Asn
1775             1780                 1785 ggg cat cat tct tcc cac aag cat gac cgg gag cct cag aga agg       5409
Gly His His Ser Ser His Lys His Asp Arg Glu Pro Gln Arg Arg
1790             1795                 1800 tcc agt gtg aaa aga acc cgc tat tat gaa act tac att agg tcc       5454
Ser Ser Val Lys Arg Thr Arg Tyr Tyr Glu Thr Tyr Ile Arg Ser
1805             1810                 1815 gac tca gga gat gaa cag ctc cca act att tgc cgg gaa gac cca       5499
Asp Ser Gly Asp Glu Gln Leu Pro Thr Ile Cys Arg Glu Asp Pro
1820             1825                 1830 gag ata cat ggc tat ttc agg gac ccc cac tgc ttg ggg gag cag       5544
Glu Ile His Gly Tyr Phe Arg Asp Pro His Cys Leu Gly Glu Gln
1835             1840                 1845 gag tat ttc agt agt gag gaa tgc tac gag gat gac agc tcg ccc       5589
Glu Tyr Phe Ser Ser Glu Glu Cys Tyr Glu Asp Asp Ser Ser Pro
1850             1855                 1860 acc tgg agc agg caa aac tat ggc tac tac agc aga tac cca ggc       5634
Thr Trp Ser Arg Gln Asn Tyr Gly Tyr Tyr Ser Arg Tyr Pro Gly
1865             1870                 1875 aga aac atc gac tct gag agg ccc cga ggc tac cat cat ccc caa       5679
Arg Asn Ile Asp Ser Glu Arg Pro Arg Gly Tyr His His Pro Gln
1880             1885                 1890 gga ttc ttg gag gac gat gac tcg ccc gtt tgc tat gat tca cgg       5724
```

-continued

| | | | | | | | | | | | |
|---|---|---|---|---|---|---|---|---|---|---|---|
| Gly | Phe | Leu | Glu | Asp | Asp | Ser | Pro | Val | Cys | Tyr | Asp Ser Arg |
| 1895 | | | | 1900 | | | | 1905 | | | |

```
aga  tct  cca  agg  aga  cgc  cta  cta  cct  ccc  acc  cca  gca  tcc  cac       5769
Arg  Ser  Pro  Arg  Arg  Arg  Leu  Leu  Pro  Pro  Thr  Pro  Ala  Ser  His
     1910                1915                    1920 cgg  aga  tcc  tcc  ttc  aac  ttt  gag  tgc  ctg  cgc  cgg  cag  agc  agc       5814
Arg  Arg  Ser  Ser  Phe  Asn  Phe  Glu  Cys  Leu  Arg  Arg  Gln  Ser  Ser
     1925                1930                    1935 cag  gaa  gag  gtc  ccg  tcg  tct  ccc  atc  ttc  ccc  cat  cgc  acg  gcc       5859
Gln  Glu  Glu  Val  Pro  Ser  Ser  Pro  Ile  Phe  Pro  His  Arg  Thr  Ala
     1940                1945                    1950 ctg  cct  ctg  cat  cta  atg  cag  caa  cag  atc  atg  gca  gtt  gcc  ggc       5904
Leu  Pro  Leu  His  Leu  Met  Gln  Gln  Gln  Ile  Met  Ala  Val  Ala  Gly
     1955                1960                    1965 cta  gat  tca  agt  aaa  gcc  cag  aag  tac  tca  ccg  agt  cac  tcg  acc       5949
Leu  Asp  Ser  Ser  Lys  Ala  Gln  Lys  Tyr  Ser  Pro  Ser  His  Ser  Thr
     1970                1975                    1980 cgg  tcg  tgg  gcc  acc  cct  cca  gca  acc  cct  ccc  tac  cgg  gac  tgg       5994
Arg  Ser  Trp  Ala  Thr  Pro  Pro  Ala  Thr  Pro  Pro  Tyr  Arg  Asp  Trp
     1985                1990                    1995 aca  ccg  tgc  tac  acc  ccc  ctg  atc  caa  gtg  gag  cag  tca  gag  gcc       6039
Thr  Pro  Cys  Tyr  Thr  Pro  Leu  Ile  Gln  Val  Glu  Gln  Ser  Glu  Ala
     2000                2005                    2010 ctg  gac  cag  gtg  aac  ggc  agc  ctg  ccg  tcc  ctg  cac  cgc  agc  tcc       6084
Leu  Asp  Gln  Val  Asn  Gly  Ser  Leu  Pro  Ser  Leu  His  Arg  Ser  Ser
     2015                2020                    2025 tgg  tac  aca  gac  gag  ccc  gac  atc  tcc  tac  cgg  act  ttc  aca  cca       6129
Trp  Tyr  Thr  Asp  Glu  Pro  Asp  Ile  Ser  Tyr  Arg  Thr  Phe  Thr  Pro
     2030                2035                    2040 gcc  agc  ctg  act  gtc  ccc  agc  agc  ttc  cgg  aac  aaa  aac  agc  gac       6174
Ala  Ser  Leu  Thr  Val  Pro  Ser  Ser  Phe  Arg  Asn  Lys  Asn  Ser  Asp
     2045                2050                    2055 aag  cag  agg  agt  gcg  gac  agc  ttg  gtg  gag  gca  gtc  ctg  ata  tcc       6219
Lys  Gln  Arg  Ser  Ala  Asp  Ser  Leu  Val  Glu  Ala  Val  Leu  Ile  Ser
     2060                2065                    2070 gaa  ggc  ttg  gga  cgc  tat  gca  agg  gac  cca  aaa  ttt  gtg  tca  gca       6264
Glu  Gly  Leu  Gly  Arg  Tyr  Ala  Arg  Asp  Pro  Lys  Phe  Val  Ser  Ala
     2075                2080                    2085 aca  aaa  cac  gaa  atc  gct  gat  gcc  tgt  gac  ctc  acc  atc  gac  gag       6309
Thr  Lys  His  Glu  Ile  Ala  Asp  Ala  Cys  Asp  Leu  Thr  Ile  Asp  Glu
     2090                2095                    2100 atg  gag  agt  gca  gcc  agc  acc  ctg  ctt  aat  ggg  aac  gtg  cgt  ccc       6354
Met  Glu  Ser  Ala  Ala  Ser  Thr  Leu  Leu  Asn  Gly  Asn  Val  Arg  Pro
     2105                2110                    2115 cga  gcc  aac  ggg  gat  gtg  ggc  ccc  ctc  tca  cac  cgg  cag  gac  tat       6399
Arg  Ala  Asn  Gly  Asp  Val  Gly  Pro  Leu  Ser  His  Arg  Gln  Asp  Tyr
     2120                2125                    2130 gag  cta  cag  gac  ttt  ggt  cct  ggc  tac  agc  gac  gaa  gag  cca  gac       6444
Glu  Leu  Gln  Asp  Phe  Gly  Pro  Gly  Tyr  Ser  Asp  Glu  Glu  Pro  Asp
     2135                2140                    2145 cct  ggg  agg  gat  gag  gag  gac  ctg  gcg  gat  gaa  atg  ata  tgc  atc       6489
Pro  Gly  Arg  Asp  Glu  Glu  Asp  Leu  Ala  Asp  Glu  Met  Ile  Cys  Ile
     2150                2155                    2160 acc  acc  ttg  tag                                                              6501
Thr  Thr  Leu
     2165
```

<210> SEQ ID NO 4
<211> LENGTH: 2166
<212> TYPE: PRT

<213> ORGANISM: Homo sapiens

<400> SEQUENCE: 4

```
Met Met Met Met Met Met Met Lys Lys Met Gln His Gln Arg Gln Gln
1               5                   10                  15

Gln Ala Asp His Ala Asn Glu Ala Asn Tyr Ala Arg Gly Thr Arg Leu
            20                  25                  30

Pro Leu Ser Gly Glu Gly Pro Thr Ser Gln Pro Asn Ser Ser Lys Gln
        35                  40                  45

Thr Val Leu Ser Trp Gln Ala Ile Asp Ala Ala Arg Gln Ala Lys
50                  55                  60

Ala Ala Gln Thr Met Ser Thr Ser Ala Pro Pro Val Gly Ser Leu
65              70                  75                  80

Ser Gln Arg Lys Arg Gln Gln Tyr Ala Lys Ser Lys Gln Gly Asn
                85                  90                  95

Ser Ser Asn Ser Arg Pro Ala Arg Ala Leu Phe Cys Leu Ser Leu Asn
            100                 105                 110

Asn Pro Ile Arg Arg Ala Cys Ile Ser Ile Val Glu Trp Lys Pro Phe
        115                 120                 125

Asp Ile Phe Ile Leu Leu Ala Ile Phe Ala Asn Cys Val Ala Leu Ala
130                 135                 140

Ile Tyr Ile Pro Phe Pro Glu Asp Asp Ser Asn Ser Thr Asn His Asn
145                 150                 155                 160

Leu Glu Lys Val Glu Tyr Ala Phe Leu Ile Ile Phe Thr Val Glu Thr
                165                 170                 175

Phe Leu Lys Ile Ile Ala Tyr Gly Leu Leu Leu His Pro Asn Ala Tyr
            180                 185                 190

Val Arg Asn Gly Trp Asn Leu Leu Asp Phe Val Ile Val Ile Val Gly
        195                 200                 205

Leu Phe Ser Val Ile Leu Glu Gln Leu Thr Lys Glu Thr Glu Gly Gly
210                 215                 220

Asn His Ser Ser Gly Lys Ser Gly Gly Phe Asp Val Lys Ala Leu Arg
225                 230                 235                 240

Ala Phe Arg Val Leu Arg Pro Leu Arg Leu Val Ser Gly Val Pro Ser
                245                 250                 255

Leu Gln Val Val Leu Asn Ser Ile Ile Lys Ala Met Val Pro Leu Leu
            260                 265                 270

His Ile Ala Leu Leu Val Leu Phe Val Ile Ile Tyr Ala Ile Ile
        275                 280                 285

Gly Leu Glu Leu Phe Ile Gly Lys Met His Lys Thr Cys Phe Phe Ala
290                 295                 300

Asp Ser Asp Ile Val Ala Glu Glu Asp Pro Ala Pro Cys Ala Phe Ser
305                 310                 315                 320

Gly Asn Gly Arg Gln Cys Thr Ala Asn Gly Thr Glu Cys Arg Ser Gly
                325                 330                 335

Trp Val Gly Pro Asn Gly Gly Ile Thr Asn Phe Asp Asn Phe Ala Phe
            340                 345                 350

Ala Met Leu Thr Val Phe Gln Cys Ile Thr Met Glu Gly Trp Thr Asp
        355                 360                 365

Val Leu Tyr Trp Val Asn Asp Ala Ile Gly Trp Glu Trp Pro Trp Val
370                 375                 380

Tyr Phe Val Ser Leu Ile Ile Leu Gly Ser Phe Phe Val Leu Asn Leu
385                 390                 395                 400
```

-continued

```
Val Leu Gly Val Leu Ser Gly Glu Phe Ser Lys Arg Glu Lys Ala
                405                 410                 415
Lys Ala Arg Gly Asp Phe Gln Lys Leu Arg Glu Lys Gln Gln Leu Glu
            420                 425                 430
Glu Asp Leu Lys Gly Tyr Leu Asp Trp Ile Thr Gln Ala Glu Asp Ile
                435                 440                 445
Asp Pro Glu Asn Glu Glu Gly Glu Glu Gly Lys Arg Asn Thr
450                 455                 460
Ser Met Pro Thr Ser Glu Thr Glu Ser Val Asn Thr Glu Asn Val Ser
465                 470                 475                 480
Gly Glu Gly Glu Asn Arg Gly Cys Cys Gly Ser Leu Trp Cys Trp Trp
                485                 490                 495
Arg Arg Arg Gly Ala Ala Lys Ala Gly Pro Ser Gly Cys Arg Arg Trp
                500                 505                 510
Gly Gln Ala Ile Ser Lys Ser Lys Leu Ser Arg Arg Trp Arg Arg Trp
                515                 520                 525
Asn Arg Phe Asn Arg Arg Cys Arg Ala Ala Val Lys Ser Val Thr
            530                 535                 540
Phe Tyr Trp Leu Val Ile Val Leu Val Phe Leu Asn Thr Leu Thr Ile
545                 550                 555                 560
Ser Ser Glu His Tyr Asn Gln Pro Asp Trp Leu Thr Gln Ile Gln Asp
                565                 570                 575
Ile Ala Asn Lys Val Leu Leu Ala Leu Phe Thr Cys Glu Met Leu Val
                580                 585                 590
Lys Met Tyr Ser Leu Gly Leu Gln Ala Tyr Phe Val Ser Leu Phe Asn
                595                 600                 605
Arg Phe Asp Cys Phe Val Val Cys Gly Gly Ile Thr Glu Thr Ile Leu
            610                 615                 620
Val Glu Leu Glu Ile Met Ser Pro Leu Gly Ile Ser Val Phe Arg Cys
625                 630                 635                 640
Val Arg Leu Leu Arg Ile Phe Lys Val Thr Arg His Trp Thr Ser Leu
                645                 650                 655
Ser Asn Leu Val Ala Ser Leu Leu Asn Ser Met Lys Ser Ile Ala Ser
                660                 665                 670
Leu Leu Leu Leu Leu Phe Leu Phe Ile Ile Ile Phe Ser Leu Leu Gly
                675                 680                 685
Met Gln Leu Phe Gly Gly Lys Phe Asn Phe Asp Glu Thr Gln Thr Lys
            690                 695                 700
Arg Ser Thr Phe Asp Asn Phe Pro Gln Ala Leu Leu Thr Val Phe Gln
705                 710                 715                 720
Ile Leu Thr Gly Glu Asp Trp Asn Ala Val Met Tyr Asp Gly Ile Met
                725                 730                 735
Ala Tyr Gly Gly Pro Ser Ser Ser Gly Met Ile Val Cys Ile Tyr Phe
            740                 745                 750
Ile Ile Leu Phe Ile Cys Gly Asn Tyr Ile Leu Leu Asn Val Phe Leu
                755                 760                 765
Ala Ile Ala Val Asp Asn Leu Ala Asp Ala Glu Ser Leu Asn Thr Ala
            770                 775                 780
Gln Lys Glu Glu Ala Glu Glu Lys Glu Arg Lys Lys Ile Ala Arg Lys
785                 790                 795                 800
Glu Ser Leu Glu Asn Lys Lys Asn Asn Lys Pro Glu Val Asn Gln Ile
                805                 810                 815
Ala Asn Ser Asp Asn Lys Val Thr Ile Asp Asp Tyr Arg Glu Glu Asp
```

-continued

```
                820                 825                 830
Glu Asp Lys Asp Pro Tyr Pro Pro Cys Asp Val Pro Val Gly Glu Glu
            835                 840                 845
Glu Glu Glu Glu Glu Glu Asp Glu Pro Glu Val Pro Ala Gly Pro Arg
850                 855                 860
Pro Arg Arg Ile Ser Glu Leu Asn Met Lys Glu Lys Ile Ala Pro Ile
865                 870                 875                 880
Pro Glu Gly Ser Ala Phe Phe Ile Leu Ser Lys Thr Asn Pro Ile Arg
                885                 890                 895
Val Gly Cys His Lys Leu Ile Asn His His Ile Phe Thr Asn Leu Ile
            900                 905                 910
Leu Val Phe Ile Met Leu Ser Ser Ala Ala Leu Ala Ala Glu Asp Pro
        915                 920                 925
Ile Arg Ser His Ser Phe Arg Asn Thr Ile Leu Gly Tyr Phe Asp Tyr
    930                 935                 940
Ala Phe Thr Ala Ile Phe Thr Val Glu Ile Leu Leu Lys Met Thr Thr
945                 950                 955                 960
Phe Gly Ala Phe Leu His Lys Gly Ala Phe Cys Arg Asn Tyr Phe Asn
                965                 970                 975
Leu Leu Asp Met Leu Val Val Gly Val Ser Leu Val Ser Phe Gly Ile
            980                 985                 990
Gln Ser Ser Ala Ile Ser Val Val Lys Ile Leu Arg Val Leu Arg Val
        995                 1000                1005
Leu Arg Pro Leu Arg Ala Ile Asn Arg Ala Lys Gly Leu Lys His
    1010                1015                1020
Val Val Gln Cys Val Phe Val Ala Ile Arg Thr Ile Gly Asn Ile
    1025                1030                1035
Met Ile Val Thr Thr Leu Leu Gln Phe Met Phe Ala Cys Ile Gly
    1040                1045                1050
Val Gln Leu Phe Lys Gly Lys Phe Tyr Arg Cys Thr Asp Glu Ala
    1055                1060                1065
Lys Ser Asn Pro Glu Glu Cys Arg Gly Leu Phe Ile Leu Tyr Lys
    1070                1075                1080
Asp Gly Asp Val Asp Ser Pro Val Val Arg Glu Arg Ile Trp Gln
    1085                1090                1095
Asn Ser Asp Phe Asn Phe Asp Asn Val Leu Ser Ala Met Met Ala
    1100                1105                1110
Leu Phe Thr Val Ser Thr Phe Glu Gly Trp Pro Ala Leu Leu Tyr
    1115                1120                1125
Lys Ala Ile Asp Ser Asn Gly Glu Asn Ile Gly Pro Ile Tyr Asn
    1130                1135                1140
His Arg Val Glu Ile Ser Ile Phe Phe Ile Ile Tyr Ile Ile Ile
    1145                1150                1155
Val Ala Phe Phe Met Met Asn Ile Phe Val Gly Phe Val Ile Val
    1160                1165                1170
Thr Phe Gln Glu Gln Gly Glu Lys Glu Tyr Lys Asn Cys Glu Leu
    1175                1180                1185
Asp Lys Asn Gln Arg Gln Cys Val Glu Tyr Ala Leu Lys Ala Arg
    1190                1195                1200
Pro Leu Arg Arg Tyr Ile Pro Lys Asn Pro Tyr Gln Tyr Lys Phe
    1205                1210                1215
Trp Tyr Val Val Asn Ser Ser Pro Phe Glu Tyr Met Met Phe Val
    1220                1225                1230
```

```
Leu Ile Met Leu Asn Thr Leu Cys Leu Ala Met Gln His Tyr Glu
    1235                1240                1245

Gln Ser Lys Met Phe Asn Asp Ala Met Asp Ile Leu Asn Met Val
    1250                1255                1260

Phe Thr Gly Val Phe Thr Val Glu Met Val Leu Lys Val Ile Ala
    1265                1270                1275

Phe Lys Pro Lys Gly Tyr Phe Ser Asp Ala Trp Asn Thr Phe Asp
    1280                1285                1290

Ser Leu Ile Val Ile Gly Ser Ile Ile Asp Val Ala Leu Ser Glu
    1295                1300                1305

Ala Asp Asn Ser Glu Glu Ser Asn Arg Ile Ser Ile Thr Phe Phe
    1310                1315                1320

Arg Leu Phe Arg Val Met Arg Leu Val Lys Leu Leu Ser Arg Gly
    1325                1330                1335

Glu Gly Ile Arg Thr Leu Leu Trp Thr Phe Ile Lys Ser Phe Gln
    1340                1345                1350

Ala Leu Pro Tyr Val Ala Leu Leu Ile Ala Met Leu Phe Phe Ile
    1355                1360                1365

Tyr Ala Val Ile Gly Met Gln Met Phe Gly Lys Val Ala Met Arg
    1370                1375                1380

Asp Asn Asn Gln Ile Asn Arg Asn Asn Asn Phe Gln Thr Phe Pro
    1385                1390                1395

Gln Ala Val Leu Leu Leu Phe Arg Cys Ala Thr Gly Glu Ala Trp
    1400                1405                1410

Gln Glu Ile Met Leu Ala Cys Leu Pro Gly Lys Leu Cys Asp Pro
    1415                1420                1425

Glu Ser Asp Tyr Asn Pro Gly Glu Glu Tyr Thr Cys Gly Ser Asn
    1430                1435                1440

Phe Ala Ile Val Tyr Phe Ile Ser Phe Tyr Met Leu Cys Ala Phe
    1445                1450                1455

Leu Ile Ile Asn Leu Phe Val Ala Val Ile Met Asp Asn Phe Asp
    1460                1465                1470

Tyr Leu Thr Arg Asp Trp Ser Ile Leu Gly Pro His His Leu Asp
    1475                1480                1485

Glu Phe Lys Arg Ile Trp Ser Glu Tyr Asp Pro Glu Ala Lys Gly
    1490                1495                1500

Arg Ile Lys His Leu Asp Val Val Thr Leu Leu Arg Arg Ile Gln
    1505                1510                1515

Pro Pro Leu Gly Phe Gly Lys Leu Cys Pro His Arg Val Ala Cys
    1520                1525                1530

Lys Arg Leu Val Ala Met Asn Met Pro Leu Asn Ser Asp Gly Thr
    1535                1540                1545

Val Met Phe Asn Ala Thr Leu Phe Ala Leu Val Arg Thr Ala Leu
    1550                1555                1560

Lys Ile Lys Thr Glu Gly Asn Leu Glu Gln Ala Asn Glu Glu Leu
    1565                1570                1575

Arg Ala Val Ile Lys Lys Ile Trp Lys Lys Thr Ser Met Lys Leu
    1580                1585                1590

Leu Asp Gln Val Val Pro Pro Ala Gly Asp Asp Glu Val Thr Val
    1595                1600                1605

Gly Lys Phe Tyr Ala Thr Phe Leu Ile Gln Asp Tyr Phe Arg Lys
    1610                1615                1620
```

```
Phe Lys Lys Arg Lys Glu Gln Gly Leu Val Gly Lys Tyr Pro Ala
1625                1630                1635

Lys Asn Thr Thr Ile Ala Leu Gln Ala Gly Leu Arg Thr Leu His
1640                1645                1650

Asp Ile Gly Pro Glu Ile Arg Arg Ala Ile Ser Cys Asp Leu Gln
1655                1660                1665

Asp Asp Glu Pro Glu Glu Thr Lys Arg Glu Glu Glu Asp Asp Val
1670                1675                1680

Phe Lys Arg Asn Gly Ala Leu Leu Gly Asn His Val Asn His Val
1685                1690                1695

Asn Ser Asp Arg Arg Asp Ser Leu Gln Gln Thr Asn Thr Thr His
1700                1705                1710

Arg Pro Leu His Val Gln Arg Pro Ser Ile Pro Ala Ser Asp
1715                1720                1725

Thr Glu Lys Pro Leu Phe Pro Pro Ala Gly Asn Ser Val Cys His
1730                1735                1740

Asn His His Asn His Asn Ser Ile Gly Lys Gln Val Pro Thr Ser
1745                1750                1755

Thr Asn Ala Asn Leu Asn Asn Ala Asn Met Ser Lys Ala Ala His
1760                1765                1770

Gly Lys Arg Pro Ser Ile Gly Asn Leu Glu His Val Ser Glu Asn
1775                1780                1785

Gly His His Ser Ser His Lys His Asp Arg Glu Pro Gln Arg Arg
1790                1795                1800

Ser Ser Val Lys Arg Thr Arg Tyr Tyr Glu Thr Tyr Ile Arg Ser
1805                1810                1815

Asp Ser Gly Asp Glu Gln Leu Pro Thr Ile Cys Arg Glu Asp Pro
1820                1825                1830

Glu Ile His Gly Tyr Phe Arg Asp Pro His Cys Leu Gly Glu Gln
1835                1840                1845

Glu Tyr Phe Ser Ser Glu Glu Cys Tyr Glu Asp Asp Ser Ser Pro
1850                1855                1860

Thr Trp Ser Arg Gln Asn Tyr Gly Tyr Tyr Ser Arg Tyr Pro Gly
1865                1870                1875

Arg Asn Ile Asp Ser Glu Arg Pro Arg Gly Tyr His His Pro Gln
1880                1885                1890

Gly Phe Leu Glu Asp Asp Ser Pro Val Cys Tyr Asp Ser Arg
1895                1900                1905

Arg Ser Pro Arg Arg Arg Leu Leu Pro Pro Thr Pro Ala Ser His
1910                1915                1920

Arg Arg Ser Ser Phe Asn Phe Glu Cys Leu Arg Arg Gln Ser Ser
1925                1930                1935

Gln Glu Glu Val Pro Ser Ser Pro Ile Phe Pro His Arg Thr Ala
1940                1945                1950

Leu Pro Leu His Leu Met Gln Gln Ile Met Ala Val Ala Gly
1955                1960                1965

Leu Asp Ser Ser Lys Ala Gln Lys Tyr Ser Pro Ser His Ser Thr
1970                1975                1980

Arg Ser Trp Ala Thr Pro Pro Ala Thr Pro Pro Tyr Arg Asp Trp
1985                1990                1995

Thr Pro Cys Tyr Thr Pro Leu Ile Gln Val Glu Gln Ser Glu Ala
2000                2005                2010

Leu Asp Gln Val Asn Gly Ser Leu Pro Ser Leu His Arg Ser Ser
```

```
            2015                2020                2025

Trp Tyr Thr Asp Glu Pro Asp Ile Ser Tyr Arg Thr Phe Thr Pro
    2030                2035                2040

Ala Ser Leu Thr Val Pro Ser Ser Phe Arg Asn Lys Asn Ser Asp
    2045                2050                2055

Lys Gln Arg Ser Ala Asp Ser Leu Val Glu Ala Val Leu Ile Ser
    2060                2065                2070

Glu Gly Leu Gly Arg Tyr Ala Arg Asp Pro Lys Phe Val Ser Ala
    2075                2080                2085

Thr Lys His Glu Ile Ala Asp Ala Cys Asp Leu Thr Ile Asp Glu
    2090                2095                2100

Met Glu Ser Ala Ala Ser Thr Leu Leu Asn Gly Asn Val Arg Pro
    2105                2110                2115

Arg Ala Asn Gly Asp Val Gly Pro Leu Ser His Arg Gln Asp Tyr
    2120                2125                2130

Glu Leu Gln Asp Phe Gly Pro Gly Tyr Ser Asp Glu Glu Pro Asp
    2135                2140                2145

Pro Gly Arg Asp Glu Glu Asp Leu Ala Asp Glu Met Ile Cys Ile
    2150                2155                2160

Thr Thr Leu
    2165

<210> SEQ ID NO 5
<211> LENGTH: 557
<212> TYPE: DNA
<213> ORGANISM: Homo sapiens
<220> FEATURE:
<221> NAME/KEY: partial_cDNA
<222> LOCATION: (1)..(557)

<400> SEQUENCE: 5
ctgattgtca tcggcagcat cattgacgtc atcctcagtg agatcgacga ccccgacgag     60
agtgcccgca tctccagcgc cttcttccgc ctgttccggg tcatgaggtt gatcaagctg    120
ctgagccgcg ccgagggcgt gcgcacgctg ctccggacct tcatcaagtc cttccaggcc    180
ctgccctacg tggctctgct catcgtcatg ctcttcttca tctatgctgt catcggcatg    240
cagatgtttg gaagatcgc catggtggac ggaacccaga taaaccggaa caacaatttc    300
cagaccttcc ctcaggctgt gctgctgctc ttcaggtgcg ccacgggtga ggcgtggcag    360
gagatcctgc tggcctgcag gtacgggcag ctgtgcgacc ccgagtcaga ctacctccct    420
ggggaggagt ataccctgcgg caccgacttc gcctactact acttcatcag cttctacatg    480
ctctgtgcct tcctgatcat caacctcttt gtggctgtga tcatggacaa ttttgactac    540
ctcacccgga ctggtcc                                                   557

<210> SEQ ID NO 6
<211> LENGTH: 553
<212> TYPE: DNA
<213> ORGANISM: Homo sapiens
<220> FEATURE:
<221> NAME/KEY: partial_cDNA
<222> LOCATION: (1)..(553)
<220> FEATURE:
<221> NAME/KEY: misc_feature
<222> LOCATION: (1)..(553)
<223> OTHER INFORMATION: n is dATP, dCTP, dGTP, or dTTP

<400> SEQUENCE: 6
ctcatcgtaa tcggcagcat tatagacgtg gccctcagcg aagcagacaa ctctgaagag     60
```

```
agcaatagaa tctccatcac cttttccgt cttttccgag tgatgcgatt ggtgaagctt      120
ctcagcaggg gggaaggcat ccggacattg ctgtggactt ttattaagtc ctttcaggcg      180
ctcccgtatg tggccctcct catagccatg ctgttcttca tctatgcggt cattggcatg      240
cagatgtttg ggaaagttgc catgagagat aacaaccaga tcaataggaa caataacttc      300
cagacgtttc cccaggcggt gctgctgctc ttcaggtgtg caacaggtga ggcctggcag      360
gagatcatgc tggcctgtct cccagggaag ctctgtgacc ctgagtcaga ttacaacctc      420
ggggaggagt atacatgtgg gagcaacttt gccattgtct atttcatcag nttttacatg      480
ctctgtgcat ttctgacatc aatctgtttg gtggctgtca tcatggataa tttcgactat      540
ctgaccccng gac                                                          553
```

```
<210> SEQ ID NO 7
<211> LENGTH: 498
<212> TYPE: DNA
<213> ORGANISM: pig
<220> FEATURE:
<221> NAME/KEY: partial_cDNA
<222> LOCATION: (1)..(498)

<400> SEQUENCE: 7
```

```
tggaatgtgt tcgacttcct gattgtcatc ggcagcatca ttgacgtcat cctcagtgag      60
atcgacgacc ccgacgagag tgcccgcatc tccagcgcct tcttccgcct gttccgggtc     120
atgaggttga tcaagctgct gagccgcgcc gagggcgtgc gcacgctgct ctggaccttc     180
atcaagtcct tccaggccct gccctacgtg gctctgctca tcgtcatgct cttcttcatc     240
tatgctgtca tcggcatgca gatgtttggg aagatcgcca tggtggacgg aacccagata     300
aaccggaaca acaatttcca gaccttccct caggctgtgc tgctgctctt caggtgcgcc     360
acgggtgagg cgtggcagga gatcctgctg gcctgcaggt acgggcagct gtgcgacccc     420
gagtcagact acctccctgg ggaggagtat acctgcggca ccgacttcgc ctactactac     480
ttcatcagct tctacatg                                                    498
```

```
<210> SEQ ID NO 8
<211> LENGTH: 573
<212> TYPE: DNA
<213> ORGANISM: pig
<220> FEATURE:
<221> NAME/KEY: partial_cDNA
<222> LOCATION: (1)..(573)
<220> FEATURE:
<221> NAME/KEY: misc_feature
<222> LOCATION: (1)..(573)
<223> OTHER INFORMATION: n is dATP, dCTP, dGTP, or dTTP
<220> FEATURE:
<221> NAME/KEY: misc_feature
<222> LOCATION: (1)..(573)
<223> OTHER INFORMATION: Xaa is any amino acid

<400> SEQUENCE: 8
```

```
tggcgggatg acctggtcca ggagcttcat gctggttctc ttccagatct tcttgataat       60
ggccctcagc tcctcgttgg cctgctcaaa gttaccttcc gtcttgatct tgagtgccgt      120
tcggaccagg gcgaagaggg tggcattgaa ggtgaccgag ccatcgctat tcaggggcat      180
gttcatgccc accagccgct tacatgccac ccggtgtgga caaaatttcc caaagcccag      240 aggggggctgg atccttctca gcagggtcac cacgtccagg tgcttgattc tgcccttagc    300
ttctgggtcg tactctgccc agatggcctt gaactcgtcc aggtgatgtg ggcccaggat    360
```

| | |
|---|---:|
| ggaccagtcc cgggtgaggt agtcaaaatt gtccatgatc acagccacaa agaggttgat | 420 |
| gatcaggaag gcacagagca tgtagaagct gatgaagtag tagtaggcga agtcggtgcc | 480 |
| cgcaggtata ctcctcccca gggaggtagt ctgactcggg gtcgcacagc ttgccgtacc | 540 |
| tgcaggccan caggatctcc tgcacgcctt acc | 573 |

<210> SEQ ID NO 9
<211> LENGTH: 6615
<212> TYPE: DNA
<213> ORGANISM: Homo sapiens
<220> FEATURE:
<221> NAME/KEY: gene
<222> LOCATION: (1)..(6615)
<223> OTHER INFORMATION: n is dATP, dCTP, dGTP, or dTTP
<220> FEATURE:
<221> NAME/KEY: CDS
<222> LOCATION: (2282)..(6298)
<220> FEATURE:
<221> NAME/KEY: misc_feature
<222> LOCATION: (2282)..(6298)
<223> OTHER INFORMATION: n is dATP, dCTP, dGTP, or dTTP
<220> FEATURE:
<221> NAME/KEY: misc_feature
<222> LOCATION: (2282)..(6298)
<223> OTHER INFORMATION: Xaa is any amino acid

<400> SEQUENCE: 9

| | |
|---|---:|
| caggcccggc agcggggagc cgagtggagg ctaattttac ttgctggag cgaggagagt | 60 |
| aatcctcctg cccccactcc tgccccgcc ccctggctgg ctcagcaggg caggctcagc | 120 |
| cgacagcctc agccagccta gtccccaagg cgggggcatt gggacacag gaagggaaa | 180 |
| gcactggggt gggggagcag gagaaagcca gattcccagg gaagccatgg agccatcctc | 240 |
| accccaggat gaaggcctga ggaagaaaca gcccaagaag ccagttcctg agattctgcc | 300 |
| aaggccaccc cgggccttgt tctgcctgac cctggagaac cccctgagga aggcctgcat | 360 |
| cagcattgta gaatgaaagc ccttcgagac gatcatcttg ctcaccatct ttgccaattg | 420 |
| tgtggccctg ccgtgtacc tgccatgcc ggaagatgac aacaactctc tgaacctcgg | 480 |
| cctggagaag ctggagtatt tcttcctcat tgtcttctcg attgaagccg ccatgaagat | 540 |
| cattgcctac ggcttcttat tccaccagga cgcttacctg cgcagtggct ggaatgtgct | 600 |
| ggacttcacc attgtcttcc tgggggtctt caccgtgatt ctggacaagg ttaacgtcat | 660 |
| ccaaagccac acagccccat gagcagcaaa ggagccggct tggatgtcaa ggccctcaga | 720 |
| gccttccgag tgctcagacc cctccggctg gtgtcggggg tgcctagcct gcaggtggtc | 780 |
| ctgaactcca tcttcaaggc catgctcccc ctctttcaca tcgccctgct ggtcctcttt | 840 |
| atggtcatca tctatgccat catcgggctg gagctcttca agggcaagat gcacaagacc | 900 |
| tgctacttca ttggtacaga tatcgtggcc acggtggaga atgaagagcc atcgccctgc | 960 |
| gccaggacgg gctcagggcg ccggtgcacc atcaatggca gtgagtgccg gggcggctgg | 1020 |
| ccagggccca accatggcat cacccacttc gacaacttcg gcttctccat gctcaccgtg | 1080 |
| taccagtgca ttaccatgga gggatggact gacgtccttt actgggtcaa tgatgccatc | 1140 |
| gggaatgagt ggcctggat ctatttgtc accctcattt tgctgggatc cttcttcatc | 1200 |
| ctcaacctgg tgctgggtgt cctgagtggg gaattcacca aggagcggga aaggccaag | 1260 |
| tccaggggaa ccttccagaa gctccggag aagcagcaac tagatgagga ccttcggggc | 1320 |
| tacatgagct ggatcacgca gggcgaggtc atggatgttg aggacttcag agaaggaaaa | 1380 |
| ctgtctttgg atgaaggtgg ctctgacaca gagagcctgt atgaaattgc aggcttgaac | 1440 |

-continued

```
aaaatcatcc agttcatccg acattggagg cagtggaacc gcatctttcg ctggaagtgc      1500
catgacatcg tgaagtccaa ggtcttctat tggctggtga ttctcatcgt tgccctcaac      1560
accctgtcta tcgcctcaga gcaccacaac cagcctctct ggctgacccg tttgcaagac      1620
attgccaacc gggtgctgct gtccctcttc accactgaga tgctgatgaa gatgtacggg      1680
ctgggcctgc gccagtactt catgtctatc ttcaaccgct tcgactgctt cgtggtgtgc      1740
agcggtatcc tggagatcct gctggtggag tcggcgccca tgacacccct gggcatctcc      1800
gtgctccgct gcatccgcct cctgaggatc ttcaagatca ccaaatattg gacgtcgctg      1860
agcaacctgg tggcatccct gctcaactcc atccgctcca tcgcctccct gctgctgctg      1920
ctcttcctct tcatcgtcat cttcgccctc ctgggcatgc agctctttgg ggggaggtat      1980
gactttgaag acacagaagt acggcgcagc aactttgaca actttcccca gccctcatc       2040 agcgtcttcc aggtactgac aggggaagac tggacctcaa tgatgtacaa tgggatcatg      2100
gcctacggcg gccgtccta ccctggcatg cttgtgtgca tttacttcat catccttttc       2160
gtctgtggca actacatcct gctcaatgtc ttcctggcca ttgccgtgga caacctggcc      2220
gaggcggaga gcctgacttc tgcccagaac ggccaaggct gaggagaaaa aacgcaggaa      2280
```

| g atg tcc aag ggt ctc cca gac aag tca gaa gag gag aag tca acg atg | 2329 |
|---|---|
| Met Ser Lys Gly Leu Pro Asp Lys Ser Glu Glu Glu Lys Ser Thr Met | |
| 1               5                   10                  15 | |

| gcc aag aag ctg gag cag aaa ccc aag ggt gag ggc atc ccc acc act | 2377 |
|---|---|
| Ala Lys Lys Leu Glu Gln Lys Pro Lys Gly Glu Gly Ile Pro Thr Thr | |
|         20                  25                  30 | |

| gcc aag ctg ana atc gat gag ttn gaa tct aat gtc aat gag gtg aag | 2425 |
|---|---|
| Ala Lys Leu Xaa Ile Asp Glu Xaa Glu Ser Asn Val Asn Glu Val Lys | |
|         35                  40                  45 | |

| gat ccc tac ccc tca gcc gac ttc cca ggg gat gac gag gaa gat gag | 2473 |
|---|---|
| Asp Pro Tyr Pro Ser Ala Asp Phe Pro Gly Asp Asp Glu Glu Asp Glu | |
| 50                  55                  60 | |

| cct gag atc ccg ctg agc ccc cga cca cgt ccc ctg gct gag ctg cag | 2521 |
|---|---|
| Pro Glu Ile Pro Leu Ser Pro Arg Pro Arg Pro Leu Ala Glu Leu Gln | |
| 65                  70                  75              80 | |

| ctg aaa gag aag gcc gtg ccc att cca gaa gcc agc tcc ttc ttc atc | 2569 |
|---|---|
| Leu Lys Glu Lys Ala Val Pro Ile Pro Glu Ala Ser Ser Phe Phe Ile | |
|         85                  90                  95 | |

| ttc agc ccc acc aat aag atc cgt gtc ctg tgt cac cgc atc gtc aat | 2617 |
|---|---|
| Phe Ser Pro Thr Asn Lys Ile Arg Val Leu Cys His Arg Ile Val Asn | |
|         100                 105                 110 | |

| gcc acc tgg ttc acc aac ttc atc ctg ctc ttc atc ctg ctc agc agc | 2665 |
|---|---|
| Ala Thr Trp Phe Thr Asn Phe Ile Leu Leu Phe Ile Leu Leu Ser Ser | |
|         115                 120                 125 | |

| gct gca ctg gct gcg gaa gac ccc atc cgg gct gat tcc atg aga aat | 2713 |
|---|---|
| Ala Ala Leu Ala Ala Glu Asp Pro Ile Arg Ala Asp Ser Met Arg Asn | |
| 130                 135                 140 | |

| cag atc ctt aaa cac ttt gac atc ggg ttc acc tct gtc ttc act gtg | 2761 |
|---|---|
| Gln Ile Leu Lys His Phe Asp Ile Gly Phe Thr Ser Val Phe Thr Val | |
| 145                 150                 155                 160 | |

| gag att gtc ctc aag atg acg acc tac gga gcc ttc ctg cac aag ggt | 2809 |
|---|---|
| Glu Ile Val Leu Lys Met Thr Thr Tyr Gly Ala Phe Leu His Lys Gly | |
|         165                 170                 175 | |

| tcc ttc tgc cgc aat tac ttc aac atg ctg gac ctg ctg gtg gtg gcc | 2857 |
|---|---|
| Ser Phe Cys Arg Asn Tyr Phe Asn Met Leu Asp Leu Leu Val Val Ala | |
|         180                 185                 190 | |

| gtg tcc ctc atc tcc atg gga ctt gag tcc agt gcc atc tcc gtg gtg | 2905 |
|---|---|
| Val Ser Leu Ile Ser Met Gly Leu Glu Ser Ser Ala Ile Ser Val Val | |
|         195                 200                 205 | |

-continued

```
aag atc ctg agg gtg ctg agg gtg ctc cga cca ctc aga gcc atc aac      2953
Lys Ile Leu Arg Val Leu Arg Val Leu Arg Pro Leu Arg Ala Ile Asn
    210                 215                 220 aga gcc aag ggg ttg aag gtg agn nnn nnn nnn nnn nnn nnn nnn nnn      3001
Arg Ala Lys Gly Leu Lys Val Xaa Xaa Xaa Xaa Xaa Xaa Xaa Xaa Xaa
225                 230                 235                 240 nnn nnn nnn nnn nnn nnn nnn nnn nnn nnn nnn nnn nnn nnn nnn nnn      3049
Xaa Xaa Xaa Xaa Xaa Xaa Xaa Xaa Xaa Xaa Xaa Xaa Xaa Xaa Xaa Xaa
                245                 250                 255 nnn nnn nnn nnn nnn nnn nnn nnn nnn nnn nnn nnn nnn nnn nnn nnn      3097
Xaa Xaa Xaa Xaa Xaa Xaa Xaa Xaa Xaa Xaa Xaa Xaa Xaa Xaa Xaa Xaa
            260                 265                 270 nnn nnn nnn nnn nnn nnn nnn nnn nnn nnn nnn nnn nnn nnn nnn nnn      3145
Xaa Xaa Xaa Xaa Xaa Xaa Xaa Xaa Xaa Xaa Xaa Xaa Xaa Xaa Xaa Xaa
        275                 280                 285 nnn nnn nnn nnn nnn nnn nnn nnn nnn nnn nnn nnn nnn nnn nnn nnn      3193
Xaa Xaa Xaa Xaa Xaa Xaa Xaa Xaa Xaa Xaa Xaa Xaa Xaa Xaa Xaa Xaa
    290                 295                 300 nnn nnn nnn nnn nnn nnn nnn nnn nnn nnn nnn nnn nnn nnn nnn nnn      3241
Xaa Xaa Xaa Xaa Xaa Xaa Xaa Xaa Xaa Xaa Xaa Xaa Xaa Xaa Xaa Xaa
305                 310                 315                 320 nnn nnn nnn nnn nnn nnn nnn nnn nnn nnn tgc cac agg ggc tac          3289
Xaa Xaa Xaa Xaa Xaa Xaa Xaa Xaa Xaa Xaa Cys His Arg Gly Tyr
                325                 330                 335 tac tac gtg tac aag gac ggg gac ccc atg cag ata gag ctg cgt cac      3337
Tyr Tyr Val Tyr Lys Asp Gly Asp Pro Met Gln Ile Glu Leu Arg His
            340                 345                 350 cgc gag tgg gta cac agc gac ttc cac ttc gac aat gtg ctc tca gcc      3385
Arg Glu Trp Val His Ser Asp Phe His Phe Asp Asn Val Leu Ser Ala
        355                 360                 365 atg atg tcc ctc ttc acg gtc tcc acc ttc gag gga tgg cct cag ctg      3433
Met Met Ser Leu Phe Thr Val Ser Thr Phe Glu Gly Trp Pro Gln Leu
    370                 375                 380 ctg tac aag gcc ata gac tcc aat gcg gag gac gtg ggt ccc atc tac      3481
Leu Tyr Lys Ala Ile Asp Ser Asn Ala Glu Asp Val Gly Pro Ile Tyr
385                 390                 395                 400 aac aac cgt gtg gag atg gcc atc ttc ttc atc atc tac atc atc ctc      3529
Asn Asn Arg Val Glu Met Ala Ile Phe Phe Ile Ile Tyr Ile Ile Leu
                405                 410                 415 att gcc ttc ttc atg atg aac atc ttt gtg ggc ttc gtc att gtc acc      3577
Ile Ala Phe Phe Met Met Asn Ile Phe Val Gly Phe Val Ile Val Thr
            420                 425                 430 ttc cag gag cag gga gag act gag tac aag aac tgt gag ctg gac aag      3625
Phe Gln Glu Gln Gly Glu Thr Glu Tyr Lys Asn Cys Glu Leu Asp Lys
        435                 440                 445 aac cag cgc caa tgt gta cag tat gcc ctg aag gcc cgc cca ctg agg      3673
Asn Gln Arg Gln Cys Val Gln Tyr Ala Leu Lys Ala Arg Pro Leu Arg
    450                 455                 460 tgc tac att ccc aaa aac cca tac cag tac cag gtg tgg tac att gtc      3721
Cys Tyr Ile Pro Lys Asn Pro Tyr Gln Tyr Gln Val Trp Tyr Ile Val
465                 470                 475                 480 acc tcc tcc tac ttt gaa tac ctg atg ttt gcc ctc atc atg ctc aac      3769
Thr Ser Ser Tyr Phe Glu Tyr Leu Met Phe Ala Leu Ile Met Leu Asn
                485                 490                 495 acc atc tgc ctc ggc atg cag cac tac aac cag tcg gag cag atg aac      3817
Thr Ile Cys Leu Gly Met Gln His Tyr Asn Gln Ser Glu Gln Met Asn
            500                 505                 510 cac atc tca gac atc ctc aat gtg gcc ttc act atc atc ttc acc ctg      3865
His Ile Ser Asp Ile Leu Asn Val Ala Phe Thr Ile Ile Phe Thr Leu
```

-continued

```
              515                 520                 525
gag atg atc ctc aag ctc atg gcc ttc aag gcc agg ggc tac ttt gga      3913
Glu Met Ile Leu Lys Leu Met Ala Phe Lys Ala Arg Gly Tyr Phe Gly
    530                 535                 540 gac ccc tgg aat gtg ttt gac ttc ctg att gtc att ggc agc atc att      3961
Asp Pro Trp Asn Val Phe Asp Phe Leu Ile Val Ile Gly Ser Ile Ile
545                 550                 555                 560 gat gtc atc ctc agt gag atc gac act ttc ctg gcc tcc agc ggg gga      4009
Asp Val Ile Leu Ser Glu Ile Asp Thr Phe Leu Ala Ser Ser Gly Gly
                565                 570                 575 ctg tat tgc ctg ggt gga ggc tgc ggg aac gtt gac cca gat gag agt      4057
Leu Tyr Cys Leu Gly Gly Gly Cys Gly Asn Val Asp Pro Asp Glu Ser
            580                 585                 590 gcc cgc atc tcc agc gcc ttc ttc cgc ctg ttc cgt gtc atg agg ctg      4105
Ala Arg Ile Ser Ser Ala Phe Phe Arg Leu Phe Arg Val Met Arg Leu
        595                 600                 605 atc aag ctg ctg agc cgg gca gaa gga gtg cga acc ctc ctg tgg acg      4153
Ile Lys Leu Leu Ser Arg Ala Glu Gly Val Arg Thr Leu Leu Trp Thr
    610                 615                 620 ttc atc aag tcc ttc cag gcc cta ccc tac gtg gct ctg ctc atc gtc      4201
Phe Ile Lys Ser Phe Gln Ala Leu Pro Tyr Val Ala Leu Leu Ile Val
625                 630                 635                 640 atg ctc ttc ttc atc tac gct gtc atc ggc atg cag atg ttt ggg aag      4249
Met Leu Phe Phe Ile Tyr Ala Val Ile Gly Met Gln Met Phe Gly Lys
                645                 650                 655 atc gcc ttg gtg gat ggg acc caa ata aac cgg aac aac aac ttc cag      4297
Ile Ala Leu Val Asp Gly Thr Gln Ile Asn Arg Asn Asn Asn Phe Gln
            660                 665                 670 acc ttc cca caa gct gtg cta ctg ctc ttc agg tgt gca aca ggt gag      4345
Thr Phe Pro Gln Ala Val Leu Leu Leu Phe Arg Cys Ala Thr Gly Glu
        675                 680                 685 gcc tgg cag gag atc cta ctg gcc tgc agc tat ggg aag ctg tgt gac      4393
Ala Trp Gln Glu Ile Leu Leu Ala Cys Ser Tyr Gly Lys Leu Cys Asp
    690                 695                 700 cca gag tcg gac tat gcc cca ggg gag gag tac aca tgt ggc acc aac      4441
Pro Glu Ser Asp Tyr Ala Pro Gly Glu Glu Tyr Thr Cys Gly Thr Asn
705                 710                 715                 720 ttt gca tac tac tac ttc atc agc ttc tac atg ctc tgt gcc ttc ctg      4489
Phe Ala Tyr Tyr Tyr Phe Ile Ser Phe Tyr Met Leu Cys Ala Phe Leu
                725                 730                 735 gtc atc aac ctc ttt gtg gct gtc atc atg gac aat ttt gac tac ctc      4537
Val Ile Asn Leu Phe Val Ala Val Ile Met Asp Asn Phe Asp Tyr Leu
            740                 745                 750 acc cgg gac tgg tcc atc ctg ggc cct cat cac ctg gat gag ttc aag      4585
Thr Arg Asp Trp Ser Ile Leu Gly Pro His His Leu Asp Glu Phe Lys
        755                 760                 765 gcc atc tgg gca gag tat gac cca gag gct aag ggg aga atc aaa cac      4633
Ala Ile Trp Ala Glu Tyr Asp Pro Glu Ala Lys Gly Arg Ile Lys His
    770                 775                 780 ctg gac gtg gtg acc ctg ctg aga agg att cag ccc cct ctg ggc ttt      4681
Leu Asp Val Val Thr Leu Leu Arg Arg Ile Gln Pro Pro Leu Gly Phe
785                 790                 795                 800 ggg aag ttc tgc cca cat cgg gta gct tgt aag cgg ctg gtg ggc atg      4729
Gly Lys Phe Cys Pro His Arg Val Ala Cys Lys Arg Leu Val Gly Met
                805                 810                 815 aac atg ccc ctg aac agc gac ggc aca gtc acc ttc aat gcc aca ctc      4777
Asn Met Pro Leu Asn Ser Asp Gly Thr Val Thr Phe Asn Ala Thr Leu
            820                 825                 830 ttt gcc ctg gtc cgc acg gca ctc aag atc aag acg gaa ggt aac ttt      4825
```

```
Phe Ala Leu Val Arg Thr Ala Leu Lys Ile Lys Thr Glu Gly Asn Phe
        835                 840                 845 gag cag gcc aac gag gag ctg agg gcc atc atc aag aag atc tgg aag        4873
Glu Gln Ala Asn Glu Glu Leu Arg Ala Ile Ile Lys Lys Ile Trp Lys
    850                 855                 860 aga acc agc atg aag ctc ttg gac cag gtc atc cct cca ata gga gat        4921
Arg Thr Ser Met Lys Leu Leu Asp Gln Val Ile Pro Pro Ile Gly Asp
865                 870                 875                 880 gat gag gtg aca gtg ggg aag ttc tac gcc aca ttc ctc atc cag gag        4969
Asp Glu Val Thr Val Gly Lys Phe Tyr Ala Thr Phe Leu Ile Gln Glu
                885                 890                 895 cac ttc cgg aag ttc atg aaa cgc caa gag gag tat tat ggc tat cgg        5017
His Phe Arg Lys Phe Met Lys Arg Gln Glu Glu Tyr Tyr Gly Tyr Arg
            900                 905                 910 ccc aag aag gac att gta cag atc cag gca ggg ctg cgg acc att gag        5065
Pro Lys Lys Asp Ile Val Gln Ile Gln Ala Gly Leu Arg Thr Ile Glu
        915                 920                 925 gaa gag gca gcc ccc gag atc tgt cgc acg gtc tca gga gac ctg gct        5113
Glu Glu Ala Ala Pro Glu Ile Cys Arg Thr Val Ser Gly Asp Leu Ala
    930                 935                 940 gct gag gag gag ctg gag aga gcc atg gtg gag gct gcg atg gag gag        5161
Ala Glu Glu Glu Leu Glu Arg Ala Met Val Glu Ala Ala Met Glu Glu
945                 950                 955                 960 gga ata ttc cgg agg act gga ggc ctg ttt ggc cag gtg gac aac ttc        5209
Gly Ile Phe Arg Arg Thr Gly Gly Leu Phe Gly Gln Val Asp Asn Phe
                965                 970                 975 ctg gaa agg acc aac tcc ctg ccc ccc gtc atg gcc aat cag aga ccc        5257
Leu Glu Arg Thr Asn Ser Leu Pro Pro Val Met Ala Asn Gln Arg Pro
            980                 985                 990 ctc cag ttt gct gag ata gag atg gaa gag atg gag tca cct gtc ttc        5305
Leu Gln Phe Ala Glu Ile Glu Met Glu Glu Met Glu Ser Pro Val Phe
        995                 1000                1005 ttg gag gac ttc cca caa gat cca cgc acc aac ccc ctg gct cgt           5350
Leu Glu Asp Phe Pro Gln Asp Pro Arg Thr Asn Pro Leu Ala Arg
    1010                1015                1020 gcc aat acc aac aat gcc aac gcc aat gtc gcc tat ggc aac agc           5395
Ala Asn Thr Asn Asn Ala Asn Ala Asn Val Ala Tyr Gly Asn Ser
1025                1030                1035 aac cat agc aac agc cat gtg ttt tcc agt gtc cac tat gaa agg           5440
Asn His Ser Asn Ser His Val Phe Ser Ser Val His Tyr Glu Arg
    1040                1045                1050 gag ttc cca gaa gag aca gag acg cct gct acc aga gga cga gcc           5485
Glu Phe Pro Glu Glu Thr Glu Thr Pro Ala Thr Arg Gly Arg Ala
    1055                1060                1065 ctt ggc caa ccc tgc agg gtc cnn nnn nnn nnn nnn nnn nnn              5530
Leu Gly Gln Pro Cys Arg Val Xaa Xaa Xaa Xaa Xaa Xaa Xaa
    1070                1075                1080 nnn nnn nnn nnn nnn nnn nnn nnn nnn nnn nnn nnn nnn nnn nnn          5575
Xaa Xaa Xaa Xaa Xaa Xaa Xaa Xaa Xaa Xaa Xaa Xaa Xaa Xaa Xaa
1085                1090                1095 nnn nnn nnn nnn nnn nnn nnn nnn nnn nnn nnn nnn nnn nnn nnn          5620
Xaa Xaa Xaa Xaa Xaa Xaa Xaa Xaa Xaa Xaa Xaa Xaa Xaa Xaa Xaa
1100                1105                1110 nnn nnn nnn nnn nnn nnn nnn nnn nnn nnn nnn nnn nnn nnn nnn          5665
Xaa Xaa Xaa Xaa Xaa Xaa Xaa Xaa Xaa Xaa Xaa Xaa Xaa Xaa Xaa
    1115                1120                1125 nnn nnn nnn nnn nnn nnn nnn nnn nnn nnn nnn nnn nnn nnn nnn          5710
Xaa Xaa Xaa Xaa Xaa Xaa Xaa Xaa Xaa Xaa Xaa Xaa Xaa Xaa Xaa
        1130                1135                1140
```

```
nnn nnn nnn nnn nnn nnn nnn nnn nnn nnn nnn nnn nnn nnn nnn      5755
Xaa Xaa Xaa Xaa Xaa Xaa Xaa Xaa Xaa Xaa Xaa Xaa Xaa Xaa Xaa
    1145                1150                1155 nnn nnn nnn nnn nnn nnn nnn nnn nnn nnn nnn nnn nnn nnn nnn      5800
Xaa Xaa Xaa Xaa Xaa Xaa Xaa Xaa Xaa Xaa Xaa Xaa Xaa Xaa Xaa
1160                1165                1170 nnn nnn aca gga ccc cac agc aaa ccc tgt gtg gag atg ctg aag      5845
Xaa Xaa Thr Gly Pro His Ser Lys Pro Cys Val Glu Met Leu Lys
    1175                1180                1185 gga ctg ctg acc cag agg gca atg ccc aga ggc cag gca cct cct      5890
Gly Leu Leu Thr Gln Arg Ala Met Pro Arg Gly Gln Ala Pro Pro
1190                1195                1200 gcc ccc tgc cag tgc ccc agg gtg gag tcc tcc atg cct gag gac      5935
Ala Pro Cys Gln Cys Pro Arg Val Glu Ser Ser Met Pro Glu Asp
    1205                1210                1215 aga aag agc tcc aca cca ggg tct ctt cat gag gag aca ccc cac      5980
Arg Lys Ser Ser Thr Pro Gly Ser Leu His Glu Glu Thr Pro His
1220                1225                1230 agc agg agc acc agg gag aat act tcc agg tgc tca gca cca gct      6025
Ser Arg Ser Thr Arg Glu Asn Thr Ser Arg Cys Ser Ala Pro Ala
    1235                1240                1245 aca gcc ctg ctg atc caa aag gct ctg gtt cga ggg ggc ctg ggc      6070
Thr Ala Leu Leu Ile Gln Lys Ala Leu Val Arg Gly Gly Leu Gly
1250                1255                1260 acc ttg gca gct gat gca aac ttc atc atg gca aca ggc cag gcc      6115
Thr Leu Ala Ala Asp Ala Asn Phe Ile Met Ala Thr Gly Gln Ala
    1265                1270                1275 ctg gca gat gcc tgc caa atg gaa cca gag gaa gtg gag atc atg      6160
Leu Ala Asp Ala Cys Gln Met Glu Pro Glu Glu Val Glu Ile Met
1280                1285                1290 gca aca gag cta ctg aaa gga cga gag gcc cca gag ggc atg gcc      6205
Ala Thr Glu Leu Leu Lys Gly Arg Glu Ala Pro Glu Gly Met Ala
    1295                1300                1305 agc tcc ctg gga tgc ctg aac ctc ggg tcc tcc ctg ggc agc ctc      6250
Ser Ser Leu Gly Cys Leu Asn Leu Gly Ser Ser Leu Gly Ser Leu
1310                1315                1320 gac caa cac cag ggc tcc cag gag acc ctt att cct cca agg ctg      6295
Asp Gln His Gln Gly Ser Gln Glu Thr Leu Ile Pro Pro Arg Leu
    1325                1330                1335 tga tgcccacaca gcatcagcat gggcttagag ctggcatgac caatgggggt       6348
ggggaagttg ctggggtgga gaagggctag cccaccgcag cagcctccct cctctcagc 6408 agctagatgc atggcctgag gcaggtggt caggaaccac ctcaaaaagt gcggaggaag 6468 tagctggaca ggccctgccc ctcaccagca agaggcatga ttggatggag cttctaatgt 6528 cattcaaaaa ggcctggtca gtgcctgtct ggcctagggc cactcccacc tgcaggacat 6588 taaaatctcc aggcctgtga cactggc                                    6615
```

<210> SEQ ID NO 10
<211> LENGTH: 1338
<212> TYPE: PRT
<213> ORGANISM: Homo sapiens
<220> FEATURE:
<221> NAME/KEY: misc_feature
<222> LOCATION: (36)..(36)
<223> OTHER INFORMATION: The 'Xaa' at location 36 stands for Lys, Arg, Thr, or Ile.
<220> FEATURE:
<221> NAME/KEY: misc_feature
<222> LOCATION: (40)..(40)
<223> OTHER INFORMATION: The 'Xaa' at location 40 stands for Leu, or Phe.

```
<220> FEATURE:
<221> NAME/KEY: misc_feature
<222> LOCATION: (232)..(232)
<223> OTHER INFORMATION: The 'Xaa' at location 232 stands for Arg, or
      Ser.
<220> FEATURE:
<221> NAME/KEY: misc_feature
<222> LOCATION: (233)..(233)
<223> OTHER INFORMATION: The 'Xaa' at location 233 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (234)..(234)
<223> OTHER INFORMATION: The 'Xaa' at location 234 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (235)..(235)
<223> OTHER INFORMATION: The 'Xaa' at location 235 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (236)..(236)
<223> OTHER INFORMATION: The 'Xaa' at location 236 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (237)..(237)
<223> OTHER INFORMATION: The 'Xaa' at location 237 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (238)..(238)
<223> OTHER INFORMATION: The 'Xaa' at location 238 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (239)..(239)
<223> OTHER INFORMATION: The 'Xaa' at location 239 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (240)..(240)
<223> OTHER INFORMATION: The 'Xaa' at location 240 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (241)..(241)
<223> OTHER INFORMATION: The 'Xaa' at location 241 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (242)..(242)
<223> OTHER INFORMATION: The 'Xaa' at location 242 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (243)..(243)
<223> OTHER INFORMATION: The 'Xaa' at location 243 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (244)..(244)
<223> OTHER INFORMATION: The 'Xaa' at location 244 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
```

```
<222> LOCATION: (245)..(245)
<223> OTHER INFORMATION: The 'Xaa' at location 245 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (246)..(246)
<223> OTHER INFORMATION: The 'Xaa' at location 246 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (247)..(247)
<223> OTHER INFORMATION: The 'Xaa' at location 247 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (248)..(248)
<223> OTHER INFORMATION: The 'Xaa' at location 248 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (249)..(249)
<223> OTHER INFORMATION: The 'Xaa' at location 249 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (250)..(250)
<223> OTHER INFORMATION: The 'Xaa' at location 250 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (251)..(251)
<223> OTHER INFORMATION: The 'Xaa' at location 251 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (252)..(252)
<223> OTHER INFORMATION: The 'Xaa' at location 252 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (253)..(253)
<223> OTHER INFORMATION: The 'Xaa' at location 253 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (254)..(254)
<223> OTHER INFORMATION: The 'Xaa' at location 254 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (255)..(255)
<223> OTHER INFORMATION: The 'Xaa' at location 255 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (256)..(256)
<223> OTHER INFORMATION: The 'Xaa' at location 256 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (257)..(257)
<223> OTHER INFORMATION: The 'Xaa' at location 257 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (258)..(258)
```

```
<223> OTHER INFORMATION: The 'Xaa' at location 258 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (259)..(259)
<223> OTHER INFORMATION: The 'Xaa' at location 259 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (260)..(260)
<223> OTHER INFORMATION: The 'Xaa' at location 260 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (261)..(261)
<223> OTHER INFORMATION: The 'Xaa' at location 261 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (262)..(262)
<223> OTHER INFORMATION: The 'Xaa' at location 262 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (263)..(263)
<223> OTHER INFORMATION: The 'Xaa' at location 263 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (264)..(264)
<223> OTHER INFORMATION: The 'Xaa' at location 264 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (265)..(265)
<223> OTHER INFORMATION: The 'Xaa' at location 265 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (266)..(266)
<223> OTHER INFORMATION: The 'Xaa' at location 266 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (267)..(267)
<223> OTHER INFORMATION: The 'Xaa' at location 267 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (268)..(268)
<223> OTHER INFORMATION: The 'Xaa' at location 268 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (269)..(269)
<223> OTHER INFORMATION: The 'Xaa' at location 269 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (270)..(270)
<223> OTHER INFORMATION: The 'Xaa' at location 270 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (271)..(271)
<223> OTHER INFORMATION: The 'Xaa' at location 271 stands for Lys, Asn,
```

-continued

```
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (272)..(272)
<223> OTHER INFORMATION: The 'Xaa' at location 272 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (273)..(273)
<223> OTHER INFORMATION: The 'Xaa' at location 273 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (274)..(274)
<223> OTHER INFORMATION: The 'Xaa' at location 274 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (275)..(275)
<223> OTHER INFORMATION: The 'Xaa' at location 275 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (276)..(276)
<223> OTHER INFORMATION: The 'Xaa' at location 276 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (277)..(277)
<223> OTHER INFORMATION: The 'Xaa' at location 277 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (278)..(278)
<223> OTHER INFORMATION: The 'Xaa' at location 278 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (279)..(279)
<223> OTHER INFORMATION: The 'Xaa' at location 279 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (280)..(280)
<223> OTHER INFORMATION: The 'Xaa' at location 280 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (281)..(281)
<223> OTHER INFORMATION: The 'Xaa' at location 281 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (282)..(282)
<223> OTHER INFORMATION: The 'Xaa' at location 282 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (283)..(283)
<223> OTHER INFORMATION: The 'Xaa' at location 283 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (284)..(284)
<223> OTHER INFORMATION: The 'Xaa' at location 284 stands for Lys, Asn,
      Arg, Ser, Thr, Ile, Met, Glu, Asp, Gly, Ala, Val, Gln, His, Pro,
```

```
            Leu, Tyr, Trp, Cys, or Phe.
<220> FEATURE:
<221> NAME/KEY: misc_feature
<222> LOCATION: (285)..(285)
<223> OTHER INFORMATION: The 'Xaa' at location 285 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (286)..(286)
<223> OTHER INFORMATION: The 'Xaa' at location 286 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (287)..(287)
<223> OTHER INFORMATION: The 'Xaa' at location 287 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (288)..(288)
<223> OTHER INFORMATION: The 'Xaa' at location 288 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (289)..(289)
<223> OTHER INFORMATION: The 'Xaa' at location 289 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (290)..(290)
<223> OTHER INFORMATION: The 'Xaa' at location 290 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (291)..(291)
<223> OTHER INFORMATION: The 'Xaa' at location 291 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (292)..(292)
<223> OTHER INFORMATION: The 'Xaa' at location 292 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (293)..(293)
<223> OTHER INFORMATION: The 'Xaa' at location 293 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (294)..(294)
<223> OTHER INFORMATION: The 'Xaa' at location 294 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (295)..(295)
<223> OTHER INFORMATION: The 'Xaa' at location 295 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (296)..(296)
<223> OTHER INFORMATION: The 'Xaa' at location 296 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (297)..(297)
<223> OTHER INFORMATION: The 'Xaa' at location 297 stands for Lys, Asn,
      Arg, Ser, Thr, Ile, Met, Glu, Asp, Gly, Ala, Val, Gln, His, Pro,
      Leu, Tyr, Trp, Cys, or Phe.
```

-continued

```
<220> FEATURE:
<221> NAME/KEY: misc_feature
<222> LOCATION: (298)..(298)
<223> OTHER INFORMATION: The 'Xaa' at location 298 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (299)..(299)
<223> OTHER INFORMATION: The 'Xaa' at location 299 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (300)..(300)
<223> OTHER INFORMATION: The 'Xaa' at location 300 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (301)..(301)
<223> OTHER INFORMATION: The 'Xaa' at location 301 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (302)..(302)
<223> OTHER INFORMATION: The 'Xaa' at location 302 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (303)..(303)
<223> OTHER INFORMATION: The 'Xaa' at location 303 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (304)..(304)
<223> OTHER INFORMATION: The 'Xaa' at location 304 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (305)..(305)
<223> OTHER INFORMATION: The 'Xaa' at location 305 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (306)..(306)
<223> OTHER INFORMATION: The 'Xaa' at location 306 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (307)..(307)
<223> OTHER INFORMATION: The 'Xaa' at location 307 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (308)..(308)
<223> OTHER INFORMATION: The 'Xaa' at location 308 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (309)..(309)
<223> OTHER INFORMATION: The 'Xaa' at location 309 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (310)..(310)
<223> OTHER INFORMATION: The 'Xaa' at location 310 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
```

```
<221> NAME/KEY: misc_feature
<222> LOCATION: (311)..(311)
<223> OTHER INFORMATION: The 'Xaa' at location 311 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (312)..(312)
<223> OTHER INFORMATION: The 'Xaa' at location 312 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (313)..(313)
<223> OTHER INFORMATION: The 'Xaa' at location 313 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (314)..(314)
<223> OTHER INFORMATION: The 'Xaa' at location 314 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (315)..(315)
<223> OTHER INFORMATION: The 'Xaa' at location 315 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (316)..(316)
<223> OTHER INFORMATION: The 'Xaa' at location 316 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (317)..(317)
<223> OTHER INFORMATION: The 'Xaa' at location 317 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (318)..(318)
<223> OTHER INFORMATION: The 'Xaa' at location 318 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (319)..(319)
<223> OTHER INFORMATION: The 'Xaa' at location 319 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (320)..(320)
<223> OTHER INFORMATION: The 'Xaa' at location 320 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (321)..(321)
<223> OTHER INFORMATION: The 'Xaa' at location 321 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (322)..(322)
<223> OTHER INFORMATION: The 'Xaa' at location 322 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (323)..(323)
<223> OTHER INFORMATION: The 'Xaa' at location 323 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
```

```
<222> LOCATION: (324)..(324)
<223> OTHER INFORMATION: The 'Xaa' at location 324 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (325)..(325)
<223> OTHER INFORMATION: The 'Xaa' at location 325 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (326)..(326)
<223> OTHER INFORMATION: The 'Xaa' at location 326 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (327)..(327)
<223> OTHER INFORMATION: The 'Xaa' at location 327 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (328)..(328)
<223> OTHER INFORMATION: The 'Xaa' at location 328 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (329)..(329)
<223> OTHER INFORMATION: The 'Xaa' at location 329 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (330)..(330)
<223> OTHER INFORMATION: The 'Xaa' at location 330 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (331)..(331)
<223> OTHER INFORMATION: The 'Xaa' at location 331 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (1076)..(1076)
<223> OTHER INFORMATION: The 'Xaa' at location 1076 stands for Gln, His,
      Arg, Pro, or Leu.
<220> FEATURE:
<221> NAME/KEY: misc_feature
<222> LOCATION: (1077)..(1077)
<223> OTHER INFORMATION: The 'Xaa' at location 1077 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (1078)..(1078)
<223> OTHER INFORMATION: The 'Xaa' at location 1078 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (1079)..(1079)
<223> OTHER INFORMATION: The 'Xaa' at location 1079 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (1080)..(1080)
<223> OTHER INFORMATION: The 'Xaa' at location 1080 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (1081)..(1081)
<223> OTHER INFORMATION: The 'Xaa' at location 1081 stands for Lys, Asn,
```

```
        Arg, Ser, Thr, Ile, Met, Glu, Asp, Gly, Ala, Val, Gln, His, Pro,
        Leu, Tyr, Trp, Cys, or Phe.
<220> FEATURE:
<221> NAME/KEY: misc_feature
<222> LOCATION: (1082)..(1082)
<223> OTHER INFORMATION: The 'Xaa' at location 1082 stands for Lys, Asn,
        Arg, Ser, Thr, Ile, Met, Glu, Asp, Gly, Ala, Val, Gln, His, Pro,
        Leu, Tyr, Trp, Cys, or Phe.
<220> FEATURE:
<221> NAME/KEY: misc_feature
<222> LOCATION: (1083)..(1083)
<223> OTHER INFORMATION: The 'Xaa' at location 1083 stands for Lys, Asn,
        Arg, Ser, Thr, Ile, Met, Glu, Asp, Gly, Ala, Val, Gln, His, Pro,
        Leu, Tyr, Trp, Cys, or Phe.
<220> FEATURE:
<221> NAME/KEY: misc_feature
<222> LOCATION: (1084)..(1084)
<223> OTHER INFORMATION: The 'Xaa' at location 1084 stands for Lys, Asn,
        Arg, Ser, Thr, Ile, Met, Glu, Asp, Gly, Ala, Val, Gln, His, Pro,
        Leu, Tyr, Trp, Cys, or Phe.
<220> FEATURE:
<221> NAME/KEY: misc_feature
<222> LOCATION: (1085)..(1085)
<223> OTHER INFORMATION: The 'Xaa' at location 1085 stands for Lys, Asn,
        Arg, Ser, Thr, Ile, Met, Glu, Asp, Gly, Ala, Val, Gln, His, Pro,
        Leu, Tyr, Trp, Cys, or Phe.
<220> FEATURE:
<221> NAME/KEY: misc_feature
<222> LOCATION: (1086)..(1086)
<223> OTHER INFORMATION: The 'Xaa' at location 1086 stands for Lys, Asn,
        Arg, Ser, Thr, Ile, Met, Glu, Asp, Gly, Ala, Val, Gln, His, Pro,
        Leu, Tyr, Trp, Cys, or Phe.
<220> FEATURE:
<221> NAME/KEY: misc_feature
<222> LOCATION: (1087)..(1087)
<223> OTHER INFORMATION: The 'Xaa' at location 1087 stands for Lys, Asn,
        Arg, Ser, Thr, Ile, Met, Glu, Asp, Gly, Ala, Val, Gln, His, Pro,
        Leu, Tyr, Trp, Cys, or Phe.
<220> FEATURE:
<221> NAME/KEY: misc_feature
<222> LOCATION: (1088)..(1088)
<223> OTHER INFORMATION: The 'Xaa' at location 1088 stands for Lys, Asn,
        Arg, Ser, Thr, Ile, Met, Glu, Asp, Gly, Ala, Val, Gln, His, Pro,
        Leu, Tyr, Trp, Cys, or Phe.
<220> FEATURE:
<221> NAME/KEY: misc_feature
<222> LOCATION: (1089)..(1089)
<223> OTHER INFORMATION: The 'Xaa' at location 1089 stands for Lys, Asn,
        Arg, Ser, Thr, Ile, Met, Glu, Asp, Gly, Ala, Val, Gln, His, Pro,
        Leu, Tyr, Trp, Cys, or Phe.
<220> FEATURE:
<221> NAME/KEY: misc_feature
<222> LOCATION: (1090)..(1090)
<223> OTHER INFORMATION: The 'Xaa' at location 1090 stands for Lys, Asn,
        Arg, Ser, Thr, Ile, Met, Glu, Asp, Gly, Ala, Val, Gln, His, Pro,
        Leu, Tyr, Trp, Cys, or Phe.
<220> FEATURE:
<221> NAME/KEY: misc_feature
<222> LOCATION: (1091)..(1091)
<223> OTHER INFORMATION: The 'Xaa' at location 1091 stands for Lys, Asn,
        Arg, Ser, Thr, Ile, Met, Glu, Asp, Gly, Ala, Val, Gln, His, Pro,
        Leu, Tyr, Trp, Cys, or Phe.
<220> FEATURE:
<221> NAME/KEY: misc_feature
<222> LOCATION: (1092)..(1092)
<223> OTHER INFORMATION: The 'Xaa' at location 1092 stands for Lys, Asn,
        Arg, Ser, Thr, Ile, Met, Glu, Asp, Gly, Ala, Val, Gln, His, Pro,
        Leu, Tyr, Trp, Cys, or Phe.
<220> FEATURE:
<221> NAME/KEY: misc_feature
<222> LOCATION: (1093)..(1093)
<223> OTHER INFORMATION: The 'Xaa' at location 1093 stands for Lys, Asn,
        Arg, Ser, Thr, Ile, Met, Glu, Asp, Gly, Ala, Val, Gln, His, Pro,
        Leu, Tyr, Trp, Cys, or Phe.
<220> FEATURE:
<221> NAME/KEY: misc_feature
<222> LOCATION: (1094)..(1094)
<223> OTHER INFORMATION: The 'Xaa' at location 1094 stands for Lys, Asn,
        Arg, Ser, Thr, Ile, Met, Glu, Asp, Gly, Ala, Val, Gln, His, Pro,
```

```
      Leu, Tyr, Trp, Cys, or Phe.
<220> FEATURE:
<221> NAME/KEY: misc_feature
<222> LOCATION: (1095)..(1095)
<223> OTHER INFORMATION: The 'Xaa' at location 1095 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (1096)..(1096)
<223> OTHER INFORMATION: The 'Xaa' at location 1096 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (1097)..(1097)
<223> OTHER INFORMATION: The 'Xaa' at location 1097 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (1098)..(1098)
<223> OTHER INFORMATION: The 'Xaa' at location 1098 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (1099)..(1099)
<223> OTHER INFORMATION: The 'Xaa' at location 1099 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (1100)..(1100)
<223> OTHER INFORMATION: The 'Xaa' at location 1100 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (1101)..(1101)
<223> OTHER INFORMATION: The 'Xaa' at location 1101 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (1102)..(1102)
<223> OTHER INFORMATION: The 'Xaa' at location 1102 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (1103)..(1103)
<223> OTHER INFORMATION: The 'Xaa' at location 1103 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (1104)..(1104)
<223> OTHER INFORMATION: The 'Xaa' at location 1104 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (1105)..(1105)
<223> OTHER INFORMATION: The 'Xaa' at location 1105 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (1106)..(1106)
<223> OTHER INFORMATION: The 'Xaa' at location 1106 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (1107)..(1107)
<223> OTHER INFORMATION: The 'Xaa' at location 1107 stands for Lys, Asn,
      Arg, Ser, Thr, Ile, Met, Glu, Asp, Gly, Ala, Val, Gln, His, Pro,
      Leu, Tyr, Trp, Cys, or Phe.
```

-continued

```
<220> FEATURE:
<221> NAME/KEY: misc_feature
<222> LOCATION: (1108)..(1108)
<223> OTHER INFORMATION: The 'Xaa' at location 1108 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (1109)..(1109)
<223> OTHER INFORMATION: The 'Xaa' at location 1109 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (1110)..(1110)
<223> OTHER INFORMATION: The 'Xaa' at location 1110 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (1111)..(1111)
<223> OTHER INFORMATION: The 'Xaa' at location 1111 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (1112)..(1112)
<223> OTHER INFORMATION: The 'Xaa' at location 1112 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (1113)..(1113)
<223> OTHER INFORMATION: The 'Xaa' at location 1113 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (1114)..(1114)
<223> OTHER INFORMATION: The 'Xaa' at location 1114 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (1115)..(1115)
<223> OTHER INFORMATION: The 'Xaa' at location 1115 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (1116)..(1116)
<223> OTHER INFORMATION: The 'Xaa' at location 1116 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (1117)..(1117)
<223> OTHER INFORMATION: The 'Xaa' at location 1117 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (1118)..(1118)
<223> OTHER INFORMATION: The 'Xaa' at location 1118 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (1119)..(1119)
<223> OTHER INFORMATION: The 'Xaa' at location 1119 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (1120)..(1120)
<223> OTHER INFORMATION: The 'Xaa' at location 1120 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
```

```
<221> NAME/KEY: misc_feature
<222> LOCATION: (1121)..(1121)
<223> OTHER INFORMATION: The 'Xaa' at location 1121 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (1122)..(1122)
<223> OTHER INFORMATION: The 'Xaa' at location 1122 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (1123)..(1123)
<223> OTHER INFORMATION: The 'Xaa' at location 1123 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (1124)..(1124)
<223> OTHER INFORMATION: The 'Xaa' at location 1124 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (1125)..(1125)
<223> OTHER INFORMATION: The 'Xaa' at location 1125 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (1126)..(1126)
<223> OTHER INFORMATION: The 'Xaa' at location 1126 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (1127)..(1127)
<223> OTHER INFORMATION: The 'Xaa' at location 1127 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (1128)..(1128)
<223> OTHER INFORMATION: The 'Xaa' at location 1128 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (1129)..(1129)
<223> OTHER INFORMATION: The 'Xaa' at location 1129 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (1130)..(1130)
<223> OTHER INFORMATION: The 'Xaa' at location 1130 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (1131)..(1131)
<223> OTHER INFORMATION: The 'Xaa' at location 1131 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (1132)..(1132)
<223> OTHER INFORMATION: The 'Xaa' at location 1132 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (1133)..(1133)
<223> OTHER INFORMATION: The 'Xaa' at location 1133 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
```

```
<222> LOCATION: (1134)..(1134)
<223> OTHER INFORMATION: The 'Xaa' at location 1134 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (1135)..(1135)
<223> OTHER INFORMATION: The 'Xaa' at location 1135 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (1136)..(1136)
<223> OTHER INFORMATION: The 'Xaa' at location 1136 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (1137)..(1137)
<223> OTHER INFORMATION: The 'Xaa' at location 1137 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (1138)..(1138)
<223> OTHER INFORMATION: The 'Xaa' at location 1138 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (1139)..(1139)
<223> OTHER INFORMATION: The 'Xaa' at location 1139 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (1140)..(1140)
<223> OTHER INFORMATION: The 'Xaa' at location 1140 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (1141)..(1141)
<223> OTHER INFORMATION: The 'Xaa' at location 1141 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (1142)..(1142)
<223> OTHER INFORMATION: The 'Xaa' at location 1142 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (1143)..(1143)
<223> OTHER INFORMATION: The 'Xaa' at location 1143 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (1144)..(1144)
<223> OTHER INFORMATION: The 'Xaa' at location 1144 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (1145)..(1145)
<223> OTHER INFORMATION: The 'Xaa' at location 1145 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (1146)..(1146)
<223> OTHER INFORMATION: The 'Xaa' at location 1146 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (1147)..(1147)
```

-continued

```
<223> OTHER INFORMATION: The 'Xaa' at location 1147 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (1148)..(1148)
<223> OTHER INFORMATION: The 'Xaa' at location 1148 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (1149)..(1149)
<223> OTHER INFORMATION: The 'Xaa' at location 1149 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (1150)..(1150)
<223> OTHER INFORMATION: The 'Xaa' at location 1150 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (1151)..(1151)
<223> OTHER INFORMATION: The 'Xaa' at location 1151 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (1152)..(1152)
<223> OTHER INFORMATION: The 'Xaa' at location 1152 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (1153)..(1153)
<223> OTHER INFORMATION: The 'Xaa' at location 1153 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (1154)..(1154)
<223> OTHER INFORMATION: The 'Xaa' at location 1154 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (1155)..(1155)
<223> OTHER INFORMATION: The 'Xaa' at location 1155 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (1156)..(1156)
<223> OTHER INFORMATION: The 'Xaa' at location 1156 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (1157)..(1157)
<223> OTHER INFORMATION: The 'Xaa' at location 1157 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (1158)..(1158)
<223> OTHER INFORMATION: The 'Xaa' at location 1158 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (1159)..(1159)
<223> OTHER INFORMATION: The 'Xaa' at location 1159 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (1160)..(1160)
<223> OTHER INFORMATION: The 'Xaa' at location 1160 stands for Lys, Asn,
```

-continued

```
        Arg, Ser, Thr, Ile, Met, Glu, Asp, Gly, Ala, Val, Gln, His, Pro,
        Leu, Tyr, Trp, Cys, or Phe.
<220> FEATURE:
<221> NAME/KEY: misc_feature
<222> LOCATION: (1161)..(1161)
<223> OTHER INFORMATION: The 'Xaa' at location 1161 stands for Lys, Asn,
        Arg, Ser, Thr, Ile, Met, Glu, Asp, Gly, Ala, Val, Gln, His, Pro,
        Leu, Tyr, Trp, Cys, or Phe.
<220> FEATURE:
<221> NAME/KEY: misc_feature
<222> LOCATION: (1162)..(1162)
<223> OTHER INFORMATION: The 'Xaa' at location 1162 stands for Lys, Asn,
        Arg, Ser, Thr, Ile, Met, Glu, Asp, Gly, Ala, Val, Gln, His, Pro,
        Leu, Tyr, Trp, Cys, or Phe.
<220> FEATURE:
<221> NAME/KEY: misc_feature
<222> LOCATION: (1163)..(1163)
<223> OTHER INFORMATION: The 'Xaa' at location 1163 stands for Lys, Asn,
        Arg, Ser, Thr, Ile, Met, Glu, Asp, Gly, Ala, Val, Gln, His, Pro,
        Leu, Tyr, Trp, Cys, or Phe.
<220> FEATURE:
<221> NAME/KEY: misc_feature
<222> LOCATION: (1164)..(1164)
<223> OTHER INFORMATION: The 'Xaa' at location 1164 stands for Lys, Asn,
        Arg, Ser, Thr, Ile, Met, Glu, Asp, Gly, Ala, Val, Gln, His, Pro,
        Leu, Tyr, Trp, Cys, or Phe.
<220> FEATURE:
<221> NAME/KEY: misc_feature
<222> LOCATION: (1165)..(1165)
<223> OTHER INFORMATION: The 'Xaa' at location 1165 stands for Lys, Asn,
        Arg, Ser, Thr, Ile, Met, Glu, Asp, Gly, Ala, Val, Gln, His, Pro,
        Leu, Tyr, Trp, Cys, or Phe.
<220> FEATURE:
<221> NAME/KEY: misc_feature
<222> LOCATION: (1166)..(1166)
<223> OTHER INFORMATION: The 'Xaa' at location 1166 stands for Lys, Asn,
        Arg, Ser, Thr, Ile, Met, Glu, Asp, Gly, Ala, Val, Gln, His, Pro,
        Leu, Tyr, Trp, Cys, or Phe.
<220> FEATURE:
<221> NAME/KEY: misc_feature
<222> LOCATION: (1167)..(1167)
<223> OTHER INFORMATION: The 'Xaa' at location 1167 stands for Lys, Asn,
        Arg, Ser, Thr, Ile, Met, Glu, Asp, Gly, Ala, Val, Gln, His, Pro,
        Leu, Tyr, Trp, Cys, or Phe.
<220> FEATURE:
<221> NAME/KEY: misc_feature
<222> LOCATION: (1168)..(1168)
<223> OTHER INFORMATION: The 'Xaa' at location 1168 stands for Lys, Asn,
        Arg, Ser, Thr, Ile, Met, Glu, Asp, Gly, Ala, Val, Gln, His, Pro,
        Leu, Tyr, Trp, Cys, or Phe.
<220> FEATURE:
<221> NAME/KEY: misc_feature
<222> LOCATION: (1169)..(1169)
<223> OTHER INFORMATION: The 'Xaa' at location 1169 stands for Lys, Asn,
        Arg, Ser, Thr, Ile, Met, Glu, Asp, Gly, Ala, Val, Gln, His, Pro,
        Leu, Tyr, Trp, Cys, or Phe.
<220> FEATURE:
<221> NAME/KEY: misc_feature
<222> LOCATION: (1170)..(1170)
<223> OTHER INFORMATION: The 'Xaa' at location 1170 stands for Lys, Asn,
        Arg, Ser, Thr, Ile, Met, Glu, Asp, Gly, Ala, Val, Gln, His, Pro,
        Leu, Tyr, Trp, Cys, or Phe.
<220> FEATURE:
<221> NAME/KEY: misc_feature
<222> LOCATION: (1171)..(1171)
<223> OTHER INFORMATION: The 'Xaa' at location 1171 stands for Lys, Asn,
        Arg, Ser, Thr, Ile, Met, Glu, Asp, Gly, Ala, Val, Gln, His, Pro,
        Leu, Tyr, Trp, Cys, or Phe.
<220> FEATURE:
<221> NAME/KEY: misc_feature
<222> LOCATION: (1172)..(1172)
<223> OTHER INFORMATION: The 'Xaa' at location 1172 stands for Lys, Asn,
        Arg, Ser, Thr, Ile, Met, Glu, Asp, Gly, Ala, Val, Gln, His, Pro,
        Leu, Tyr, Trp, Cys, or Phe.
<220> FEATURE:
<221> NAME/KEY: misc_feature
<222> LOCATION: (1173)..(1173)
<223> OTHER INFORMATION: The 'Xaa' at location 1173 stands for Lys, Asn,
        Arg, Ser, Thr, Ile, Met, Glu, Asp, Gly, Ala, Val, Gln, His, Pro,
```

-continued

```
         Leu, Tyr, Trp, Cys, or Phe.
<220> FEATURE:
<221> NAME/KEY: misc_feature
<222> LOCATION: (1174)..(1174)
<223> OTHER INFORMATION: The 'Xaa' at location 1174 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (1175)..(1175)
<223> OTHER INFORMATION: The 'Xaa' at location 1175 stands for Lys, Asn,
      Arg, Ser, Thr, Ile, Met, Glu, Asp, Gly, Ala, Val, Gln, His, Pro,
      Leu, Tyr, Trp, Cys, or Phe.

<400> SEQUENCE: 10

Met Ser Lys Gly Leu Pro Asp Lys Ser Glu Glu Lys Ser Thr Met
1               5                  10                  15

Ala Lys Lys Leu Glu Gln Lys Pro Lys Gly Glu Gly Ile Pro Thr Thr
                20                  25                  30

Ala Lys Leu Xaa Ile Asp Glu Xaa Glu Ser Asn Val Asn Glu Val Lys
                35                  40                  45

Asp Pro Tyr Pro Ser Ala Asp Phe Pro Gly Asp Asp Glu Glu Asp Glu
50                  55                  60

Pro Glu Ile Pro Leu Ser Pro Arg Pro Arg Pro Leu Ala Glu Leu Gln
65                  70                  75                  80

Leu Lys Glu Lys Ala Val Pro Ile Pro Glu Ala Ser Ser Phe Phe Ile
                85                  90                  95

Phe Ser Pro Thr Asn Lys Ile Arg Val Leu Cys His Arg Ile Val Asn
                100                 105                 110

Ala Thr Trp Phe Thr Asn Phe Ile Leu Leu Phe Ile Leu Leu Ser Ser
                115                 120                 125

Ala Ala Leu Ala Ala Glu Asp Pro Ile Arg Ala Asp Ser Met Arg Asn
                130                 135                 140

Gln Ile Leu Lys His Phe Asp Ile Gly Phe Thr Ser Val Phe Thr Val
145                 150                 155                 160

Glu Ile Val Leu Lys Met Thr Thr Tyr Gly Ala Phe Leu His Lys Gly
                165                 170                 175

Ser Phe Cys Arg Asn Tyr Phe Asn Met Leu Asp Leu Leu Val Val Ala
                180                 185                 190

Val Ser Leu Ile Ser Met Gly Leu Glu Ser Ser Ala Ile Ser Val Val
                195                 200                 205

Lys Ile Leu Arg Val Leu Arg Val Leu Arg Pro Leu Arg Ala Ile Asn
                210                 215                 220

Arg Ala Lys Gly Leu Lys Val Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Xaa Xaa
                245                 250                 255

Xaa Xaa Xaa Xaa Xaa Xaa Xaa Xaa Xaa Xaa Xaa Xaa Xaa Xaa Xaa
                260                 265                 270

Xaa Xaa Xaa Xaa Xaa Xaa Xaa Xaa Xaa Xaa Xaa Xaa Xaa Xaa Xaa
                275                 280                 285

Xaa Xaa Xaa Xaa Xaa Xaa Xaa Xaa Xaa Xaa Xaa Xaa Xaa Xaa Xaa
                290                 295                 300

Xaa Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Xaa Xaa Xaa Xaa Xaa Cys His Arg Gly Tyr
                325                 330                 335
```

-continued

Tyr Tyr Val Tyr Lys Asp Gly Asp Pro Met Gln Ile Glu Leu Arg His
        340                 345                 350

Arg Glu Trp Val His Ser Asp Phe His Phe Asp Asn Val Leu Ser Ala
        355                 360                 365

Met Met Ser Leu Phe Thr Val Ser Thr Phe Glu Gly Trp Pro Gln Leu
        370                 375                 380

Leu Tyr Lys Ala Ile Asp Ser Asn Ala Glu Asp Val Gly Pro Ile Tyr
385                 390                 395                 400

Asn Asn Arg Val Glu Met Ala Ile Phe Phe Ile Ile Tyr Ile Ile Leu
                405                 410                 415

Ile Ala Phe Phe Met Met Asn Ile Phe Val Gly Phe Val Ile Val Thr
                420                 425                 430

Phe Gln Glu Gln Gly Glu Thr Glu Tyr Lys Asn Cys Glu Leu Asp Lys
        435                 440                 445

Asn Gln Arg Gln Cys Val Gln Tyr Ala Leu Lys Ala Arg Pro Leu Arg
        450                 455                 460

Cys Tyr Ile Pro Lys Asn Pro Tyr Gln Tyr Gln Val Trp Tyr Ile Val
465                 470                 475                 480

Thr Ser Ser Tyr Phe Glu Tyr Leu Met Phe Ala Leu Ile Met Leu Asn
                485                 490                 495

Thr Ile Cys Leu Gly Met Gln His Tyr Asn Gln Ser Glu Gln Met Asn
                500                 505                 510

His Ile Ser Asp Ile Leu Asn Val Ala Phe Thr Ile Ile Phe Thr Leu
        515                 520                 525

Glu Met Ile Leu Lys Leu Met Ala Phe Lys Ala Arg Gly Tyr Phe Gly
        530                 535                 540

Asp Pro Trp Asn Val Phe Asp Phe Leu Ile Val Ile Gly Ser Ile Ile
545                 550                 555                 560

Asp Val Ile Leu Ser Glu Ile Asp Thr Phe Leu Ala Ser Ser Gly Gly
                565                 570                 575

Leu Tyr Cys Leu Gly Gly Gly Cys Gly Asn Val Asp Pro Asp Glu Ser
                580                 585                 590

Ala Arg Ile Ser Ser Ala Phe Phe Arg Leu Phe Arg Val Met Arg Leu
        595                 600                 605

Ile Lys Leu Leu Ser Arg Ala Glu Gly Val Arg Thr Leu Leu Trp Thr
        610                 615                 620

Phe Ile Lys Ser Phe Gln Ala Leu Pro Tyr Val Ala Leu Leu Ile Val
625                 630                 635                 640

Met Leu Phe Phe Ile Tyr Ala Val Ile Gly Met Gln Met Phe Gly Lys
                645                 650                 655

Ile Ala Leu Val Asp Gly Thr Gln Ile Asn Arg Asn Asn Asn Phe Gln
                660                 665                 670

Thr Phe Pro Gln Ala Val Leu Leu Leu Phe Arg Cys Ala Thr Gly Glu
        675                 680                 685

Ala Trp Gln Glu Ile Leu Leu Ala Cys Ser Tyr Gly Lys Leu Cys Asp
        690                 695                 700

Pro Glu Ser Asp Tyr Ala Pro Gly Glu Glu Tyr Thr Cys Gly Thr Asn
705                 710                 715                 720

Phe Ala Tyr Tyr Tyr Phe Ile Ser Phe Tyr Met Leu Cys Ala Phe Leu
                725                 730                 735

Val Ile Asn Leu Phe Val Ala Val Ile Met Asp Asn Phe Asp Tyr Leu
                740                 745                 750

Thr Arg Asp Trp Ser Ile Leu Gly Pro His His Leu Asp Glu Phe Lys

-continued

```
                755                 760                 765
Ala Ile Trp Ala Glu Tyr Asp Pro Glu Ala Lys Gly Arg Ile Lys His
        770                 775                 780
Leu Asp Val Val Thr Leu Leu Arg Arg Ile Gln Pro Pro Leu Gly Phe
785                 790                 795                 800
Gly Lys Phe Cys Pro His Arg Val Ala Cys Lys Arg Leu Val Gly Met
                805                 810                 815
Asn Met Pro Leu Asn Ser Asp Gly Thr Val Thr Phe Asn Ala Thr Leu
        820                 825                 830
Phe Ala Leu Val Arg Thr Ala Leu Lys Ile Lys Thr Glu Gly Asn Phe
        835                 840                 845
Glu Gln Ala Asn Glu Glu Leu Arg Ala Ile Ile Lys Lys Ile Trp Lys
850                 855                 860
Arg Thr Ser Met Lys Leu Leu Asp Gln Val Ile Pro Pro Ile Gly Asp
865                 870                 875                 880
Asp Glu Val Thr Val Gly Lys Phe Tyr Ala Thr Phe Leu Ile Gln Glu
                885                 890                 895
His Phe Arg Lys Phe Met Lys Arg Gln Glu Glu Tyr Tyr Gly Tyr Arg
                900                 905                 910
Pro Lys Lys Asp Ile Val Gln Ile Gln Ala Gly Leu Arg Thr Ile Glu
                915                 920                 925
Glu Glu Ala Ala Pro Glu Ile Cys Arg Thr Val Ser Gly Asp Leu Ala
        930                 935                 940
Ala Glu Glu Glu Leu Glu Arg Ala Met Val Glu Ala Ala Met Glu Glu
945                 950                 955                 960
Gly Ile Phe Arg Arg Thr Gly Gly Leu Phe Gly Gln Val Asp Asn Phe
                965                 970                 975
Leu Glu Arg Thr Asn Ser Leu Pro Pro Val Met Ala Asn Gln Arg Pro
        980                 985                 990
Leu Gln Phe Ala Glu Ile Glu Met  Glu Glu Met Glu Ser  Pro Val Phe
        995                 1000                1005
Leu Glu Asp Phe Pro Gln Asp  Pro Arg Thr Asn Pro  Leu Ala Arg
1010                1015                1020
Ala Asn  Thr Asn Asn Ala Asn  Ala Asn Val Ala Tyr  Gly Asn Ser
1025                1030                1035
Asn His  Ser Asn Ser His Val  Phe Ser Ser Val His  Tyr Glu Arg
1040                1045                1050
Glu Phe  Pro Glu Glu Thr Glu  Thr Pro Ala Thr Arg  Gly Arg Ala
1055                1060                1065
Leu Gly  Gln Pro Cys Arg Val  Xaa Xaa Xaa Xaa Xaa  Xaa Xaa Xaa
1070                1075                1080
Xaa Xaa  Xaa Xaa Xaa Xaa Xaa  Xaa Xaa Xaa Xaa Xaa  Xaa Xaa
        1085                1090                1095
Xaa Xaa  Xaa Xaa Xaa Xaa Xaa  Xaa Xaa Xaa Xaa Xaa  Xaa Xaa Xaa
        1100                1105                1110
Xaa Xaa  Xaa Xaa Xaa Xaa Xaa  Xaa Xaa Xaa Xaa Xaa  Xaa Xaa Xaa
        1115                1120                1125
Xaa Xaa  Xaa Xaa Xaa Xaa Xaa  Xaa Xaa Xaa Xaa Xaa  Xaa Xaa Xaa
        1130                1135                1140
Xaa Xaa  Xaa Xaa Xaa Xaa Xaa  Xaa Xaa Xaa Xaa Xaa  Xaa Xaa Xaa
        1145                1150                1155
Xaa Xaa  Xaa Xaa Xaa Xaa Xaa  Xaa Xaa Xaa Xaa  Xaa Xaa Xaa
        1160                1165                1170
```

```
Xaa Xaa Thr Gly Pro His Ser Lys Pro Cys Val Glu  Met Leu Lys
    1175                1180                 1185

Gly Leu Leu Thr Gln Arg Ala Met Pro Arg Gly Gln  Ala Pro Pro
    1190                1195                 1200

Ala Pro Cys Gln Cys Pro Arg Val Glu Ser Ser Met  Pro Glu Asp
    1205                1210                 1215

Arg Lys Ser Ser Thr Pro Gly Ser Leu His Glu Glu  Thr Pro His
    1220                1225                 1230

Ser Arg Ser Thr Arg Glu Asn Thr Ser Arg Cys Ser  Ala Pro Ala
    1235                1240                 1245

Thr Ala Leu Leu Ile Gln Lys Ala Leu Val Arg Gly  Gly Leu Gly
    1250                1255                 1260

Thr Leu Ala Ala Asp Ala Asn Phe Ile Met Ala Thr  Gly Gln Ala
    1265                1270                 1275

Leu Ala Asp Ala Cys Gln Met Glu Pro Glu Glu Val  Glu Ile Met
    1280                1285                 1290

Ala Thr Glu Leu Leu Lys Gly Arg Glu Ala Pro Glu  Gly Met Ala
    1295                1300                 1305

Ser Ser Leu Gly Cys Leu Asn Leu Gly Ser Ser Leu  Gly Ser Leu
    1310                1315                 1320

Asp Gln His Gln Gly Ser Gln Glu Thr Leu Ile Pro  Pro Arg Leu
    1325                1330                 1335

<210> SEQ ID NO 11
<211> LENGTH: 6160
<212> TYPE: DNA
<213> ORGANISM: Homo sapiens
<220> FEATURE:
<221> NAME/KEY: gene
<222> LOCATION: (1)..(6160)
<220> FEATURE:
<221> NAME/KEY: CDS
<222> LOCATION: (226)..(5847)

<400> SEQUENCE: 11
tcaggccggc agcggggagc cgagtggagg ctaattttac ttgctgggag cgaggagagt      60
aatcctcctg ccccccactc ctgccccgcc cctggctgg tcagcaggg cagctcagcc      120 gacagcctca gccagcctag tccccaaggc gggggcattg gggacacagg gaagggaaag      180
cactggggtg ggggagcagg agaaagccag attcccaggg aagcc atg gag cca tcc      237
                                                  Met Glu Pro Ser
                                                   1 tca ccc cag gat gaa ggc ctg agg aag aaa cag ccc aag aag cca gtt      285
Ser Pro Gln Asp Glu Gly Leu Arg Lys Lys Gln Pro Lys Lys Pro Val
  5              10                  15                  20 cct gag att ctg cca agg cca ccc cgg gct ttg ttc tgc ctg acc ctg      333
Pro Glu Ile Leu Pro Arg Pro Pro Arg Ala Leu Phe Cys Leu Thr Leu
             25                  30                  35 gag aac ccc ctg agg aag gcc tgc atc agc att gta gaa tgg aag ccc      381
Glu Asn Pro Leu Arg Lys Ala Cys Ile Ser Ile Val Glu Trp Lys Pro
         40                  45                  50 ttc gag acg atc atc ttg ctc acc atc ttt gcc aat tgt gtg gcc ctg      429
Phe Glu Thr Ile Ile Leu Leu Thr Ile Phe Ala Asn Cys Val Ala Leu
     55                  60                  65 gcc gtg tac ctg ccc atg ccg gaa gat gac aac aac tct ctg aac ctc      477
Ala Val Tyr Leu Pro Met Pro Glu Asp Asp Asn Asn Ser Leu Asn Leu
 70                  75                  80 ggc ctg gag aag ctg gag tat ttc ttc ctc att gtc ttc tcg att gaa      525
```

-continued

| | | |
|---|---|---|
| Gly Leu Glu Lys Leu Glu Tyr Phe Phe Leu Ile Val Phe Ser Ile Glu<br>85                           90                             95                        100 | | |
| gcc gcc atg aag atc att gcc tac ggc ttc tta ttc cac cag gac gct<br>Ala Ala Met Lys Ile Ile Ala Tyr Gly Phe Leu Phe His Gln Asp Ala<br>                     105                          110                     115 | 573 | |
| tac ctg cgc agt ggc tgg aat gtg ctg gac ttc acc att gtc ttc ctg<br>Tyr Leu Arg Ser Gly Trp Asn Val Leu Asp Phe Thr Ile Val Phe Leu<br>           120                        125                      130 | 621 | |
| ggg gtc ttc acc gtg att ctg gaa cag gtt aac gtg atc caa agc cac<br>Gly Val Phe Thr Val Ile Leu Glu Gln Val Asn Val Ile Gln Ser His<br>         135                      140                     145 | 669 | |
| aca gcc cca atg agc agc aaa gga gcc ggc ttg gat gtc aag gcc ctc<br>Thr Ala Pro Met Ser Ser Lys Gly Ala Gly Leu Asp Val Lys Ala Leu<br>150                          155                        160 | 717 | |
| aga gcc ttc cga gtg ctc aga ccc ctc cgg ctg gtg tcg ggg gtg cct<br>Arg Ala Phe Arg Val Leu Arg Pro Leu Arg Leu Val Ser Gly Val Pro<br>165                          170                        175                     180 | 765 | |
| agc ctg cag gtg gtc ctg aac tcc atc ttc aag gcc atg ctc ccc ctc<br>Ser Leu Gln Val Val Leu Asn Ser Ile Phe Lys Ala Met Leu Pro Leu<br>                     185                          190                     195 | 813 | |
| ttt cac atc gcc ctg ctg gtc ctc ttt atg gtc atc atc tat gcc atc<br>Phe His Ile Ala Leu Leu Val Leu Phe Met Val Ile Ile Tyr Ala Ile<br>              200                         205                       210 | 861 | |
| atc ggg ctg gag ctc ttc aag ggc aag atg cac aag acc tgc tac ttc<br>Ile Gly Leu Glu Leu Phe Lys Gly Lys Met His Lys Thr Cys Tyr Phe<br>         215                      220                      225 | 909 | |
| att ggt aca gat atc gtg gcc acg gtg gag aat gaa gag cca tcg ccc<br>Ile Gly Thr Asp Ile Val Ala Thr Val Glu Asn Glu Glu Pro Ser Pro<br>230                          235                        240 | 957 | |
| tgc gcc agg acg ggc tca ggg cgc cgg tgc acc atc aat ggc agt gag<br>Cys Ala Arg Thr Gly Ser Gly Arg Arg Cys Thr Ile Asn Gly Ser Glu<br>245                          250                        255                     260 | 1005 | |
| tgc cgg ggc ggc tgc cca ggg ccc aac cat ggc atc acc cac ttc gac<br>Cys Arg Gly Gly Cys Pro Gly Pro Asn His Gly Ile Thr His Phe Asp<br>                     265                          270                     275 | 1053 | |
| aac ttc ggc ttc tcc atg ctc acc gtg tac cag tgc att acc atg gag<br>Asn Phe Gly Phe Ser Met Leu Thr Val Tyr Gln Cys Ile Thr Met Glu<br>                   280                          285                     290 | 1101 | |
| gga tgg act gac gtc ctt tac tgg gtc aat gat gcc atc ggg aat gag<br>Gly Trp Thr Asp Val Leu Tyr Trp Val Asn Asp Ala Ile Gly Asn Glu<br>         295                      300                      305 | 1149 | |
| tgg ccc tgg atc tat ttt gtc acc ctc att ttg ctg gga tcc ttc ttc<br>Trp Pro Trp Ile Tyr Phe Val Thr Leu Ile Leu Leu Gly Ser Phe Phe<br>310                          315                        320 | 1197 | |
| atc ctc aac ctg gtg ctg ggt gtc ctg agt ggg gaa ttc acc aag gag<br>Ile Leu Asn Leu Val Leu Gly Val Leu Ser Gly Glu Phe Thr Lys Glu<br>325                          330                        335                     340 | 1245 | |
| cgg gag aag gcc aag tcc agg gga acc ttc cag aag ctc cgg gag aag<br>Arg Glu Lys Ala Lys Ser Arg Gly Thr Phe Gln Lys Leu Arg Glu Lys<br>                   345                          350                     355 | 1293 | |
| cag caa cta gat gag gac ctt cgg ggc tac atg agc tgg atc acg cag<br>Gln Gln Leu Asp Glu Asp Leu Arg Gly Tyr Met Ser Trp Ile Thr Gln<br>                     360                          365                     370 | 1341 | |
| ggc gag gtc atg gat gtt gag gac ttc aga gaa gga aaa ctg tct ttg<br>Gly Glu Val Met Asp Val Glu Asp Phe Arg Glu Gly Lys Leu Ser Leu<br>                     375                          380                     385 | 1389 | |
| gat gaa ggt ggc tct gac aca gag agc ctg tat gaa att gca ggc ttg<br>Asp Glu Gly Gly Ser Asp Thr Glu Ser Leu Tyr Glu Ile Ala Gly Leu<br>390                          395                        400 | 1437 | |

```
aac aaa atc atc cag ttc atc cga cat tgg agg cag tgg aac cgc atc    1485
Asn Lys Ile Ile Gln Phe Ile Arg His Trp Arg Gln Trp Asn Arg Ile
405                 410                 415                 420 ttt cgc tgg aag tgc cat gac atc gtg aag tcc aag gtc ttc tat tgg    1533
Phe Arg Trp Lys Cys His Asp Ile Val Lys Ser Lys Val Phe Tyr Trp
                425                 430                 435 ctg gtg att ctc atc gtt gcc ctc aac acc ctg tct atc gcc tca gag    1581
Leu Val Ile Leu Ile Val Ala Leu Asn Thr Leu Ser Ile Ala Ser Glu
        440                 445                 450 cac cac aac cag ccg cac tgg ctg acc cgt ttg caa gac att gcc aac    1629
His His Asn Gln Pro His Trp Leu Thr Arg Leu Gln Asp Ile Ala Asn
                455                 460                 465 cgg gtg ctg ctg tcc ctc ttc acc act gag atg ctg atg aag atg tac    1677
Arg Val Leu Leu Ser Leu Phe Thr Thr Glu Met Leu Met Lys Met Tyr
    470                 475                 480 ggg ctg ggc ctg cgc cag tac ttc atg tct atc ttc aac cgc ttc gac    1725
Gly Leu Gly Leu Arg Gln Tyr Phe Met Ser Ile Phe Asn Arg Phe Asp
485                 490                 495                 500 tgc ttc gtg gtg tgc agc ggt atc ctg gag atc ctg ctg gtg gag tcg    1773
Cys Phe Val Val Cys Ser Gly Ile Leu Glu Ile Leu Leu Val Glu Ser
                505                 510                 515 ggc gcc atg aca ccc ctg ggc atc tcc gtg ctc cgc tgc atc cgc ctc    1821
Gly Ala Met Thr Pro Leu Gly Ile Ser Val Leu Arg Cys Ile Arg Leu
        520                 525                 530 ctg agg atc ttc aag atc acc aaa tat tgg acg tcg ctg agc aac ctg    1869
Leu Arg Ile Phe Lys Ile Thr Lys Tyr Trp Thr Ser Leu Ser Asn Leu
                535                 540                 545 gtg gca tcc ctg ctc aac tcc atc cgc tcc atc gcc tcc ctg ctg ctg    1917
Val Ala Ser Leu Leu Asn Ser Ile Arg Ser Ile Ala Ser Leu Leu Leu
    550                 555                 560 ctg ctc ttc ctc ttc atc gtc atc ttc cgc ctc ggc atg cag ctc        1965
Leu Leu Phe Leu Phe Ile Val Ile Phe Arg Leu Gly Met Gln Leu
565                 570                 575                 580 ttt ggg ggg agg tat gac ttt gaa gac aca gaa gta cgg cgc agc aac    2013
Phe Gly Gly Arg Tyr Asp Phe Glu Asp Thr Glu Val Arg Arg Ser Asn
                585                 590                 595 ttt gac aac ttt ccc caa gcc ctc atc agc gtc ttc cag gta ctg aca    2061
Phe Asp Asn Phe Pro Gln Ala Leu Ile Ser Val Phe Gln Val Leu Thr
        600                 605                 610 ggg gaa gac tgg acc tca atg atg tac aat ggg atc atg gcc tcg agc    2109
Gly Glu Asp Trp Thr Ser Met Met Tyr Asn Gly Ile Met Ala Ser Ser
                615                 620                 625 ggg ccg tcc tac cct ggc atg ctt gtg tgc att tac ttc atc atc ctt    2157
Gly Pro Ser Tyr Pro Gly Met Leu Val Cys Ile Tyr Phe Ile Ile Leu
    630                 635                 640 ttc gtc tgt ggc aac tac atc ctg ctc aat gtc ttc ctg gcc att gcc    2205
Phe Val Cys Gly Asn Tyr Ile Leu Leu Asn Val Phe Leu Ala Ile Ala
645                 650                 655                 660 gtg gac aac ctg gcc gag gcg gag agc ctg act tct gcc cag aag gcc    2253
Val Asp Asn Leu Ala Glu Ala Glu Ser Leu Thr Ser Ala Gln Lys Ala
                665                 670                 675 aag gct gag gag aaa aaa cgc agg aag atg tcc aag ggt ctc cca gac    2301
Lys Ala Glu Glu Lys Lys Arg Arg Lys Met Ser Lys Gly Leu Pro Asp
        680                 685                 690 aag tca gaa gag gag aag tca acg atg gcc aag aag ctg gag cag aaa    2349
Lys Ser Glu Glu Glu Lys Ser Thr Met Ala Lys Lys Leu Glu Gln Lys
                695                 700                 705 ccc aag ggt gag ggc atc ccc acc act gcc aag ctg aaa atc gat gag    2397
Pro Lys Gly Glu Gly Ile Pro Thr Thr Ala Lys Leu Lys Ile Asp Glu
    710                 715                 720
```

-continued

| | |
|---|---|
| ttt gaa tct aat gtc aat gag gtg aag gat ccc tac ccc tca gcc gac<br>Phe Glu Ser Asn Val Asn Glu Val Lys Asp Pro Tyr Pro Ser Ala Asp<br>725                   730                  735                    740 | 2445 |
| ttc cca ggg gat gac gag gaa gat gag cct gag atc ccg ctg agc ccc<br>Phe Pro Gly Asp Asp Glu Glu Asp Glu Pro Glu Ile Pro Leu Ser Pro<br>                 745                  750                  755 | 2493 |
| cga cca cgt ccc ctg gct gag ctg cag ctg aaa gag aag gcc gtg ccc<br>Arg Pro Arg Pro Leu Ala Glu Leu Gln Leu Lys Glu Lys Ala Val Pro<br>        760                  765                  770 | 2541 |
| att cca gaa gcc agc tcc ttc ttc atc ttc agc ccc acc aat aag atc<br>Ile Pro Glu Ala Ser Ser Phe Phe Ile Phe Ser Pro Thr Asn Lys Ile<br>775                   780                  785 | 2589 |
| cgt gtc ctg tgt cac cgc atc gtc aat gcc acc tgg ttc acc aac ttc<br>Arg Val Leu Cys His Arg Ile Val Asn Ala Thr Trp Phe Thr Asn Phe<br>        790                  795                  800 | 2637 |
| atc ctc ctc ttc atc ctg ctc agc agc gct gca ctg gct gcg gaa gac<br>Ile Leu Leu Phe Ile Leu Leu Ser Ser Ala Ala Leu Ala Ala Glu Asp<br>805                   810                  815                  820 | 2685 |
| ccc atc cgg gct gat tcc atg aga aat cag atc ctt aaa cac ttt gac<br>Pro Ile Arg Ala Asp Ser Met Arg Asn Gln Ile Leu Lys His Phe Asp<br>                 825                  830                  835 | 2733 |
| atc ggg ttc acc tct gtc ttc act gtg gag att gtc ctc aag atg acg<br>Ile Gly Phe Thr Ser Val Phe Thr Val Glu Ile Val Leu Lys Met Thr<br>        840                  845                  850 | 2781 |
| acc tac gga gcc ttc ctg cac aag ggt tcc ttc tgc cgc aat tac ttc<br>Thr Tyr Gly Ala Phe Leu His Lys Gly Ser Phe Cys Arg Asn Tyr Phe<br>855                   860                  865 | 2829 |
| aac atg ctg gac ctg ctg gtg gtg gcc gtg tcc ctc atc tcc atg gga<br>Asn Met Leu Asp Leu Leu Val Val Ala Val Ser Leu Ile Ser Met Gly<br>                 870                  875                  880 | 2877 |
| ctt gag tcc agt gcc atc tcc gtg gtg aag atc ctg agg gtg ctg agg<br>Leu Glu Ser Ser Ala Ile Ser Val Val Lys Ile Leu Arg Val Leu Arg<br>885                   890                  895                  900 | 2925 |
| gtg ctc cga cca ctc aga gcc atc aac aga gcc aag ggg ttg aag cac<br>Val Leu Arg Pro Leu Arg Ala Ile Asn Arg Ala Lys Gly Leu Lys His<br>                 905                  910                  915 | 2973 |
| gtg gct agg tgc atg ttc gtg gcc atc agc acc atc ggg aac atc gtg<br>Val Ala Arg Cys Met Phe Val Ala Ile Ser Thr Ile Gly Asn Ile Val<br>        920                  925                  930 | 3021 |
| ctg gtc act acc ctc cta cag ttc atg ttt gcc tgc atc ggc gtc cag<br>Leu Val Thr Thr Leu Leu Gln Phe Met Phe Ala Cys Ile Gly Val Gln<br>935                   940                  945 | 3069 |
| ctc ttc aag ggg aag ttc ttc agg tgc acc gac ttg tcc aag atg aca<br>Leu Phe Lys Gly Lys Phe Phe Arg Cys Thr Asp Leu Ser Lys Met Thr<br>950                   955                  960 | 3117 |
| gag gag gag tgc agg ggc tac tac tac gtg tac aag gac ggg gac ccc<br>Glu Glu Glu Cys Arg Gly Tyr Tyr Tyr Val Tyr Lys Asp Gly Asp Pro<br>965                 970                  975                  980 | 3165 |
| atg cag ata gag ctg cgt cac cgc gag tgg gta cac agc gac ttc cac<br>Met Gln Ile Glu Leu Arg His Arg Glu Trp Val His Ser Asp Phe His<br>                 985                  990                  995 | 3213 |
| ttc gac aat gtg ctc tca gcc atg atg tcc ctc ttc acg gtc tcc<br>Phe Asp Asn Val Leu Ser Ala Met Met Ser Leu Phe Thr Val Ser<br>                1000                1005                1010 | 3258 |
| acc ttc gag gga tgg cct cag ctg ctg tac aag gcc ata gac tcc<br>Thr Phe Glu Gly Trp Pro Gln Leu Leu Tyr Lys Ala Ile Asp Ser<br>                1015                1020                1025 | 3303 |
| aat gcg gag gac gtg ggt ccc atc tac aac aac cgt gtg gag atg<br>Asn Ala Glu Asp Val Gly Pro Ile Tyr Asn Asn Arg Val Glu Met | 3348 |

-continued

```
                1030                1035                1040
gcc atc ttc ttc atc atc tac atc atc ctc att gcc ttc ttc atg              3393
Ala Ile Phe Phe Ile Ile Tyr Ile Ile Leu Ile Ala Phe Phe Met
            1045                1050                1055 atg aac atc ttt gtg ggc ttc gtc att gtc acc ttc cag gag cag              3438
Met Asn Ile Phe Val Gly Phe Val Ile Val Thr Phe Gln Glu Gln
            1060                1065                1070 gga gag act gag tac aag aac tgt gag ctg gac aag aac cag cgc              3483
Gly Glu Thr Glu Tyr Lys Asn Cys Glu Leu Asp Lys Asn Gln Arg
            1075                1080                1085 caa tgt gta cag tat gcc ctg aag gcc cgc cca ctg agg tgc tac              3528
Gln Cys Val Gln Tyr Ala Leu Lys Ala Arg Pro Leu Arg Cys Tyr
            1090                1095                1100 att ccc aaa aac cca tac cag tac cag gtg tgg tac att gtc acc              3573
Ile Pro Lys Asn Pro Tyr Gln Tyr Gln Val Trp Tyr Ile Val Thr
            1105                1110                1115 tcc tcc tac ttt gaa tac ctg atg ttt gcc ctc atc atg ctc aac              3618
Ser Ser Tyr Phe Glu Tyr Leu Met Phe Ala Leu Ile Met Leu Asn
            1120                1125                1130 acc atc tgc ctc ggc atg cag cac tac aac cag tcg gag cag atg              3663
Thr Ile Cys Leu Gly Met Gln His Tyr Asn Gln Ser Glu Gln Met
            1135                1140                1145 aac cac atc tca gac atc ctc aat gtg gcc ttc act atc atc ttc              3708
Asn His Ile Ser Asp Ile Leu Asn Val Ala Phe Thr Ile Ile Phe
            1150                1155                1160 acc ctg gag atg atc ctc aag ctc atg gcc ttc aag gcc agg ggc              3753
Thr Leu Glu Met Ile Leu Lys Leu Met Ala Phe Lys Ala Arg Gly
            1165                1170                1175 tac ttt gga aac ccc tgg aat gtg ttt gac ttc ctg att gtc att              3798
Tyr Phe Gly Asn Pro Trp Asn Val Phe Asp Phe Leu Ile Val Ile
            1180                1185                1190 ggc agc atc att gat gtc atc ctc agt gag atc gac act ttc ctg              3843
Gly Ser Ile Ile Asp Val Ile Leu Ser Glu Ile Asp Thr Phe Leu
            1195                1200                1205 gcc tcc agc ggg gga ctg tat tgc ctg ggt gga ggc tgc ggg aac              3888
Ala Ser Ser Gly Gly Leu Tyr Cys Leu Gly Gly Gly Cys Gly Asn
            1210                1215                1220 gtt gac cca gat gag agt gcc cgc atc tcc agc gcc ttc ttc cgc              3933
Val Asp Pro Asp Glu Ser Ala Arg Ile Ser Ser Ala Phe Phe Arg
            1225                1230                1235 ctg ttc cgt gtc atg agg ctg atc aag ctg ctg agc cgg gca gaa              3978
Leu Phe Arg Val Met Arg Leu Ile Lys Leu Leu Ser Arg Ala Glu
            1240                1245                1250 gga gtg cga acc ctc ctg tgg acg ttc atc aag tcc ttc cag gcc              4023
Gly Val Arg Thr Leu Leu Trp Thr Phe Ile Lys Ser Phe Gln Ala
            1255                1260                1265 cta ccc tac gtg gct ctg ctc atc gtc atg ctc ttc ttc atc tac              4068
Leu Pro Tyr Val Ala Leu Leu Ile Val Met Leu Phe Phe Ile Tyr
            1270                1275                1280 gct gtc atc ggc atg cag atg ttt ggg aag atc gcc ttg gtg gat              4113
Ala Val Ile Gly Met Gln Met Phe Gly Lys Ile Ala Leu Val Asp
            1285                1290                1295 ggg acc caa ata aac cgg aac aac aac ttc cag acc ttc cca caa              4158
Gly Thr Gln Ile Asn Arg Asn Asn Asn Phe Gln Thr Phe Pro Gln
            1300                1305                1310 gct gtg cta ctg ctc ttc agg tgt gca aca ggt gag gcc tgg cag              4203
Ala Val Leu Leu Leu Phe Arg Cys Ala Thr Gly Glu Ala Trp Gln
            1315                1320                1325 gag atc cta ctg gcc tgc agc tat ggg aag ctg tgt gac cca gag              4248
```

```
               Glu Ile Leu Leu Ala Cys Ser Tyr Gly Lys Leu Cys Asp Pro Glu
                       1330                1335                1340 tcg gac tat gcc cca ggg gag gag tac aca tgt ggc acc aac ttt                    4293
Ser Asp Tyr Ala Pro Gly Glu Glu Tyr Thr Cys Gly Thr Asn Phe
            1345                1350                1355 gca tac tac tac ttc atc agc ttc tac atg ctc tgt gcc ttc ctg                    4338
Ala Tyr Tyr Tyr Phe Ile Ser Phe Tyr Met Leu Cys Ala Phe Leu
            1360                1365                1370 gtc atc aac ctc ttt gtg gct gtc atc atg gac aat ttt gac tac                    4383
Val Ile Asn Leu Phe Val Ala Val Ile Met Asp Asn Phe Asp Tyr
            1375                1380                1385 ctc acc cgg gac tgg tcc atc ctg ggc cct cat cac ctg gat gag                    4428
Leu Thr Arg Asp Trp Ser Ile Leu Gly Pro His His Leu Asp Glu
            1390                1395                1400 ttc aag gcc atc tgg gca gag tat gac cca gag gct aag ggg agg                    4473
Phe Lys Ala Ile Trp Ala Glu Tyr Asp Pro Glu Ala Lys Gly Arg
            1405                1410                1415 atc aaa cac ctg gac gtg gtg acc ctg ctg aga agg att cag ccc                    4518
Ile Lys His Leu Asp Val Val Thr Leu Leu Arg Arg Ile Gln Pro
            1420                1425                1430 cct ctg ggc ttt ggg aag ttc tgc cca cat cgg gta gct tgt aag                    4563
Pro Leu Gly Phe Gly Lys Phe Cys Pro His Arg Val Ala Cys Lys
            1435                1440                1445 cgg ctg gtg ggc atg aac atg ccc ctg aac agc gac ggc aca gtc                    4608
Arg Leu Val Gly Met Asn Met Pro Leu Asn Ser Asp Gly Thr Val
            1450                1455                1460 acc ttc aat gcc aca ctc ttt gcc ctg gtc cgc acg gca ctc aag                    4653
Thr Phe Asn Ala Thr Leu Phe Ala Leu Val Arg Thr Ala Leu Lys
            1465                1470                1475 atc aag acg gaa ggt aac ttt gag cag gcc aac gag gag ctg agg                    4698
Ile Lys Thr Glu Gly Asn Phe Glu Gln Ala Asn Glu Glu Leu Arg
            1480                1485                1490 gcc atc atc aag aag atc tgg aag aga acc agc atg aag ctc ttg                    4743
Ala Ile Ile Lys Lys Ile Trp Lys Arg Thr Ser Met Lys Leu Leu
            1495                1500                1505 gac cag gtc atc cct cca ata gga gat gat gag gtg aca gtg ggg                    4788
Asp Gln Val Ile Pro Pro Ile Gly Asp Asp Glu Val Thr Val Gly
            1510                1515                1520 aag ttc tac gcc aca ttc ctc atc cag gag cac ttc cgg aag ttc                    4833
Lys Phe Tyr Ala Thr Phe Leu Ile Gln Glu His Phe Arg Lys Phe
            1525                1530                1535 atg aaa cgc caa gag gag tat tat ggc tat cgg ccc aag aag gac                    4878
Met Lys Arg Gln Glu Glu Tyr Tyr Gly Tyr Arg Pro Lys Lys Asp
            1540                1545                1550 att gta cag atc cag gca ggg ctg cgg acc att gag gaa gag gca                    4923
Ile Val Gln Ile Gln Ala Gly Leu Arg Thr Ile Glu Glu Glu Ala
            1555                1560                1565 gcc ccc gag atc tgt cgc acg gtc tca gga gac ctg gct gct gag                    4968
Ala Pro Glu Ile Cys Arg Thr Val Ser Gly Asp Leu Ala Ala Glu
            1570                1575                1580 gag gag ctg gag aga gcc atg gtg gag gct gcg atg gag gag ggg                    5013
Glu Glu Leu Glu Arg Ala Met Val Glu Ala Ala Met Glu Glu Gly
            1585                1590                1595 ata ttc cgg agg act gga ggc ctg ttt ggc cag gtg gac aac ttc                    5058
Ile Phe Arg Arg Thr Gly Gly Leu Phe Gly Gln Val Asp Asn Phe
            1600                1605                1610 ctg gaa agg acc aac tcc ctg ccc cct gtc atg gcc aat cag aga                    5103
Leu Glu Arg Thr Asn Ser Leu Pro Pro Val Met Ala Asn Gln Arg
            1615                1620                1625
```

```
                                           -continued
ccc ctc cag ttt  gct gag ata gag atg  gaa gag atg gag tca  cct        5148
Pro Leu Gln Phe  Ala Glu Ile Glu Met  Glu Glu Met Glu Ser  Pro
            1630             1635              1640 gtc ttc ttg gag  gac ttc cca caa gat  cca cgc acc aac ccc  ctg        5193
Val Phe Leu Glu  Asp Phe Pro Gln Asp  Pro Arg Thr Asn Pro  Leu
            1645             1650              1655 gct cgt gcc aat  acc aac aat gcc aac  gcc aat gtc gcc tat  gcg        5238
Ala Arg Ala Asn  Thr Asn Asn Ala Asn  Ala Asn Val Ala Tyr  Ala
            1660             1665              1670 aac agc aac cat  agc aac agc cat gtg  ttt tcc agt gtc cac  tat        5283
Asn Ser Asn His  Ser Asn Ser His Val  Phe Ser Ser Val His  Tyr
            1675             1680              1685 gaa agg gag ttc  cca gaa gag aca gag  acg cct gct acc aga  gga        5328
Glu Arg Glu Phe  Pro Glu Glu Thr Glu  Thr Pro Ala Thr Arg  Gly
            1690             1695              1700 cga gcc ctt ggc  caa ccc tgc agg tcc  ctg gga ccc cac agc  aaa        5373
Arg Ala Leu Gly  Gln Pro Cys Arg Ser  Leu Gly Pro His Ser  Lys
            1705             1710              1715 ccc tgt gtg gag  atg ctg aag gga ctg  ctg acc cag agg gca  atg        5418
Pro Cys Val Glu  Met Leu Lys Gly Leu  Leu Thr Gln Arg Ala  Met
            1720             1725              1730 ccc aga ggc cag  gca cct cct gcc ccc  tgc cag tgc ccc agg  gtg        5463
Pro Arg Gly Gln  Ala Pro Pro Ala Pro  Cys Gln Cys Pro Arg  Val
            1735             1740              1745 gag tcc tcc atg  cct gag gac aga aag  agc tcc aca cca ggg  tct        5508
Glu Ser Ser Met  Pro Glu Asp Arg Lys  Ser Ser Thr Pro Gly  Ser
            1750             1755              1760 ctt cat gag gag  aca ccc cac agc agg  agc acc agg gag aat  act        5553
Leu His Glu Glu  Thr Pro His Ser Arg  Ser Thr Arg Glu Asn  Thr
            1765             1770              1775 tcc agg tgc tca  gca cca gct aca gcc  ctg ctg atc caa aag  gct        5598
Ser Arg Cys Ser  Ala Pro Ala Thr Ala  Leu Leu Ile Gln Lys  Ala
            1780             1785              1790 ctg gtt cga ggg  ggc ctg ggc acc ttg  gca gct gat gca aac  ttc        5643
Leu Val Arg Gly  Gly Leu Gly Thr Leu  Ala Ala Asp Ala Asn  Phe
            1795             1800              1805 atc atg gca aca  ggc cag gcc ctc gga  gat gcc tgc caa atg  gaa        5688
Ile Met Ala Thr  Gly Gln Ala Leu Gly  Asp Ala Cys Gln Met  Glu
            1810             1815              1820 cca gag gaa gtg  gag atc atg gca aca  gag cta ctg aaa gga  cga        5733
Pro Glu Glu Val  Glu Ile Met Ala Thr  Glu Leu Leu Lys Gly  Arg
            1825             1830              1835 gag gcc cca gac  ggc atg gcc agc tcc  ctg gga tgc ctg aac  ctc        5778
Glu Ala Pro Asp  Gly Met Ala Ser Ser  Leu Gly Cys Leu Asn  Leu
            1840             1845              1850 ggg tcc tcc ctg  ggc agc ctc gac caa  cac cag ggc tcc cag  gag        5823
Gly Ser Ser Leu  Gly Ser Leu Asp Gln  His Gln Gly Ser Gln  Glu
            1855             1860              1865 acc ctt att cct  cca agg ctg tga tgcccacaca gcatcagcat gggcttagag      5877
Thr Leu Ile Pro  Pro Arg Leu
            1870 ctggcatgac caatgggggt ggggaagttg ctggggtgga gaagggctag cccaccgcag      5937 cagcctccct ccctctcagc agctagatgc atgcctgagg cagggtggtc aggaaccacc      5997 tcaaaaagtg cggaggaagt agctggacag gccctgcccc tcaccagcaa gaggcatgat      6057 tggatggagc ttctaatgtc attcaaaaag gcctggtcag tgcctgtccc tagggccact      6117 cccacctgca ggacattaaa atctccaggc ctgtgacact ggc                        6160
```

<210> SEQ ID NO 12
<211> LENGTH: 1873
<212> TYPE: PRT
<213> ORGANISM: Homo sapiens

<400> SEQUENCE: 12

```
Met Glu Pro Ser Ser Pro Gln Asp Glu Gly Leu Arg Lys Lys Gln Pro
1               5                   10                  15

Lys Lys Pro Val Pro Glu Ile Leu Pro Arg Pro Arg Ala Leu Phe
            20                  25                  30

Cys Leu Thr Leu Glu Asn Pro Leu Arg Lys Ala Cys Ile Ser Ile Val
            35                  40                  45

Glu Trp Lys Pro Phe Glu Thr Ile Ile Leu Leu Thr Ile Phe Ala Asn
    50                  55                  60

Cys Val Ala Leu Ala Val Tyr Leu Pro Met Pro Glu Asp Asp Asn Asn
65                  70                  75                  80

Ser Leu Asn Leu Gly Leu Glu Lys Leu Glu Tyr Phe Phe Leu Ile Val
                85                  90                  95

Phe Ser Ile Glu Ala Ala Met Lys Ile Ile Ala Tyr Gly Phe Leu Phe
            100                 105                 110

His Gln Asp Ala Tyr Leu Arg Ser Gly Trp Asn Val Leu Asp Phe Thr
        115                 120                 125

Ile Val Phe Leu Gly Val Phe Thr Val Ile Leu Glu Gln Val Asn Val
    130                 135                 140

Ile Gln Ser His Thr Ala Pro Met Ser Ser Lys Gly Ala Gly Leu Asp
145                 150                 155                 160

Val Lys Ala Leu Arg Ala Phe Arg Val Leu Arg Pro Leu Arg Leu Val
                165                 170                 175

Ser Gly Val Pro Ser Leu Gln Val Val Leu Asn Ser Ile Phe Lys Ala
            180                 185                 190

Met Leu Pro Leu Phe His Ile Ala Leu Leu Val Leu Phe Met Val Ile
        195                 200                 205

Ile Tyr Ala Ile Ile Gly Leu Glu Leu Phe Lys Gly Lys Met His Lys
    210                 215                 220

Thr Cys Tyr Phe Ile Gly Thr Asp Ile Val Ala Thr Val Glu Asn Glu
225                 230                 235                 240

Glu Pro Ser Pro Cys Ala Arg Thr Gly Ser Gly Arg Arg Cys Thr Ile
                245                 250                 255

Asn Gly Ser Glu Cys Arg Gly Gly Cys Pro Gly Pro Asn His Gly Ile
            260                 265                 270

Thr His Phe Asp Asn Phe Gly Phe Ser Met Leu Thr Val Tyr Gln Cys
        275                 280                 285

Ile Thr Met Glu Gly Trp Thr Asp Val Leu Tyr Trp Val Asn Asp Ala
    290                 295                 300

Ile Gly Asn Glu Trp Pro Trp Ile Tyr Phe Val Thr Leu Ile Leu Leu
305                 310                 315                 320

Gly Ser Phe Phe Ile Leu Asn Leu Val Leu Gly Val Leu Ser Gly Glu
                325                 330                 335

Phe Thr Lys Glu Arg Glu Lys Ala Lys Ser Arg Gly Thr Phe Gln Lys
            340                 345                 350

Leu Arg Glu Lys Gln Gln Leu Asp Glu Asp Leu Arg Gly Tyr Met Ser
        355                 360                 365

Trp Ile Thr Gln Gly Glu Val Met Asp Val Glu Asp Phe Arg Glu Gly
    370                 375                 380
```

-continued

```
Lys Leu Ser Leu Asp Glu Gly Gly Ser Asp Thr Glu Ser Leu Tyr Glu
385                 390                 395                 400

Ile Ala Gly Leu Asn Lys Ile Ile Gln Phe Ile Arg His Trp Arg Gln
                405                 410                 415

Trp Asn Arg Ile Phe Arg Trp Lys Cys His Asp Ile Val Lys Ser Lys
            420                 425                 430

Val Phe Tyr Trp Leu Val Ile Leu Ile Val Ala Leu Asn Thr Leu Ser
        435                 440                 445

Ile Ala Ser Glu His His Asn Gln Pro His Trp Leu Thr Arg Leu Gln
    450                 455                 460

Asp Ile Ala Asn Arg Val Leu Leu Ser Leu Phe Thr Thr Glu Met Leu
465                 470                 475                 480

Met Lys Met Tyr Gly Leu Gly Leu Arg Gln Tyr Phe Met Ser Ile Phe
                485                 490                 495

Asn Arg Phe Asp Cys Phe Val Val Cys Ser Gly Ile Leu Glu Ile Leu
            500                 505                 510

Leu Val Glu Ser Gly Ala Met Thr Pro Leu Gly Ile Ser Val Leu Arg
        515                 520                 525

Cys Ile Arg Leu Leu Arg Ile Phe Lys Ile Thr Lys Tyr Trp Thr Ser
    530                 535                 540

Leu Ser Asn Leu Val Ala Ser Leu Leu Asn Ser Ile Arg Ser Ile Ala
545                 550                 555                 560

Ser Leu Leu Leu Leu Phe Leu Phe Ile Val Ile Phe Arg Leu Leu
                565                 570                 575

Gly Met Gln Leu Phe Gly Gly Arg Tyr Asp Phe Glu Asp Thr Glu Val
            580                 585                 590

Arg Arg Ser Asn Phe Asp Asn Phe Pro Gln Ala Leu Ile Ser Val Phe
        595                 600                 605

Gln Val Leu Thr Gly Glu Asp Trp Thr Ser Met Met Tyr Asn Gly Ile
    610                 615                 620

Met Ala Ser Ser Gly Pro Ser Tyr Pro Gly Met Leu Val Cys Ile Tyr
625                 630                 635                 640

Phe Ile Ile Leu Phe Val Cys Gly Asn Tyr Ile Leu Leu Asn Val Phe
                645                 650                 655

Leu Ala Ile Ala Val Asp Asn Leu Ala Glu Ala Glu Ser Leu Thr Ser
            660                 665                 670

Ala Gln Lys Ala Lys Ala Glu Glu Lys Lys Arg Arg Lys Met Ser Lys
        675                 680                 685

Gly Leu Pro Asp Lys Ser Glu Glu Lys Ser Thr Met Ala Lys Lys
    690                 695                 700

Leu Glu Gln Lys Pro Lys Gly Glu Gly Ile Pro Thr Thr Ala Lys Leu
705                 710                 715                 720

Lys Ile Asp Glu Phe Glu Ser Asn Val Asn Glu Val Lys Asp Pro Tyr
                725                 730                 735

Pro Ser Ala Asp Phe Pro Gly Asp Asp Glu Glu Asp Glu Pro Glu Ile
            740                 745                 750

Pro Leu Ser Pro Arg Pro Arg Pro Leu Ala Glu Leu Gln Leu Lys Glu
        755                 760                 765

Lys Ala Val Pro Ile Pro Glu Ala Ser Ser Phe Phe Ile Phe Ser Pro
    770                 775                 780

Thr Asn Lys Ile Arg Val Leu Cys His Arg Ile Val Asn Ala Thr Trp
785                 790                 795                 800

Phe Thr Asn Phe Ile Leu Leu Phe Ile Leu Leu Ser Ser Ala Ala Leu
```

-continued

```
                805                 810                 815
Ala Ala Glu Asp Pro Ile Arg Ala Asp Ser Met Arg Asn Gln Ile Leu
                820                 825                 830

Lys His Phe Asp Ile Gly Phe Thr Ser Val Phe Thr Val Glu Ile Val
                835                 840                 845

Leu Lys Met Thr Thr Tyr Gly Ala Phe Leu His Lys Gly Ser Phe Cys
                850                 855                 860

Arg Asn Tyr Phe Asn Met Leu Asp Leu Leu Val Val Ala Val Ser Leu
865                 870                 875                 880

Ile Ser Met Gly Leu Glu Ser Ser Ala Ile Ser Val Val Lys Ile Leu
                885                 890                 895

Arg Val Leu Arg Val Leu Arg Pro Leu Arg Ala Ile Asn Arg Ala Lys
                900                 905                 910

Gly Leu Lys His Val Ala Arg Cys Met Phe Val Ala Ile Ser Thr Ile
                915                 920                 925

Gly Asn Ile Val Leu Val Thr Thr Leu Leu Gln Phe Met Phe Ala Cys
                930                 935                 940

Ile Gly Val Gln Leu Phe Lys Gly Lys Phe Phe Arg Cys Thr Asp Leu
945                 950                 955                 960

Ser Lys Met Thr Glu Glu Cys Arg Gly Tyr Tyr Val Tyr Lys
                965                 970                 975

Asp Gly Asp Pro Met Gln Ile Glu Leu Arg His Arg Glu Trp Val His
                980                 985                 990

Ser Asp Phe His Phe Asp Asn Val Leu Ser Ala Met Met Ser Leu Phe
                995                1000                1005

Thr Val Ser Thr Phe Glu Gly Trp Pro Gln Leu Leu Tyr Lys Ala
                1010                1015                1020

Ile Asp Ser Asn Ala Glu Asp Val Gly Pro Ile Tyr Asn Asn Arg
                1025                1030                1035

Val Glu Met Ala Ile Phe Phe Ile Ile Tyr Ile Ile Leu Ile Ala
                1040                1045                1050

Phe Phe Met Met Asn Ile Phe Val Gly Phe Val Ile Val Thr Phe
                1055                1060                1065

Gln Glu Gln Gly Glu Thr Glu Tyr Lys Asn Cys Glu Leu Asp Lys
                1070                1075                1080

Asn Gln Arg Gln Cys Val Gln Tyr Ala Leu Lys Ala Arg Pro Leu
                1085                1090                1095

Arg Cys Tyr Ile Pro Lys Asn Pro Tyr Gln Tyr Gln Val Trp Tyr
                1100                1105                1110

Ile Val Thr Ser Ser Tyr Phe Glu Tyr Leu Met Phe Ala Leu Ile
                1115                1120                1125

Met Leu Asn Thr Ile Cys Leu Gly Met Gln His Tyr Asn Gln Ser
                1130                1135                1140

Glu Gln Met Asn His Ile Ser Asp Ile Leu Asn Val Ala Phe Thr
                1145                1150                1155

Ile Ile Phe Thr Leu Glu Met Ile Leu Lys Leu Met Ala Phe Lys
                1160                1165                1170

Ala Arg Gly Tyr Phe Gly Asn Pro Trp Asn Val Phe Asp Phe Leu
                1175                1180                1185

Ile Val Ile Gly Ser Ile Ile Asp Val Ile Leu Ser Glu Ile Asp
                1190                1195                1200

Thr Phe Leu Ala Ser Ser Gly Gly Leu Tyr Cys Leu Gly Gly Gly
                1205                1210                1215
```

```
        -continued

Cys Gly Asn Val Asp Pro Asp Glu Ser Ala Arg Ile  Ser Ser Ala
    1220             1225             1230

Phe Phe Arg Leu Phe Arg Val Met Arg Leu Ile Lys  Leu Leu Ser
    1235             1240             1245

Arg Ala Glu Gly Val Arg Thr Leu Leu Trp Thr Phe  Ile Lys Ser
    1250             1255             1260

Phe Gln Ala Leu Pro Tyr Val Ala Leu Leu Ile Val  Met Leu Phe
    1265             1270             1275

Phe Ile Tyr Ala Val Ile Gly Met Gln Met Phe Gly  Lys Ile Ala
    1280             1285             1290

Leu Val Asp Gly Thr Gln Ile Asn Arg Asn Asn Asn  Phe Gln Thr
    1295             1300             1305

Phe Pro Gln Ala Val Leu Leu Leu Phe Arg Cys Ala  Thr Gly Glu
    1310             1315             1320

Ala Trp Gln Glu Ile Leu Leu Ala Cys Ser Tyr Gly  Lys Leu Cys
    1325             1330             1335

Asp Pro Glu Ser Asp Tyr Ala Pro Gly Glu Glu Tyr  Thr Cys Gly
    1340             1345             1350

Thr Asn Phe Ala Tyr Tyr Tyr Phe Ile Ser Phe Tyr  Met Leu Cys
    1355             1360             1365

Ala Phe Leu Val Ile Asn Leu Phe Val Ala Val Ile  Met Asp Asn
    1370             1375             1380

Phe Asp Tyr Leu Thr Arg Asp Trp Ser Ile Leu Gly  Pro His His
    1385             1390             1395

Leu Asp Glu Phe Lys Ala Ile Trp Ala Glu Tyr Asp  Pro Glu Ala
    1400             1405             1410

Lys Gly Arg Ile Lys His Leu Asp Val Val Thr Leu  Leu Arg Arg
    1415             1420             1425

Ile Gln Pro Pro Leu Gly Phe Gly Lys Phe Cys Pro  His Arg Val
    1430             1435             1440

Ala Cys Lys Arg Leu Val Gly Met Asn Met Pro Leu  Asn Ser Asp
    1445             1450             1455

Gly Thr Val Thr Phe Asn Ala Thr Leu Phe Ala Leu  Val Arg Thr
    1460             1465             1470

Ala Leu Lys Ile Lys Thr Glu Gly Asn Phe Glu Gln  Ala Asn Glu
    1475             1480             1485

Glu Leu Arg Ala Ile Ile Lys Lys Ile Trp Lys Arg  Thr Ser Met
    1490             1495             1500

Lys Leu Leu Asp Gln Val Ile Pro Pro Ile Gly Asp  Asp Glu Val
    1505             1510             1515

Thr Val Gly Lys Phe Tyr Ala Thr Phe Leu Ile Gln  Glu His Phe
    1520             1525             1530

Arg Lys Phe Met Lys Arg Gln Glu Glu Tyr Tyr Gly  Tyr Arg Pro
    1535             1540             1545

Lys Lys Asp Ile Val Gln Ile Gln Ala Gly Leu Arg  Thr Ile Glu
    1550             1555             1560

Glu Glu Ala Ala Pro Glu Ile Cys Arg Thr Val Ser  Gly Asp Leu
    1565             1570             1575

Ala Ala Glu Glu Glu Leu Glu Arg Ala Met Val Glu  Ala Ala Met
    1580             1585             1590

Glu Glu Gly Ile Phe Arg Arg Thr Gly Gly Leu Phe  Gly Gln Val
    1595             1600             1605
```

| Asp | Asn | Phe | Leu | Glu | Arg | Thr | Asn | Ser | Leu | Pro | Pro | Val | Met | Ala |
|-----|-----|-----|-----|-----|-----|-----|-----|-----|-----|-----|-----|-----|-----|-----|
| 1610 | | | | 1615 | | | | | 1620 | | | | | |

| Asn | Gln | Arg | Pro | Leu | Gln | Phe | Ala | Glu | Ile | Glu | Met | Glu | Glu | Met |
|-----|-----|-----|-----|-----|-----|-----|-----|-----|-----|-----|-----|-----|-----|-----|
| 1625 | | | | 1630 | | | | | 1635 | | | | | |

| Glu | Ser | Pro | Val | Phe | Leu | Glu | Asp | Phe | Pro | Gln | Asp | Pro | Arg | Thr |
|-----|-----|-----|-----|-----|-----|-----|-----|-----|-----|-----|-----|-----|-----|-----|
| 1640 | | | | 1645 | | | | | 1650 | | | | | |

| Asn | Pro | Leu | Ala | Arg | Ala | Asn | Thr | Asn | Asn | Ala | Asn | Ala | Asn | Val |
|-----|-----|-----|-----|-----|-----|-----|-----|-----|-----|-----|-----|-----|-----|-----|
| 1655 | | | | 1660 | | | | | 1665 | | | | | |

| Ala | Tyr | Ala | Asn | Ser | Asn | His | Ser | Asn | Ser | His | Val | Phe | Ser | Ser |
|-----|-----|-----|-----|-----|-----|-----|-----|-----|-----|-----|-----|-----|-----|-----|
| 1670 | | | | 1675 | | | | | 1680 | | | | | |

| Val | His | Tyr | Glu | Arg | Glu | Phe | Pro | Glu | Glu | Thr | Glu | Thr | Pro | Ala |
|-----|-----|-----|-----|-----|-----|-----|-----|-----|-----|-----|-----|-----|-----|-----|
| 1685 | | | | 1690 | | | | | 1695 | | | | | |

| Thr | Arg | Gly | Arg | Ala | Leu | Gly | Gln | Pro | Cys | Arg | Ser | Leu | Gly | Pro |
|-----|-----|-----|-----|-----|-----|-----|-----|-----|-----|-----|-----|-----|-----|-----|
| 1700 | | | | 1705 | | | | | 1710 | | | | | |

| His | Ser | Lys | Pro | Cys | Val | Glu | Met | Leu | Lys | Gly | Leu | Leu | Thr | Gln |
|-----|-----|-----|-----|-----|-----|-----|-----|-----|-----|-----|-----|-----|-----|-----|
| 1715 | | | | 1720 | | | | | 1725 | | | | | |

| Arg | Ala | Met | Pro | Arg | Gly | Gln | Ala | Pro | Pro | Ala | Pro | Cys | Gln | Cys |
|-----|-----|-----|-----|-----|-----|-----|-----|-----|-----|-----|-----|-----|-----|-----|
| 1730 | | | | 1735 | | | | | 1740 | | | | | |

| Pro | Arg | Val | Glu | Ser | Ser | Met | Pro | Glu | Asp | Arg | Lys | Ser | Ser | Thr |
|-----|-----|-----|-----|-----|-----|-----|-----|-----|-----|-----|-----|-----|-----|-----|
| 1745 | | | | 1750 | | | | | 1755 | | | | | |

| Pro | Gly | Ser | Leu | His | Glu | Glu | Thr | Pro | His | Ser | Arg | Ser | Thr | Arg |
|-----|-----|-----|-----|-----|-----|-----|-----|-----|-----|-----|-----|-----|-----|-----|
| 1760 | | | | 1765 | | | | | 1770 | | | | | |

| Glu | Asn | Thr | Ser | Arg | Cys | Ser | Ala | Pro | Ala | Thr | Ala | Leu | Leu | Ile |
|-----|-----|-----|-----|-----|-----|-----|-----|-----|-----|-----|-----|-----|-----|-----|
| 1775 | | | | 1780 | | | | | 1785 | | | | | |

| Gln | Lys | Ala | Leu | Val | Arg | Gly | Gly | Leu | Gly | Thr | Leu | Ala | Ala | Asp |
|-----|-----|-----|-----|-----|-----|-----|-----|-----|-----|-----|-----|-----|-----|-----|
| 1790 | | | | 1795 | | | | | 1800 | | | | | |

| Ala | Asn | Phe | Ile | Met | Ala | Thr | Gly | Gln | Ala | Leu | Gly | Asp | Ala | Cys |
|-----|-----|-----|-----|-----|-----|-----|-----|-----|-----|-----|-----|-----|-----|-----|
| 1805 | | | | 1810 | | | | | 1815 | | | | | |

| Gln | Met | Glu | Pro | Glu | Glu | Val | Glu | Ile | Met | Ala | Thr | Glu | Leu | Leu |
|-----|-----|-----|-----|-----|-----|-----|-----|-----|-----|-----|-----|-----|-----|-----|
| 1820 | | | | 1825 | | | | | 1830 | | | | | |

| Lys | Gly | Arg | Glu | Ala | Pro | Asp | Gly | Met | Ala | Ser | Ser | Leu | Gly | Cys |
|-----|-----|-----|-----|-----|-----|-----|-----|-----|-----|-----|-----|-----|-----|-----|
| 1835 | | | | 1840 | | | | | 1845 | | | | | |

| Leu | Asn | Leu | Gly | Ser | Ser | Leu | Gly | Ser | Leu | Asp | Gln | His | Gln | Gly |
|-----|-----|-----|-----|-----|-----|-----|-----|-----|-----|-----|-----|-----|-----|-----|
| 1850 | | | | 1855 | | | | | 1860 | | | | | |

| Ser | Gln | Glu | Thr | Leu | Ile | Pro | Pro | Arg | Leu |
|-----|-----|-----|-----|-----|-----|-----|-----|-----|-----|
| 1865 | | | | 1870 | | | | | |

```
<210> SEQ ID NO 13
<211> LENGTH: 6160
<212> TYPE: DNA
<213> ORGANISM: Homo sapiens
<220> FEATURE:
<221> NAME/KEY: gene
<222> LOCATION: (1)..(6160)
<220> FEATURE:
<221> NAME/KEY: CDS
<222> LOCATION: (226)..(5847)

<400> SEQUENCE: 13
tcaggccggc agcggggagc cgagtggagg ctaattttac ttgctgggag cgaggagagt      60
aatcctcctg cccccactc ctgccccgcc ccctggctgg ctcagcaggg cagctcagcc     120
gacagcctca gccagcctag tccccaaggc gggggcattg gggacacagg gaagggaaag    180
cactggggtg ggggagcagg agaaagccag attcccaggg aagcc atg gag cca tcc    237
                                                    Met Glu Pro Ser
                                                      1 tca ccc cag gat gaa ggc ctg agg aag aaa cag ccc aag aag cca gtt      285
```

```
                Ser Pro Gln Asp Glu Gly Leu Arg Lys Lys Gln Pro Lys Lys Pro Val
                5                   10                  15                  20 cct gag att ctg cca agg cca ccc cgg gct ttg ttc tgc ctg acc ctg             333
Pro Glu Ile Leu Pro Arg Pro Pro Arg Ala Leu Phe Cys Leu Thr Leu
                    25                  30                  35 gag aac ccc ctg agg aag gcc tgc atc agc att gta gaa tgg aag ccc             381
Glu Asn Pro Leu Arg Lys Ala Cys Ile Ser Ile Val Glu Trp Lys Pro
            40                  45                  50 ttc gag acg atc atc ttg ctc acc atc ttt gcc aat tgt gtg gcc ctg             429
Phe Glu Thr Ile Ile Leu Leu Thr Ile Phe Ala Asn Cys Val Ala Leu
        55                  60                  65 gcc gtg tac ctg ccc atg ccg gaa gat gac aac aac tct ctg aac ctc             477
Ala Val Tyr Leu Pro Met Pro Glu Asp Asp Asn Asn Ser Leu Asn Leu
    70                  75                  80 ggc ctg gag aag ctg gag tat ttc ttc ctc att gtc ttc tcg att gaa             525
Gly Leu Glu Lys Leu Glu Tyr Phe Phe Leu Ile Val Phe Ser Ile Glu
85                  90                  95                  100 gcc gcc atg aag atc att gcc tac ggc tta ttc cac cag gac gct                 573
Ala Ala Met Lys Ile Ile Ala Tyr Gly Leu Phe His Gln Asp Ala
                105                 110                 115 tac ctg cgc agt ggc tgg aat gtg ctg gac ttc acc att gtc ttc ctg             621
Tyr Leu Arg Ser Gly Trp Asn Val Leu Asp Phe Thr Ile Val Phe Leu
            120                 125                 130 ggg gtc ttc acc gtg att ctg gaa cag gtt aac gtc atc caa agc cac             669
Gly Val Phe Thr Val Ile Leu Glu Gln Val Asn Val Ile Gln Ser His
        135                 140                 145 aca gcc cca atg agc agc aaa gga gcc ggc ttg gat gtc aag gcc ctc             717
Thr Ala Pro Met Ser Ser Lys Gly Ala Gly Leu Asp Val Lys Ala Leu
    150                 155                 160 aga gcc ttc cga gtg ctc aga ccc ctc cgg ctg gtg tcg ggg gtg cct             765
Arg Ala Phe Arg Val Leu Arg Pro Leu Arg Leu Val Ser Gly Val Pro
165                 170                 175                 180 agc ctg cag gtg gtc ctg aac tcc atc ttc aag gcc atg ctc ccc ctc             813
Ser Leu Gln Val Val Leu Asn Ser Ile Phe Lys Ala Met Leu Pro Leu
                185                 190                 195 ttt cac atc gcc ctg ctg gtc ctc ttt atg gtc atc atc tat gcc atc             861
Phe His Ile Ala Leu Leu Val Leu Phe Met Val Ile Ile Tyr Ala Ile
            200                 205                 210 atc ggg ctg gag ctc ttc aag ggc aag atg cac aag acc tgc tac ttc             909
Ile Gly Leu Glu Leu Phe Lys Gly Lys Met His Lys Thr Cys Tyr Phe
        215                 220                 225 att ggt aca gat atc gtg gcc acg gtg gag aat gaa gag cca tcg ccc             957
Ile Gly Thr Asp Ile Val Ala Thr Val Glu Asn Glu Glu Pro Ser Pro
    230                 235                 240 tgc gcc agg acg ggc tca ggg cgc cgg tgc acc atc aat ggc agt gag            1005
Cys Ala Arg Thr Gly Ser Gly Arg Arg Cys Thr Ile Asn Gly Ser Glu
245                 250                 255                 260 tgc cgg ggc ggc tgc cca ggg ccc aac cat ggc atc acc cac ttc gac            1053
Cys Arg Gly Gly Cys Pro Gly Pro Asn His Gly Ile Thr His Phe Asp
                265                 270                 275 aac ttc ggc ttc tcc atg ctc acc gtg tac cag tgc att acc atg gag            1101
Asn Phe Gly Phe Ser Met Leu Thr Val Tyr Gln Cys Ile Thr Met Glu
            280                 285                 290 gga tgg act gac gtc ctt tac tgg gtc aat gat gcc atc ggg aat gag            1149
Gly Trp Thr Asp Val Leu Tyr Trp Val Asn Asp Ala Ile Gly Asn Glu
        295                 300                 305 tgg ccc tgg atc tat ttt gtc acc ctc att ttg ctg gga tcc ttc ttc            1197
Trp Pro Trp Ile Tyr Phe Val Thr Leu Ile Leu Leu Gly Ser Phe Phe
    310                 315                 320
```

```
atc ctc aac ctg gtg ctg ggt gtc ctg agt ggg gaa ttc acc aag gag       1245
Ile Leu Asn Leu Val Leu Gly Val Leu Ser Gly Glu Phe Thr Lys Glu
325                 330                 335                 340 cgg gag aag gcc aag tcc agg gga acc ttc cag aag ctc cgg gag aag       1293
Arg Glu Lys Ala Lys Ser Arg Gly Thr Phe Gln Lys Leu Arg Glu Lys
            345                 350                 355 cag caa cta gat gag gac ctt cgg ggc tac atg agc tgg atc acg cag       1341
Gln Gln Leu Asp Glu Asp Leu Arg Gly Tyr Met Ser Trp Ile Thr Gln
        360                 365                 370 ggc gag gtc atg gat gtt gag gac ttc aga gaa gga aaa ctg tct ttg       1389
Gly Glu Val Met Asp Val Glu Asp Phe Arg Glu Gly Lys Leu Ser Leu
    375                 380                 385 gat gaa ggt ggc tct gac aca gag agc ctg tat gaa att gca ggc ttg       1437
Asp Glu Gly Gly Ser Asp Thr Glu Ser Leu Tyr Glu Ile Ala Gly Leu
390                 395                 400 aac aaa atc atc cag ttc atc cga cat tgg agg cag tgg aac cgc atc       1485
Asn Lys Ile Ile Gln Phe Ile Arg His Trp Arg Gln Trp Asn Arg Ile
405                 410                 415                 420 ttt cgc tgg aag tgc cat gac atc gtg aag tcc aag gtc ttc tat tgg       1533
Phe Arg Trp Lys Cys His Asp Ile Val Lys Ser Lys Val Phe Tyr Trp
            425                 430                 435 ctg gtg att ctc atc gtt gcc ctc aac acc ctg tct atc gcc tca gag       1581
Leu Val Ile Leu Ile Val Ala Leu Asn Thr Leu Ser Ile Ala Ser Glu
        440                 445                 450 cac cac aac cag ccg cac tgg ctg acc cgt ttg caa gac att gcc aac       1629
His His Asn Gln Pro His Trp Leu Thr Arg Leu Gln Asp Ile Ala Asn
    455                 460                 465 cgg gtg ctg ctg tcc ctc ttc acc act gag atg ctg atg aag atg tac       1677
Arg Val Leu Leu Ser Leu Phe Thr Thr Glu Met Leu Met Lys Met Tyr
470                 475                 480 ggg ctg ggc ctg cgc cag tac ttc atg tct atc ttc aac cgc ttc gac       1725
Gly Leu Gly Leu Arg Gln Tyr Phe Met Ser Ile Phe Asn Arg Phe Asp
485                 490                 495                 500 tgc ttc gtg gtg tgc agc ggt atc ctg gag atc ctg ctg gtg gag tcg       1773
Cys Phe Val Val Cys Ser Gly Ile Leu Glu Ile Leu Leu Val Glu Ser
            505                 510                 515 ggc gcc atg aca ccc ctg ggc atc tcc gtg ctc cgc tgc atc cgc ctc       1821
Gly Ala Met Thr Pro Leu Gly Ile Ser Val Leu Arg Cys Ile Arg Leu
        520                 525                 530 ctg agg atc ttc aag atc acc aaa tat tgg acg tcg ctg agc aac ctg       1869
Leu Arg Ile Phe Lys Ile Thr Lys Tyr Trp Thr Ser Leu Ser Asn Leu
    535                 540                 545 gtg gca tcc ctg ctc aac tcc atc cgc tcc atc gcc tcc ctg ctg ctg       1917
Val Ala Ser Leu Leu Asn Ser Ile Arg Ser Ile Ala Ser Leu Leu Leu
550                 555                 560 ctg ctc ttc ctc ttc atc gtc atc ttc cgc ctc ctg ggc atg cag ctc       1965
Leu Leu Phe Leu Phe Ile Val Ile Phe Arg Leu Leu Gly Met Gln Leu
565                 570                 575                 580 ttt ggg ggg agg tat gac ttt gaa gac aca gaa gta cgg cgc agc aac       2013
Phe Gly Gly Arg Tyr Asp Phe Glu Asp Thr Glu Val Arg Arg Ser Asn
            585                 590                 595 ttt gac aac ttt ccc caa gcc ctc atc agc gtc ttc cag gta ctg aca       2061
Phe Asp Asn Phe Pro Gln Ala Leu Ile Ser Val Phe Gln Val Leu Thr
        600                 605                 610 ggg gaa gac tgg acc tca atg atg tac aat ggg atc atg gcc tcg agc       2109
Gly Glu Asp Trp Thr Ser Met Met Tyr Asn Gly Ile Met Ala Ser Ser
    615                 620                 625 ggg ccg tcc tac cct ggc atg ctt gtg tgc att tac ttc atc atc ctt       2157
Gly Pro Ser Tyr Pro Gly Met Leu Val Cys Ile Tyr Phe Ile Ile Leu
630                 635                 640
```

| | |
|---|---:|
| ttc gtc tgt ggc aac tac atc ctg ctc aat gtc ttc ctg gcc att gcc<br>Phe Val Cys Gly Asn Tyr Ile Leu Leu Asn Val Phe Leu Ala Ile Ala<br>645                         650                    655                  660 | 2205 |
| gtg gac aac ctg gcc gag gcg gag agc ctg act tct gcc cag aag gcc<br>Val Asp Asn Leu Ala Glu Ala Glu Ser Leu Thr Ser Ala Gln Lys Ala<br>                   665                    670                    675 | 2253 |
| aag gct gag gag aaa aaa cgc agg aag atg tcc aag ggt ctc cca gac<br>Lys Ala Glu Glu Lys Lys Arg Arg Lys Met Ser Lys Gly Leu Pro Asp<br>680                         685                    690 | 2301 |
| aag tca gaa gag gag aag tca acg atg gcc aag aag ctg gag cag aaa<br>Lys Ser Glu Glu Lys Ser Thr Met Ala Lys Lys Leu Glu Gln Lys<br>         695                    700                    705 | 2349 |
| ccc aag ggt gag ggc atc ccc acc act gcc aag ctg aaa atc gat gag<br>Pro Lys Gly Glu Gly Ile Pro Thr Thr Ala Lys Leu Lys Ile Asp Glu<br>710                         715                    720 | 2397 |
| ttt gaa tct aat gtc aat gag gtg aag gat ccc tac ccc tca gcc gac<br>Phe Glu Ser Asn Val Asn Glu Val Lys Asp Pro Tyr Pro Ser Ala Asp<br>725                         730                    735                  740 | 2445 |
| ttc cca ggg gat gac gag gaa gat gag cct gag atc ccg ctg agc ccc<br>Phe Pro Gly Asp Asp Glu Glu Asp Glu Pro Glu Ile Pro Leu Ser Pro<br>                        745                    750                    755 | 2493 |
| cga cca cgt ccc ctg gct gag ctg cag ctg aaa gag aag gcc gtg ccc<br>Arg Pro Arg Pro Leu Ala Glu Leu Gln Leu Lys Glu Lys Ala Val Pro<br>                 760                    765                    770 | 2541 |
| att cca gaa gcc agc tcc ttc ttc atc ttc agc ccc acc aat aag atc<br>Ile Pro Glu Ala Ser Ser Phe Phe Ile Phe Ser Pro Thr Asn Lys Ile<br>775                         780                    785 | 2589 |
| cgt gtc ctg tgt cac cgc atc gtc aat gcc acc tgg ttc acc aac ttc<br>Arg Val Leu Cys His Arg Ile Val Asn Ala Thr Trp Phe Thr Asn Phe<br>790                         795                    800 | 2637 |
| atc ctg ctc ttc atc ctg ctc agc agc gct gca ctg gct gcg gaa gac<br>Ile Leu Leu Phe Ile Leu Leu Ser Ser Ala Ala Leu Ala Ala Glu Asp<br>805                         810                    815                  820 | 2685 |
| ccc atc cgg gct gat tcc atg aga aat cag atc ctt aaa cac ttt gac<br>Pro Ile Arg Ala Asp Ser Met Arg Asn Gln Ile Leu Lys His Phe Asp<br>                   825                    830                    835 | 2733 |
| atc ggg ttc acc tct gtc ttc act gtg gag att gtc ctc aag atg acg<br>Ile Gly Phe Thr Ser Val Phe Thr Val Glu Ile Val Leu Lys Met Thr<br>                 840                    845                    850 | 2781 |
| acc tac gga gcc ttc ctg cac aag ggt tcc ttc tgc cgc aat tac ttc<br>Thr Tyr Gly Ala Phe Leu His Lys Gly Ser Phe Cys Arg Asn Tyr Phe<br>855                         860                    865 | 2829 |
| aac atg ctg gac ctg ctg gtg gtg gcc gtg tcc ctc atc tcc atg gga<br>Asn Met Leu Asp Leu Leu Val Val Ala Val Ser Leu Ile Ser Met Gly<br>870                         875                    880 | 2877 |
| ctt gag tcc agt gcc atc tcc gtg gtg aag atc ctg agg gtg ctg agg<br>Leu Glu Ser Ser Ala Ile Ser Val Val Lys Ile Leu Arg Val Leu Arg<br>885                         890                    895                  900 | 2925 |
| gtg ctc cga cca ctc aga gcc atc aac aga gcc aag ggg ttg aag cac<br>Val Leu Arg Pro Leu Arg Ala Ile Asn Arg Ala Lys Gly Leu Lys His<br>                   905                    910                    915 | 2973 |
| gtg gct agg tgc atg ttc gtg gcc atc agc acc atc ggg aac atc gtg<br>Val Ala Arg Cys Met Phe Val Ala Ile Ser Thr Ile Gly Asn Ile Val<br>                 920                    925                    930 | 3021 |
| ctg gtc act acc ctc cta cag ttc atg ttt gcc tgc atc ggc gtc cag<br>Leu Val Thr Thr Leu Leu Gln Phe Met Phe Ala Cys Ile Gly Val Gln<br>935                         940                    945 | 3069 |
| ctc ttc aag ggg aag ttc ttc agg tgc acc gac ttg tcc aag atg aca<br>Leu Phe Lys Gly Lys Phe Phe Arg Cys Thr Asp Leu Ser Lys Met Thr | 3117 |

-continued

```
        950                 955                 960
gag gag gag tgc agg ggc tac tac tac gtg tac aag gac ggg gac ccc      3165
Glu Glu Glu Cys Arg Gly Tyr Tyr Tyr Val Tyr Lys Asp Gly Asp Pro
965                 970                 975                 980 atg cag ata gag ctg cgt cac cgc gag tgg gta cac agc gac ttc cac      3213
Met Gln Ile Glu Leu Arg His Arg Glu Trp Val His Ser Asp Phe His
                985                 990                 995 ttc gac aat gtg ctc tca gcc atg atg tcc ctc ttc acg gtc tcc          3258
Phe Asp Asn Val Leu Ser Ala Met Met Ser Leu Phe Thr Val Ser
            1000                1005                1010 acc ttc gag gga tgg cct cag ctg ctg tac aag gcc ata gac tcc          3303
Thr Phe Glu Gly Trp Pro Gln Leu Leu Tyr Lys Ala Ile Asp Ser
            1015                1020                1025 aat gcg gag gac gtg ggt ccc atc tac aac aac cgt gtg gag atg          3348
Asn Ala Glu Asp Val Gly Pro Ile Tyr Asn Asn Arg Val Glu Met
            1030                1035                1040 gcc atc ttc ttc atc atc tac atc atc ctc att gcc ttc ttc atg          3393
Ala Ile Phe Phe Ile Ile Tyr Ile Ile Leu Ile Ala Phe Phe Met
            1045                1050                1055 atg aac atc ttt gtg ggc ttc gtc att gtc acc ttc cag gag cag          3438
Met Asn Ile Phe Val Gly Phe Val Ile Val Thr Phe Gln Glu Gln
            1060                1065                1070 gga gag act gag tac aag aac tgt gag ctg gac aag aac cag cgc          3483
Gly Glu Thr Glu Tyr Lys Asn Cys Glu Leu Asp Lys Asn Gln Arg
            1075                1080                1085 caa tgt gta cag tat gcc ctg aag gcc cgc cca ctg agg tgc tac          3528
Gln Cys Val Gln Tyr Ala Leu Lys Ala Arg Pro Leu Arg Cys Tyr
            1090                1095                1100 att ccc aaa aac cca tac cag tac cag gtg tgg tac att gtc acc          3573
Ile Pro Lys Asn Pro Tyr Gln Tyr Gln Val Trp Tyr Ile Val Thr
            1105                1110                1115 tcc tcc tac ttt gaa tac ctg atg ttt gcc ctc atc atg ctc aac          3618
Ser Ser Tyr Phe Glu Tyr Leu Met Phe Ala Leu Ile Met Leu Asn
            1120                1125                1130 acc atc tgc ctc ggc atg cag cac tac aac cag tcg gag cag atg          3663
Thr Ile Cys Leu Gly Met Gln His Tyr Asn Gln Ser Glu Gln Met
            1135                1140                1145 aac cac atc tca gac atc ctc aat gtg gcc ttc act atc atc ttc          3708
Asn His Ile Ser Asp Ile Leu Asn Val Ala Phe Thr Ile Ile Phe
            1150                1155                1160 acc ctg gag atg atc ctc aag ctc atg gcc ttc aag gcc agg ggc          3753
Thr Leu Glu Met Ile Leu Lys Leu Met Ala Phe Lys Ala Arg Gly
            1165                1170                1175 tac ttt gga aac ccc tgg aat gtg ttt gac ttc ctg att gtc att          3798
Tyr Phe Gly Asn Pro Trp Asn Val Phe Asp Phe Leu Ile Val Ile
            1180                1185                1190 ggc agc atc att gat gtc atc ctc agt gag atc gac act ttc ctg          3843
Gly Ser Ile Ile Asp Val Ile Leu Ser Glu Ile Asp Thr Phe Leu
            1195                1200                1205 gcc tcc agc ggg gga ctg tat tgc ctg ggt gga ggc tgc ggg aac          3888
Ala Ser Ser Gly Gly Leu Tyr Cys Leu Gly Gly Gly Cys Gly Asn
            1210                1215                1220 gtt gac cca gat gag agt gcc cgc atc tcc agc gcc ttc ttc cgc          3933
Val Asp Pro Asp Glu Ser Ala Arg Ile Ser Ser Ala Phe Phe Arg
            1225                1230                1235 ctg ttc cgt gtc atg agg ctg atc aag ctg ctg agc cgg gca gaa          3978
Leu Phe Arg Val Met Arg Leu Ile Lys Leu Leu Ser Arg Ala Glu
            1240                1245                1250 gga gtg cga acc ctc ctg tgg acg ttc atc aag tcc ttc cag gcc          4023
```

```
                Gly Val Arg Thr Leu Leu Trp Thr Phe Ile Lys Ser Phe Gln Ala
                        1255                1260                1265 cta ccc tac gtg gct ctg ctc atc gtc atg ctc ttc ttc atc tac          4068
Leu Pro Tyr Val Ala Leu Leu Ile Val Met Leu Phe Phe Ile Tyr
            1270                1275                1280 gct gtc atc ggc atg cag atg ttt ggg aag atc gcc ttg gtg gat          4113
Ala Val Ile Gly Met Gln Met Phe Gly Lys Ile Ala Leu Val Asp
        1285                1290                1295 ggg acc caa ata aac cgg aac aac aac ttc cag acc ttc cca caa          4158
Gly Thr Gln Ile Asn Arg Asn Asn Asn Phe Gln Thr Phe Pro Gln
        1300                1305                1310 gct gtg cta ctg ctc ttc agg tgt gca aca ggt gag gcc tgg cag          4203
Ala Val Leu Leu Leu Phe Arg Cys Ala Thr Gly Glu Ala Trp Gln
        1315                1320                1325 gag atc cta ctg gcc tgc agc tat ggg aag ctg tgt gac cca gag          4248
Glu Ile Leu Leu Ala Cys Ser Tyr Gly Lys Leu Cys Asp Pro Glu
        1330                1335                1340 tcg gac tat gcc cca ggg gag gag tac aca tgt ggc acc aac ttt          4293
Ser Asp Tyr Ala Pro Gly Glu Glu Tyr Thr Cys Gly Thr Asn Phe
        1345                1350                1355 gca tac tac tac ttc atc agc ttc tac atg ctc tgt gcc ttc ctg          4338
Ala Tyr Tyr Tyr Phe Ile Ser Phe Tyr Met Leu Cys Ala Phe Leu
        1360                1365                1370 gtc atc aac ctc ttt gtg gct gtc atc atg gac aat ttt gac tac          4383
Val Ile Asn Leu Phe Val Ala Val Ile Met Asp Asn Phe Asp Tyr
        1375                1380                1385 ctc acc cgg gac tgg tcc atc ctg ggc cct cat cac ctg gat gag          4428
Leu Thr Arg Asp Trp Ser Ile Leu Gly Pro His His Leu Asp Glu
        1390                1395                1400 ttc aag gcc atc tgg gca gag tat gac cca gag gct aag ggg agg          4473
Phe Lys Ala Ile Trp Ala Glu Tyr Asp Pro Glu Ala Lys Gly Arg
        1405                1410                1415 atc aaa cac ctg gac gtg gtg acc ctg ctg aga agg att cag ccc          4518
Ile Lys His Leu Asp Val Val Thr Leu Leu Arg Arg Ile Gln Pro
        1420                1425                1430 cct ctg ggc ttt ggg aag ttc tgc cca cat cgg gta gct tgt aag          4563
Pro Leu Gly Phe Gly Lys Phe Cys Pro His Arg Val Ala Cys Lys
        1435                1440                1445 cgg ctg gtg ggc atg aac atg ccc ctg aac agc gac ggc aca gtc          4608
Arg Leu Val Gly Met Asn Met Pro Leu Asn Ser Asp Gly Thr Val
        1450                1455                1460 acc ttc aat gcc aca ctc ttt gcc ctg gtc cgc acg gca ctc aag          4653
Thr Phe Asn Ala Thr Leu Phe Ala Leu Val Arg Thr Ala Leu Lys
        1465                1470                1475 atc aag acg gaa ggt aac ttt gag cag gcc aac gag gag ctg agg          4698
Ile Lys Thr Glu Gly Asn Phe Glu Gln Ala Asn Glu Glu Leu Arg
        1480                1485                1490 gcc atc atc aag aag atc tgg aag aga acc agc atg aag ctc ttg          4743
Ala Ile Ile Lys Lys Ile Trp Lys Arg Thr Ser Met Lys Leu Leu
        1495                1500                1505 gac cag gtc atc cct cca ata gga gat gat gag gtg aca gtg ggg          4788
Asp Gln Val Ile Pro Pro Ile Gly Asp Asp Glu Val Thr Val Gly
        1510                1515                1520 aag ttc tac gcc aca ttc ctc atc cag gag cac ttc cgg aag ttc          4833
Lys Phe Tyr Ala Thr Phe Leu Ile Gln Glu His Phe Arg Lys Phe
        1525                1530                1535 atg aaa cgc caa gag gag tat tat ggc tat cgg ccc aag aag gac          4878
Met Lys Arg Gln Glu Glu Tyr Tyr Gly Tyr Arg Pro Lys Lys Asp
        1540                1545                1550
```

```
att gta cag atc cag gca ggg ctg cgg acc att gag gaa gag gca      4923
Ile Val Gln Ile Gln Ala Gly Leu Arg Thr Ile Glu Glu Glu Ala
        1555                1560                1565 gcc ccc gag atc tgt cgc acg gtc tca gga gac ctg gct gct gag      4968
Ala Pro Glu Ile Cys Arg Thr Val Ser Gly Asp Leu Ala Ala Glu
1570                1575                1580 gag gag ctg gag aga gcc atg gtg gag gct gcg atg gag gag ggg      5013
Glu Glu Leu Glu Arg Ala Met Val Glu Ala Ala Met Glu Glu Gly
    1585                1590                1595 ata ttc cgg agg act gga ggc ctg ttt ggc cag gtg gac aac ttc      5058
Ile Phe Arg Arg Thr Gly Gly Leu Phe Gly Gln Val Asp Asn Phe
1600                1605                1610 ctg gaa agg acc aac tcc ctg ccc cct gtc atg gcc aat cag aga      5103
Leu Glu Arg Thr Asn Ser Leu Pro Pro Val Met Ala Asn Gln Arg
    1615                1620                1625 ccc ctc cag ttt gct gag ata gag atg gaa gag atg gag tca cct      5148
Pro Leu Gln Phe Ala Glu Ile Glu Met Glu Glu Met Glu Ser Pro
1630                1635                1640 gtc ttc ttg gag gac ttc cca caa gat cca cgc acc aac ccc ctg      5193
Val Phe Leu Glu Asp Phe Pro Gln Asp Pro Arg Thr Asn Pro Leu
    1645                1650                1655 gct cgt gcc aat acc aac aat gcc aac gcc aat gtc gcc tat gcg      5238
Ala Arg Ala Asn Thr Asn Asn Ala Asn Ala Asn Val Ala Tyr Ala
1660                1665                1670 aac agc aac cat agc aac agc cat gtg ttt tcc agt gtc cac tat      5283
Asn Ser Asn His Ser Asn Ser His Val Phe Ser Ser Val His Tyr
    1675                1680                1685 gaa agg gag ttc cca gaa gag aca gag acg cct gct acc aga gga      5328
Glu Arg Glu Phe Pro Glu Glu Thr Glu Thr Pro Ala Thr Arg Gly
1690                1695                1700 cga gcc ctt ggc caa ccc tgc agg tcc ctg gga ccc cac agc aaa      5373
Arg Ala Leu Gly Gln Pro Cys Arg Ser Leu Gly Pro His Ser Lys
    1705                1710                1715 ccc tgt gtg gag atg ctg aag gga ctg ctg acc cag agg gca atg      5418
Pro Cys Val Glu Met Leu Lys Gly Leu Leu Thr Gln Arg Ala Met
1720                1725                1730 ccc aga ggc cag gca cct cct gcc ccc tgc cag tgc ccc agg gtg      5463
Pro Arg Gly Gln Ala Pro Pro Ala Pro Cys Gln Cys Pro Arg Val
    1735                1740                1745 gag tcc tcc atg cct gag gac aga aag agc tcc aca cca ggg tct      5508
Glu Ser Ser Met Pro Glu Asp Arg Lys Ser Ser Thr Pro Gly Ser
1750                1755                1760 ctt cat gag gag aca ccc cac agc agg agc acc agg gag aat act      5553
Leu His Glu Glu Thr Pro His Ser Arg Ser Thr Arg Glu Asn Thr
    1765                1770                1775 tcc agg tgc tca gca cca gct aca gcc ctg ctg atc caa aag gct      5598
Ser Arg Cys Ser Ala Pro Ala Thr Ala Leu Leu Ile Gln Lys Ala
1780                1785                1790 ctg gtt cga ggg ggc ctg ggc acc ttg gca gct gat gca aac ttc      5643
Leu Val Arg Gly Gly Leu Gly Thr Leu Ala Ala Asp Ala Asn Phe
    1795                1800                1805 atc atg gca aca ggc cag gcc ctc gga gat gcc tgc caa atg gaa      5688
Ile Met Ala Thr Gly Gln Ala Leu Gly Asp Ala Cys Gln Met Glu
1810                1815                1820 cca gag gaa gtg gag atc atg gca aca gag cta ctg aaa gga cga      5733
Pro Glu Glu Val Glu Ile Met Ala Thr Glu Leu Leu Lys Gly Arg
    1825                1830                1835 gag gcc cca gac ggc atg gcc agc tcc ctg gga tgc ctg aac ctc      5778
Glu Ala Pro Asp Gly Met Ala Ser Ser Leu Gly Cys Leu Asn Leu
1840                1845                1850
```

```
ggg tcc tcc ctg  ggc agc ctc gac caa  cac cag ggc tcc cag  gag        5823
Gly Ser Ser Leu  Gly Ser Leu Asp Gln  His Gln Gly Ser Gln  Glu
            1855                 1860                 1865 acc ctt att cct  cca agg ctg tga tgcccacaca gcatcagcat gggcttagag     5877
Thr Leu Ile Pro  Pro Arg Leu
            1870 ctggcatgac caatgggggt ggggaagttg ctggggtgga gaagggctag cccaccgcag     5937 cagcctccct ccctctcagc agctagatgc atgcctgagg cagggtggtc aggaaccacc     5997 tcaaaaagtg cggaggaagt agctggacag gccctgcccc tcaccagcaa gaggcatgat     6057 tggatggagc ttctaatgtc attcaaaaag gcctggtcag tgcctgtccc tagggccact     6117 cccacctgca ggacattaaa atctccaggc ctgtgacact ggc                      6160

<210> SEQ ID NO 14
<211> LENGTH: 1873
<212> TYPE: PRT
<213> ORGANISM: Homo sapiens

<400> SEQUENCE: 14

Met Glu Pro Ser Ser Pro Gln Asp Glu Gly Leu Arg Lys Lys Gln Pro
1               5                   10                  15

Lys Lys Pro Val Pro Glu Ile Leu Pro Arg Pro Pro Arg Ala Leu Phe
            20                  25                  30

Cys Leu Thr Leu Glu Asn Pro Leu Arg Lys Ala Cys Ile Ser Ile Val
        35                  40                  45

Glu Trp Lys Pro Phe Glu Thr Ile Ile Leu Thr Ile Phe Ala Asn
    50                  55                  60

Cys Val Ala Leu Ala Val Tyr Leu Pro Met Pro Glu Asp Asp Asn Asn
65                  70                  75                  80

Ser Leu Asn Leu Gly Leu Glu Lys Leu Glu Tyr Phe Phe Leu Ile Val
                85                  90                  95

Phe Ser Ile Glu Ala Ala Met Lys Ile Ile Ala Tyr Gly Phe Leu Phe
            100                 105                 110

His Gln Asp Ala Tyr Leu Arg Ser Gly Trp Asn Val Leu Asp Phe Thr
        115                 120                 125

Ile Val Phe Leu Gly Val Phe Thr Val Ile Leu Glu Gln Val Asn Val
    130                 135                 140

Ile Gln Ser His Thr Ala Pro Met Ser Ser Lys Gly Ala Gly Leu Asp
145                 150                 155                 160

Val Lys Ala Leu Arg Ala Phe Arg Val Leu Arg Pro Leu Arg Leu Val
                165                 170                 175

Ser Gly Val Pro Ser Leu Gln Val Leu Asn Ser Ile Phe Lys Ala
            180                 185                 190

Met Leu Pro Leu Phe His Ile Ala Leu Leu Val Leu Phe Met Val Ile
        195                 200                 205

Ile Tyr Ala Ile Ile Gly Leu Glu Leu Phe Lys Gly Lys Met His Lys
    210                 215                 220

Thr Cys Tyr Phe Ile Gly Thr Asp Ile Val Ala Thr Val Glu Asn Glu
225                 230                 235                 240

Glu Pro Ser Pro Cys Ala Arg Thr Gly Ser Gly Arg Arg Cys Thr Ile
                245                 250                 255

Asn Gly Ser Glu Cys Arg Gly Gly Cys Pro Gly Pro Asn His Gly Ile
            260                 265                 270

Thr His Phe Asp Asn Phe Gly Phe Ser Met Leu Thr Val Tyr Gln Cys
```

```
                275                 280                 285
Ile Thr Met Glu Gly Trp Thr Asp Val Leu Tyr Trp Val Asn Asp Ala
290                 295                 300
Ile Gly Asn Glu Trp Pro Trp Ile Tyr Phe Val Thr Leu Ile Leu Leu
305                 310                 315                 320
Gly Ser Phe Phe Ile Leu Asn Leu Val Leu Gly Val Leu Ser Gly Glu
                325                 330                 335
Phe Thr Lys Glu Arg Glu Lys Ala Lys Ser Arg Gly Thr Phe Gln Lys
                340                 345                 350
Leu Arg Glu Lys Gln Gln Leu Asp Glu Asp Leu Arg Gly Tyr Met Ser
            355                 360                 365
Trp Ile Thr Gln Gly Glu Val Met Asp Val Glu Asp Phe Arg Glu Gly
370                 375                 380
Lys Leu Ser Leu Asp Glu Gly Ser Asp Thr Glu Ser Leu Tyr Glu
385                 390                 395                 400
Ile Ala Gly Leu Asn Lys Ile Ile Gln Phe Ile Arg His Trp Arg Gln
                405                 410                 415
Trp Asn Arg Ile Phe Arg Trp Lys Cys His Asp Ile Val Lys Ser Lys
                420                 425                 430
Val Phe Tyr Trp Leu Val Ile Leu Ile Val Ala Leu Asn Thr Leu Ser
            435                 440                 445
Ile Ala Ser Glu His His Asn Gln Pro His Trp Leu Thr Arg Leu Gln
        450                 455                 460
Asp Ile Ala Asn Arg Val Leu Leu Ser Leu Phe Thr Thr Glu Met Leu
465                 470                 475                 480
Met Lys Met Tyr Gly Leu Gly Leu Arg Gln Tyr Phe Met Ser Ile Phe
                485                 490                 495
Asn Arg Phe Asp Cys Phe Val Val Cys Ser Gly Ile Leu Glu Ile Leu
                500                 505                 510
Leu Val Glu Ser Gly Ala Met Thr Pro Leu Gly Ile Ser Val Leu Arg
            515                 520                 525
Cys Ile Arg Leu Leu Arg Ile Phe Lys Ile Thr Lys Tyr Trp Thr Ser
        530                 535                 540
Leu Ser Asn Leu Val Ala Ser Leu Leu Asn Ser Ile Arg Ser Ile Ala
545                 550                 555                 560
Ser Leu Leu Leu Leu Leu Phe Leu Phe Ile Val Ile Phe Arg Leu Leu
                565                 570                 575
Gly Met Gln Leu Phe Gly Gly Arg Tyr Asp Phe Glu Asp Thr Glu Val
                580                 585                 590
Arg Arg Ser Asn Phe Asp Asn Phe Pro Gln Ala Leu Ile Ser Val Phe
            595                 600                 605
Gln Val Leu Thr Gly Glu Asp Trp Thr Ser Met Met Tyr Asn Gly Ile
        610                 615                 620
Met Ala Ser Ser Gly Pro Ser Tyr Pro Gly Met Leu Val Cys Ile Tyr
625                 630                 635                 640
Phe Ile Ile Leu Phe Val Cys Gly Asn Tyr Ile Leu Leu Asn Val Phe
                645                 650                 655
Leu Ala Ile Ala Val Asp Asn Leu Ala Glu Ala Glu Ser Leu Thr Ser
                660                 665                 670
Ala Gln Lys Ala Lys Ala Glu Glu Lys Lys Arg Arg Lys Met Ser Lys
            675                 680                 685
Gly Leu Pro Asp Lys Ser Glu Glu Glu Lys Ser Thr Met Ala Lys Lys
        690                 695                 700
```

-continued

```
Leu Glu Gln Lys Pro Lys Gly Glu Gly Ile Pro Thr Thr Ala Lys Leu
705                 710                 715                 720

Lys Ile Asp Glu Phe Glu Ser Asn Val Asn Glu Val Lys Asp Pro Tyr
            725                 730                 735

Pro Ser Ala Asp Phe Pro Gly Asp Glu Glu Asp Glu Pro Glu Ile
            740                 745                 750

Pro Leu Ser Pro Arg Pro Arg Pro Leu Ala Glu Leu Gln Leu Lys Glu
            755                 760                 765

Lys Ala Val Pro Ile Pro Glu Ala Ser Ser Phe Phe Ile Phe Ser Pro
770                 775                 780

Thr Asn Lys Ile Arg Val Leu Cys His Arg Ile Val Asn Ala Thr Trp
785                 790                 795                 800

Phe Thr Asn Phe Ile Leu Leu Phe Ile Leu Leu Ser Ser Ala Ala Leu
                805                 810                 815

Ala Ala Glu Asp Pro Ile Arg Ala Asp Ser Met Arg Asn Gln Ile Leu
            820                 825                 830

Lys His Phe Asp Ile Gly Phe Thr Ser Val Phe Thr Val Glu Ile Val
835                 840                 845

Leu Lys Met Thr Thr Tyr Gly Ala Phe Leu His Lys Gly Ser Phe Cys
850                 855                 860

Arg Asn Tyr Phe Asn Met Leu Asp Leu Leu Val Val Ala Val Ser Leu
865                 870                 875                 880

Ile Ser Met Gly Leu Glu Ser Ser Ala Ile Ser Val Val Lys Ile Leu
                885                 890                 895

Arg Val Leu Arg Val Leu Arg Pro Leu Arg Ala Ile Asn Arg Ala Lys
            900                 905                 910

Gly Leu Lys His Val Ala Arg Cys Met Phe Val Ala Ile Ser Thr Ile
            915                 920                 925

Gly Asn Ile Val Leu Val Thr Thr Leu Leu Gln Phe Met Phe Ala Cys
            930                 935                 940

Ile Gly Val Gln Leu Phe Lys Gly Lys Phe Phe Arg Cys Thr Asp Leu
945                 950                 955                 960

Ser Lys Met Thr Glu Glu Cys Arg Gly Tyr Tyr Val Tyr Lys
                965                 970                 975

Asp Gly Asp Pro Met Gln Ile Glu Leu Arg His Arg Glu Trp Val His
                980                 985                 990

Ser Asp Phe His Phe Asp Asn Val  Leu Ser Ala Met Met  Ser Leu Phe
                995                 1000                1005

Thr Val  Ser Thr Phe Glu Gly  Trp Pro Gln Leu Leu  Tyr Lys Ala
    1010                1015                1020

Ile Asp  Ser Asn Ala Glu Asp  Val Gly Pro Ile Tyr  Asn Asn Arg
    1025                1030                1035

Val Glu  Met Ala Ile Phe Phe  Ile Ile Tyr Ile Ile  Leu Ile Ala
    1040                1045                1050

Phe Phe  Met Met Asn Ile Phe  Val Gly Phe Val Ile  Val Thr Phe
    1055                1060                1065

Gln Glu  Gln Gly Glu Thr Glu  Tyr Lys Asn Cys Glu  Leu Asp Lys
    1070                1075                1080

Asn Gln  Arg Gln Cys Val Gln  Tyr Ala Leu Lys Ala  Arg Pro Leu
    1085                1090                1095

Arg Cys  Tyr Ile Pro Lys Asn  Pro Tyr Gln Tyr Gln  Val Trp Tyr
    1100                1105                1110
```

```
Ile Val Thr Ser Ser Tyr Phe Glu Tyr Leu Met Phe Ala Leu Ile
1115                1120                1125

Met Leu Asn Thr Ile Cys Leu Gly Met Gln His Tyr Asn Gln Ser
1130                1135                1140

Glu Gln Met Asn His Ile Ser Asp Ile Leu Asn Val Ala Phe Thr
1145                1150                1155

Ile Ile Phe Thr Leu Glu Met Ile Leu Lys Leu Met Ala Phe Lys
1160                1165                1170

Ala Arg Gly Tyr Phe Gly Asn Pro Trp Asn Val Phe Asp Phe Leu
1175                1180                1185

Ile Val Ile Gly Ser Ile Ile Asp Val Ile Leu Ser Glu Ile Asp
1190                1195                1200

Thr Phe Leu Ala Ser Ser Gly Gly Leu Tyr Cys Leu Gly Gly Gly
1205                1210                1215

Cys Gly Asn Val Asp Pro Asp Glu Ser Ala Arg Ile Ser Ser Ala
1220                1225                1230

Phe Phe Arg Leu Phe Arg Val Met Arg Leu Ile Lys Leu Leu Ser
1235                1240                1245

Arg Ala Glu Gly Val Arg Thr Leu Leu Trp Thr Phe Ile Lys Ser
1250                1255                1260

Phe Gln Ala Leu Pro Tyr Val Ala Leu Leu Ile Val Met Leu Phe
1265                1270                1275

Phe Ile Tyr Ala Val Ile Gly Met Gln Met Phe Gly Lys Ile Ala
1280                1285                1290

Leu Val Asp Gly Thr Gln Ile Asn Arg Asn Asn Asn Phe Gln Thr
1295                1300                1305

Phe Pro Gln Ala Val Leu Leu Leu Phe Arg Cys Ala Thr Gly Glu
1310                1315                1320

Ala Trp Gln Glu Ile Leu Leu Ala Cys Ser Tyr Gly Lys Leu Cys
1325                1330                1335

Asp Pro Glu Ser Asp Tyr Ala Pro Gly Glu Glu Tyr Thr Cys Gly
1340                1345                1350

Thr Asn Phe Ala Tyr Tyr Tyr Phe Ile Ser Phe Tyr Met Leu Cys
1355                1360                1365

Ala Phe Leu Val Ile Asn Leu Phe Val Ala Val Ile Met Asp Asn
1370                1375                1380

Phe Asp Tyr Leu Thr Arg Asp Trp Ser Ile Leu Gly Pro His His
1385                1390                1395

Leu Asp Glu Phe Lys Ala Ile Trp Ala Glu Tyr Asp Pro Glu Ala
1400                1405                1410

Lys Gly Arg Ile Lys His Leu Asp Val Val Thr Leu Leu Arg Arg
1415                1420                1425

Ile Gln Pro Pro Leu Gly Phe Gly Lys Phe Cys Pro His Arg Val
1430                1435                1440

Ala Cys Lys Arg Leu Val Gly Met Asn Met Pro Leu Asn Ser Asp
1445                1450                1455

Gly Thr Val Thr Phe Asn Ala Thr Leu Phe Ala Leu Val Arg Thr
1460                1465                1470

Ala Leu Lys Ile Lys Thr Glu Gly Asn Phe Glu Gln Ala Asn Glu
1475                1480                1485

Glu Leu Arg Ala Ile Ile Lys Lys Ile Trp Lys Arg Thr Ser Met
1490                1495                1500

Lys Leu Leu Asp Gln Val Ile Pro Pro Ile Gly Asp Asp Glu Val
```

```
                1505                1510                1515

Thr Val Gly Lys Phe Tyr Ala Thr Phe Leu Ile Gln Glu His Phe
    1520                1525                1530

Arg Lys Phe Met Lys Arg Gln Glu Glu Tyr Tyr Gly Tyr Arg Pro
    1535                1540                1545

Lys Lys Asp Ile Val Gln Ile Gln Ala Gly Leu Arg Thr Ile Glu
    1550                1555                1560

Glu Glu Ala Ala Pro Glu Ile Cys Arg Thr Val Ser Gly Asp Leu
    1565                1570                1575

Ala Ala Glu Glu Glu Leu Glu Arg Ala Met Val Glu Ala Ala Met
    1580                1585                1590

Glu Glu Gly Ile Phe Arg Arg Thr Gly Gly Leu Phe Gly Gln Val
    1595                1600                1605

Asp Asn Phe Leu Glu Arg Thr Asn Ser Leu Pro Pro Val Met Ala
    1610                1615                1620

Asn Gln Arg Pro Leu Gln Phe Ala Glu Ile Glu Met Glu Glu Met
    1625                1630                1635

Glu Ser Pro Val Phe Leu Glu Asp Phe Pro Gln Asp Pro Arg Thr
    1640                1645                1650

Asn Pro Leu Ala Arg Ala Asn Thr Asn Asn Ala Asn Ala Asn Val
    1655                1660                1665

Ala Tyr Ala Asn Ser Asn His Ser Asn Ser His Val Phe Ser Ser
    1670                1675                1680

Val His Tyr Glu Arg Glu Phe Pro Glu Glu Thr Glu Thr Pro Ala
    1685                1690                1695

Thr Arg Gly Arg Ala Leu Gly Gln Pro Cys Arg Ser Leu Gly Pro
    1700                1705                1710

His Ser Lys Pro Cys Val Glu Met Leu Lys Gly Leu Leu Thr Gln
    1715                1720                1725

Arg Ala Met Pro Arg Gly Gln Ala Pro Pro Ala Pro Cys Gln Cys
    1730                1735                1740

Pro Arg Val Glu Ser Ser Met Pro Glu Asp Arg Lys Ser Ser Thr
    1745                1750                1755

Pro Gly Ser Leu His Glu Glu Thr Pro His Ser Arg Ser Thr Arg
    1760                1765                1770

Glu Asn Thr Ser Arg Cys Ser Ala Pro Ala Thr Ala Leu Leu Ile
    1775                1780                1785

Gln Lys Ala Leu Val Arg Gly Gly Leu Gly Thr Leu Ala Ala Asp
    1790                1795                1800

Ala Asn Phe Ile Met Ala Thr Gly Gln Ala Leu Gly Asp Ala Cys
    1805                1810                1815

Gln Met Glu Pro Glu Glu Val Glu Ile Met Ala Thr Glu Leu Leu
    1820                1825                1830

Lys Gly Arg Glu Ala Pro Asp Gly Met Ala Ser Ser Leu Gly Cys
    1835                1840                1845

Leu Asn Leu Gly Ser Ser Leu Gly Ser Leu Asp Gln His Gln Gly
    1850                1855                1860

Ser Gln Glu Thr Leu Ile Pro Pro Arg Leu
    1865                1870

<210> SEQ ID NO 15
<211> LENGTH: 7362
<212> TYPE: DNA
<213> ORGANISM: Homo sapiens
```

```
<220> FEATURE:
<221> NAME/KEY: gene
<222> LOCATION: (1)..(7362)
<220> FEATURE:
<221> NAME/KEY: CDS
<222> LOCATION: (1516)..(6834)
<220> FEATURE:
<221> NAME/KEY: misc_feature
<222> LOCATION: (1516)..(6834)
<223> OTHER INFORMATION: n is dATP, dCTP, dGTP, or dTTP
<220> FEATURE:
<221> NAME/KEY: misc_feature
<222> LOCATION: (1516)..(6834)
<223> OTHER INFORMATION: Xaa is any amino acid

<400> SEQUENCE: 15
```

| | | |
|---|---|---|
| agaataaggg cagggaccgc ggctcctacc tcttggtgat ccccttcccc attccgcccc | 60 |
| cgcctcaacg cccagcacag tgccctgcac acagtagtcg ctcaataaat gttcgtggat | 120 |
| gatgatgatg atgatgatga aaaaaatgca gcatcaacgg cagcagcaag cggaccacgc | 180 |
| gaacgaggca aactatgcaa gaggcaccag acttcctctt tctggtgaag gaccaacttc | 240 |
| tcagccgaat agctccaagc aaactgtcct gtcttggcaa gctgcaatcg atgctgctag | 300 |
| acaggccaag gctgcccaaa ctatgagcac ctctgcaccc ccacctgtag gatctctctc | 360 |
| ccaaagaaaa cgtcagcaat acgccaagag caaaaaacag ggtaactcgt ccaacagccg | 420 |
| acctgcccgc gcccttttct gtttatcact caataacccc atccgaagag cctgcattag | 480 |
| tatagtggaa tggaaaccat ttgacatatt tatattattg gctattttg ccaattgtgt | 540 |
| ggccttagct atttacatcc cattccctga agatgattca aattcaacaa atcataactt | 600 |
| ggaaaaagta gaatatgcct tcctgattat ttttacagtc gagacatttt tgaagattat | 660 |
| agcgtatgga ttattgctac atcctaatgc ttatgttagg aatggatgga atttactgga | 720 |
| ttttgttata gtaatagtag gattgtttag tgtaattttg gaacaattaa ccaaagaaac | 780 |
| agaaggcggg aaccactcaa gcggcaaatc tggaggcttt gatgtcaaag ccctccgtgc | 840 |
| ctttcgagtg ttgcgaccac ttcgactagt gtcaggagtg cccagtttac aagttgtcct | 900 |
| gaactccatt ataaaagcca tggttcccct ccttcacata gcccttttgg tattatttgt | 960 |
| aatcataatc tatgctatta taggattgga acttttatt ggaaaaatgc acaaaacatg | 1020 |
| ttttttgct gactcagata tcgtagctga agaggaccca gctccatgtg cgttctcagg | 1080 |
| gaatggacgc cagtgtactg ccaatggcac ggaatgtagg agtggctggg ttggcccgaa | 1140 |
| cggaggcatc accaactttg ataactttgc ctttgccatg cttactgtgt ttcagtgcat | 1200 |
| caccatggag ggctggacag atgtgctcta ctgggtaaat gatgcgatag gatgggaatg | 1260 |
| gccatgggtg tattttgtta gtctgatcat ccttggctca ttttcgtcc ttaacctggc | 1320 |
| tcattttcg tccttatcag agaattctca aggaaagag agaaggcaaa agcacgggga | 1380 |
| gatttccaga agctccggga gaagcagcag ctggaggagg atctaaaggg ctacttggat | 1440 |
| tggatcaccc aagctgagga catcgatccg gagaatgagg aagaaggagg agaggaaggc | 1500 |

```
aaacgaaata ctagc atg ccc acc agc gag act gag tct gtg aac aca gag      1551
               Met Pro Thr Ser Glu Thr Glu Ser Val Asn Thr Glu
                 1               5                  10 aac gtc agc ggt gaa ggc gag aac cga ggc tgc tgt gga agt ctc tgg        1599
Asn Val Ser Gly Glu Gly Glu Asn Arg Gly Cys Cys Gly Ser Leu Trp
            15                  20                  25 tgc tgg tgg aga cgg aga ggc gcg gcc aag gcg ggg ccc tct ggg tgt        1647
Cys Trp Trp Arg Arg Arg Gly Ala Ala Lys Ala Gly Pro Ser Gly Cys
        30                  35                  40
```

-continued

| | |
|---|---|
| cgg cgg tgg ggt caa gcc atc tca aaa tcc aaa ctc agc cga cgc tgg<br>Arg Arg Trp Gly Gln Ala Ile Ser Lys Ser Lys Leu Ser Arg Arg Trp<br>45                                  50                          55                          60 | 1695 |
| cgt cgc tgg aac cga ttc aat cgc aga aga tgt agg gcc gcc gtg aag<br>Arg Arg Trp Asn Arg Phe Asn Arg Arg Arg Cys Arg Ala Ala Val Lys<br>                          65                          70                          75 | 1743 |
| tct gtc acg ttt tac tgg ctg gtt atc gtc ctg gtg ttt ctg aac acc<br>Ser Val Thr Phe Tyr Trp Leu Val Ile Val Leu Val Phe Leu Asn Thr<br>               80                          85                          90 | 1791 |
| tta acc att tcc tct gag cac tac aat cag cca gat tgg ttg aca cag<br>Leu Thr Ile Ser Ser Glu His Tyr Asn Gln Pro Asp Trp Leu Thr Gln<br>             95                          100                        105 | 1839 |
| att caa gat atg ccc aac aaa gtc ctc ttg gct ctg ttc acc tgc gag<br>Ile Gln Asp Met Pro Asn Lys Val Leu Leu Ala Leu Phe Thr Cys Glu<br>110                              115                        120 | 1887 |
| atg ctg gta aaa atg tac agc ttg ggc ctc caa gca tat ttc gtc tct<br>Met Leu Val Lys Met Tyr Ser Leu Gly Leu Gln Ala Tyr Phe Val Ser<br>125                              130                        135                        140 | 1935 |
| ctt ttc aac cgg ttt gat tgc ttc gtg gtg tgt ggt gga atc act gag<br>Leu Phe Asn Arg Phe Asp Cys Phe Val Val Cys Gly Gly Ile Thr Glu<br>                          145                        150                        155 | 1983 |
| acg atc ttg gtg gaa ctg gaa atc atg tct ccc ctg ggg atc tct gtg<br>Thr Ile Leu Val Glu Leu Glu Ile Met Ser Pro Leu Gly Ile Ser Val<br>                    160                        165                        170 | 2031 |
| ttt cgg tgt gtg cgc ctc tta aga atc ttc aaa gtg acc agg cac tgg<br>Phe Arg Cys Val Arg Leu Leu Arg Ile Phe Lys Val Thr Arg His Trp<br>               175                        180                        185 | 2079 |
| act tcc ctg agc aac tta gtg gca tcc tta tta aac tcc atg aag tcc<br>Thr Ser Leu Ser Asn Leu Val Ala Ser Leu Leu Asn Ser Met Lys Ser<br>          190                        195                        200 | 2127 |
| atc gct tcg ctg ttg ctt ctg ctt ttt ctc ttc att atc atc ttt tcc<br>Ile Ala Ser Leu Leu Leu Leu Leu Phe Leu Phe Ile Ile Ile Phe Ser<br>205                              210                        215                        220 | 2175 |
| ttg ctt ggg atg cag ctg ttt ggc ggc aag ttt aat ttt gat gaa acg<br>Leu Leu Gly Met Gln Leu Phe Gly Gly Lys Phe Asn Phe Asp Glu Thr<br>                          225                        230                        235 | 2223 |
| caa acc aag cgg agc acc ttt gac aat ttc cct caa gca ctt ctc aca<br>Gln Thr Lys Arg Ser Thr Phe Asp Asn Phe Pro Gln Ala Leu Leu Thr<br>                    240                        245                        250 | 2271 |
| gtg ttc cag atc ctg aca ggc gaa gac tgg aat gct gtg atg tac gat<br>Val Phe Gln Ile Leu Thr Gly Glu Asp Trp Asn Ala Val Met Tyr Asp<br>          255                        260                        265 | 2319 |
| ggc atc atg gct tac ggg ggc cca tcc tct tca gga atg atc gtc tgc<br>Gly Ile Met Ala Tyr Gly Gly Pro Ser Ser Ser Gly Met Ile Val Cys<br>270                              275                        280 | 2367 |
| atc tac ttc atc atc ctc ttc att tgt ggt aac tat att cta ctg aat<br>Ile Tyr Phe Ile Ile Leu Phe Ile Cys Gly Asn Tyr Ile Leu Leu Asn<br>285                              290                        295                        300 | 2415 |
| gtc ttc ttg gcc atc gct gta gac aat ttg gct gat gct gaa agt ctg<br>Val Phe Leu Ala Ile Ala Val Asp Asn Leu Ala Asp Ala Glu Ser Leu<br>                          305                        310                        315 | 2463 |
| aac act gct cag aaa gaa gaa gcg gaa gaa aag gag agg aaa aag att<br>Asn Thr Ala Gln Lys Glu Glu Ala Glu Glu Lys Glu Arg Lys Lys Ile<br>                    320                        325                        330 | 2511 |
| gcc aga aaa gag agc cta gaa aat aaa aag aac aac aaa cca gaa gtc<br>Ala Arg Lys Glu Ser Leu Glu Asn Lys Lys Asn Asn Lys Pro Glu Val<br>               335                        340                        345 | 2559 |
| aac cag ata gcc aac agt gac aac aag gtt aca att gat gac tat aga<br>Asn Gln Ile Ala Asn Ser Asp Asn Lys Val Thr Ile Asp Asp Tyr Arg<br>350                              355                        360 | 2607 |

```
gaa gag gat gaa gac aag gac ccc tat ccg cct tgc gat gtg cca ggt    2655
Glu Glu Asp Glu Asp Lys Asp Pro Tyr Pro Pro Cys Asp Val Pro Gly
365                 370                 375                 380 atg gtg gnn nnn nnn nnn nnn nnn nnn nnn nnn nnn nnn nnn nnn nnn    2703
Met Val Xaa Xaa Xaa Xaa Xaa Xaa Xaa Xaa Xaa Xaa Xaa Xaa Xaa Xaa
            385                 390                 395 nnn nnn nnn nnn nnn nnn nnn nnn nnn nnn nnn nnn nnn nnn nnn nnn    2751
Xaa Xaa Xaa Xaa Xaa Xaa Xaa Xaa Xaa Xaa Xaa Xaa Xaa Xaa Xaa Xaa
                400                 405                 410 nnn nnn nnn nnn nnn nnn nnn nnn nnn nnn nnn nnn nnn nnn nnn nnn    2799
Xaa Xaa Xaa Xaa Xaa Xaa Xaa Xaa Xaa Xaa Xaa Xaa Xaa Xaa Xaa Xaa
            415                 420                 425 nnn nnn nnn nnn nnn nnn nnn nnn nnn nnn nnn nnn nnn nnn nnn nnn    2847
Xaa Xaa Xaa Xaa Xaa Xaa Xaa Xaa Xaa Xaa Xaa Xaa Xaa Xaa Xaa Xaa
        430                 435                 440 nnn nnn nnn nnn nnn nnn nnn nnn nnn nnn nnn nnn nnn nnn nnn nnn    2895
Xaa Xaa Xaa Xaa Xaa Xaa Xaa Xaa Xaa Xaa Xaa Xaa Xaa Xaa Xaa Xaa
445                 450                 455                 460 nnn nnn nnn nnn nnn nnn nnn nnn nnn nnn nnn nnn nnn nnn nnn nnn    2943
Xaa Xaa Xaa Xaa Xaa Xaa Xaa Xaa Xaa Xaa Xaa Xaa Xaa Xaa Xaa Xaa
                465                 470                 475 nnn nnn nnn nnn nnn nnn ccc tgc agg atc cgc gta ggc tgc cac aag    2991
Xaa Xaa Xaa Xaa Xaa Xaa Pro Cys Arg Ile Arg Val Gly Cys His Lys
            480                 485                 490 ctc atc aac cac cac atc ttc acc aac ctc atc ctt gtc ttc atc atg    3039
Leu Ile Asn His His Ile Phe Thr Asn Leu Ile Leu Val Phe Ile Met
                495                 500                 505 ctg agc agc gct gcc ctg gcc gca gag gac ccc atc cgc agc cac tcc    3087
Leu Ser Ser Ala Ala Leu Ala Ala Glu Asp Pro Ile Arg Ser His Ser
        510                 515                 520 ttc cgg aac acg ata ctg ggt tac ttt gac tat gcc ttc aca gcc atc    3135
Phe Arg Asn Thr Ile Leu Gly Tyr Phe Asp Tyr Ala Phe Thr Ala Ile
525                 530                 535                 540 ttt act gtt gag atc ctg ttg aag atg aca act ttt gga gct ttc ctc    3183
Phe Thr Val Glu Ile Leu Leu Lys Met Thr Thr Phe Gly Ala Phe Leu
                545                 550                 555 cac aaa ggg gcc ttc tgc agg aac tac ttc aat ttg ctg gat atg ctg    3231
His Lys Gly Ala Phe Cys Arg Asn Tyr Phe Asn Leu Leu Asp Met Leu
            560                 565                 570 gtg gtt ggg gtg tct ctg gtg tca ttt ggg att caa tcc agt gcc atc    3279
Val Val Gly Val Ser Leu Val Ser Phe Gly Ile Gln Ser Ser Ala Ile
        575                 580                 585 tcc gtt gtg aag att ctg agg gtc tta agg gtc ctg cgt ccc ctc agg    3327
Ser Val Val Lys Ile Leu Arg Val Leu Arg Val Leu Arg Pro Leu Arg
590                 595                 600 gcc atc aac aga gca aaa gga ctt aag cac gtg gtc cag tgc gtc ttc    3375
Ala Ile Asn Arg Ala Lys Gly Leu Lys His Val Val Gln Cys Val Phe
                605                 610                 615                 620 gtg gcc atc cgg acc atc ggc aac atc atg atc gtc acc acc ctc ctg    3423
Val Ala Ile Arg Thr Ile Gly Asn Ile Met Ile Val Thr Thr Leu Leu
            625                 630                 635 cag ttc atg ttt gcc tgt atc ggg gtc cag ttg ttc aag ggg aag ttc    3471
Gln Phe Met Phe Ala Cys Ile Gly Val Gln Leu Phe Lys Gly Lys Phe
        640                 645                 650 tat cgc tgt acg gat gaa gcc aaa agt aac cct gaa gaa tgc agg gga    3519
Tyr Arg Cys Thr Asp Glu Ala Lys Ser Asn Pro Glu Glu Cys Arg Gly
655                 660                 665 ctt ttc atc ctc tac aag gat ggg gat gtt gac agt cct gtg gtc cgt    3567
Leu Phe Ile Leu Tyr Lys Asp Gly Asp Val Asp Ser Pro Val Val Arg
```

```
                                                     -continued
        670                  675                  680
gaa cgg atc tgg caa aac agt gat ttc aac ttc gac aac gtc ctc tct    3615
Glu Arg Ile Trp Gln Asn Ser Asp Phe Asn Phe Asp Asn Val Leu Ser
685                 690                 695                 700 gct atg atg gcg ctc ttc aca gtc tcc acg ttt gag ggc tgg cct gcg    3663
Ala Met Met Ala Leu Phe Thr Val Ser Thr Phe Glu Gly Trp Pro Ala
                705                 710                 715 ttg ctg tat aaa gcc atc gac tcg aat gga gag aac atc ggc cca atc    3711
Leu Leu Tyr Lys Ala Ile Asp Ser Asn Gly Glu Asn Ile Gly Pro Ile
            720                 725                 730 tac aac cac cgc gtg gag atc tcc atc ttc ttc atc atc tac atc atc    3759
Tyr Asn His Arg Val Glu Ile Ser Ile Phe Phe Ile Ile Tyr Ile Ile
        735                 740                 745 att gta gct ttc ttc atg atg aac atc ttt gtg ggc ttt gtc atc gtt    3807
Ile Val Ala Phe Phe Met Met Asn Ile Phe Val Gly Phe Val Ile Val
    750                 755                 760 aca ttt cag gaa caa gga gaa aaa gag tat aag aac tgt gag ctg gac    3855
Thr Phe Gln Glu Gln Gly Glu Lys Glu Tyr Lys Asn Cys Glu Leu Asp
765                 770                 775                 780 aaa aat cag cgt cag tgt gtt gaa tac gcc ttg aaa gca cgt ccc ttg    3903
Lys Asn Gln Arg Gln Cys Val Glu Tyr Ala Leu Lys Ala Arg Pro Leu
                785                 790                 795 cgg aga tac atc ccc aaa aac ccc tac cag tac aag ttc tgg tac gtg    3951
Arg Arg Tyr Ile Pro Lys Asn Pro Tyr Gln Tyr Lys Phe Trp Tyr Val
            800                 805                 810 gtg aac tct tcg cct ttc gaa tac atg atg ttt gtc ctc atc atg ctc    3999
Val Asn Ser Ser Pro Phe Glu Tyr Met Met Phe Val Leu Ile Met Leu
        815                 820                 825 aac aca ctc tgc ttg gcc atg cag cac tac gag cag tcc aag atg ttc    4047
Asn Thr Leu Cys Leu Ala Met Gln His Tyr Glu Gln Ser Lys Met Phe
    830                 835                 840 aat gat gcc atg gac att ctg aac atg gtc ttc acc ggg gtg ttc acc    4095
Asn Asp Ala Met Asp Ile Leu Asn Met Val Phe Thr Gly Val Phe Thr
845                 850                 855                 860 gtc gag atg gtt ttg aaa gtc atc gca ttt aag cct aag ggg tat ttt    4143
Val Glu Met Val Leu Lys Val Ile Ala Phe Lys Pro Lys Gly Tyr Phe
                865                 870                 875 agt gac gcc tgg aac acg ttt gac tcc ctc atc gta atc ggc agc att    4191
Ser Asp Ala Trp Asn Thr Phe Asp Ser Leu Ile Val Ile Gly Ser Ile
            880                 885                 890 ata gac gtg gcc ctc agc gaa gca aag cca act gaa agt gaa aat gtc    4239
Ile Asp Val Ala Leu Ser Glu Ala Lys Pro Thr Glu Ser Glu Asn Val
        895                 900                 905 cct gtc cca act gct aca cct ggg aac tct gaa gag agc aat aga atc    4287
Pro Val Pro Thr Ala Thr Pro Gly Asn Ser Glu Glu Ser Asn Arg Ile
    910                 915                 920 tcc atc acc ttt ttc cgt ctt ttc cga gtg atg cga ttg gtg aag ctt    4335
Ser Ile Thr Phe Phe Arg Leu Phe Arg Val Met Arg Leu Val Lys Leu
925                 930                 935                 940 ctc agc agg ggg gaa ggc atc cgg aca ttg ctg tgg act ttt att aag    4383
Leu Ser Arg Gly Glu Gly Ile Arg Thr Leu Leu Trp Thr Phe Ile Lys
                945                 950                 955 tcc ttt cag gcg ctc ccg tat gtg gcc ctc ctc ata gcc atg ctg ttc    4431
Ser Phe Gln Ala Leu Pro Tyr Val Ala Leu Leu Ile Ala Met Leu Phe
            960                 965                 970 ttc atc tat gcg gtc att ggc atg cag atg ttt ggg aaa gtt gcc atg    4479
Phe Ile Tyr Ala Val Ile Gly Met Gln Met Phe Gly Lys Val Ala Met
        975                 980                 985 aga gat aac aac cag atc aat agg aac aat aac ttc cag acg ttt ccc    4527
```

```
                Arg Asp Asn Asn Gln Ile Asn Arg Asn Asn Asn Phe  Gln Thr Phe Pro
                    990                 995                 1000 cag gcg gtg ctg ctg ctc ttc agg tgt gca aca  ggt gag gcc tgg         4572
Gln Ala Val Leu Leu Leu Phe Arg Cys Ala Thr  Gly Glu Ala Trp
1005                1010                1015 cag gag atc atg ctg gcc tgt ctc cca ggg aag  ctc tgt gac cct         4617
Gln Glu Ile Met Leu Ala Cys Leu Pro Gly Lys  Leu Cys Asp Pro
1020                1025                1030 gag tca gat tac aac ccc ggg gag gag tat aca  tgt ggg agc aac         4662
Glu Ser Asp Tyr Asn Pro Gly Glu Glu Tyr Thr  Cys Gly Ser Asn
1035                1040                1045 ttt gcc att gtc tat ttc atc agt ttt tac atg  ctc tgt gca ttt         4707
Phe Ala Ile Val Tyr Phe Ile Ser Phe Tyr Met  Leu Cys Ala Phe
1050                1055                1060 ctg atc atc aat ctg ttt gtg gct gtc atc atg  gat aat ttc gac         4752
Leu Ile Ile Asn Leu Phe Val Ala Val Ile Met  Asp Asn Phe Asp
1065                1070                1075 tat ctg acc cgg gac tgg tct att ttg ggg cct  cac cat tta gat         4797
Tyr Leu Thr Arg Asp Trp Ser Ile Leu Gly Pro  His His Leu Asp
1080                1085                1090 gaa ttc aaa aga ata tgg tca gaa tat gac cct  gag gca aag gga         4842
Glu Phe Lys Arg Ile Trp Ser Glu Tyr Asp Pro  Glu Ala Lys Gly
1095                1100                1105 agg ata aaa cac ctt gat gtg gtc act ctg ctt  cga cgc atc cag         4887
Arg Ile Lys His Leu Asp Val Val Thr Leu Leu  Arg Arg Ile Gln
1110                1115                1120 cct ccc ctg ggg ttt ggg aag tta tgt cca cac  agg gta gcg tgc         4932
Pro Pro Leu Gly Phe Gly Lys Leu Cys Pro His  Arg Val Ala Cys
1125                1130                1135 aag aga tta gtt gcc atg aac atg cct ctc aac  agt gac ggg aca         4977
Lys Arg Leu Val Ala Met Asn Met Pro Leu Asn  Ser Asp Gly Thr
1140                1145                1150 gtc atg ttt aat gca acc ctg ttt gct ttg gtt  cga acg gct ctt         5022
Val Met Phe Asn Ala Thr Leu Phe Ala Leu Val  Arg Thr Ala Leu
1155                1160                1165 aag atc aag acc gaa ggg aac ctg gag caa gct  aat gaa gaa ctt         5067
Lys Ile Lys Thr Glu Gly Asn Leu Glu Gln Ala  Asn Glu Glu Leu
1170                1175                1180 cgg gct gtg ata aag aaa att tgg aag aaa acc  agc atg aaa tta         5112
Arg Ala Val Ile Lys Lys Ile Trp Lys Lys Thr  Ser Met Lys Leu
1185                1190                1195 ctt gac caa gtt gtc cct cca gct ggt gat gat  gag gta acc gtg         5157
Leu Asp Gln Val Val Pro Pro Ala Gly Asp Asp  Glu Val Thr Val
1200                1205                1210 ggg aag ttc tat gcc act ttc ctg ata cag gac  tac ttt agg aaa         5202
Gly Lys Phe Tyr Ala Thr Phe Leu Ile Gln Asp  Tyr Phe Arg Lys
1215                1220                1225 ttc aag aaa cgg aaa gaa caa gga ctg gtg gga  aag tac cct gcg         5247
Phe Lys Lys Arg Lys Glu Gln Gly Leu Val Gly  Lys Tyr Pro Ala
1230                1235                1240 aag aac aca aca att gcc cta cag gcg gga tta  agg aca ctg cat         5292
Lys Asn Thr Thr Ile Ala Leu Gln Ala Gly Leu  Arg Thr Leu His
1245                1250                1255 gac att ggg cca gaa atc cgg cgt gct ata tcg  tgt gat ttg caa         5337
Asp Ile Gly Pro Glu Ile Arg Arg Ala Ile Ser  Cys Asp Leu Gln
1260                1265                1270 gat gac gag cct gag gaa aca aaa cga gaa gaa  gaa gat gat gtg         5382
Asp Asp Glu Pro Glu Glu Thr Lys Arg Glu Glu  Glu Asp Asp Val
1275                1280                1285
```

```
ttc aaa aga aat ggt gcc ctg ctt gga aac cat gtc aat cat gtt       5427
Phe Lys Arg Asn Gly Ala Leu Leu Gly Asn His Val Asn His Val
1290                1295                1300 aat agt gat agg aga gat tcc ctt cag cag acc aat acc acc cac       5472
Asn Ser Asp Arg Arg Asp Ser Leu Gln Gln Thr Asn Thr Thr His
1305                1310                1315 cgt ccc ctg cat gtc caa agg cct tca att cca cct gca agt gat       5517
Arg Pro Leu His Val Gln Arg Pro Ser Ile Pro Pro Ala Ser Asp
1320                1325                1330 act gag aaa ccg ctg ttt cct cca gca gga aat tcg gtg tgt cat       5562
Thr Glu Lys Pro Leu Phe Pro Pro Ala Gly Asn Ser Val Cys His
1335                1340                1345 aac cat cat aac cat aat tcc ata gga aag caa gtt ccc acc tca       5607
Asn His His Asn His Asn Ser Ile Gly Lys Gln Val Pro Thr Ser
1350                1355                1360 aca aat gcc aat ctc aat aat gcc aat atg tcc aaa gct gcc cat       5652
Thr Asn Ala Asn Leu Asn Asn Ala Asn Met Ser Lys Ala Ala His
1365                1370                1375 gga aag cgg ccc agc att ggg aac ctt gag cat gtg tct gaa aat       5697
Gly Lys Arg Pro Ser Ile Gly Asn Leu Glu His Val Ser Glu Asn
1380                1385                1390 ggg cat cat tct tcc cac aag cat gac cgg gag cct cag aga agg       5742
Gly His His Ser Ser His Lys His Asp Arg Glu Pro Gln Arg Arg
1395                1400                1405 tcc agt gtg aaa aga acc cgc tat tat gaa act tac att agg tcc       5787
Ser Ser Val Lys Arg Thr Arg Tyr Tyr Glu Thr Tyr Ile Arg Ser
1410                1415                1420 gac tca gga gat gaa cag ctc cca act att tgc cgg gaa gac cca       5832
Asp Ser Gly Asp Glu Gln Leu Pro Thr Ile Cys Arg Glu Asp Pro
1425                1430                1435 gag ata cat ggc tat ttc agg gac ccc cac tgc ttg ggg gag cag       5877
Glu Ile His Gly Tyr Phe Arg Asp Pro His Cys Leu Gly Glu Gln
1440                1445                1450 gag tat ttc agt agt gag gaa tgc tac gag gat gac agc tcg ccc       5922
Glu Tyr Phe Ser Ser Glu Glu Cys Tyr Glu Asp Asp Ser Ser Pro
1455                1460                1465 acc tgg agc agg caa aac tat ggc tac tac agc aga tac cca ggc       5967
Thr Trp Ser Arg Gln Asn Tyr Gly Tyr Tyr Ser Arg Tyr Pro Gly
1470                1475                1480 aga aac atc gac tct gag agg ccc cga ggc tac cat cat ccc caa       6012
Arg Asn Ile Asp Ser Glu Arg Pro Arg Gly Tyr His His Pro Gln
1485                1490                1495 gga ttc ttg gag gac gat gac tcg ccc gtt tgc tat gat tca cgg       6057
Gly Phe Leu Glu Asp Asp Asp Ser Pro Val Cys Tyr Asp Ser Arg
1500                1505                1510 aga tct cca agg aga cgc cta cta cct ccc acc cca gca tcc cac       6102
Arg Ser Pro Arg Arg Arg Leu Leu Pro Pro Thr Pro Ala Ser His
1515                1520                1525 cgg aga tcc tcc ttc aac ttt gag tgc ctg cgc cgg cag agc agc       6147
Arg Arg Ser Ser Phe Asn Phe Glu Cys Leu Arg Arg Gln Ser Ser
1530                1535                1540 cag gaa gag gtc ccg tcg tct ccc atc ttc ccc cat cgc acg gcc       6192
Gln Glu Glu Val Pro Ser Ser Pro Ile Phe Pro His Arg Thr Ala
1545                1550                1555 ctg cct ctg cat cta atg cag caa cag atc atg gca gtt gcc ggc       6237
Leu Pro Leu His Leu Met Gln Gln Gln Ile Met Ala Val Ala Gly
1560                1565                1570 cta gat tca agt aaa gcc cag aag tac tca ccg agt cac tcg acc       6282
Leu Asp Ser Ser Lys Ala Gln Lys Tyr Ser Pro Ser His Ser Thr
1575                1580                1585
```

| | | | | | | | | | | |
|---|---|---|---|---|---|---|---|---|---|---|
| cgg | tcg | tgg | gcc | acc | cct | cca | gca | acc | cct | ccc | tac | cgg | gac | tgg | 6327 |
| Arg | Ser | Trp | Ala | Thr | Pro | Pro | Ala | Thr | Pro | Pro | Tyr | Arg | Asp | Trp | |
| 1590 | | | | 1595 | | | | | 1600 | | | | | | |
| aca | ccg | tgc | tac | acc | ccc | ctg | atc | caa | gtg | gag | cag | tca | gag | gcc | 6372 |
| Thr | Pro | Cys | Tyr | Thr | Pro | Leu | Ile | Gln | Val | Glu | Gln | Ser | Glu | Ala | |
| 1605 | | | | 1610 | | | | | 1615 | | | | | | |
| ctg | gac | cag | gtg | aac | ggc | agc | ctg | ccg | tcc | ctg | cac | cgc | agc | tcc | 6417 |
| Leu | Asp | Gln | Val | Asn | Gly | Ser | Leu | Pro | Ser | Leu | His | Arg | Ser | Ser | |
| 1620 | | | | 1625 | | | | | 1630 | | | | | | |
| tgg | tac | aca | gac | gag | ccc | gac | atc | tcc | tac | cgg | act | ttc | aca | cca | 6462 |
| Trp | Tyr | Thr | Asp | Glu | Pro | Asp | Ile | Ser | Tyr | Arg | Thr | Phe | Thr | Pro | |
| 1635 | | | | 1640 | | | | | 1645 | | | | | | |
| gcc | agc | ctg | act | gtc | ccc | agc | agc | ttc | cgg | aac | aaa | aac | agc | gac | 6507 |
| Ala | Ser | Leu | Thr | Val | Pro | Ser | Ser | Phe | Arg | Asn | Lys | Asn | Ser | Asp | |
| 1650 | | | | 1655 | | | | | 1660 | | | | | | |
| aag | cag | agg | agt | gcg | gac | agc | ttg | gtg | gag | gca | gtc | ctg | ata | tcc | 6552 |
| Lys | Gln | Arg | Ser | Ala | Asp | Ser | Leu | Val | Glu | Ala | Val | Leu | Ile | Ser | |
| 1665 | | | | 1670 | | | | | 1675 | | | | | | |
| gaa | ggc | ttg | gga | cgc | tat | gca | agg | gac | cca | aaa | ttt | gtg | tca | gca | 6597 |
| Glu | Gly | Leu | Gly | Arg | Tyr | Ala | Arg | Asp | Pro | Lys | Phe | Val | Ser | Ala | |
| 1680 | | | | 1685 | | | | | 1690 | | | | | | |
| aca | aaa | cac | gaa | atc | gct | gat | gcc | tgt | gac | ctc | acc | atc | gac | gag | 6642 |
| Thr | Lys | His | Glu | Ile | Ala | Asp | Ala | Cys | Asp | Leu | Thr | Ile | Asp | Glu | |
| 1695 | | | | 1700 | | | | | 1705 | | | | | | |
| atg | gag | agt | gca | gcc | agc | acc | ctg | ctt | aat | ggg | aac | gtg | cgt | ccc | 6687 |
| Met | Glu | Ser | Ala | Ala | Ser | Thr | Leu | Leu | Asn | Gly | Asn | Val | Arg | Pro | |
| 1710 | | | | 1715 | | | | | 1720 | | | | | | |
| cga | gcc | aac | ggg | gat | gtg | ggc | ccc | ctc | tca | cac | cgg | cag | gac | tat | 6732 |
| Arg | Ala | Asn | Gly | Asp | Val | Gly | Pro | Leu | Ser | His | Arg | Gln | Asp | Tyr | |
| 1725 | | | | 1730 | | | | | 1735 | | | | | | |
| gag | cta | cag | gac | ttt | ggt | cct | ggc | tac | agc | gac | gaa | gag | cca | gac | 6777 |
| Glu | Leu | Gln | Asp | Phe | Gly | Pro | Gly | Tyr | Ser | Asp | Glu | Glu | Pro | Asp | |
| 1740 | | | | 1745 | | | | | 1750 | | | | | | |
| cct | ggg | agg | gat | gag | gag | gac | ctg | gcg | gat | gaa | atg | ata | tgc | atc | 6822 |
| Pro | Gly | Arg | Asp | Glu | Glu | Asp | Leu | Ala | Asp | Glu | Met | Ile | Cys | Ile | |
| 1755 | | | | 1760 | | | | | 1765 | | | | | | |
| acc | acc | ttg | tag | cccccagcga | ggggcagact | ggctctggcc | tcaggtgggg | | | | | | | | 6874 |
| Thr | Thr | Leu | | | | | | | | | | | | | |
| 1770 | | | | | | | | | | | | | | | | cgcaggagag ccaggggaaa agtgcctcat agttaggaaa gtttaggcac tagttgggag 6934 taatattcaa ttaattagac ttttgtataa gagatgtcat gcctcaagaa agccataaac 6994 ctggtaggaa caggtcccaa gcggttgagc ctggcagagt accatgcgct cggccccagc 7054 tgcaggaaac agcaggcccc gccctctcac agaggatggg tgaggaggcc agacctgccc 7114 tgccccattg tccagatggg cactgctgtg gagtctgctt ctccatgta ccagggcacc 7174 aggcccaccc aactgaaggc atggcggcgg ggtgcagggg aaagttaaag gtgatgacga 7234 tcatcacacc tgtgtcgtta cctcagccat cggtctagca tatcagtcac tgggcccaac 7294 atatccattt ttaaacccctt tcccccaaat acactgcgtc ctggttcctg tttagctgtt 7354 ctgaaata 7362

<210> SEQ ID NO 16
<211> LENGTH: 1772
<212> TYPE: PRT
<213> ORGANISM: Homo sapiens
<220> FEATURE:
<221> NAME/KEY: misc_feature
<222> LOCATION: (383)..(383)

-continued

```
<223> OTHER INFORMATION: The 'Xaa' at location 383 stands for Glu, Asp,
      Gly, Ala, or Val.
<220> FEATURE:
<221> NAME/KEY: misc_feature
<222> LOCATION: (384)..(384)
<223> OTHER INFORMATION: The 'Xaa' at location 384 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (385)..(385)
<223> OTHER INFORMATION: The 'Xaa' at location 385 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (386)..(386)
<223> OTHER INFORMATION: The 'Xaa' at location 386 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (387)..(387)
<223> OTHER INFORMATION: The 'Xaa' at location 387 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (388)..(388)
<223> OTHER INFORMATION: The 'Xaa' at location 388 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (389)..(389)
<223> OTHER INFORMATION: The 'Xaa' at location 389 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (390)..(390)
<223> OTHER INFORMATION: The 'Xaa' at location 390 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (391)..(391)
<223> OTHER INFORMATION: The 'Xaa' at location 391 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (392)..(392)
<223> OTHER INFORMATION: The 'Xaa' at location 392 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (393)..(393)
<223> OTHER INFORMATION: The 'Xaa' at location 393 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (394)..(394)
<223> OTHER INFORMATION: The 'Xaa' at location 394 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (395)..(395)
<223> OTHER INFORMATION: The 'Xaa' at location 395 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (396)..(396)
<223> OTHER INFORMATION: The 'Xaa' at location 396 stands for Lys, Asn,
      Arg, Ser, Thr, Ile, Met, Glu, Asp, Gly, Ala, Val, Gln, His, Pro,
```

```
        Leu, Tyr, Trp, Cys, or Phe.
<220> FEATURE:
<221> NAME/KEY: misc_feature
<222> LOCATION: (397)..(397)
<223> OTHER INFORMATION: The 'Xaa' at location 397 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (398)..(398)
<223> OTHER INFORMATION: The 'Xaa' at location 398 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (399)..(399)
<223> OTHER INFORMATION: The 'Xaa' at location 399 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (400)..(400)
<223> OTHER INFORMATION: The 'Xaa' at location 400 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (401)..(401)
<223> OTHER INFORMATION: The 'Xaa' at location 401 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (402)..(402)
<223> OTHER INFORMATION: The 'Xaa' at location 402 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (403)..(403)
<223> OTHER INFORMATION: The 'Xaa' at location 403 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (404)..(404)
<223> OTHER INFORMATION: The 'Xaa' at location 404 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (405)..(405)
<223> OTHER INFORMATION: The 'Xaa' at location 405 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (406)..(406)
<223> OTHER INFORMATION: The 'Xaa' at location 406 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (407)..(407)
<223> OTHER INFORMATION: The 'Xaa' at location 407 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (408)..(408)
<223> OTHER INFORMATION: The 'Xaa' at location 408 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (409)..(409)
<223> OTHER INFORMATION: The 'Xaa' at location 409 stands for Lys, Asn,
      Arg, Ser, Thr, Ile, Met, Glu, Asp, Gly, Ala, Val, Gln, His, Pro,
      Leu, Tyr, Trp, Cys, or Phe.
```

```
<220> FEATURE:
<221> NAME/KEY: misc_feature
<222> LOCATION: (410)..(410)
<223> OTHER INFORMATION: The 'Xaa' at location 410 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (411)..(411)
<223> OTHER INFORMATION: The 'Xaa' at location 411 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (412)..(412)
<223> OTHER INFORMATION: The 'Xaa' at location 412 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (413)..(413)
<223> OTHER INFORMATION: The 'Xaa' at location 413 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (414)..(414)
<223> OTHER INFORMATION: The 'Xaa' at location 414 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (415)..(415)
<223> OTHER INFORMATION: The 'Xaa' at location 415 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (416)..(416)
<223> OTHER INFORMATION: The 'Xaa' at location 416 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (417)..(417)
<223> OTHER INFORMATION: The 'Xaa' at location 417 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (418)..(418)
<223> OTHER INFORMATION: The 'Xaa' at location 418 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (419)..(419)
<223> OTHER INFORMATION: The 'Xaa' at location 419 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (420)..(420)
<223> OTHER INFORMATION: The 'Xaa' at location 420 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (421)..(421)
<223> OTHER INFORMATION: The 'Xaa' at location 421 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (422)..(422)
<223> OTHER INFORMATION: The 'Xaa' at location 422 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
```

```
<221> NAME/KEY: misc_feature
<222> LOCATION: (423)..(423)
<223> OTHER INFORMATION: The 'Xaa' at location 423 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (424)..(424)
<223> OTHER INFORMATION: The 'Xaa' at location 424 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (425)..(425)
<223> OTHER INFORMATION: The 'Xaa' at location 425 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (426)..(426)
<223> OTHER INFORMATION: The 'Xaa' at location 426 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (427)..(427)
<223> OTHER INFORMATION: The 'Xaa' at location 427 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (428)..(428)
<223> OTHER INFORMATION: The 'Xaa' at location 428 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (429)..(429)
<223> OTHER INFORMATION: The 'Xaa' at location 429 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (430)..(430)
<223> OTHER INFORMATION: The 'Xaa' at location 430 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (431)..(431)
<223> OTHER INFORMATION: The 'Xaa' at location 431 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (432)..(432)
<223> OTHER INFORMATION: The 'Xaa' at location 432 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (433)..(433)
<223> OTHER INFORMATION: The 'Xaa' at location 433 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (434)..(434)
<223> OTHER INFORMATION: The 'Xaa' at location 434 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (435)..(435)
<223> OTHER INFORMATION: The 'Xaa' at location 435 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
```

```
<222> LOCATION: (436)..(436)
<223> OTHER INFORMATION: The 'Xaa' at location 436 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (437)..(437)
<223> OTHER INFORMATION: The 'Xaa' at location 437 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (438)..(438)
<223> OTHER INFORMATION: The 'Xaa' at location 438 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (439)..(439)
<223> OTHER INFORMATION: The 'Xaa' at location 439 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (440)..(440)
<223> OTHER INFORMATION: The 'Xaa' at location 440 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (441)..(441)
<223> OTHER INFORMATION: The 'Xaa' at location 441 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (442)..(442)
<223> OTHER INFORMATION: The 'Xaa' at location 442 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (443)..(443)
<223> OTHER INFORMATION: The 'Xaa' at location 443 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (444)..(444)
<223> OTHER INFORMATION: The 'Xaa' at location 444 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (445)..(445)
<223> OTHER INFORMATION: The 'Xaa' at location 445 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (446)..(446)
<223> OTHER INFORMATION: The 'Xaa' at location 446 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (447)..(447)
<223> OTHER INFORMATION: The 'Xaa' at location 447 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (448)..(448)
<223> OTHER INFORMATION: The 'Xaa' at location 448 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (449)..(449)
```

-continued

```
<223> OTHER INFORMATION: The 'Xaa' at location 449 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (450)..(450)
<223> OTHER INFORMATION: The 'Xaa' at location 450 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (451)..(451)
<223> OTHER INFORMATION: The 'Xaa' at location 451 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (452)..(452)
<223> OTHER INFORMATION: The 'Xaa' at location 452 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (453)..(453)
<223> OTHER INFORMATION: The 'Xaa' at location 453 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (454)..(454)
<223> OTHER INFORMATION: The 'Xaa' at location 454 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (455)..(455)
<223> OTHER INFORMATION: The 'Xaa' at location 455 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (456)..(456)
<223> OTHER INFORMATION: The 'Xaa' at location 456 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (457)..(457)
<223> OTHER INFORMATION: The 'Xaa' at location 457 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (458)..(458)
<223> OTHER INFORMATION: The 'Xaa' at location 458 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (459)..(459)
<223> OTHER INFORMATION: The 'Xaa' at location 459 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (460)..(460)
<223> OTHER INFORMATION: The 'Xaa' at location 460 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (461)..(461)
<223> OTHER INFORMATION: The 'Xaa' at location 461 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (462)..(462)
<223> OTHER INFORMATION: The 'Xaa' at location 462 stands for Lys, Asn,
```

```
        Arg, Ser, Thr, Ile, Met, Glu, Asp, Gly, Ala, Val, Gln, His, Pro,
        Leu, Tyr, Trp, Cys, or Phe.
<220> FEATURE:
<221> NAME/KEY: misc_feature
<222> LOCATION: (463)..(463)
<223> OTHER INFORMATION: The 'Xaa' at location 463 stands for Lys, Asn,
        Arg, Ser, Thr, Ile, Met, Glu, Asp, Gly, Ala, Val, Gln, His, Pro,
        Leu, Tyr, Trp, Cys, or Phe.
<220> FEATURE:
<221> NAME/KEY: misc_feature
<222> LOCATION: (464)..(464)
<223> OTHER INFORMATION: The 'Xaa' at location 464 stands for Lys, Asn,
        Arg, Ser, Thr, Ile, Met, Glu, Asp, Gly, Ala, Val, Gln, His, Pro,
        Leu, Tyr, Trp, Cys, or Phe.
<220> FEATURE:
<221> NAME/KEY: misc_feature
<222> LOCATION: (465)..(465)
<223> OTHER INFORMATION: The 'Xaa' at location 465 stands for Lys, Asn,
        Arg, Ser, Thr, Ile, Met, Glu, Asp, Gly, Ala, Val, Gln, His, Pro,
        Leu, Tyr, Trp, Cys, or Phe.
<220> FEATURE:
<221> NAME/KEY: misc_feature
<222> LOCATION: (466)..(466)
<223> OTHER INFORMATION: The 'Xaa' at location 466 stands for Lys, Asn,
        Arg, Ser, Thr, Ile, Met, Glu, Asp, Gly, Ala, Val, Gln, His, Pro,
        Leu, Tyr, Trp, Cys, or Phe.
<220> FEATURE:
<221> NAME/KEY: misc_feature
<222> LOCATION: (467)..(467)
<223> OTHER INFORMATION: The 'Xaa' at location 467 stands for Lys, Asn,
        Arg, Ser, Thr, Ile, Met, Glu, Asp, Gly, Ala, Val, Gln, His, Pro,
        Leu, Tyr, Trp, Cys, or Phe.
<220> FEATURE:
<221> NAME/KEY: misc_feature
<222> LOCATION: (468)..(468)
<223> OTHER INFORMATION: The 'Xaa' at location 468 stands for Lys, Asn,
        Arg, Ser, Thr, Ile, Met, Glu, Asp, Gly, Ala, Val, Gln, His, Pro,
        Leu, Tyr, Trp, Cys, or Phe.
<220> FEATURE:
<221> NAME/KEY: misc_feature
<222> LOCATION: (469)..(469)
<223> OTHER INFORMATION: The 'Xaa' at location 469 stands for Lys, Asn,
        Arg, Ser, Thr, Ile, Met, Glu, Asp, Gly, Ala, Val, Gln, His, Pro,
        Leu, Tyr, Trp, Cys, or Phe.
<220> FEATURE:
<221> NAME/KEY: misc_feature
<222> LOCATION: (470)..(470)
<223> OTHER INFORMATION: The 'Xaa' at location 470 stands for Lys, Asn,
        Arg, Ser, Thr, Ile, Met, Glu, Asp, Gly, Ala, Val, Gln, His, Pro,
        Leu, Tyr, Trp, Cys, or Phe.
<220> FEATURE:
<221> NAME/KEY: misc_feature
<222> LOCATION: (471)..(471)
<223> OTHER INFORMATION: The 'Xaa' at location 471 stands for Lys, Asn,
        Arg, Ser, Thr, Ile, Met, Glu, Asp, Gly, Ala, Val, Gln, His, Pro,
        Leu, Tyr, Trp, Cys, or Phe.
<220> FEATURE:
<221> NAME/KEY: misc_feature
<222> LOCATION: (472)..(472)
<223> OTHER INFORMATION: The 'Xaa' at location 472 stands for Lys, Asn,
        Arg, Ser, Thr, Ile, Met, Glu, Asp, Gly, Ala, Val, Gln, His, Pro,
        Leu, Tyr, Trp, Cys, or Phe.
<220> FEATURE:
<221> NAME/KEY: misc_feature
<222> LOCATION: (473)..(473)
<223> OTHER INFORMATION: The 'Xaa' at location 473 stands for Lys, Asn,
        Arg, Ser, Thr, Ile, Met, Glu, Asp, Gly, Ala, Val, Gln, His, Pro,
        Leu, Tyr, Trp, Cys, or Phe.
<220> FEATURE:
<221> NAME/KEY: misc_feature
<222> LOCATION: (474)..(474)
<223> OTHER INFORMATION: The 'Xaa' at location 474 stands for Lys, Asn,
        Arg, Ser, Thr, Ile, Met, Glu, Asp, Gly, Ala, Val, Gln, His, Pro,
        Leu, Tyr, Trp, Cys, or Phe.
<220> FEATURE:
<221> NAME/KEY: misc_feature
<222> LOCATION: (475)..(475)
<223> OTHER INFORMATION: The 'Xaa' at location 475 stands for Lys, Asn,
        Arg, Ser, Thr, Ile, Met, Glu, Asp, Gly, Ala, Val, Gln, His, Pro,
```

```
        Leu, Tyr, Trp, Cys, or Phe.
<220> FEATURE:
<221> NAME/KEY: misc_feature
<222> LOCATION: (476)..(476)
<223> OTHER INFORMATION: The 'Xaa' at location 476 stands for Lys, Asn,
        Arg, Ser, Thr, Ile, Met, Glu, Asp, Gly, Ala, Val, Gln, His, Pro,
        Leu, Tyr, Trp, Cys, or Phe.
<220> FEATURE:
<221> NAME/KEY: misc_feature
<222> LOCATION: (477)..(477)
<223> OTHER INFORMATION: The 'Xaa' at location 477 stands for Lys, Asn,
        Arg, Ser, Thr, Ile, Met, Glu, Asp, Gly, Ala, Val, Gln, His, Pro,
        Leu, Tyr, Trp, Cys, or Phe.
<220> FEATURE:
<221> NAME/KEY: misc_feature
<222> LOCATION: (478)..(478)
<223> OTHER INFORMATION: The 'Xaa' at location 478 stands for Lys, Asn,
        Arg, Ser, Thr, Ile, Met, Glu, Asp, Gly, Ala, Val, Gln, His, Pro,
        Leu, Tyr, Trp, Cys, or Phe.
<220> FEATURE:
<221> NAME/KEY: misc_feature
<222> LOCATION: (479)..(479)
<223> OTHER INFORMATION: The 'Xaa' at location 479 stands for Lys, Asn,
        Arg, Ser, Thr, Ile, Met, Glu, Asp, Gly, Ala, Val, Gln, His, Pro,
        Leu, Tyr, Trp, Cys, or Phe.
<220> FEATURE:
<221> NAME/KEY: misc_feature
<222> LOCATION: (480)..(480)
<223> OTHER INFORMATION: The 'Xaa' at location 480 stands for Lys, Asn,
        Arg, Ser, Thr, Ile, Met, Glu, Asp, Gly, Ala, Val, Gln, His, Pro,
        Leu, Tyr, Trp, Cys, or Phe.
<220> FEATURE:
<221> NAME/KEY: misc_feature
<222> LOCATION: (481)..(481)
<223> OTHER INFORMATION: The 'Xaa' at location 481 stands for Lys, Asn,
        Arg, Ser, Thr, Ile, Met, Glu, Asp, Gly, Ala, Val, Gln, His, Pro,
        Leu, Tyr, Trp, Cys, or Phe.
<220> FEATURE:
<221> NAME/KEY: misc_feature
<222> LOCATION: (482)..(482)
<223> OTHER INFORMATION: The 'Xaa' at location 482 stands for Lys, Asn,
        Arg, Ser, Thr, Ile, Met, Glu, Asp, Gly, Ala, Val, Gln, His, Pro,
        Leu, Tyr, Trp, Cys, or Phe.

<400> SEQUENCE: 16

Met Pro Thr Ser Glu Thr Glu Ser Val Asn Thr Glu Asn Val Ser Gly
1               5                   10                  15

Glu Gly Glu Asn Arg Gly Cys Cys Gly Ser Leu Trp Cys Trp Trp Arg
            20                  25                  30

Arg Arg Gly Ala Ala Lys Ala Gly Pro Ser Gly Cys Arg Arg Trp Gly
        35                  40                  45

Gln Ala Ile Ser Lys Ser Lys Leu Ser Arg Arg Trp Arg Arg Trp Asn
    50                  55                  60

Arg Phe Asn Arg Arg Arg Cys Arg Ala Ala Val Lys Ser Val Thr Phe
65                  70                  75                  80

Tyr Trp Leu Val Ile Val Leu Val Phe Leu Asn Thr Leu Thr Ile Ser
                85                  90                  95

Ser Glu His Tyr Asn Gln Pro Asp Trp Leu Thr Gln Ile Gln Asp Met
            100                 105                 110

Pro Asn Lys Val Leu Leu Ala Leu Phe Thr Cys Glu Met Leu Val Lys
        115                 120                 125

Met Tyr Ser Leu Gly Leu Gln Ala Tyr Phe Val Ser Leu Phe Asn Arg
    130                 135                 140

Phe Asp Cys Phe Val Val Cys Gly Gly Ile Thr Glu Thr Ile Leu Val
145                 150                 155                 160

Glu Leu Glu Ile Met Ser Pro Leu Gly Ile Ser Val Phe Arg Cys Val
                165                 170                 175
```

```
Arg Leu Leu Arg Ile Phe Lys Val Thr Arg His Trp Thr Ser Leu Ser
            180                 185                 190

Asn Leu Val Ala Ser Leu Leu Asn Ser Met Lys Ser Ile Ala Ser Leu
        195                 200                 205

Leu Leu Leu Leu Phe Leu Phe Ile Ile Ile Phe Ser Leu Leu Gly Met
    210                 215                 220

Gln Leu Phe Gly Gly Lys Phe Asn Phe Asp Glu Thr Gln Thr Lys Arg
225                 230                 235                 240

Ser Thr Phe Asp Asn Phe Pro Gln Ala Leu Leu Thr Val Phe Gln Ile
                245                 250                 255

Leu Thr Gly Glu Asp Trp Asn Ala Val Met Tyr Asp Gly Ile Met Ala
            260                 265                 270

Tyr Gly Gly Pro Ser Ser Gly Met Ile Val Cys Ile Tyr Phe Ile
        275                 280                 285

Ile Leu Phe Ile Cys Gly Asn Tyr Ile Leu Leu Asn Val Phe Leu Ala
    290                 295                 300

Ile Ala Val Asp Asn Leu Ala Asp Ala Glu Ser Leu Asn Thr Ala Gln
305                 310                 315                 320

Lys Glu Glu Ala Glu Lys Glu Arg Lys Ile Ala Arg Lys Glu
                325                 330                 335

Ser Leu Glu Asn Lys Lys Asn Asn Lys Pro Glu Val Asn Gln Ile Ala
            340                 345                 350

Asn Ser Asp Asn Lys Val Thr Ile Asp Asp Tyr Arg Glu Glu Asp Glu
        355                 360                 365

Asp Lys Asp Pro Tyr Pro Pro Cys Asp Val Pro Gly Met Val Xaa Xaa
    370                 375                 380

Xaa Xaa Xaa Xaa Xaa Xaa Xaa Xaa Xaa Xaa Xaa Xaa Xaa Xaa Xaa Xaa
385                 390                 395                 400

Xaa Xaa Xaa Xaa Xaa Xaa Xaa Xaa Xaa Xaa Xaa Xaa Xaa Xaa Xaa Xaa
                405                 410                 415

Xaa Xaa Xaa Xaa Xaa Xaa Xaa Xaa Xaa Xaa Xaa Xaa Xaa Xaa Xaa Xaa
            420                 425                 430

Xaa Xaa Xaa Xaa Xaa Xaa Xaa Xaa Xaa Xaa Xaa Xaa Xaa Xaa Xaa Xaa
        435                 440                 445

Xaa Xaa Xaa Xaa Xaa Xaa Xaa Xaa Xaa Xaa Xaa Xaa Xaa Xaa Xaa Xaa
    450                 455                 460

Xaa Xaa Xaa Xaa Xaa Xaa Xaa Xaa Xaa Xaa Xaa Xaa Xaa Xaa Xaa Xaa
465                 470                 475                 480

Xaa Xaa Pro Cys Arg Ile Arg Val Gly Cys His Lys Leu Ile Asn His
                485                 490                 495

His Ile Phe Thr Asn Leu Ile Leu Val Phe Ile Met Leu Ser Ser Ala
            500                 505                 510

Ala Leu Ala Ala Glu Asp Pro Ile Arg Ser His Ser Phe Arg Asn Thr
        515                 520                 525

Ile Leu Gly Tyr Phe Asp Tyr Ala Phe Thr Ala Ile Phe Thr Val Glu
    530                 535                 540

Ile Leu Leu Lys Met Thr Thr Phe Gly Ala Phe Leu His Lys Gly Ala
545                 550                 555                 560

Phe Cys Arg Asn Tyr Phe Asn Leu Leu Asp Met Leu Val Val Gly Val
                565                 570                 575

Ser Leu Val Ser Phe Gly Ile Gln Ser Ser Ala Ile Ser Val Val Lys
            580                 585                 590

Ile Leu Arg Val Leu Arg Val Leu Arg Pro Leu Arg Ala Ile Asn Arg
```

-continued

```
            595                 600                 605
Ala Lys Gly Leu Lys His Val Val Gln Cys Val Phe Val Ala Ile Arg
            610                 615                 620
Thr Ile Gly Asn Ile Met Ile Val Thr Thr Leu Leu Gln Phe Met Phe
625                 630                 635                 640
Ala Cys Ile Gly Val Gln Leu Phe Lys Gly Lys Phe Tyr Arg Cys Thr
                    645                 650                 655
Asp Glu Ala Lys Ser Asn Pro Glu Glu Cys Arg Gly Leu Phe Ile Leu
                660                 665                 670
Tyr Lys Asp Gly Asp Val Asp Ser Pro Val Val Arg Glu Arg Ile Trp
            675                 680                 685
Gln Asn Ser Asp Phe Asn Phe Asp Asn Val Leu Ser Ala Met Met Ala
            690                 695                 700
Leu Phe Thr Val Ser Thr Phe Glu Gly Trp Pro Ala Leu Leu Tyr Lys
705                 710                 715                 720
Ala Ile Asp Ser Asn Gly Glu Asn Ile Gly Pro Ile Tyr Asn His Arg
                725                 730                 735
Val Glu Ile Ser Ile Phe Phe Ile Ile Tyr Ile Ile Val Ala Phe
                740                 745                 750
Phe Met Met Asn Ile Phe Val Gly Phe Val Ile Val Thr Phe Gln Glu
            755                 760                 765
Gln Gly Glu Lys Glu Tyr Lys Asn Cys Glu Leu Asp Lys Asn Gln Arg
770                 775                 780
Gln Cys Val Glu Tyr Ala Leu Lys Ala Arg Pro Leu Arg Arg Tyr Ile
785                 790                 795                 800
Pro Lys Asn Pro Tyr Gln Tyr Lys Phe Trp Tyr Val Val Asn Ser Ser
                805                 810                 815
Pro Phe Glu Tyr Met Met Phe Val Leu Ile Met Leu Asn Thr Leu Cys
            820                 825                 830
Leu Ala Met Gln His Tyr Glu Gln Ser Lys Met Phe Asn Asp Ala Met
            835                 840                 845
Asp Ile Leu Asn Met Val Phe Thr Gly Val Phe Thr Val Glu Met Val
850                 855                 860
Leu Lys Val Ile Ala Phe Lys Pro Lys Gly Tyr Phe Ser Asp Ala Trp
865                 870                 875                 880
Asn Thr Phe Asp Ser Leu Ile Val Ile Gly Ser Ile Ile Asp Val Ala
                    885                 890                 895
Leu Ser Glu Ala Lys Pro Thr Glu Ser Glu Asn Val Pro Val Pro Thr
                900                 905                 910
Ala Thr Pro Gly Asn Ser Glu Glu Ser Asn Arg Ile Ser Ile Thr Phe
            915                 920                 925
Phe Arg Leu Phe Arg Val Met Arg Leu Val Lys Leu Leu Ser Arg Gly
            930                 935                 940
Glu Gly Ile Arg Thr Leu Leu Trp Thr Phe Ile Lys Ser Phe Gln Ala
945                 950                 955                 960
Leu Pro Tyr Val Ala Leu Leu Ile Ala Met Leu Phe Phe Ile Tyr Ala
                    965                 970                 975
Val Ile Gly Met Gln Met Phe Gly Lys Val Ala Met Arg Asp Asn Asn
                980                 985                 990
Gln Ile Asn Arg Asn Asn Asn Phe  Gln Thr Phe Pro Gln Ala Val Leu
            995                 1000                1005
Leu Leu  Phe Arg Cys Ala Thr Gly Glu Ala Trp Gln  Glu Ile Met
            1010                1015                1020
```

-continued

```
Leu Ala Cys Leu Pro Gly Lys Leu Cys Asp Pro Glu Ser Asp Tyr
    1025                1030                1035
Asn Pro Gly Glu Glu Tyr Thr Cys Gly Ser Asn Phe Ala Ile Val
    1040                1045                1050
Tyr Phe Ile Ser Phe Tyr Met Leu Cys Ala Phe Leu Ile Ile Asn
    1055                1060                1065
Leu Phe Val Ala Val Ile Met Asp Asn Phe Asp Tyr Leu Thr Arg
    1070                1075                1080
Asp Trp Ser Ile Leu Gly Pro His His Leu Asp Glu Phe Lys Arg
    1085                1090                1095
Ile Trp Ser Glu Tyr Asp Pro Glu Ala Lys Gly Arg Ile Lys His
    1100                1105                1110
Leu Asp Val Val Thr Leu Leu Arg Arg Ile Gln Pro Pro Leu Gly
    1115                1120                1125
Phe Gly Lys Leu Cys Pro His Arg Val Ala Cys Lys Arg Leu Val
    1130                1135                1140
Ala Met Asn Met Pro Leu Asn Ser Asp Gly Thr Val Met Phe Asn
    1145                1150                1155
Ala Thr Leu Phe Ala Leu Val Arg Thr Ala Leu Lys Ile Lys Thr
    1160                1165                1170
Glu Gly Asn Leu Glu Gln Ala Asn Glu Glu Leu Arg Ala Val Ile
    1175                1180                1185
Lys Lys Ile Trp Lys Lys Thr Ser Met Lys Leu Leu Asp Gln Val
    1190                1195                1200
Val Pro Pro Ala Gly Asp Asp Glu Val Thr Val Gly Lys Phe Tyr
    1205                1210                1215
Ala Thr Phe Leu Ile Gln Asp Tyr Phe Arg Lys Phe Lys Lys Arg
    1220                1225                1230
Lys Glu Gln Gly Leu Val Gly Lys Tyr Pro Ala Lys Asn Thr Thr
    1235                1240                1245
Ile Ala Leu Gln Ala Gly Leu Arg Thr Leu His Asp Ile Gly Pro
    1250                1255                1260
Glu Ile Arg Arg Ala Ile Ser Cys Asp Leu Gln Asp Asp Glu Pro
    1265                1270                1275
Glu Glu Thr Lys Arg Glu Glu Asp Asp Val Phe Lys Arg Asn
    1280                1285                1290
Gly Ala Leu Leu Gly Asn His Val Asn His Val Asn Ser Asp Arg
    1295                1300                1305
Arg Asp Ser Leu Gln Gln Thr Asn Thr Thr His Arg Pro Leu His
    1310                1315                1320
Val Gln Arg Pro Ser Ile Pro Pro Ala Ser Asp Thr Glu Lys Pro
    1325                1330                1335
Leu Phe Pro Pro Ala Gly Asn Ser Val Cys His Asn His His Asn
    1340                1345                1350
His Asn Ser Ile Gly Lys Gln Val Pro Thr Ser Thr Asn Ala Asn
    1355                1360                1365
Leu Asn Asn Ala Asn Met Ser Lys Ala Ala His Gly Lys Arg Pro
    1370                1375                1380
Ser Ile Gly Asn Leu Glu His Val Ser Glu Asn Gly His His Ser
    1385                1390                1395
Ser His Lys His Asp Arg Glu Pro Gln Arg Arg Ser Ser Val Lys
    1400                1405                1410
```

```
Arg  Thr  Arg  Tyr  Tyr  Glu  Thr  Tyr  Ile  Arg  Ser  Asp  Ser  Gly  Asp
1415                1420                1425

Glu  Gln  Leu  Pro  Thr  Ile  Cys  Arg  Glu  Asp  Pro  Glu  Ile  His  Gly
    1430                1435                1440

Tyr  Phe  Arg  Asp  Pro  His  Cys  Leu  Gly  Glu  Gln  Glu  Tyr  Phe  Ser
1445                1450                1455

Ser  Glu  Glu  Cys  Tyr  Glu  Asp  Asp  Ser  Ser  Pro  Thr  Trp  Ser  Arg
    1460                1465                1470

Gln  Asn  Tyr  Gly  Tyr  Tyr  Ser  Arg  Tyr  Pro  Gly  Arg  Asn  Ile  Asp
1475                1480                1485

Ser  Glu  Arg  Pro  Arg  Gly  Tyr  His  His  Pro  Gln  Gly  Phe  Leu  Glu
    1490                1495                1500

Asp  Asp  Asp  Ser  Pro  Val  Cys  Tyr  Asp  Ser  Arg  Arg  Ser  Pro  Arg
1505                1510                1515

Arg  Arg  Leu  Leu  Pro  Pro  Thr  Pro  Ala  Ser  His  Arg  Arg  Ser  Ser
    1520                1525                1530

Phe  Asn  Phe  Glu  Cys  Leu  Arg  Arg  Gln  Ser  Ser  Gln  Glu  Glu  Val
1535                1540                1545

Pro  Ser  Ser  Pro  Ile  Phe  Pro  His  Arg  Thr  Ala  Leu  Pro  Leu  His
    1550                1555                1560

Leu  Met  Gln  Gln  Gln  Ile  Met  Ala  Val  Ala  Gly  Leu  Asp  Ser  Ser
1565                1570                1575

Lys  Ala  Gln  Lys  Tyr  Ser  Pro  Ser  His  Ser  Thr  Arg  Ser  Trp  Ala
    1580                1585                1590

Thr  Pro  Pro  Ala  Thr  Pro  Pro  Tyr  Arg  Asp  Trp  Thr  Pro  Cys  Tyr
1595                1600                1605

Thr  Pro  Leu  Ile  Gln  Val  Glu  Gln  Ser  Glu  Ala  Leu  Asp  Gln  Val
    1610                1615                1620

Asn  Gly  Ser  Leu  Pro  Ser  Leu  His  Arg  Ser  Ser  Trp  Tyr  Thr  Asp
1625                1630                1635

Glu  Pro  Asp  Ile  Ser  Tyr  Arg  Thr  Phe  Thr  Pro  Ala  Ser  Leu  Thr
    1640                1645                1650

Val  Pro  Ser  Ser  Phe  Arg  Asn  Lys  Asn  Ser  Asp  Lys  Gln  Arg  Ser
1655                1660                1665

Ala  Asp  Ser  Leu  Val  Glu  Ala  Val  Leu  Ile  Ser  Glu  Gly  Leu  Gly
    1670                1675                1680

Arg  Tyr  Ala  Arg  Asp  Pro  Lys  Phe  Val  Ser  Ala  Thr  Lys  His  Glu
1685                1690                1695

Ile  Ala  Asp  Ala  Cys  Asp  Leu  Thr  Ile  Asp  Glu  Met  Glu  Ser  Ala
    1700                1705                1710

Ala  Ser  Thr  Leu  Leu  Asn  Gly  Asn  Val  Arg  Pro  Arg  Ala  Asn  Gly
1715                1720                1725

Asp  Val  Gly  Pro  Leu  Ser  His  Arg  Gln  Asp  Tyr  Glu  Leu  Gln  Asp
    1730                1735                1740

Phe  Gly  Pro  Gly  Tyr  Ser  Asp  Glu  Glu  Pro  Asp  Pro  Gly  Arg  Asp
1745                1750                1755

Glu  Glu  Asp  Leu  Ala  Asp  Glu  Met  Ile  Cys  Ile  Thr  Thr  Leu
    1760                1765                1770

<210> SEQ ID NO 17
<211> LENGTH: 7193
<212> TYPE: DNA
<213> ORGANISM: Homo sapiens
<220> FEATURE:
<221> NAME/KEY: gene
```

```
<222> LOCATION: (1)..(7193)
<220> FEATURE:
<221> NAME/KEY: CDS
<222> LOCATION: (119)..(6664)

<400> SEQUENCE: 17
agaataaggg cagggaccgc ggctcctatc tcttggtgat ccccttcccc attccgcccc        60
cgcctcaacg cccagcacag tgccctgcac acagtagtcg ctcaataaat gttcgtgg        118 atg atg atg atg atg atg atg aaa aaa atg cag cat caa cgg cag cag        166
Met Met Met Met Met Met Met Lys Lys Met Gln His Gln Arg Gln Gln
  1               5                  10                  15 caa gcg gac cac gcg aac gag gca aac tat gca aga ggc acc aga ctt        214
Gln Ala Asp His Ala Asn Glu Ala Asn Tyr Ala Arg Gly Thr Arg Leu
             20                  25                  30 cct ctt tct ggt gaa gga cca act tct cag ccg aat agc tcc aag caa        262
Pro Leu Ser Gly Glu Gly Pro Thr Ser Gln Pro Asn Ser Ser Lys Gln
         35                  40                  45 act gtc ctg tct tgg caa gct gca atc gat gct gct aga cag gcc aag        310
Thr Val Leu Ser Trp Gln Ala Ala Ile Asp Ala Ala Arg Gln Ala Lys
     50                  55                  60 gct gcc caa act atg agc acc tct gca ccc cca cct gta gga tct ctc        358
Ala Ala Gln Thr Met Ser Thr Ser Ala Pro Pro Pro Val Gly Ser Leu
 65                  70                  75                  80 tcc caa aga aaa cgt cag caa tac gcc aag agc aaa aaa cag ggt aac        406
Ser Gln Arg Lys Arg Gln Gln Tyr Ala Lys Ser Lys Lys Gln Gly Asn
                 85                  90                  95 tcg tcc aac agc cga cct gcc cgc gcc ctt ttc tgt tta tca ctc aat        454
Ser Ser Asn Ser Arg Pro Ala Arg Ala Leu Phe Cys Leu Ser Leu Asn
            100                 105                 110 aac ccc atc cga aga gcc tgc att agt ata gtg gaa tgg aaa cca ttt        502
Asn Pro Ile Arg Arg Ala Cys Ile Ser Ile Val Glu Trp Lys Pro Phe
        115                 120                 125 gac ata ttt ata tta ttg gct att ttt gcc aat tgt gtg gcc tta gct        550
Asp Ile Phe Ile Leu Leu Ala Ile Phe Ala Asn Cys Val Ala Leu Ala
    130                 135                 140 att tac atc cca ttc cct gaa gat gat tct aat tca aca aat cat aac        598
Ile Tyr Ile Pro Phe Pro Glu Asp Asp Ser Asn Ser Thr Asn His Asn
145                 150                 155                 160 ttg gaa aaa gta gaa tat gcc ttc ctg att att ttt aca gtc gag aca        646
Leu Glu Lys Val Glu Tyr Ala Phe Leu Ile Ile Phe Thr Val Glu Thr
                165                 170                 175 ttt ttg aag att ata gcg tat gga tta ttg cta cat cct aat gct tat        694
Phe Leu Lys Ile Ile Ala Tyr Gly Leu Leu Leu His Pro Asn Ala Tyr
            180                 185                 190 gtt agg aat gga tgg aat tta ctg gat ttt gtt ata gta ata gta gga        742
Val Arg Asn Gly Trp Asn Leu Leu Asp Phe Val Ile Val Ile Val Gly
        195                 200                 205 ttg ttt agt gta att ttg gaa caa tta acc aaa gaa aca gaa ggc ggg        790
Leu Phe Ser Val Ile Leu Glu Gln Leu Thr Lys Glu Thr Glu Gly Gly
    210                 215                 220 aac cac tca agc ggc aaa tct gga ggc ttt gat gtc aaa gcc ctc cgt        838
Asn His Ser Ser Gly Lys Ser Gly Gly Phe Asp Val Lys Ala Leu Arg
225                 230                 235                 240 gcc ttt cga gtg ttg cga cca ctt cga cta gtg tca ggg gtg ccc agt        886
Ala Phe Arg Val Leu Arg Pro Leu Arg Leu Val Ser Gly Val Pro Ser
                245                 250                 255 tta caa gtt gtc ctg aac tcc att ata aaa gcc atg gtt ccc ctc ctt        934
Leu Gln Val Val Leu Asn Ser Ile Ile Lys Ala Met Val Pro Leu Leu
            260                 265                 270
```

```
                                             -continued cac ata gcc ctt ttg gta tta ttt gta atc ata atc tat gct att ata       982
His Ile Ala Leu Leu Val Leu Phe Val Ile Ile Ile Tyr Ala Ile Ile
            275                 280                 285 gga ttg gaa ctt ttt att gga aaa atg cac aaa aca tgt ttt ttt gct      1030
Gly Leu Glu Leu Phe Ile Gly Lys Met His Lys Thr Cys Phe Phe Ala
290                 295                 300 gac tca gat atc gta gct gaa gag gac cca gct cca tgt gcg ttc tca      1078
Asp Ser Asp Ile Val Ala Glu Glu Asp Pro Ala Pro Cys Ala Phe Ser
305                 310                 315                 320 ggg aat gga cgc cag tgt act gcc aat ggc acg gaa tgt agg agt ggc      1126
Gly Asn Gly Arg Gln Cys Thr Ala Asn Gly Thr Glu Cys Arg Ser Gly
                325                 330                 335 tgg gtt ggc ccg aac gga ggc atc acc aac ttt gat aac ttt gcc ttt      1174
Trp Val Gly Pro Asn Gly Gly Ile Thr Asn Phe Asp Asn Phe Ala Phe
            340                 345                 350 gcc atg ctt act gtg ttt cag tgc atc acc atg gag ggc tgg aca gac      1222
Ala Met Leu Thr Val Phe Gln Cys Ile Thr Met Glu Gly Trp Thr Asp
355                 360                 365 gtg ctc tac tgg gta aat gat gcg ata gga tgg gaa tgg cca tgg gtg      1270
Val Leu Tyr Trp Val Asn Asp Ala Ile Gly Trp Glu Trp Pro Trp Val
370                 375                 380 tat ttt gtt agt ctg atc atc ctt ggc tca ttt ttc gtc ctt aac ctg      1318
Tyr Phe Val Ser Leu Ile Ile Leu Gly Ser Phe Phe Val Leu Asn Leu
385                 390                 395                 400 gtt ctt ggt gtc ctt agt gga gaa ttc tca aag gaa aga gag aag gca      1366
Val Leu Gly Val Leu Ser Gly Glu Phe Ser Lys Glu Arg Glu Lys Ala
                405                 410                 415 aaa gca cgg gga gat ttc cag aag ctc cgg gag aag cag cag ctg gag      1414
Lys Ala Arg Gly Asp Phe Gln Lys Leu Arg Glu Lys Gln Gln Leu Glu
            420                 425                 430 gag gat cta aag ggc tac ttg gat tgg atc acc caa gct gag gac atc      1462
Glu Asp Leu Lys Gly Tyr Leu Asp Trp Ile Thr Gln Ala Glu Asp Ile
435                 440                 445 gat ccg gag aat gag gaa gaa gga gga gag gaa ggc aaa cga aat act      1510
Asp Pro Glu Asn Glu Glu Glu Gly Gly Glu Glu Gly Lys Arg Asn Thr
450                 455                 460 agc atg ccc acc agc gag act gag tct gtg aac aca gag aac gtc agc      1558
Ser Met Pro Thr Ser Glu Thr Glu Ser Val Asn Thr Glu Asn Val Ser
465                 470                 475                 480 ggt gaa ggc gag aac cga ggc tgc tgt gga agt ctc tgg tgc tgg tgg      1606
Gly Glu Gly Glu Asn Arg Gly Cys Cys Gly Ser Leu Trp Cys Trp Trp
                485                 490                 495 aga cgg aga ggc gcg gcc aag gcg ggg ccc tct ggg tgt cgg cgg tgg      1654
Arg Arg Arg Gly Ala Ala Lys Ala Gly Pro Ser Gly Cys Arg Arg Trp
            500                 505                 510 ggt caa gcc atc tca aaa tcc aaa ctc agc cga cgc tgg cgt cgc tgg      1702
Gly Gln Ala Ile Ser Lys Ser Lys Leu Ser Arg Arg Trp Arg Arg Trp
515                 520                 525 aac cga ttc aat cgc aga aga tgt agg gcc gcc gtg aag tct gtc acg      1750
Asn Arg Phe Asn Arg Arg Arg Cys Arg Ala Ala Val Lys Ser Val Thr
530                 535                 540 ttt tac tgg ctg gtt atc gtc ctg gtg ttt ctg aac acc tta acc att      1798
Phe Tyr Trp Leu Val Ile Val Leu Val Phe Leu Asn Thr Leu Thr Ile
545                 550                 555                 560 tcc tct gag cac tac aat cag cca gat tgg ttg aca cag att caa gat      1846
Ser Ser Glu His Tyr Asn Gln Pro Asp Trp Leu Thr Gln Ile Gln Asp
                565                 570                 575 att gcc aac aaa gtc ctc ttg gct ctg ttc acc tgc gag atg ctg gta      1894
Ile Ala Asn Lys Val Leu Leu Ala Leu Phe Thr Cys Glu Met Leu Val
            580                 585                 590
```

```
aaa atg tac agc ttg ggc ctc caa gca tat ttc gtc tct ctt ttc aac      1942
Lys Met Tyr Ser Leu Gly Leu Gln Ala Tyr Phe Val Ser Leu Phe Asn
        595                 600                 605 cgg ttt gat tgc ttc gtg gtg tgt ggt gga atc act gag acg atc ctg      1990
Arg Phe Asp Cys Phe Val Val Cys Gly Gly Ile Thr Glu Thr Ile Leu
610                 615                 620 gtg gaa ctg gaa atc atg tct ccc ctg ggg atc tct gtg ttt cgg tgt      2038
Val Glu Leu Glu Ile Met Ser Pro Leu Gly Ile Ser Val Phe Arg Cys
625                 630                 635                 640 gtg cgc ctc tta aga atc ttc aaa gtg acc agg cac tgg act tcc ctg      2086
Val Arg Leu Leu Arg Ile Phe Lys Val Thr Arg His Trp Thr Ser Leu
                645                 650                 655 agc aac tta gtg gca tcc tta tta aac tcc atg aag tcc atc gct tcg      2134
Ser Asn Leu Val Ala Ser Leu Leu Asn Ser Met Lys Ser Ile Ala Ser
        660                 665                 670 ctg ttg ctt ctg ctt ttt ctc ttc att atc atc ttt tcc ttg ctt ggg      2182
Leu Leu Leu Leu Leu Phe Leu Phe Ile Ile Ile Phe Ser Leu Leu Gly
    675                 680                 685 atg cag ctg ttt ggc ggc aag ttt aat ttt gat gaa acg caa acc aag      2230
Met Gln Leu Phe Gly Gly Lys Phe Asn Phe Asp Glu Thr Gln Thr Lys
690                 695                 700 cgg agc acc ttt gac aat ttc cct caa gca ctt ctc aca gtg ttc cag      2278
Arg Ser Thr Phe Asp Asn Phe Pro Gln Ala Leu Leu Thr Val Phe Gln
705                 710                 715                 720 atc ctg aca ggc gaa gac tgg aat gct gtg atg tac gat ggc atc atg      2326
Ile Leu Thr Gly Glu Asp Trp Asn Ala Val Met Tyr Asp Gly Ile Met
                725                 730                 735 gct tac ggg ggc cca tcc tct tca gga atg atc gtc tgc atc tac ttc      2374
Ala Tyr Gly Gly Pro Ser Ser Ser Gly Met Ile Val Cys Ile Tyr Phe
        740                 745                 750 atc atc ctc ttc att tgt ggt aac tat att cta ctg aat gtc ttc ttg      2422
Ile Ile Leu Phe Ile Cys Gly Asn Tyr Ile Leu Leu Asn Val Phe Leu
    755                 760                 765 gcc atc gct gta gac aat ttg gct gat gct gaa agt ctg aac act gct      2470
Ala Ile Ala Val Asp Asn Leu Ala Asp Ala Glu Ser Leu Asn Thr Ala
770                 775                 780 cag aaa gaa gaa gcg gaa gaa aag gag agg aaa aag att gcc aga aaa      2518
Gln Lys Glu Glu Ala Glu Glu Lys Glu Arg Lys Lys Ile Ala Arg Lys
785                 790                 795                 800 gag agc cta gaa aat aaa aag aac aac aaa cca gaa gtc aac cag ata      2566
Glu Ser Leu Glu Asn Lys Lys Asn Asn Lys Pro Glu Val Asn Gln Ile
                805                 810                 815 gcc aac agt gac aac aag gtt aca att gat gac tat aga gaa gag gat      2614
Ala Asn Ser Asp Asn Lys Val Thr Ile Asp Asp Tyr Arg Glu Glu Asp
        820                 825                 830 gaa gac aag gac ccc tat ccg cct tgc gat gtg cca gta ggg gaa gag      2662
Glu Asp Lys Asp Pro Tyr Pro Pro Cys Asp Val Pro Val Gly Glu Glu
    835                 840                 845 gaa gag gaa gag gag gag gat gaa cct gag gtt cct gcc gga ccc cgt      2710
Glu Glu Glu Glu Glu Glu Asp Glu Pro Glu Val Pro Ala Gly Pro Arg
850                 855                 860 cct cga agg atc tcg gag ttg aac atg aag gaa aaa att gcc ccc atc      2758
Pro Arg Arg Ile Ser Glu Leu Asn Met Lys Glu Lys Ile Ala Pro Ile
865                 870                 875                 880 cct gaa ggg agc gct ttc ttc att ctt agc aag acc aac ccg atc cgc      2806
Pro Glu Gly Ser Ala Phe Phe Ile Leu Ser Lys Thr Asn Pro Ile Arg
                885                 890                 895 gta ggc tgc cac aag ctc atc aac cac cac atc ttc acc aac ctc atc      2854
Val Gly Cys His Lys Leu Ile Asn His His Ile Phe Thr Asn Leu Ile
```

```
                  900               905                 910
ctt gtc ttc atc atg ctg agc agc gct gcc ctg gcc gca gag gac ccc    2902
Leu Val Phe Ile Met Leu Ser Ser Ala Ala Leu Ala Ala Glu Asp Pro
                915                 920                 925 atc cgc agc cac tcc ttc cgg aac acg ata ctg ggt tac ttt gac tat    2950
Ile Arg Ser His Ser Phe Arg Asn Thr Ile Leu Gly Tyr Phe Asp Tyr
            930                 935                 940 gcc ttc aca gcc atc ttt act gtt gag atc ctg ttg aag atg aca act    2998
Ala Phe Thr Ala Ile Phe Thr Val Glu Ile Leu Leu Lys Met Thr Thr
945                 950                 955                 960 ttt gga gct ttc ctc cac aaa ggg gcc ttc tgc agg aac tac ttc aat    3046
Phe Gly Ala Phe Leu His Lys Gly Ala Phe Cys Arg Asn Tyr Phe Asn
                965                 970                 975 ttg ctg gat atg ctg gtg gtt ggg gtg tct ctg gtg tca ttt ggg att    3094
Leu Leu Asp Met Leu Val Val Gly Val Ser Leu Val Ser Phe Gly Ile
            980                 985                 990 caa tcc agt gcc atc tcc gtt gtg  aag att ctg agg gtc  tta agg gtc   3142
Gln Ser Ser Ala Ile Ser Val Val  Lys Ile Leu Arg Val  Leu Arg Val
                995                 1000                1005 ctg cgt  ccc ctc agg gcc atc  aac aga gca aaa gga  ctt aag cac      3187
Leu Arg  Pro Leu Arg Ala Ile  Asn Arg Ala Lys Gly  Leu Lys His
    1010                 1015                 1020 gtg gtc  cag tgc gtc ttc gtg  gcc atc cgg acc atc  ggc aac atc      3232
Val Val  Gln Cys Val Phe Val  Ala Ile Arg Thr Ile  Gly Asn Ile
    1025                 1030                 1035 atg atc  gtc act acc ctc ctg  cag ttc atg ttt gcc  tgt atc ggg      3277
Met Ile  Val Thr Thr Leu Leu  Gln Phe Met Phe Ala  Cys Ile Gly
    1040                 1045                 1050 gtc cag  ttg ttc aag ggg aag  ttc tat cgc tgt acg  gat gaa gcc      3322
Val Gln  Leu Phe Lys Gly Lys  Phe Tyr Arg Cys Thr  Asp Glu Ala
    1055                 1060                 1065 aaa agt  aac cct gaa gaa tgc  agg gga ctt ttc atc  ctc tac aag      3367
Lys Ser  Asn Pro Glu Glu Cys  Arg Gly Leu Phe Ile  Leu Tyr Lys
    1070                 1075                 1080 gat ggg  gat gtt gac agt cct  gtg gtc cgt gaa cgg  atc tgg caa      3412
Asp Gly  Asp Val Asp Ser Pro  Val Val Arg Glu Arg  Ile Trp Gln
    1085                 1090                 1095 aac agt  gat ttc aac ttc gac  aac gtc ctc tct gct  atg atg gcg      3457
Asn Ser  Asp Phe Asn Phe Asp  Asn Val Leu Ser Ala  Met Met Ala
    1100                 1105                 1110 ctc ttc  aca gtc tcc acg ttt  gag ggc tgg cct gcg  ttg ctg tat      3502
Leu Phe  Thr Val Ser Thr Phe  Glu Gly Trp Pro Ala  Leu Leu Tyr
    1115                 1120                 1125 aaa gcc  atc gac tcg aat gga  gag aac atc ggc cca  atc tac aac      3547
Lys Ala  Ile Asp Ser Asn Gly  Glu Asn Ile Gly Pro  Ile Tyr Asn
    1130                 1135                 1140 cac cgc  gtg gag atc tcc atc  ttc ttc atc atc tac  atc atc att      3592
His Arg  Val Glu Ile Ser Ile  Phe Phe Ile Ile Tyr  Ile Ile Ile
    1145                 1150                 1155 gta gct  ttc ttc atg atg aac  atc ttt gtg ggc ttt  gtc atc gtt      3637
Val Ala  Phe Phe Met Met Asn  Ile Phe Val Gly Phe  Val Ile Val
    1160                 1165                 1170 aca ttt  cag gaa caa gga gaa  aaa gag tat aag aac  tgt gag ctg      3682
Thr Phe  Gln Glu Gln Gly Glu  Lys Glu Tyr Lys Asn  Cys Glu Leu
    1175                 1180                 1185 gac aaa  aat cag cgt cag tgt  gtt gaa tac gcc ttg  aaa gca cgt      3727
Asp Lys  Asn Gln Arg Gln Cys  Val Glu Tyr Ala Leu  Lys Ala Arg
    1190                 1195                 1200 ccc ttg  cgg aga tac atc ccc  aaa aac ccc tac cag  tac aag ttc      3772
```

```
                                        -continued

Pro Leu Arg Arg Tyr Ile Pro Lys Asn Pro Tyr Gln Tyr Lys Phe
    1205                1210                1215 tgg tac gtg gtg aac tct tcg cct ttc gaa tac atg atg ttt gtc      3817
Trp Tyr Val Val Asn Ser Ser Pro Phe Glu Tyr Met Met Phe Val
    1220                1225                1230 ctc atc atg ctc aac aca ctc tgc ttg gcc atg cag cac tac gag      3862
Leu Ile Met Leu Asn Thr Leu Cys Leu Ala Met Gln His Tyr Glu
    1235                1240                1245 cag tcc aag atg ttc aat gat gcc atg gac att ctg aac atg gtc      3907
Gln Ser Lys Met Phe Asn Asp Ala Met Asp Ile Leu Asn Met Val
    1250                1255                1260 ttc acc ggg gtg ttc acc gtc gag atg gtt ttg aaa gtc atc gca      3952
Phe Thr Gly Val Phe Thr Val Glu Met Val Leu Lys Val Ile Ala
    1265                1270                1275 ttt aag cct aag ggg tat ttt agt gac gcc tgg aac acg ttt gac      3997
Phe Lys Pro Lys Gly Tyr Phe Ser Asp Ala Trp Asn Thr Phe Asp
    1280                1285                1290 tcc ctc atc gta atc ggc agc att ata gac gtg gcc ctc agc gaa      4042
Ser Leu Ile Val Ile Gly Ser Ile Ile Asp Val Ala Leu Ser Glu
    1295                1300                1305 gcg gac cca act gaa agt gaa aat gtc cct gtc cca act gct aca      4087
Ala Asp Pro Thr Glu Ser Glu Asn Val Pro Val Pro Thr Ala Thr
    1310                1315                1320 cct ggg aac tct gaa gag agc aat aga atc tcc atc acc ttt ttc      4132
Pro Gly Asn Ser Glu Glu Ser Asn Arg Ile Ser Ile Thr Phe Phe
    1325                1330                1335 cgt ctt ttc cga gtg atg cga ttg gtg aag ctt ctc agc agg ggg      4177
Arg Leu Phe Arg Val Met Arg Leu Val Lys Leu Leu Ser Arg Gly
    1340                1345                1350 gaa ggc atc cgg aca ttg ctg tgg act ttt att aag tcc ttt cag      4222
Glu Gly Ile Arg Thr Leu Leu Trp Thr Phe Ile Lys Ser Phe Gln
    1355                1360                1365 gcg ctc ccg tat gtg gcc ctc ctc ata gcc atg ctg ttc ttc atc      4267
Ala Leu Pro Tyr Val Ala Leu Leu Ile Ala Met Leu Phe Phe Ile
    1370                1375                1380 tat gcg gtc att ggc atg cag atg ttt ggg aaa gtt gcc atg aga      4312
Tyr Ala Val Ile Gly Met Gln Met Phe Gly Lys Val Ala Met Arg
    1385                1390                1395 gat aac aac cag atc aat agg aac aat aac ttc cag acg ttt ccc      4357
Asp Asn Asn Gln Ile Asn Arg Asn Asn Asn Phe Gln Thr Phe Pro
    1400                1405                1410 cag gcg gtg ctg ctc ctc ttc agg tgt gca aca ggt gag gcc tgg      4402
Gln Ala Val Leu Leu Leu Phe Arg Cys Ala Thr Gly Glu Ala Trp
    1415                1420                1425 cag gag atc atg ctg gcc tgt ctc cca ggg aag ctc tgt gac cct      4447
Gln Glu Ile Met Leu Ala Cys Leu Pro Gly Lys Leu Cys Asp Pro
    1430                1435                1440 gag tca gat tac aac ccc ggg gag gag tat aca tgt ggg agc aac      4492
Glu Ser Asp Tyr Asn Pro Gly Glu Glu Tyr Thr Cys Gly Ser Asn
    1445                1450                1455 ttt gcc att gtc tat ttc atc agt ttt tac atg ctc tgt gca ttt      4537
Phe Ala Ile Val Tyr Phe Ile Ser Phe Tyr Met Leu Cys Ala Phe
    1460                1465                1470 ctg atc atc aat ctg ttt gtg gct gtc atc atg gat aat ttc gac      4582
Leu Ile Ile Asn Leu Phe Val Ala Val Ile Met Asp Asn Phe Asp
    1475                1480                1485 tat ctg acc cgg gac tgg tct att ttg ggg cct cac cat tta gat      4627
Tyr Leu Thr Arg Asp Trp Ser Ile Leu Gly Pro His His Leu Asp
    1490                1495                1500
```

```
gaa ttc aaa aga ata tgg tca gaa tat gac cct gag gca aag gga        4672
Glu Phe Lys Arg Ile Trp Ser Glu Tyr Asp Pro Glu Ala Lys Gly
1505                1510                1515 agg ata aaa cac ctt gat gtg gtc act ctg ctt cga cgc atc cag        4717
Arg Ile Lys His Leu Asp Val Val Thr Leu Leu Arg Arg Ile Gln
    1520                1525                1530 cct ccc ctg ggg ttt ggg aag tta tgt cca cac agg gta gcg tgc        4762
Pro Pro Leu Gly Phe Gly Lys Leu Cys Pro His Arg Val Ala Cys
1535                1540                1545 aag aga tta gtt gcc atg aac atg cct ctc aac agt gac ggg aca        4807
Lys Arg Leu Val Ala Met Asn Met Pro Leu Asn Ser Asp Gly Thr
    1550                1555                1560 gtc atg ttt aat gca acc ctg ttt gct ttg gtt cga acg gct ctt        4852
Val Met Phe Asn Ala Thr Leu Phe Ala Leu Val Arg Thr Ala Leu
1565                1570                1575 aag atc aag acc gaa ggg aac ctg gag caa gct aat gaa gaa ctt        4897
Lys Ile Lys Thr Glu Gly Asn Leu Glu Gln Ala Asn Glu Glu Leu
    1580                1585                1590 cgg gct gtg ata aag aaa att tgg aag aaa acc agc atg aaa tta        4942
Arg Ala Val Ile Lys Lys Ile Trp Lys Lys Thr Ser Met Lys Leu
1595                1600                1605 ctt gac caa gtt gtc cct cca gct ggt gat gat gag gta acc gtg        4987
Leu Asp Gln Val Val Pro Pro Ala Gly Asp Asp Glu Val Thr Val
    1610                1615                1620 ggg aag ttc tat gcc act ttc ctg ata cag gac tac ttt agg aaa        5032
Gly Lys Phe Tyr Ala Thr Phe Leu Ile Gln Asp Tyr Phe Arg Lys
1625                1630                1635 ttc aag aaa cgg aaa gaa caa gga ctg gtg gga aag tac cct gcg        5077
Phe Lys Lys Arg Lys Glu Gln Gly Leu Val Gly Lys Tyr Pro Ala
    1640                1645                1650 aag aac acc aca att gcc cta cag gcg gga tta agg aca ctg cat        5122
Lys Asn Thr Thr Ile Ala Leu Gln Ala Gly Leu Arg Thr Leu His
1655                1660                1665 gac att ggg cca gaa atc cgg cgt gct ata tcg tgt gat ttg caa        5167
Asp Ile Gly Pro Glu Ile Arg Arg Ala Ile Ser Cys Asp Leu Gln
    1670                1675                1680 gat gac gag cct gag gaa aca aaa cga gaa gaa gaa gat gat gtg        5212
Asp Asp Glu Pro Glu Glu Thr Lys Arg Glu Glu Glu Asp Asp Val
1685                1690                1695 ttc aaa aga aat ggt gcc ctg ctt gga aac cat gtc aat cat gtt        5257
Phe Lys Arg Asn Gly Ala Leu Leu Gly Asn His Val Asn His Val
    1700                1705                1710 aat agt gat agg aga gat tcc ctt cag cag acc aat acc acc cac        5302
Asn Ser Asp Arg Arg Asp Ser Leu Gln Gln Thr Asn Thr Thr His
1715                1720                1725 cgt ccc ctg cat gtc caa agg cct tca att cca cct gca agt gat        5347
Arg Pro Leu His Val Gln Arg Pro Ser Ile Pro Pro Ala Ser Asp
    1730                1735                1740 act gag aaa ccg ctg ttt cct cca gca gga aat tcg gtg tgt cat        5392
Thr Glu Lys Pro Leu Phe Pro Pro Ala Gly Asn Ser Val Cys His
1745                1750                1755 aac cat cat aac cat aat tcc ata gga aag caa gtt ccc acc tca        5437
Asn His His Asn His Asn Ser Ile Gly Lys Gln Val Pro Thr Ser
    1760                1765                1770 aca aat gcc aat ctc aat aat gcc aat atg tcc aaa gct gcc cat        5482
Thr Asn Ala Asn Leu Asn Asn Ala Asn Met Ser Lys Ala Ala His
1775                1780                1785 gga aag cgg ccc agc att ggg aac ctt gag cat gtg tct gaa aat        5527
Gly Lys Arg Pro Ser Ile Gly Asn Leu Glu His Val Ser Glu Asn
1790                1795                1800
```

```
ggg cat cat tct tcc cac aag cat gac cgg gag cct cag aga agg      5572
Gly His His Ser Ser His Lys His Asp Arg Glu Pro Gln Arg Arg
    1805            1810                1815 tcc agt gtg aaa aga acc cgc tat tat gaa act tac att agg tcc      5617
Ser Ser Val Lys Arg Thr Arg Tyr Tyr Glu Thr Tyr Ile Arg Ser
    1820            1825                1830 gac tca gga gat gaa cag ctc cca act att tgc cgg gaa gac cca      5662
Asp Ser Gly Asp Glu Gln Leu Pro Thr Ile Cys Arg Glu Asp Pro
    1835            1840                1845 gag ata cat ggc tat ttc agg gac ccc cac tgc ttg ggg gag cag      5707
Glu Ile His Gly Tyr Phe Arg Asp Pro His Cys Leu Gly Glu Gln
    1850            1855                1860 gag tat ttc agt agt gag gaa tgc tac gag gat gac agc tcg ccc      5752
Glu Tyr Phe Ser Ser Glu Glu Cys Tyr Glu Asp Asp Ser Ser Pro
    1865            1870                1875 acc tgg agc agg caa aac tat ggc tac tac agc aga tac cca ggc      5797
Thr Trp Ser Arg Gln Asn Tyr Gly Tyr Tyr Ser Arg Tyr Pro Gly
    1880            1885                1890 aga aac atc gac tct gag agg ccc cga ggc tac cat cat ccc caa      5842
Arg Asn Ile Asp Ser Glu Arg Pro Arg Gly Tyr His His Pro Gln
    1895            1900                1905 gga ttc ttg gag gac gat gac tcg ccc gtt tgc tat gat tca cgg      5887
Gly Phe Leu Glu Asp Asp Asp Ser Pro Val Cys Tyr Asp Ser Arg
    1910            1915                1920 aga tct cca agg aga cgc cta cta cct ccc acc cca gca tcc cac      5932
Arg Ser Pro Arg Arg Arg Leu Leu Pro Pro Thr Pro Ala Ser His
    1925            1930                1935 cgg aga tcc tcc ttc aac ttt gag tgc ctg cgc cgg cag agc agc      5977
Arg Arg Ser Ser Phe Asn Phe Glu Cys Leu Arg Arg Gln Ser Ser
    1940            1945                1950 cag gaa gag gtc ccg tcg tct ccc atc ttc ccc cat cgc acg gcc      6022
Gln Glu Glu Val Pro Ser Ser Pro Ile Phe Pro His Arg Thr Ala
    1955            1960                1965 ctg cct ctg cat cta atg cag caa cag atc atg gca gtt gcc ggc      6067
Leu Pro Leu His Leu Met Gln Gln Gln Ile Met Ala Val Ala Gly
    1970            1975                1980 cta gat tca agt aaa gcc cag aag tac tca ccg agt cac tcg acc      6112
Leu Asp Ser Ser Lys Ala Gln Lys Tyr Ser Pro Ser His Ser Thr
    1985            1990                1995 cgg tcg tgg gcc acc cct cca gca acc cct ccc tac cgg gac tgg      6157
Arg Ser Trp Ala Thr Pro Pro Ala Thr Pro Pro Tyr Arg Asp Trp
    2000            2005                2010 aca ccg tgc tac acc ccc ctg atc caa gtg gag cag tca gag gcc      6202
Thr Pro Cys Tyr Thr Pro Leu Ile Gln Val Glu Gln Ser Glu Ala
    2015            2020                2025 ctg gac cag gtg aac ggc agc ctg ccg tcc ctg cac cgc agc tcc      6247
Leu Asp Gln Val Asn Gly Ser Leu Pro Ser Leu His Arg Ser Ser
    2030            2035                2040 tgg tac aca gac gag ccc gac atc tcc tac cgg act ttc aca cca      6292
Trp Tyr Thr Asp Glu Pro Asp Ile Ser Tyr Arg Thr Phe Thr Pro
    2045            2050                2055 gcc agc ctg act gtc ccc agc agc ttc cgg aac aaa aac agc gac      6337
Ala Ser Leu Thr Val Pro Ser Ser Phe Arg Asn Lys Asn Ser Asp
    2060            2065                2070 aag cag agg agt gcg gac agc ttg gtg gag gca gtc ctg ata tcc      6382
Lys Gln Arg Ser Ala Asp Ser Leu Val Glu Ala Val Leu Ile Ser
    2075            2080                2085 gaa ggc ttg gga cgc tat gca agg gac cca aaa ttt gtg tca gca      6427
Glu Gly Leu Gly Arg Tyr Ala Arg Asp Pro Lys Phe Val Ser Ala
```

-continued

```
         2090                2095                2100
aca aaa cac gaa atc gct gat gcc tgt gac ctc acc atc gac gag      6472
Thr Lys His Glu Ile Ala Asp Ala Cys Asp Leu Thr Ile Asp Glu
    2105                2110                2115 atg gag agt gca gcc agc acc ctg ctt aat ggg aac gtg cgt ccc      6517
Met Glu Ser Ala Ala Ser Thr Leu Leu Asn Gly Asn Val Arg Pro
    2120                2125                2130 cga gcc aac ggg gat gtg ggc ccc ctc tca cac cgg cag gac tat      6562
Arg Ala Asn Gly Asp Val Gly Pro Leu Ser His Arg Gln Asp Tyr
    2135                2140                2145 gag cta cag gac ttt ggt cct ggc tac agc gac gaa gag cca gac      6607
Glu Leu Gln Asp Phe Gly Pro Gly Tyr Ser Asp Glu Glu Pro Asp
    2150                2155                2160 cct ggg agg gat gag gag gac ctg gcg gat gaa atg ata tgc atc      6652
Pro Gly Arg Asp Glu Glu Asp Leu Ala Asp Glu Met Ile Cys Ile
    2165                2170                2175 acc acc ttg tag cccccagcga ggggcagact ggctctggcc tcaggtgggg      6704
Thr Thr Leu
    2180 cgcaggagag ccaggggaaa agtgcctcat agttaggaaa gtttaggcac tagttgggag   6764 taatattcaa ttaattagac ttttgtataa gagatgtcat gcctcaagaa agccataaac   6824 ctggtaggaa caggtcccaa gcggttgagc ctggcagagt accatgcgct cggccccagc   6884 tgcaggaaac agcaggcccc gccctctcac agaggatggg tgaggaggcc agacctgccc   6944 tgccccattg tccagatggg cactgctgtg gagtctgctt ctcccatgta ccagggcacc   7004 aggcccaccc aactgaaggc atggcggcgg ggtgcagggg aaagttaaag gtgatgacga   7064 tcatcacacc tcgtgtcgtt acctcagcca tcggtctagc atatcagtca ctgggcccaa   7124 catatccatt tttaaaccct ttcccccaaa tacactgcgt cctggttcct gtttagctgt   7184 tctgaaata                                                          7193
```

<210> SEQ ID NO 18
<211> LENGTH: 2181
<212> TYPE: PRT
<213> ORGANISM: Homo sapiens

<400> SEQUENCE: 18

```
Met Met Met Met Met Met Met Lys Lys Met Gln His Gln Arg Gln Gln
1               5                   10                  15

Gln Ala Asp His Ala Asn Glu Ala Asn Tyr Ala Arg Gly Thr Arg Leu
            20                  25                  30

Pro Leu Ser Gly Glu Gly Pro Thr Ser Gln Pro Asn Ser Ser Lys Gln
        35                  40                  45

Thr Val Leu Ser Trp Gln Ala Ala Ile Asp Ala Ala Arg Gln Ala Lys
    50                  55                  60

Ala Ala Gln Thr Met Ser Thr Ser Ala Pro Pro Val Gly Ser Leu
65                  70                  75                  80

Ser Gln Arg Lys Arg Gln Gln Tyr Ala Lys Ser Lys Lys Gln Gly Asn
                85                  90                  95

Ser Ser Asn Ser Arg Pro Ala Arg Ala Leu Phe Cys Leu Ser Leu Asn
            100                 105                 110

Asn Pro Ile Arg Arg Ala Cys Ile Ser Ile Val Glu Trp Lys Pro Phe
        115                 120                 125

Asp Ile Phe Ile Leu Leu Ala Ile Phe Ala Asn Cys Val Ala Leu Ala
    130                 135                 140
```

-continued

```
Ile Tyr Ile Pro Phe Pro Glu Asp Asp Ser Asn Ser Thr Asn His Asn
145                 150                 155                 160

Leu Glu Lys Val Glu Tyr Ala Phe Leu Ile Ile Phe Thr Val Glu Thr
                165                 170                 175

Phe Leu Lys Ile Ile Ala Tyr Gly Leu Leu His Pro Asn Ala Tyr
            180                 185                 190

Val Arg Asn Gly Trp Asn Leu Leu Asp Phe Val Ile Val Ile Val Gly
        195                 200                 205

Leu Phe Ser Val Ile Leu Glu Gln Leu Thr Lys Glu Thr Glu Gly Gly
    210                 215                 220

Asn His Ser Ser Gly Lys Ser Gly Gly Phe Asp Val Lys Ala Leu Arg
225                 230                 235                 240

Ala Phe Arg Val Leu Arg Pro Leu Arg Leu Val Ser Gly Val Pro Ser
                245                 250                 255

Leu Gln Val Val Leu Asn Ser Ile Ile Lys Ala Met Val Pro Leu Leu
                260                 265                 270

His Ile Ala Leu Leu Val Leu Phe Val Ile Ile Tyr Ala Ile Ile
            275                 280                 285

Gly Leu Glu Leu Phe Ile Gly Lys Met His Lys Thr Cys Phe Phe Ala
            290                 295                 300

Asp Ser Asp Ile Val Ala Glu Asp Pro Ala Pro Cys Ala Phe Ser
305                 310                 315                 320

Gly Asn Gly Arg Gln Cys Thr Ala Asn Gly Thr Glu Cys Arg Ser Gly
                325                 330                 335

Trp Val Gly Pro Asn Gly Gly Ile Thr Asn Phe Asp Asn Phe Ala Phe
                340                 345                 350

Ala Met Leu Thr Val Phe Gln Cys Ile Thr Met Glu Gly Trp Thr Asp
            355                 360                 365

Val Leu Tyr Trp Val Asn Asp Ala Ile Gly Trp Glu Trp Pro Trp Val
        370                 375                 380

Tyr Phe Val Ser Leu Ile Ile Leu Gly Ser Phe Phe Val Leu Asn Leu
385                 390                 395                 400

Val Leu Gly Val Leu Ser Gly Glu Phe Ser Lys Glu Arg Glu Lys Ala
                405                 410                 415

Lys Ala Arg Gly Asp Phe Gln Lys Leu Arg Glu Lys Gln Gln Leu Glu
            420                 425                 430

Glu Asp Leu Lys Gly Tyr Leu Asp Trp Ile Thr Gln Ala Glu Asp Ile
        435                 440                 445

Asp Pro Glu Asn Glu Glu Gly Glu Gly Lys Arg Asn Thr
    450                 455                 460

Ser Met Pro Thr Ser Glu Thr Glu Ser Val Asn Thr Glu Asn Val Ser
465                 470                 475                 480

Gly Glu Gly Glu Asn Arg Gly Cys Cys Gly Ser Leu Trp Cys Trp Trp
                485                 490                 495

Arg Arg Arg Gly Ala Ala Lys Ala Gly Pro Ser Gly Cys Arg Arg Trp
            500                 505                 510

Gly Gln Ala Ile Ser Lys Ser Lys Leu Ser Arg Arg Trp Arg Arg Trp
        515                 520                 525

Asn Arg Phe Asn Arg Arg Cys Arg Ala Ala Val Lys Ser Val Thr
    530                 535                 540

Phe Tyr Trp Leu Val Ile Val Leu Val Phe Leu Asn Thr Leu Thr Ile
545                 550                 555                 560

Ser Ser Glu His Tyr Asn Gln Pro Asp Trp Leu Thr Gln Ile Gln Asp
```

-continued

```
                565                 570                 575
Ile Ala Asn Lys Val Leu Leu Ala Leu Phe Thr Cys Glu Met Leu Val
            580                 585                 590
Lys Met Tyr Ser Leu Gly Leu Gln Ala Tyr Phe Val Ser Leu Phe Asn
            595                 600                 605
Arg Phe Asp Cys Phe Val Val Cys Gly Gly Ile Thr Glu Thr Ile Leu
            610                 615                 620
Val Glu Leu Glu Ile Met Ser Pro Leu Gly Ile Ser Val Phe Arg Cys
625                 630                 635                 640
Val Arg Leu Leu Arg Ile Phe Lys Val Thr Arg His Trp Thr Ser Leu
            645                 650                 655
Ser Asn Leu Val Ala Ser Leu Leu Asn Ser Met Lys Ser Ile Ala Ser
            660                 665                 670
Leu Leu Leu Leu Leu Phe Leu Phe Ile Ile Ile Phe Ser Leu Leu Gly
            675                 680                 685
Met Gln Leu Phe Gly Gly Lys Phe Asn Phe Asp Glu Thr Gln Thr Lys
            690                 695                 700
Arg Ser Thr Phe Asp Asn Phe Pro Gln Ala Leu Leu Thr Val Phe Gln
705                 710                 715                 720
Ile Leu Thr Gly Glu Asp Trp Asn Ala Val Met Tyr Asp Gly Ile Met
            725                 730                 735
Ala Tyr Gly Gly Pro Ser Ser Gly Met Ile Val Cys Ile Tyr Phe
            740                 745                 750
Ile Ile Leu Phe Ile Cys Gly Asn Tyr Ile Leu Leu Asn Val Phe Leu
            755                 760                 765
Ala Ile Ala Val Asp Asn Leu Ala Asp Ala Glu Ser Leu Asn Thr Ala
            770                 775                 780
Gln Lys Glu Glu Ala Glu Lys Glu Arg Lys Ile Ala Arg Lys
785                 790                 795                 800
Glu Ser Leu Glu Asn Lys Lys Asn Asn Lys Pro Glu Val Asn Gln Ile
            805                 810                 815
Ala Asn Ser Asp Asn Lys Val Thr Ile Asp Asp Tyr Arg Glu Glu Asp
            820                 825                 830
Glu Asp Lys Asp Pro Tyr Pro Pro Cys Asp Val Pro Val Gly Glu Glu
            835                 840                 845
Glu Glu Glu Glu Glu Glu Asp Glu Pro Glu Val Pro Ala Gly Pro Arg
            850                 855                 860
Pro Arg Arg Ile Ser Glu Leu Asn Met Lys Glu Lys Ile Ala Pro Ile
865                 870                 875                 880
Pro Glu Gly Ser Ala Phe Phe Ile Leu Ser Lys Thr Asn Pro Ile Arg
            885                 890                 895
Val Gly Cys His Lys Leu Ile Asn His His Ile Phe Thr Asn Leu Ile
            900                 905                 910
Leu Val Phe Ile Met Leu Ser Ser Ala Ala Leu Ala Ala Glu Asp Pro
            915                 920                 925
Ile Arg Ser His Ser Phe Arg Asn Thr Ile Leu Gly Tyr Phe Asp Tyr
            930                 935                 940
Ala Phe Thr Ala Ile Phe Thr Val Glu Ile Leu Leu Lys Met Thr Thr
945                 950                 955                 960
Phe Gly Ala Phe Leu His Lys Gly Ala Phe Cys Arg Asn Tyr Phe Asn
            965                 970                 975
Leu Leu Asp Met Leu Val Val Gly Val Ser Leu Val Ser Phe Gly Ile
            980                 985                 990
```

```
Gln Ser Ser Ala Ile Ser Val Val  Lys Ile Leu Arg Val  Leu Arg Val
        995              1000              1005

Leu Arg  Pro Leu Arg Ala Ile  Asn Arg Ala Lys Gly  Leu Lys His
    1010              1015              1020

Val Val  Gln Cys Val Phe Val  Ala Ile Arg Thr Ile  Gly Asn Ile
    1025              1030              1035

Met Ile  Val Thr Thr Leu Leu  Gln Phe Met Phe Ala  Cys Ile Gly
    1040              1045              1050

Val Gln  Leu Phe Lys Gly Lys  Phe Tyr Arg Cys Thr  Asp Glu Ala
    1055              1060              1065

Lys Ser  Asn Pro Glu Glu Cys  Arg Gly Leu Phe Ile  Leu Tyr Lys
    1070              1075              1080

Asp Gly  Asp Val Asp Ser Pro  Val Val Arg Glu Arg  Ile Trp Gln
    1085              1090              1095

Asn Ser  Asp Phe Asn Phe Asp  Asn Val Leu Ser Ala  Met Met Ala
    1100              1105              1110

Leu Phe  Thr Val Ser Thr Phe  Glu Gly Trp Pro Ala  Leu Leu Tyr
    1115              1120              1125

Lys Ala  Ile Asp Ser Asn Gly  Glu Asn Ile Gly Pro  Ile Tyr Asn
    1130              1135              1140

His Arg  Val Glu Ile Ser Ile  Phe Phe Ile Ile Tyr  Ile Ile Ile
    1145              1150              1155

Val Ala  Phe Phe Met Met Asn  Ile Phe Val Gly Phe  Val Ile Val
    1160              1165              1170

Thr Phe  Gln Glu Gln Gly Glu  Lys Glu Tyr Lys Asn  Cys Glu Leu
    1175              1180              1185

Asp Lys  Asn Gln Arg Gln Cys  Val Glu Tyr Ala Leu  Lys Ala Arg
    1190              1195              1200

Pro Leu  Arg Arg Tyr Ile Pro  Lys Asn Pro Tyr Gln  Tyr Lys Phe
    1205              1210              1215

Trp Tyr  Val Val Asn Ser Ser  Pro Phe Glu Tyr Met  Met Phe Val
    1220              1225              1230

Leu Ile  Met Leu Asn Thr Leu  Cys Leu Ala Met Gln  His Tyr Glu
    1235              1240              1245

Gln Ser  Lys Met Phe Asn Asp  Ala Met Asp Ile Leu  Asn Met Val
    1250              1255              1260

Phe Thr  Gly Val Phe Thr Val  Glu Met Val Leu Lys  Val Ile Ala
    1265              1270              1275

Phe Lys  Pro Lys Gly Tyr Phe  Ser Asp Ala Trp Asn  Thr Phe Asp
    1280              1285              1290

Ser Leu  Ile Val Ile Gly Ser  Ile Ile Asp Val Ala  Leu Ser Glu
    1295              1300              1305

Ala Asp  Pro Thr Glu Ser Glu  Asn Val Pro Val Pro  Thr Ala Thr
    1310              1315              1320

Pro Gly  Asn Ser Glu Glu Ser  Asn Arg Ile Ser Ile  Thr Phe Phe
    1325              1330              1335

Arg Leu  Phe Arg Val Met Arg  Leu Val Lys Leu Leu  Ser Arg Gly
    1340              1345              1350

Glu Gly  Ile Arg Thr Leu Leu  Trp Thr Phe Ile Lys  Ser Phe Gln
    1355              1360              1365

Ala Leu  Pro Tyr Val Ala Leu  Leu Ile Ala Met Leu  Phe Phe Ile
    1370              1375              1380
```

```
Tyr Ala Val Ile Gly Met Gln Met Phe Gly Lys Val Ala Met Arg
1385                1390                1395

Asp Asn Asn Gln Ile Asn Arg Asn Asn Asn Phe Gln Thr Phe Pro
1400                1405                1410

Gln Ala Val Leu Leu Leu Phe Arg Cys Ala Thr Gly Glu Ala Trp
1415                1420                1425

Gln Glu Ile Met Leu Ala Cys Leu Pro Gly Lys Leu Cys Asp Pro
1430                1435                1440

Glu Ser Asp Tyr Asn Pro Gly Glu Glu Tyr Thr Cys Gly Ser Asn
1445                1450                1455

Phe Ala Ile Val Tyr Phe Ile Ser Phe Tyr Met Leu Cys Ala Phe
1460                1465                1470

Leu Ile Ile Asn Leu Phe Val Ala Val Ile Met Asp Asn Phe Asp
1475                1480                1485

Tyr Leu Thr Arg Asp Trp Ser Ile Leu Gly Pro His His Leu Asp
1490                1495                1500

Glu Phe Lys Arg Ile Trp Ser Glu Tyr Asp Pro Glu Ala Lys Gly
1505                1510                1515

Arg Ile Lys His Leu Asp Val Val Thr Leu Leu Arg Arg Ile Gln
1520                1525                1530

Pro Pro Leu Gly Phe Gly Lys Leu Cys Pro His Arg Val Ala Cys
1535                1540                1545

Lys Arg Leu Val Ala Met Asn Met Pro Leu Asn Ser Asp Gly Thr
1550                1555                1560

Val Met Phe Asn Ala Thr Leu Phe Ala Leu Val Arg Thr Ala Leu
1565                1570                1575

Lys Ile Lys Thr Glu Gly Asn Leu Glu Gln Ala Asn Glu Glu Leu
1580                1585                1590

Arg Ala Val Ile Lys Lys Ile Trp Lys Lys Thr Ser Met Lys Leu
1595                1600                1605

Leu Asp Gln Val Val Pro Pro Ala Gly Asp Asp Glu Val Thr Val
1610                1615                1620

Gly Lys Phe Tyr Ala Thr Phe Leu Ile Gln Asp Tyr Phe Arg Lys
1625                1630                1635

Phe Lys Lys Arg Lys Glu Gln Gly Leu Val Gly Lys Tyr Pro Ala
1640                1645                1650

Lys Asn Thr Thr Ile Ala Leu Gln Ala Gly Leu Arg Thr Leu His
1655                1660                1665

Asp Ile Gly Pro Glu Ile Arg Arg Ala Ile Ser Cys Asp Leu Gln
1670                1675                1680

Asp Asp Glu Pro Glu Glu Thr Lys Arg Glu Glu Glu Asp Asp Val
1685                1690                1695

Phe Lys Arg Asn Gly Ala Leu Leu Gly Asn His Val Asn His Val
1700                1705                1710

Asn Ser Asp Arg Arg Asp Ser Leu Gln Gln Thr Asn Thr Thr His
1715                1720                1725

Arg Pro Leu His Val Gln Arg Pro Ser Ile Pro Pro Ala Ser Asp
1730                1735                1740

Thr Glu Lys Pro Leu Phe Pro Pro Ala Gly Asn Ser Val Cys His
1745                1750                1755

Asn His His Asn His Asn Ser Ile Gly Lys Gln Val Pro Thr Ser
1760                1765                1770

Thr Asn Ala Asn Leu Asn Asn Ala Asn Met Ser Lys Ala Ala His
```

-continued

```
            1775                1780                1785

Gly Lys Arg Pro Ser Ile Gly Asn Leu Glu His Val Ser Glu Asn
    1790                1795                1800

Gly His His Ser Ser His Lys His Asp Arg Glu Pro Gln Arg Arg
    1805                1810                1815

Ser Ser Val Lys Arg Thr Arg Tyr Tyr Glu Thr Tyr Ile Arg Ser
    1820                1825                1830

Asp Ser Gly Asp Glu Gln Leu Pro Thr Ile Cys Arg Glu Asp Pro
    1835                1840                1845

Glu Ile His Gly Tyr Phe Arg Asp Pro His Cys Leu Gly Glu Gln
    1850                1855                1860

Glu Tyr Phe Ser Ser Glu Glu Cys Tyr Glu Asp Asp Ser Ser Pro
    1865                1870                1875

Thr Trp Ser Arg Gln Asn Tyr Gly Tyr Tyr Ser Arg Tyr Pro Gly
    1880                1885                1890

Arg Asn Ile Asp Ser Glu Arg Pro Arg Gly Tyr His His Pro Gln
    1895                1900                1905

Gly Phe Leu Glu Asp Asp Asp Ser Pro Val Cys Tyr Asp Ser Arg
    1910                1915                1920

Arg Ser Pro Arg Arg Leu Leu Pro Pro Thr Pro Ala Ser His
    1925                1930                1935

Arg Arg Ser Ser Phe Asn Phe Glu Cys Leu Arg Arg Gln Ser Ser
    1940                1945                1950

Gln Glu Glu Val Pro Ser Ser Pro Ile Phe Pro His Arg Thr Ala
    1955                1960                1965

Leu Pro Leu His Leu Met Gln Gln Ile Met Ala Val Ala Gly
    1970                1975                1980

Leu Asp Ser Ser Lys Ala Gln Lys Tyr Ser Pro Ser His Ser Thr
    1985                1990                1995

Arg Ser Trp Ala Thr Pro Pro Ala Thr Pro Pro Tyr Arg Asp Trp
    2000                2005                2010

Thr Pro Cys Tyr Thr Pro Leu Ile Gln Val Glu Gln Ser Glu Ala
    2015                2020                2025

Leu Asp Gln Val Asn Gly Ser Leu Pro Ser Leu His Arg Ser Ser
    2030                2035                2040

Trp Tyr Thr Asp Glu Pro Asp Ile Ser Tyr Arg Thr Phe Thr Pro
    2045                2050                2055

Ala Ser Leu Thr Val Pro Ser Ser Phe Arg Asn Lys Asn Ser Asp
    2060                2065                2070

Lys Gln Arg Ser Ala Asp Ser Leu Val Glu Ala Val Leu Ile Ser
    2075                2080                2085

Glu Gly Leu Gly Arg Tyr Ala Arg Asp Pro Lys Phe Val Ser Ala
    2090                2095                2100

Thr Lys His Glu Ile Ala Asp Ala Cys Asp Leu Thr Ile Asp Glu
    2105                2110                2115

Met Glu Ser Ala Ala Ser Thr Leu Leu Asn Gly Asn Val Arg Pro
    2120                2125                2130

Arg Ala Asn Gly Asp Val Gly Pro Leu Ser His Arg Gln Asp Tyr
    2135                2140                2145

Glu Leu Gln Asp Phe Gly Pro Gly Tyr Ser Asp Glu Glu Pro Asp
    2150                2155                2160

Pro Gly Arg Asp Glu Glu Asp Leu Ala Asp Glu Met Ile Cys Ile
    2165                2170                2175
```

-continued

```
Thr Thr Leu
    2180

<210> SEQ ID NO 19
<211> LENGTH: 7193
<212> TYPE: DNA
<213> ORGANISM: Homo sapiens
<220> FEATURE:
<221> NAME/KEY: gene
<222> LOCATION: (1)..(7193)
<220> FEATURE:
<221> NAME/KEY: CDS
<222> LOCATION: (119)..(6664)

<400> SEQUENCE: 19
agaataaggg cagggaccgc ggctcctatc tcttggtgat cccttcccc attccgcccc      60 cgcctcaacg cccagcacag tgccctgcac acagtagtcg ctcaataaat gttcgtgg    118 atg atg atg atg atg atg atg aaa aaa atg cag cat caa cgg cag cag     166
Met Met Met Met Met Met Met Lys Lys Met Gln His Gln Arg Gln Gln
1               5                  10                  15 caa gcg gac cac gcg aac gag gca aac tat gca aga ggc acc aga ctt     214
Gln Ala Asp His Ala Asn Glu Ala Asn Tyr Ala Arg Gly Thr Arg Leu
            20                  25                  30 cct ctt tct ggt gaa gga cca act tct cag ccg aat agc tcc aag caa     262
Pro Leu Ser Gly Glu Gly Pro Thr Ser Gln Pro Asn Ser Ser Lys Gln
        35                  40                  45 act gtc ctg tct tgg caa gct gca atc gat gct gct aga cag gcc aag     310
Thr Val Leu Ser Trp Gln Ala Ala Ile Asp Ala Ala Arg Gln Ala Lys
    50                  55                  60 gct gcc caa act atg agc acc tct gca ccc cca cct gta gga tct ctc     358
Ala Ala Gln Thr Met Ser Thr Ser Ala Pro Pro Pro Val Gly Ser Leu
65                  70                  75                  80 tcc caa aga aaa cgt cag caa tac gcc aag agc aaa aaa cag ggt aac     406
Ser Gln Arg Lys Arg Gln Gln Tyr Ala Lys Ser Lys Lys Gln Gly Asn
                85                  90                  95 tcg tcc aac agc cga cct gcc cgc gcc ctt ttc tgt tta tca ctc aat     454
Ser Ser Asn Ser Arg Pro Ala Arg Ala Leu Phe Cys Leu Ser Leu Asn
            100                 105                 110 aac ccc atc cga aga gcc tgc att agt ata gtg gaa tgg aaa cca ttt     502
Asn Pro Ile Arg Arg Ala Cys Ile Ser Ile Val Glu Trp Lys Pro Phe
        115                 120                 125 gac ata ttt ata tta ttg gct att ttt gcc aat tgt gtg gcc tta gct     550
Asp Ile Phe Ile Leu Leu Ala Ile Phe Ala Asn Cys Val Ala Leu Ala
    130                 135                 140 att tac atc cca ttc cct gaa gat gat tct aat tca aca aat cat aac     598
Ile Tyr Ile Pro Phe Pro Glu Asp Asp Ser Asn Ser Thr Asn His Asn
145                 150                 155                 160 ttg gaa aaa gta gaa tat gcc ttc ctg att att ttt aca gtc gag aca     646
Leu Glu Lys Val Glu Tyr Ala Phe Leu Ile Ile Phe Thr Val Glu Thr
                165                 170                 175 ttt ttg aag att ata gcg tat gga tta ttg cta cat cct aat gct tat     694
Phe Leu Lys Ile Ile Ala Tyr Gly Leu Leu Leu His Pro Asn Ala Tyr
            180                 185                 190 gtt agg aat gga tgg aat tta ctg gat ttt gtt ata gta ata gta gga     742
Val Arg Asn Gly Trp Asn Leu Leu Asp Phe Val Ile Val Ile Val Gly
        195                 200                 205 ttg ttt agt gta att ttg gaa caa tta acc aaa gaa aca gaa ggc ggg     790
Leu Phe Ser Val Ile Leu Glu Gln Leu Thr Lys Glu Thr Glu Gly Gly
    210                 215                 220 aac cac tca agc ggc aaa tct gga ggc ttt gat gtc aaa gcc ctc cgt     838
```

-continued

```
Asn His Ser Ser Gly Lys Ser Gly Gly Phe Asp Val Lys Ala Leu Arg
225                 230                 235                 240 gcc ttt cga gtg ttg cga cca ctt cga cta gtg tca ggg gtg ccc agt      886
Ala Phe Arg Val Leu Arg Pro Leu Arg Leu Val Ser Gly Val Pro Ser
                245                 250                 255 tta caa gtt gtc ctg aac tcc att ata aaa gcc atg gtt ccc ctc ctt      934
Leu Gln Val Val Leu Asn Ser Ile Ile Lys Ala Met Val Pro Leu Leu
            260                 265                 270 cac ata gcc ctt ttg gta tta ttt gta atc ata atc tat gct att ata      982
His Ile Ala Leu Leu Val Leu Phe Val Ile Ile Ile Tyr Ala Ile Ile
        275                 280                 285 gga ttg gaa ctt ttt att gga aaa atg cac aaa aca tgt ttt ttt gct     1030
Gly Leu Glu Leu Phe Ile Gly Lys Met His Lys Thr Cys Phe Phe Ala
    290                 295                 300 gac tca gat atc gta gct gaa gag gac cca gct cca tgt gcg ttc tca     1078
Asp Ser Asp Ile Val Ala Glu Glu Asp Pro Ala Pro Cys Ala Phe Ser
305                 310                 315                 320 ggg aat gga cgc cag tgt act gcc aat ggc acg gaa tgt agg agt ggc     1126
Gly Asn Gly Arg Gln Cys Thr Ala Asn Gly Thr Glu Cys Arg Ser Gly
                325                 330                 335 tgg gtt ggc ccg aac gga ggc atc acc aac ttt gat aac ttt gcc ttt     1174
Trp Val Gly Pro Asn Gly Gly Ile Thr Asn Phe Asp Asn Phe Ala Phe
            340                 345                 350 gcc atg ctt act gtg ttt cag tgc atc acc atg gag ggc tgg aca gac     1222
Ala Met Leu Thr Val Phe Gln Cys Ile Thr Met Glu Gly Trp Thr Asp
        355                 360                 365 gtg ctc tac tgg gta aat gat gcg ata gga tgg gaa tgg cca tgg gtg     1270
Val Leu Tyr Trp Val Asn Asp Ala Ile Gly Trp Glu Trp Pro Trp Val
    370                 375                 380 tat ttt gtt agt ctg atc atc ctt ggc tca ttt ttc gtc ctt aac ctg     1318
Tyr Phe Val Ser Leu Ile Ile Leu Gly Ser Phe Phe Val Leu Asn Leu
385                 390                 395                 400 gtt ctt ggt gtc ctt agt gga gaa ttc tca aag gaa aga gag aag gca     1366
Val Leu Gly Val Leu Ser Gly Glu Phe Ser Lys Glu Arg Glu Lys Ala
                405                 410                 415 aaa gca cgg gga gat ttc cag aag ctc cgg gag aag cag cag ctg gag     1414
Lys Ala Arg Gly Asp Phe Gln Lys Leu Arg Glu Lys Gln Gln Leu Glu
            420                 425                 430 gag gat cta aag ggc tac ttg gat tgg atc acc caa gct gag gac atc     1462
Glu Asp Leu Lys Gly Tyr Leu Asp Trp Ile Thr Gln Ala Glu Asp Ile
        435                 440                 445 gat ccg gag aat gag gaa gaa gga gga gag gaa ggc aaa cga aat act     1510
Asp Pro Glu Asn Glu Glu Glu Gly Gly Glu Glu Gly Lys Arg Asn Thr
    450                 455                 460 agc atg ccc acc agc gag act gag tct gtg aac aca gag aac gtc agc     1558
Ser Met Pro Thr Ser Glu Thr Glu Ser Val Asn Thr Glu Asn Val Ser
465                 470                 475                 480 ggt gaa ggc gag aac cga ggc tgc tgt gga agt ctc tgg tgc tgg tgg     1606
Gly Glu Gly Glu Asn Arg Gly Cys Cys Gly Ser Leu Trp Cys Trp Trp
                485                 490                 495 aga cgg aga ggc gcg gcc aag gcg ggg ccc tct ggg tgt cgg cgg tgg     1654
Arg Arg Arg Gly Ala Ala Lys Ala Gly Pro Ser Gly Cys Arg Arg Trp
            500                 505                 510 ggt caa gcc atc tca aaa tcc aaa ctc agc cga cgc tgg cgt cgc tgg     1702
Gly Gln Ala Ile Ser Lys Ser Lys Leu Ser Arg Arg Trp Arg Arg Trp
        515                 520                 525 aac cga ttc aat cgc aga aga tgt agg gcc gcc gtg aag tct gtc acg     1750
Asn Arg Phe Asn Arg Arg Arg Cys Arg Ala Ala Val Lys Ser Val Thr
    530                 535                 540
```

-continued

| | |
|---|---|
| ttt tac tgg ctg gtt atc gtc ctg gtg ttt ctg aac acc tta acc att<br>Phe Tyr Trp Leu Val Ile Val Leu Val Phe Leu Asn Thr Leu Thr Ile<br>545                      550                      555                      560 | 1798 |
| tcc tct gag cac tac aat cag cca gat tgg ttg aca cag att caa gat<br>Ser Ser Glu His Tyr Asn Gln Pro Asp Trp Leu Thr Gln Ile Gln Asp<br>                565                      570                      575 | 1846 |
| att gcc aac aaa gtc ctc ttg gct ctg ttc acc tgc gag atg ctg gta<br>Ile Ala Asn Lys Val Leu Leu Ala Leu Phe Thr Cys Glu Met Leu Val<br>                580                      585                      590 | 1894 |
| aaa atg tac agc ttg ggc ctc caa gca tat ttc gtc tct ctt ttc aac<br>Lys Met Tyr Ser Leu Gly Leu Gln Ala Tyr Phe Val Ser Leu Phe Asn<br>        595                      600                      605 | 1942 |
| cgg ttt gat tgc ttc gtg gtg tgt ggt gga atc act gag acg atc ctg<br>Arg Phe Asp Cys Phe Val Val Cys Gly Gly Ile Thr Glu Thr Ile Leu<br>610                      615                      620 | 1990 |
| gtg gaa ctg gaa atc atg tct ccc ctg ggg atc tct gtg ttt cgg tgt<br>Val Glu Leu Glu Ile Met Ser Pro Leu Gly Ile Ser Val Phe Arg Cys<br>625                      630                      635                      640 | 2038 |
| gtg cgc ctc tta aga atc ttc aaa gtg acc agg cac tgg act tcc ctg<br>Val Arg Leu Leu Arg Ile Phe Lys Val Thr Arg His Trp Thr Ser Leu<br>                      645                      650                      655 | 2086 |
| agc aac tta gtg gca tcc tta tta aac tcc atg aag tcc atc gct tcg<br>Ser Asn Leu Val Ala Ser Leu Leu Asn Ser Met Lys Ser Ile Ala Ser<br>        660                      665                      670 | 2134 |
| ctg ttg ctt ctg ctt ttt ctc ttc att atc atc ttt tcc ttg ctt ggg<br>Leu Leu Leu Leu Leu Phe Leu Phe Ile Ile Ile Phe Ser Leu Leu Gly<br>675                      680                      685 | 2182 |
| atg cag ctg ttt ggc ggc aag ttt aat ttt gat gaa acg caa acc aag<br>Met Gln Leu Phe Gly Gly Lys Phe Asn Phe Asp Glu Thr Gln Thr Lys<br>                690                      695                      700 | 2230 |
| cgg agc acc ttt gac aat ttc cct caa gca ctt ctc aca gtg ttc cag<br>Arg Ser Thr Phe Asp Asn Phe Pro Gln Ala Leu Leu Thr Val Phe Gln<br>705                      710                      715                      720 | 2278 |
| atc ctg aca ggc gaa gac tgg aat gct gtg atg tac gat ggc atc atg<br>Ile Leu Thr Gly Glu Asp Trp Asn Ala Val Met Tyr Asp Gly Ile Met<br>                      725                      730                      735 | 2326 |
| gct tac ggg ggc cca tcc tct tca gga atg atc gtc tgc atc tac ttc<br>Ala Tyr Gly Gly Pro Ser Ser Ser Gly Met Ile Val Cys Ile Tyr Phe<br>        740                      745                      750 | 2374 |
| atc atc ctc ttc att tgt ggt aac tat att cta ctg aat gtc ttc ttg<br>Ile Ile Leu Phe Ile Cys Gly Asn Tyr Ile Leu Leu Asn Val Phe Leu<br>                755                      760                      765 | 2422 |
| gcc atc gct gta gac aat ttg gct gat gct gaa agt ctg aac act gct<br>Ala Ile Ala Val Asp Asn Leu Ala Asp Ala Glu Ser Leu Asn Thr Ala<br>770                      775                      780 | 2470 |
| cag aaa gaa gaa gcg gaa gaa aag gag agg aaa aag att gcc aga aaa<br>Gln Lys Glu Glu Ala Glu Glu Lys Glu Arg Lys Lys Ile Ala Arg Lys<br>785                      790                      795                      800 | 2518 |
| gag agc cta gaa aat aaa aag aac aac aaa cca gaa gtc aac cag ata<br>Glu Ser Leu Glu Asn Lys Lys Asn Asn Lys Pro Glu Val Asn Gln Ile<br>                      805                      810                      815 | 2566 |
| gcc aac agt gac aac aag gtt aca att gat gac tat aga gaa gag gat<br>Ala Asn Ser Asp Asn Lys Val Thr Ile Asp Asp Tyr Arg Glu Glu Asp<br>        820                      825                      830 | 2614 |
| gaa gac aag gac ccc tat ccg cct tgc gat gtg cca gta ggg gaa gag<br>Glu Asp Lys Asp Pro Tyr Pro Pro Cys Asp Val Pro Val Gly Glu Glu<br>835                      840                      845 | 2662 |
| gaa gag gaa gag gag gag gat gaa cct gag gtt cct gcc gga ccc cgt<br>Glu Glu Glu Glu Glu Glu Asp Glu Pro Glu Val Pro Ala Gly Pro Arg<br>        850                      855                      860 | 2710 |

-continued

```
cct cga agg atc tcg gag ttg aac atg aag gaa aaa att gcc ccc atc      2758
Pro Arg Arg Ile Ser Glu Leu Asn Met Lys Glu Lys Ile Ala Pro Ile
865                 870                 875                 880 cct gaa ggg agc gct ttc ttc att ctt agc aag acc aac ccg atc cgc      2806
Pro Glu Gly Ser Ala Phe Phe Ile Leu Ser Lys Thr Asn Pro Ile Arg
            885                 890                 895 gta ggc tgc cac aag ctc atc aac cac cac atc ttc acc aac ctc atc      2854
Val Gly Cys His Lys Leu Ile Asn His His Ile Phe Thr Asn Leu Ile
        900                 905                 910 ctt gtc ttc atc atg ctg agc agc gct gcc ctg gcc gca gag gac ccc      2902
Leu Val Phe Ile Met Leu Ser Ser Ala Ala Leu Ala Ala Glu Asp Pro
    915                 920                 925 atc cgc agc cac tcc ttc cgg aac acg ata ctg ggt tac ttt gac tat      2950
Ile Arg Ser His Ser Phe Arg Asn Thr Ile Leu Gly Tyr Phe Asp Tyr
930                 935                 940 gcc ttc aca gcc atc ttt act gtt gag atc ctg ttg aag atg aca act      2998
Ala Phe Thr Ala Ile Phe Thr Val Glu Ile Leu Leu Lys Met Thr Thr
945                 950                 955                 960 ttt gga gct ttc ctc cac aaa ggg gcc ttc tgc agg aac tac ttc aat      3046
Phe Gly Ala Phe Leu His Lys Gly Ala Phe Cys Arg Asn Tyr Phe Asn
            965                 970                 975 ttg ctg gat atg ctg gtg gtt ggg gtg tct ctg gtg tca ttt ggg att      3094
Leu Leu Asp Met Leu Val Val Gly Val Ser Leu Val Ser Phe Gly Ile
        980                 985                 990 caa tcc agt gcc atc tcc gtt gtg  aag att ctg agg gtc  tta agg gtc    3142
Gln Ser Ser Ala Ile Ser Val Val  Lys Ile Leu Arg Val  Leu Arg Val
    995                 1000                 1005 ctg cgt ccc ctc agg gcc atc  aac aga gca aaa gga  ctt aag cac        3187
Leu Arg Pro Leu Arg Ala Ile  Asn Arg Ala Lys Gly  Leu Lys His
1010                 1015                 1020 gtg gtc cag tgc gtc ttc gtg  gcc atc cgg acc atc  ggc aac atc        3232
Val Val Gln Cys Val Phe Val  Ala Ile Arg Thr Ile  Gly Asn Ile
1025                 1030                 1035 atg atc gtc act acc ctc ctg  cag ttc atg ttt gcc  tgt atc ggg        3277
Met Ile Val Thr Thr Leu Leu  Gln Phe Met Phe Ala  Cys Ile Gly
1040                 1045                 1050 gtc cag ttg ttc aag ggg aag  ttc tat cgc tgt acg  gat gaa gcc        3322
Val Gln Leu Phe Lys Gly Lys  Phe Tyr Arg Cys Thr  Asp Glu Ala
1055                 1060                 1065 aaa agt aac cct gaa gaa tgc  agg gga ctt ttc atc  ctc tac aag        3367
Lys Ser Asn Pro Glu Glu Cys  Arg Gly Leu Phe Ile  Leu Tyr Lys
1070                 1075                 1080 gat ggg gat gtt gac agt cct  gtg gtc cgt gaa cgg  atc tgg caa        3412
Asp Gly Asp Val Asp Ser Pro  Val Val Arg Glu Arg  Ile Trp Gln
1085                 1090                 1095 aac agt gat ttc aac ttc gac  aac gtc ctc tct gct  atg atg gcg        3457
Asn Ser Asp Phe Asn Phe Asp  Asn Val Leu Ser Ala  Met Met Ala
1100                 1105                 1110 ctc ttc aca gtc tcc acg ttt  gag ggc tgg cct gcg  ttg ctg tat        3502
Leu Phe Thr Val Ser Thr Phe  Glu Gly Trp Pro Ala  Leu Leu Tyr
1115                 1120                 1125 aaa gcc atc gac tcg aat gga  gag aac atc ggc cca  atc tac aac        3547
Lys Ala Ile Asp Ser Asn Gly  Glu Asn Ile Gly Pro  Ile Tyr Asn
1130                 1135                 1140 cac cgc gtg gag atc tcc atc  ttc ttc atc atc tac  atc atc att        3592
His Arg Val Glu Ile Ser Ile  Phe Phe Ile Ile Tyr  Ile Ile Ile
1145                 1150                 1155 gta gct ttc ttc atg atg aac  atc ttt gtg ggc ttt  gtc atc gtt        3637
Val Ala Phe Phe Met Met Asn  Ile Phe Val Gly Phe  Val Ile Val
```

-continued

| | | | | | | | | | | |
|---|---|---|---|---|---|---|---|---|---|---|
| | | | 1160 | | | 1165 | | | 1170 | |
| aca | ttt | cag | gaa | caa | gga | gaa | aaa | gag | tat | aag | aac | tgt | gag | ctg | 3682 |
| Thr | Phe | Gln | Glu | Gln | Gly | Glu | Lys | Glu | Tyr | Lys | Asn | Cys | Glu | Leu | |
| | 1175 | | | | | 1180 | | | | | 1185 | | | | |
| gac | aaa | aat | cag | cgt | cag | tgt | gtt | gaa | tac | gcc | ttg | aaa | gca | cgt | 3727 |
| Asp | Lys | Asn | Gln | Arg | Gln | Cys | Val | Glu | Tyr | Ala | Leu | Lys | Ala | Arg | |
| | 1190 | | | | | 1195 | | | | | 1200 | | | | |
| ccc | ttg | cgg | aga | tac | atc | ccc | aaa | aac | ccc | tac | cag | tac | aag | ttc | 3772 |
| Pro | Leu | Arg | Arg | Tyr | Ile | Pro | Lys | Asn | Pro | Tyr | Gln | Tyr | Lys | Phe | |
| | 1205 | | | | | 1210 | | | | | 1215 | | | | |
| tgg | tac | gtg | gtg | aac | tct | tcg | cct | ttc | gaa | tac | atg | atg | ttt | gtc | 3817 |
| Trp | Tyr | Val | Val | Asn | Ser | Ser | Pro | Phe | Glu | Tyr | Met | Met | Phe | Val | |
| | 1220 | | | | | 1225 | | | | | 1230 | | | | |
| ctc | atc | atg | ctc | aac | aca | ctc | tgc | ttg | gcc | atg | cag | cac | tac | gag | 3862 |
| Leu | Ile | Met | Leu | Asn | Thr | Leu | Cys | Leu | Ala | Met | Gln | His | Tyr | Glu | |
| | 1235 | | | | | 1240 | | | | | 1245 | | | | |
| cag | tcc | aag | atg | ttc | aat | gat | gcc | atg | gac | att | ctg | aac | atg | gtc | 3907 |
| Gln | Ser | Lys | Met | Phe | Asn | Asp | Ala | Met | Asp | Ile | Leu | Asn | Met | Val | |
| | 1250 | | | | | 1255 | | | | | 1260 | | | | |
| ttc | acc | ggg | gtg | ttc | acc | gtc | gag | atg | gtt | ttg | aaa | gtc | atc | gca | 3952 |
| Phe | Thr | Gly | Val | Phe | Thr | Val | Glu | Met | Val | Leu | Lys | Val | Ile | Ala | |
| | 1265 | | | | | 1270 | | | | | 1275 | | | | |
| ttt | aag | cct | aag | ggg | tat | ttt | agt | gac | gcc | tgg | aac | acg | ttt | gac | 3997 |
| Phe | Lys | Pro | Lys | Gly | Tyr | Phe | Ser | Asp | Ala | Trp | Asn | Thr | Phe | Asp | |
| | 1280 | | | | | 1285 | | | | | 1290 | | | | |
| tcc | ctc | atc | gta | atc | ggc | agc | att | ata | gac | gtg | gcc | ctc | agc | gaa | 4042 |
| Ser | Leu | Ile | Val | Ile | Gly | Ser | Ile | Ile | Asp | Val | Ala | Leu | Ser | Glu | |
| | 1295 | | | | | 1300 | | | | | 1305 | | | | |
| gcg | gac | cca | act | gaa | agt | gaa | aat | gtc | cct | gtc | cca | act | gct | aca | 4087 |
| Ala | Asp | Pro | Thr | Glu | Ser | Glu | Asn | Val | Pro | Val | Pro | Thr | Ala | Thr | |
| | 1310 | | | | | 1315 | | | | | 1320 | | | | |
| cct | ggg | aac | tct | gaa | gag | agc | aat | aga | atc | tcc | atc | acc | ttt | ttc | 4132 |
| Pro | Gly | Asn | Ser | Glu | Glu | Ser | Asn | Arg | Ile | Ser | Ile | Thr | Phe | Phe | |
| | 1325 | | | | | 1330 | | | | | 1335 | | | | |
| cgt | ctt | ttc | cga | gtg | atg | cga | ttg | gtg | aag | ctt | ctc | agc | agg | ggg | 4177 |
| Arg | Leu | Phe | Arg | Val | Met | Arg | Leu | Val | Lys | Leu | Leu | Ser | Arg | Gly | |
| | 1340 | | | | | 1345 | | | | | 1350 | | | | |
| gaa | ggc | atc | cgg | aca | ttg | ctg | tgg | act | ttt | att | aag | tcc | ttt | cag | 4222 |
| Glu | Gly | Ile | Arg | Thr | Leu | Leu | Trp | Thr | Phe | Ile | Lys | Ser | Phe | Gln | |
| | 1355 | | | | | 1360 | | | | | 1365 | | | | |
| gcg | ctc | ccg | tat | gtg | gcc | ctc | ctc | ata | gcc | atg | ctg | ttc | ttc | atc | 4267 |
| Ala | Leu | Pro | Tyr | Val | Ala | Leu | Leu | Ile | Ala | Met | Leu | Phe | Phe | Ile | |
| | 1370 | | | | | 1375 | | | | | 1380 | | | | |
| tat | gcg | gtc | att | ggc | atg | cag | atg | ttt | ggg | aaa | gtt | gcc | atg | aga | 4312 |
| Tyr | Ala | Val | Ile | Gly | Met | Gln | Met | Phe | Gly | Lys | Val | Ala | Met | Arg | |
| | 1385 | | | | | 1390 | | | | | 1395 | | | | |
| gat | aac | aac | cag | atc | aat | agg | aac | aat | aac | ttc | cag | acg | ttt | ccc | 4357 |
| Asp | Asn | Asn | Gln | Ile | Asn | Arg | Asn | Asn | Asn | Phe | Gln | Thr | Phe | Pro | |
| | 1400 | | | | | 1405 | | | | | 1410 | | | | |
| cag | gcg | gtg | ctg | ctc | ctc | ttc | agg | tgt | gca | aca | ggt | gag | gcc | tgg | 4402 |
| Gln | Ala | Val | Leu | Leu | Leu | Phe | Arg | Cys | Ala | Thr | Gly | Glu | Ala | Trp | |
| | 1415 | | | | | 1420 | | | | | 1425 | | | | |
| cag | gag | atc | atg | ctg | gcc | tgt | ctc | cca | ggg | aag | ctc | tgt | gac | cct | 4447 |
| Gln | Glu | Ile | Met | Leu | Ala | Cys | Leu | Pro | Gly | Lys | Leu | Cys | Asp | Pro | |
| | 1430 | | | | | 1435 | | | | | 1440 | | | | |
| gag | tca | gat | tac | aac | ccc | ggg | gag | gag | tat | aca | tgt | ggg | agc | aac | 4492 |
| Glu | Ser | Asp | Tyr | Asn | Pro | Gly | Glu | Glu | Tyr | Thr | Cys | Gly | Ser | Asn | |
| | 1445 | | | | | 1450 | | | | | 1455 | | | | |
| ttt | gcc | att | gtc | tat | ttc | atc | agt | ttt | tac | atg | ctc | tgt | gca | ttt | 4537 |

```
                Phe Ala Ile Val Tyr Phe Ile Ser Phe Tyr Met Leu Cys Ala Phe
                    1460            1465                1470 ctg atc atc aat ctg ttt gtg gct gtc atc atg gat aat ttc gac       4582
Leu Ile Ile Asn Leu Phe Val Ala Val Ile Met Asp Asn Phe Asp
    1475            1480                1485 tat ctg acc cgg gac tgg tct att ttg ggg cct cac cat tta gat       4627
Tyr Leu Thr Arg Asp Trp Ser Ile Leu Gly Pro His His Leu Asp
1490                1495                1500 gaa ttc aaa aga ata tgg tca gaa tat gac cct gag gca aag gga       4672
Glu Phe Lys Arg Ile Trp Ser Glu Tyr Asp Pro Glu Ala Lys Gly
    1505            1510                1515 agg ata aaa cac ctt gat gtg gtc act ctg ctt cga cgc atc cag       4717
Arg Ile Lys His Leu Asp Val Val Thr Leu Leu Arg Arg Ile Gln
    1520            1525                1530 cct ccc ctg ggg ttt ggg aag tta tgt cca cac agg gta gcg tgc       4762
Pro Pro Leu Gly Phe Gly Lys Leu Cys Pro His Arg Val Ala Cys
1535                1540                1545 aag aga tta gtt gcc atg aac atg cct ctc aac agt gac ggg aca       4807
Lys Arg Leu Val Ala Met Asn Met Pro Leu Asn Ser Asp Gly Thr
    1550            1555                1560 gtc atg ttt aat gca acc ctg ttt gct ttg gtt cga acg gct ctt       4852
Val Met Phe Asn Ala Thr Leu Phe Ala Leu Val Arg Thr Ala Leu
1565                1570                1575 aag atc aag acc gaa ggg aac ctg gag caa gct aat gaa gaa ctt       4897
Lys Ile Lys Thr Glu Gly Asn Leu Glu Gln Ala Asn Glu Glu Leu
    1580            1585                1590 cgg gct gtg ata aag aaa att tgg aag aaa acc agc atg aaa tta       4942
Arg Ala Val Ile Lys Lys Ile Trp Lys Lys Thr Ser Met Lys Leu
1595                1600                1605 ctt gac caa gtt gtc cct cca gct ggt gat gat gag gta acc gtg       4987
Leu Asp Gln Val Val Pro Pro Ala Gly Asp Asp Glu Val Thr Val
    1610            1615                1620 ggg aag ttc tat gcc act ttc ctg ata cag gac tac ttt agg aaa       5032
Gly Lys Phe Tyr Ala Thr Phe Leu Ile Gln Asp Tyr Phe Arg Lys
1625                1630                1635 ttc aag aaa cgg aaa gaa caa gga ctg gtg gga aag tac cct gcg       5077
Phe Lys Lys Arg Lys Glu Gln Gly Leu Val Gly Lys Tyr Pro Ala
    1640            1645                1650 aag aac acc aca att gcc cta cag gcg gga tta agg aca ctg cat       5122
Lys Asn Thr Thr Ile Ala Leu Gln Ala Gly Leu Arg Thr Leu His
1655                1660                1665 gac att ggg cca gaa atc cgg cgt gct ata tcg tgt gat ttg caa       5167
Asp Ile Gly Pro Glu Ile Arg Arg Ala Ile Ser Cys Asp Leu Gln
    1670            1675                1680 gat gac gag cct gag gaa aca aaa cga gaa gaa gaa gat gat gtg       5212
Asp Asp Glu Pro Glu Glu Thr Lys Arg Glu Glu Glu Asp Asp Val
1685                1690                1695 ttc aaa aga aat ggt gcc ctg ctt gga aac cat gtc aat cat gtt       5257
Phe Lys Arg Asn Gly Ala Leu Leu Gly Asn His Val Asn His Val
    1700            1705                1710 aat agt gat agg aga gat tcc ctt cag cag acc aat acc acc cac       5302
Asn Ser Asp Arg Arg Asp Ser Leu Gln Gln Thr Asn Thr Thr His
1715                1720                1725 cgt ccc ctg cat gtc caa agg cct tca att cca cct gca agt gat       5347
Arg Pro Leu His Val Gln Arg Pro Ser Ile Pro Pro Ala Ser Asp
    1730            1735                1740 act gag aaa ccg ctg ttt cct cca gca gga aat tcg gtg tgt cat       5392
Thr Glu Lys Pro Leu Phe Pro Pro Ala Gly Asn Ser Val Cys His
1745                1750                1755
```

```
aac cat cat aac cat aat tcc ata gga aag caa gtt ccc acc tca      5437
Asn His His Asn His Asn Ser Ile Gly Lys Gln Val Pro Thr Ser
    1760            1765                1770 aca aat gcc aat ctc aat aat gcc aat atg tcc aaa gct gcc cat      5482
Thr Asn Ala Asn Leu Asn Asn Ala Asn Met Ser Lys Ala Ala His
    1775            1780                1785 gga aag cgg ccc agc att ggg aac ctt gag cat gtg tct gaa aat      5527
Gly Lys Arg Pro Ser Ile Gly Asn Leu Glu His Val Ser Glu Asn
    1790            1795                1800 ggg cat cat tct tcc cac aag cat gac cgg gag cct cag aga agg      5572
Gly His His Ser Ser His Lys His Asp Arg Glu Pro Gln Arg Arg
    1805            1810                1815 tcc agt gtg aaa aga acc cgc tat tat gaa act tac att agg tcc      5617
Ser Ser Val Lys Arg Thr Arg Tyr Tyr Glu Thr Tyr Ile Arg Ser
    1820            1825                1830 gac tca gga gat gaa cag ctc cca act att tgc cgg gaa gac cca      5662
Asp Ser Gly Asp Glu Gln Leu Pro Thr Ile Cys Arg Glu Asp Pro
    1835            1840                1845 gag ata cat ggc tat ttc agg gac ccc cac tgc ttg ggg gag cag      5707
Glu Ile His Gly Tyr Phe Arg Asp Pro His Cys Leu Gly Glu Gln
    1850            1855                1860 gag tat ttc agt agt gag gaa tgc tac gag gat gac agc tcg ccc      5752
Glu Tyr Phe Ser Ser Glu Glu Cys Tyr Glu Asp Asp Ser Ser Pro
    1865            1870                1875 acc tgg agc agg caa aac tat ggc tac tac agc aga tac cca ggc      5797
Thr Trp Ser Arg Gln Asn Tyr Gly Tyr Tyr Ser Arg Tyr Pro Gly
    1880            1885                1890 aga aac atc gac tct gag agg ccc cga ggc tac cat cat ccc caa      5842
Arg Asn Ile Asp Ser Glu Arg Pro Arg Gly Tyr His His Pro Gln
    1895            1900                1905 gga ttc ttg gag gac gat gac tcg ccc gtt tgc tat gat tca cgg      5887
Gly Phe Leu Glu Asp Asp Asp Ser Pro Val Cys Tyr Asp Ser Arg
    1910            1915                1920 aga tct cca agg aga cgc cta cta cct ccc acc cca gca tcc cac      5932
Arg Ser Pro Arg Arg Arg Leu Leu Pro Pro Thr Pro Ala Ser His
    1925            1930                1935 cgg aga tcc tcc ttc aac ttt gag tgc ctg cgc cgg cag agc agc      5977
Arg Arg Ser Ser Phe Asn Phe Glu Cys Leu Arg Arg Gln Ser Ser
    1940            1945                1950 cag gaa gag gtc ccg tcg tct ccc atc ttc ccc cat cgc acg gcc      6022
Gln Glu Glu Val Pro Ser Ser Pro Ile Phe Pro His Arg Thr Ala
    1955            1960                1965 ctg cct ctg cat cta atg cag caa cag atc atg gca gtt gcc ggc      6067
Leu Pro Leu His Leu Met Gln Gln Gln Ile Met Ala Val Ala Gly
    1970            1975                1980 cta gat tca agt aaa gcc cag aag tac tca ccg agt cac tcg acc      6112
Leu Asp Ser Ser Lys Ala Gln Lys Tyr Ser Pro Ser His Ser Thr
    1985            1990                1995 cgg tcg tgg gcc acc cct cca gca acc cct ccc tac cgg gac tgg      6157
Arg Ser Trp Ala Thr Pro Pro Ala Thr Pro Pro Tyr Arg Asp Trp
    2000            2005                2010 aca ccg tgc tac acc ccc ctg atc caa gtg gag cag tca gag gcc      6202
Thr Pro Cys Tyr Thr Pro Leu Ile Gln Val Glu Gln Ser Glu Ala
    2015            2020                2025 ctg gac cag gtg aac ggc agc ctg ccg tcc ctg cac cgc agc tcc      6247
Leu Asp Gln Val Asn Gly Ser Leu Pro Ser Leu His Arg Ser Ser
    2030            2035                2040 tgg tac aca gac gag ccc gac atc tcc tac cgg act ttc aca cca      6292
Trp Tyr Thr Asp Glu Pro Asp Ile Ser Tyr Arg Thr Phe Thr Pro
    2045            2050                2055
```

| | | |
|---|---|---|
| gcc agc ctg act gtc ccc agc agc ttc cgg aac aaa aac agc gac<br>Ala Ser Leu Thr Val Pro Ser Ser Phe Arg Asn Lys Asn Ser Asp<br>    2060                                2065                      2070 | | 6337 |
| aag cag agg agt gcg gac agc ttg gtg gag gca gtc ctg ata tcc<br>Lys Gln Arg Ser Ala Asp Ser Leu Val Glu Ala Val Leu Ile Ser<br>2075                        2080                            2085 | | 6382 |
| gaa ggc ttg gga cgc tat gca agg gac cca aaa ttt gtg tca gca<br>Glu Gly Leu Gly Arg Tyr Ala Arg Asp Pro Lys Phe Val Ser Ala<br>2090                        2095                            2100 | | 6427 |
| aca aaa cac gaa atc gct gat gcc tgt gac ctc acc atc gac gag<br>Thr Lys His Glu Ile Ala Asp Ala Cys Asp Leu Thr Ile Asp Glu<br>2105                        2110                            2115 | | 6472 |
| atg gag agt gca gcc agc acc ctg ctt aat ggg aac gtg cgt ccc<br>Met Glu Ser Ala Ala Ser Thr Leu Leu Asn Gly Asn Val Arg Pro<br>2120                        2125                            2130 | | 6517 |
| cga gcc aac ggg gat gtg ggc ccc ctc tca cac cgg cag gac tat<br>Arg Ala Asn Gly Asp Val Gly Pro Leu Ser His Arg Gln Asp Tyr<br>2135                        2140                            2145 | | 6562 |
| gag cta cag gac ttt ggt cct ggc tac agc gac gaa gag cca gac<br>Glu Leu Gln Asp Phe Gly Pro Gly Tyr Ser Asp Glu Glu Pro Asp<br>2150                        2155                            2160 | | 6607 |
| cct ggg agg gat gag gag gac ctg gcg gat gaa atg ata tgc atc<br>Pro Gly Arg Asp Glu Glu Asp Leu Ala Asp Glu Met Ile Cys Ile<br>2165                        2170                            2175 | | 6652 |
| acc acc ttg tag cccccagcga ggggcagact ggctctggcc tcaggtgggg<br>Thr Thr Leu<br>    2180 | | 6704 |
| cgcaggagag ccaggggaaa agtgcctcat agttaggaaa gtttaggcac tagttgggag | | 6764 |
| taatattcaa ttaattagac ttttgtataa gagatgtcat gcctcaagaa agccataaac | | 6824 |
| ctggtaggaa caggtcccaa gcggttgagc ctggcagagt accatgcgct cggccccagc | | 6884 |
| tgcaggaaac agcaggcccc gccctctcac agaggatggg tgaggaggcc agacctgccc | | 6944 |
| tgccccattg tccagatggg cactgctgtg gagtctgctt ctcccatgta ccagggcacc | | 7004 |
| aggcccaccc aactgaaggc atggcggcgg ggtgcagggg aaagttaaag gtgatgacga | | 7064 |
| tcatcacacc tcgtgtcgtt acctcagcca tcggtctagc atatcagtca ctgggcccaa | | 7124 |
| catatccatt tttaaaccct ttcccccaaa tacactgcgt cctggttcct gtttagctgt | | 7184 |
| tctgaaata | | 7193 |

```
<210> SEQ ID NO 20
<211> LENGTH: 2181
<212> TYPE: PRT
<213> ORGANISM: Homo sapiens

<400> SEQUENCE: 20
```

Met Met Met Met Met Met Met Lys Lys Met Gln His Gln Arg Gln Gln
1                 5                    10                  15

Gln Ala Asp His Ala Asn Glu Ala Asn Tyr Ala Arg Gly Thr Arg Leu
                20                    25                    30

Pro Leu Ser Gly Glu Gly Pro Thr Ser Gln Pro Asn Ser Ser Lys Gln
        35                    40                    45

Thr Val Leu Ser Trp Gln Ala Ala Ile Asp Ala Ala Arg Gln Ala Lys
  50                    55                    60

Ala Ala Gln Thr Met Ser Thr Ser Ala Pro Pro Pro Val Gly Ser Leu
65                70                    75                    80

Ser Gln Arg Lys Arg Gln Gln Tyr Ala Lys Ser Lys Lys Gln Gly Asn

-continued

```
                    85                  90                  95
Ser Ser Asn Ser Arg Pro Ala Arg Ala Leu Phe Cys Leu Ser Leu Asn
                100                 105                 110
Asn Pro Ile Arg Arg Ala Cys Ile Ser Ile Val Glu Trp Lys Pro Phe
                115                 120                 125
Asp Ile Phe Ile Leu Leu Ala Ile Phe Ala Asn Cys Val Ala Leu Ala
130                 135                 140
Ile Tyr Ile Pro Phe Pro Glu Asp Asp Ser Asn Ser Thr Asn His Asn
145                 150                 155                 160
Leu Glu Lys Val Glu Tyr Ala Phe Leu Ile Ile Phe Thr Val Glu Thr
                165                 170                 175
Phe Leu Lys Ile Ile Ala Tyr Gly Leu Leu Leu His Pro Asn Ala Tyr
                180                 185                 190
Val Arg Asn Gly Trp Asn Leu Leu Asp Phe Val Ile Val Ile Val Gly
                195                 200                 205
Leu Phe Ser Val Ile Leu Glu Gln Leu Thr Lys Glu Thr Glu Gly Gly
210                 215                 220
Asn His Ser Ser Gly Lys Ser Gly Phe Asp Val Lys Ala Leu Arg
225                 230                 235                 240
Ala Phe Arg Val Leu Arg Pro Leu Arg Leu Val Ser Gly Val Pro Ser
                245                 250                 255
Leu Gln Val Val Leu Asn Ser Ile Ile Lys Ala Met Val Pro Leu Leu
                260                 265                 270
His Ile Ala Leu Leu Val Leu Phe Val Ile Ile Tyr Ala Ile Ile
                275                 280                 285
Gly Leu Glu Leu Phe Ile Gly Lys Met His Lys Thr Cys Phe Phe Ala
290                 295                 300
Asp Ser Asp Ile Val Ala Glu Glu Asp Pro Ala Pro Cys Ala Phe Ser
305                 310                 315                 320
Gly Asn Gly Arg Gln Cys Thr Ala Asn Gly Thr Glu Cys Arg Ser Gly
                325                 330                 335
Trp Val Gly Pro Asn Gly Gly Ile Thr Asn Phe Asp Asn Phe Ala Phe
                340                 345                 350
Ala Met Leu Thr Val Phe Gln Cys Ile Thr Met Glu Gly Trp Thr Asp
                355                 360                 365
Val Leu Tyr Trp Val Asn Asp Ala Ile Gly Trp Glu Trp Pro Trp Val
                370                 375                 380
Tyr Phe Val Ser Leu Ile Ile Leu Gly Ser Phe Phe Val Leu Asn Leu
385                 390                 395                 400
Val Leu Gly Val Leu Ser Gly Glu Phe Ser Lys Glu Arg Glu Lys Ala
                405                 410                 415
Lys Ala Arg Gly Asp Phe Gln Lys Leu Arg Glu Lys Gln Gln Leu Glu
                420                 425                 430
Glu Asp Leu Lys Gly Tyr Leu Asp Trp Ile Thr Gln Ala Glu Asp Ile
                435                 440                 445
Asp Pro Glu Asn Glu Glu Gly Gly Glu Gly Lys Arg Asn Thr
450                 455                 460
Ser Met Pro Thr Ser Glu Thr Glu Ser Val Asn Thr Glu Asn Val Ser
465                 470                 475                 480
Gly Glu Gly Glu Asn Arg Gly Cys Cys Gly Ser Leu Trp Cys Trp Trp
                485                 490                 495
Arg Arg Arg Gly Ala Ala Lys Ala Gly Pro Ser Gly Cys Arg Arg Trp
                500                 505                 510
```

-continued

```
Gly Gln Ala Ile Ser Lys Ser Lys Leu Ser Arg Arg Trp Arg Trp
            515                 520                 525
Asn Arg Phe Asn Arg Arg Cys Arg Ala Val Lys Ser Val Thr
    530                 535                 540
Phe Tyr Trp Leu Val Ile Val Leu Val Phe Leu Asn Thr Leu Thr Ile
545                 550                 555                 560
Ser Ser Glu His Tyr Asn Gln Pro Asp Trp Leu Thr Gln Ile Gln Asp
                565                 570                 575
Ile Ala Asn Lys Val Leu Leu Ala Leu Phe Thr Cys Glu Met Leu Val
            580                 585                 590
Lys Met Tyr Ser Leu Gly Leu Gln Ala Tyr Phe Val Ser Leu Phe Asn
        595                 600                 605
Arg Phe Asp Cys Phe Val Val Cys Gly Gly Ile Thr Glu Thr Ile Leu
    610                 615                 620
Val Glu Leu Glu Ile Met Ser Pro Leu Gly Ile Ser Val Phe Arg Cys
625                 630                 635                 640
Val Arg Leu Leu Arg Ile Phe Lys Val Thr Arg His Trp Thr Ser Leu
                645                 650                 655
Ser Asn Leu Val Ala Ser Leu Leu Asn Ser Met Lys Ser Ile Ala Ser
            660                 665                 670
Leu Leu Leu Leu Leu Phe Leu Phe Ile Ile Ile Phe Ser Leu Leu Gly
        675                 680                 685
Met Gln Leu Phe Gly Gly Lys Phe Asn Phe Asp Glu Thr Gln Thr Lys
    690                 695                 700
Arg Ser Thr Phe Asp Asn Phe Pro Gln Ala Leu Leu Thr Val Phe Gln
705                 710                 715                 720
Ile Leu Thr Gly Glu Asp Trp Asn Ala Val Met Tyr Asp Gly Ile Met
                725                 730                 735
Ala Tyr Gly Gly Pro Ser Ser Ser Gly Met Ile Val Cys Ile Tyr Phe
            740                 745                 750
Ile Ile Leu Phe Ile Cys Gly Asn Tyr Ile Leu Leu Asn Val Phe Leu
        755                 760                 765
Ala Ile Ala Val Asp Asn Leu Ala Asp Ala Glu Ser Leu Asn Thr Ala
    770                 775                 780
Gln Lys Glu Glu Ala Glu Glu Lys Glu Arg Lys Lys Ile Ala Arg Lys
785                 790                 795                 800
Glu Ser Leu Glu Asn Lys Lys Asn Asn Lys Pro Glu Val Asn Gln Ile
                805                 810                 815
Ala Asn Ser Asp Asn Lys Val Thr Ile Asp Asp Tyr Arg Glu Glu Asp
            820                 825                 830
Glu Asp Lys Asp Pro Tyr Pro Pro Cys Asp Val Pro Val Gly Glu Glu
        835                 840                 845
Glu Glu Glu Glu Glu Asp Glu Pro Glu Val Pro Ala Gly Pro Arg
    850                 855                 860
Pro Arg Arg Ile Ser Glu Leu Asn Met Lys Glu Lys Ile Ala Pro Ile
865                 870                 875                 880
Pro Glu Gly Ser Ala Phe Phe Ile Leu Ser Lys Thr Asn Pro Ile Arg
                885                 890                 895
Val Gly Cys His Lys Leu Ile Asn His Ile Phe Thr Asn Leu Ile
            900                 905                 910
Leu Val Phe Ile Met Leu Ser Ser Ala Ala Leu Ala Ala Glu Asp Pro
        915                 920                 925
```

-continued

```
Ile Arg Ser His Ser Phe Arg Asn Thr Ile Leu Gly Tyr Phe Asp Tyr
    930                 935                 940

Ala Phe Thr Ala Ile Phe Thr Val Glu Ile Leu Leu Lys Met Thr Thr
945                 950                 955                 960

Phe Gly Ala Phe Leu His Lys Gly Ala Phe Cys Arg Asn Tyr Phe Asn
                965                 970                 975

Leu Leu Asp Met Leu Val Val Gly Val Ser Leu Val Ser Phe Gly Ile
                980                 985                 990

Gln Ser Ser Ala Ile Ser Val Val  Lys Ile Leu Arg Val  Leu Arg Val
            995                1000                1005

Leu Arg  Pro Leu Arg Ala Ile  Asn Arg Ala Lys Gly  Leu Lys His
    1010               1015               1020

Val Val  Gln Cys Val Phe Val  Ala Ile Arg Thr Ile  Gly Asn Ile
    1025               1030               1035

Met Ile  Val Thr Thr Leu Leu  Gln Phe Met Phe Ala  Cys Ile Gly
    1040               1045               1050

Val Gln  Leu Phe Lys Gly Lys  Phe Tyr Arg Cys Thr  Asp Glu Ala
    1055               1060               1065

Lys Ser  Asn Pro Glu Glu Cys  Arg Gly Leu Phe Ile  Leu Tyr Lys
    1070               1075               1080

Asp Gly  Asp Val Asp Ser Pro  Val Val Arg Glu Arg  Ile Trp Gln
    1085               1090               1095

Asn Ser  Asp Phe Asn Phe Asp  Asn Val Leu Ser Ala  Met Met Ala
    1100               1105               1110

Leu Phe  Thr Val Ser Thr Phe  Glu Gly Trp Pro Ala  Leu Leu Tyr
    1115               1120               1125

Lys Ala  Ile Asp Ser Asn Gly  Glu Asn Ile Gly Pro  Ile Tyr Asn
    1130               1135               1140

His Arg  Val Glu Ile Ser Ile  Phe Phe Ile Ile Tyr  Ile Ile Ile
    1145               1150               1155

Val Ala  Phe Phe Met Met Asn  Ile Phe Val Gly Phe  Val Ile Val
    1160               1165               1170

Thr Phe  Gln Glu Gln Gly Glu  Lys Glu Tyr Lys Asn  Cys Glu Leu
    1175               1180               1185

Asp Lys  Asn Gln Arg Gln Cys  Val Glu Tyr Ala Leu  Lys Ala Arg
    1190               1195               1200

Pro Leu  Arg Arg Tyr Ile Pro  Lys Asn Pro Tyr Gln  Tyr Lys Phe
    1205               1210               1215

Trp Tyr  Val Val Asn Ser Ser  Pro Phe Glu Tyr Met  Met Phe Val
    1220               1225               1230

Leu Ile  Met Leu Asn Thr Leu  Cys Leu Ala Met Gln  His Tyr Glu
    1235               1240               1245

Gln Ser  Lys Met Phe Asn Asp  Ala Met Asp Ile Leu  Asn Met Val
    1250               1255               1260

Phe Thr  Gly Val Phe Thr Val  Glu Met Val Leu Lys  Val Ile Ala
    1265               1270               1275

Phe Lys  Pro Lys Gly Tyr Phe  Ser Asp Ala Trp Asn  Thr Phe Asp
    1280               1285               1290

Ser Leu  Ile Val Ile Gly Ser  Ile Ile Asp Val Ala  Leu Ser Glu
    1295               1300               1305

Ala Asp  Pro Thr Glu Ser Glu  Asn Val Pro Val Pro  Thr Ala Thr
    1310               1315               1320

Pro Gly  Asn Ser Glu Glu Ser  Asn Arg Ile Ser Ile  Thr Phe Phe
```

-continued

```
              1325                1330                1335
Arg Leu Phe Arg Val Met Arg Leu Val Lys Leu Leu Ser Arg Gly
1340                1345                1350
Glu Gly Ile Arg Thr Leu Leu Trp Thr Phe Ile Lys Ser Phe Gln
1355                1360                1365
Ala Leu Pro Tyr Val Ala Leu Leu Ile Ala Met Leu Phe Phe Ile
1370                1375                1380
Tyr Ala Val Ile Gly Met Gln Met Phe Gly Lys Val Ala Met Arg
1385                1390                1395
Asp Asn Asn Gln Ile Asn Arg Asn Asn Asn Phe Gln Thr Phe Pro
1400                1405                1410
Gln Ala Val Leu Leu Leu Phe Arg Cys Ala Thr Gly Glu Ala Trp
1415                1420                1425
Gln Glu Ile Met Leu Ala Cys Leu Pro Gly Lys Leu Cys Asp Pro
1430                1435                1440
Glu Ser Asp Tyr Asn Pro Gly Glu Glu Tyr Thr Cys Gly Ser Asn
1445                1450                1455
Phe Ala Ile Val Tyr Phe Ile Ser Phe Tyr Met Leu Cys Ala Phe
1460                1465                1470
Leu Ile Ile Asn Leu Phe Val Ala Val Ile Met Asp Asn Phe Asp
1475                1480                1485
Tyr Leu Thr Arg Asp Trp Ser Ile Leu Gly Pro His His Leu Asp
1490                1495                1500
Glu Phe Lys Arg Ile Trp Ser Glu Tyr Asp Pro Glu Ala Lys Gly
1505                1510                1515
Arg Ile Lys His Leu Asp Val Val Thr Leu Leu Arg Arg Ile Gln
1520                1525                1530
Pro Pro Leu Gly Phe Gly Lys Leu Cys Pro His Arg Val Ala Cys
1535                1540                1545
Lys Arg Leu Val Ala Met Asn Met Pro Leu Asn Ser Asp Gly Thr
1550                1555                1560
Val Met Phe Asn Ala Thr Leu Phe Ala Leu Val Arg Thr Ala Leu
1565                1570                1575
Lys Ile Lys Thr Glu Gly Asn Leu Glu Gln Ala Asn Glu Glu Leu
1580                1585                1590
Arg Ala Val Ile Lys Lys Ile Trp Lys Lys Thr Ser Met Lys Leu
1595                1600                1605
Leu Asp Gln Val Val Pro Pro Ala Gly Asp Asp Glu Val Thr Val
1610                1615                1620
Gly Lys Phe Tyr Ala Thr Phe Leu Ile Gln Asp Tyr Phe Arg Lys
1625                1630                1635
Phe Lys Lys Arg Lys Glu Gln Gly Leu Val Gly Lys Tyr Pro Ala
1640                1645                1650
Lys Asn Thr Thr Ile Ala Leu Gln Ala Gly Leu Arg Thr Leu His
1655                1660                1665
Asp Ile Gly Pro Glu Ile Arg Arg Ala Ile Ser Cys Asp Leu Gln
1670                1675                1680
Asp Asp Glu Pro Glu Glu Thr Lys Arg Glu Glu Asp Asp Val
1685                1690                1695
Phe Lys Arg Asn Gly Ala Leu Leu Gly Asn His Val Asn His Val
1700                1705                1710
Asn Ser Asp Arg Arg Asp Ser Leu Gln Gln Thr Asn Thr Thr His
1715                1720                1725
```

-continued

```
Arg Pro Leu His Val Gln Arg Pro Ser Ile Pro Pro Ala Ser Asp
    1730                1735                1740

Thr Glu Lys Pro Leu Phe Pro Pro Ala Gly Asn Ser Val Cys His
    1745                1750                1755

Asn His His Asn His Asn Ser Ile Gly Lys Gln Val Pro Thr Ser
    1760                1765                1770

Thr Asn Ala Asn Leu Asn Asn Ala Asn Met Ser Lys Ala Ala His
    1775                1780                1785

Gly Lys Arg Pro Ser Ile Gly Asn Leu Glu His Val Ser Glu Asn
    1790                1795                1800

Gly His His Ser Ser His Lys His Asp Arg Glu Pro Gln Arg Arg
    1805                1810                1815

Ser Ser Val Lys Arg Thr Arg Tyr Tyr Glu Thr Tyr Ile Arg Ser
    1820                1825                1830

Asp Ser Gly Asp Glu Gln Leu Pro Thr Ile Cys Arg Glu Asp Pro
    1835                1840                1845

Glu Ile His Gly Tyr Phe Arg Asp Pro His Cys Leu Gly Glu Gln
    1850                1855                1860

Glu Tyr Phe Ser Ser Glu Glu Cys Tyr Glu Asp Asp Ser Ser Pro
    1865                1870                1875

Thr Trp Ser Arg Gln Asn Tyr Gly Tyr Tyr Ser Arg Tyr Pro Gly
    1880                1885                1890

Arg Asn Ile Asp Ser Glu Arg Pro Arg Gly Tyr His His Pro Gln
    1895                1900                1905

Gly Phe Leu Glu Asp Asp Asp Ser Pro Val Cys Tyr Asp Ser Arg
    1910                1915                1920

Arg Ser Pro Arg Arg Arg Leu Leu Pro Pro Thr Pro Ala Ser His
    1925                1930                1935

Arg Arg Ser Ser Phe Asn Phe Glu Cys Leu Arg Arg Gln Ser Ser
    1940                1945                1950

Gln Glu Glu Val Pro Ser Ser Pro Ile Phe Pro His Arg Thr Ala
    1955                1960                1965

Leu Pro Leu His Leu Met Gln Gln Ile Met Ala Val Ala Gly
    1970                1975                1980

Leu Asp Ser Ser Lys Ala Gln Lys Tyr Ser Pro Ser His Ser Thr
    1985                1990                1995

Arg Ser Trp Ala Thr Pro Pro Ala Thr Pro Pro Tyr Arg Asp Trp
    2000                2005                2010

Thr Pro Cys Tyr Thr Pro Leu Ile Gln Val Glu Gln Ser Glu Ala
    2015                2020                2025

Leu Asp Gln Val Asn Gly Ser Leu Pro Ser Leu His Arg Ser Ser
    2030                2035                2040

Trp Tyr Thr Asp Glu Pro Asp Ile Ser Tyr Arg Thr Phe Thr Pro
    2045                2050                2055

Ala Ser Leu Thr Val Pro Ser Ser Phe Arg Asn Lys Asn Ser Asp
    2060                2065                2070

Lys Gln Arg Ser Ala Asp Ser Leu Val Glu Ala Val Leu Ile Ser
    2075                2080                2085

Glu Gly Leu Gly Arg Tyr Ala Arg Asp Pro Lys Phe Val Ser Ala
    2090                2095                2100

Thr Lys His Glu Ile Ala Asp Ala Cys Asp Leu Thr Ile Asp Glu
    2105                2110                2115
```

```
                Met Glu Ser Ala Ala Ser Thr Leu Leu Asn Gly Asn Val Arg Pro
                2120                2125                2130

Arg Ala Asn Gly Asp Val Gly Pro Leu Ser His Arg Gln Asp Tyr
                2135                2140                2145

Glu Leu Gln Asp Phe Gly Pro Gly Tyr Ser Asp Glu Glu Pro Asp
                2150                2155                2160

Pro Gly Arg Asp Glu Glu Asp Leu Ala Asp Glu Met Ile Cys Ile
                2165                2170                2175

Thr Thr Leu
                2180

<210> SEQ ID NO 21
<211> LENGTH: 6083
<212> TYPE: DNA
<213> ORGANISM: Oryctolagus cuniculus
<220> FEATURE:
<221> NAME/KEY: gene
<222> LOCATION: (1)..(6083)
<220> FEATURE:
<221> NAME/KEY: CDS
<222> LOCATION: (226)..(5847)

<400> SEQUENCE: 21
ttccacctac atgttggcct ggacagcagg gagccgaggg gaggctaatt ttactgctgg      60
gagcagctag cataatcctc ccgcccccac cccgctggct cagcagggca ggcttcgccc     120
ggcaagctca gcggcccagt ccccaaggcg gggaacactg ggacgcagg aagagaggg      180 ccgcggggtg ggggagcagc aggaagcgcc gtggccaggg aagcc atg gag cca tcc    237
                                                   Met Glu Pro Ser
                                                    1 tca ccc cag gat gag ggc ctg agg aag aaa cag ccc aag aag ccc ctg      285
Ser Pro Gln Asp Glu Gly Leu Arg Lys Lys Gln Pro Lys Lys Pro Leu
  5                  10                  15                  20 ccc gag gtc ctg ccc agg ccg ccg cgg gct ctg ttc tgc ctg acc ctg      333
Pro Glu Val Leu Pro Arg Pro Pro Arg Ala Leu Phe Cys Leu Thr Leu
                 25                  30                  35 cag aac ccg ctg agg aag gcg tgc atc agc atc gtg gaa tgg aaa ccc      381
Gln Asn Pro Leu Arg Lys Ala Cys Ile Ser Ile Val Glu Trp Lys Pro
             40                  45                  50 ttc gag acc atc atc ctg ctc acc atc ttt gcc aac tgt gtg gcc ctg      429
Phe Glu Thr Ile Ile Leu Leu Thr Ile Phe Ala Asn Cys Val Ala Leu
         55                  60                  65 gcc gtg tac ctg ccc atg ccc gag gat gac aac aac tcc ctg aac ctg      477
Ala Val Tyr Leu Pro Met Pro Glu Asp Asp Asn Asn Ser Leu Asn Leu
     70                  75                  80 ggc ctg gag aag ctg gag tac ttc ttc ctc acc gtc ttc tcc atc gaa      525
Gly Leu Glu Lys Leu Glu Tyr Phe Phe Leu Thr Val Phe Ser Ile Glu
 85                  90                  95                 100 gcc gcc atg aag atc atc gcc tac ggc ttc ctg ttc cac cag gac gcc      573
Ala Ala Met Lys Ile Ile Ala Tyr Gly Phe Leu Phe His Gln Asp Ala
                105                 110                 115 tac ctg cgc agc ggc tgg aac gtg ctg gac ttc atc atc gtc ttc ctg      621
Tyr Leu Arg Ser Gly Trp Asn Val Leu Asp Phe Ile Ile Val Phe Leu
            120                 125                 130 ggg gtc ttc acg gcg att ctg gaa cag gtc aac gtc atc cag agc aac      669
Gly Val Phe Thr Ala Ile Leu Glu Gln Val Asn Val Ile Gln Ser Asn
        135                 140                 145 acg gcc ccg atg agc agc aaa gga gcc ggc ctg gac gtc aag gcc ctg      717
Thr Ala Pro Met Ser Ser Lys Gly Ala Gly Leu Asp Val Lys Ala Leu
    150                 155                 160
```

```
agg gcc ttc cgt gtg ctc aga ccc ctc cgg ctg gtg tcg ggg gtg cct       765
Arg Ala Phe Arg Val Leu Arg Pro Leu Arg Leu Val Ser Gly Val Pro
165             170                 175                 180 agt ttg cag gtg gtc ctc aac tcc atc ttc aag gcc atg ctc ccc ctg       813
Ser Leu Gln Val Val Leu Asn Ser Ile Phe Lys Ala Met Leu Pro Leu
                185                 190                 195 ttc cac atc gcc ctg ctc gtc ctc ttc atg gtc atc atc tac gcc atc       861
Phe His Ile Ala Leu Leu Val Leu Phe Met Val Ile Ile Tyr Ala Ile
            200                 205                 210 atc ggg ctg gag ctc ttc aag ggc aag atg cac aag acc tgc tac tac       909
Ile Gly Leu Glu Leu Phe Lys Gly Lys Met His Lys Thr Cys Tyr Tyr
            215                 220                 225 atc ggg aca gac atc gtg gcc aca gtg gag aat gag aag ccc tcg ccc       957
Ile Gly Thr Asp Ile Val Ala Thr Val Glu Asn Glu Lys Pro Ser Pro
230                 235                 240 tgc gct agg acg ggc tcg ggg cgc ccc tgc acc atc aac ggc agc gag      1005
Cys Ala Arg Thr Gly Ser Gly Arg Pro Cys Thr Ile Asn Gly Ser Glu
245                 250                 255                 260 tgc cgg ggc ggc tgg ccg ggg ccc aac cac ggc atc acg cac ttc gac      1053
Cys Arg Gly Gly Trp Pro Gly Pro Asn His Gly Ile Thr His Phe Asp
                265                 270                 275 aac ttc ggc ttc tcc atg ctc acc gtg tac cag tgc atc acc atg gag      1101
Asn Phe Gly Phe Ser Met Leu Thr Val Tyr Gln Cys Ile Thr Met Glu
            280                 285                 290 ggc tgg aca gat gtc ctc tac tgg gtc aac gat gcc atc ggg aac gag      1149
Gly Trp Thr Asp Val Leu Tyr Trp Val Asn Asp Ala Ile Gly Asn Glu
            295                 300                 305 tgg ccc tgg atc tac ttt gtc act ctc atc ctg ctg ggg tcc ttc ttc      1197
Trp Pro Trp Ile Tyr Phe Val Thr Leu Ile Leu Leu Gly Ser Phe Phe
310                 315                 320 atc ctc aac ctg gtg ctg ggc gtc ctg agt ggg gaa ttc acc aag gag      1245
Ile Leu Asn Leu Val Leu Gly Val Leu Ser Gly Glu Phe Thr Lys Glu
325                 330                 335                 340 cgg gag aag gcc aag tcc agg gga acc ttc cag aag ctg cgg gag aag      1293
Arg Glu Lys Ala Lys Ser Arg Gly Thr Phe Gln Lys Leu Arg Glu Lys
                345                 350                 355 cag cag ctg gag gag gac ctt cgg ggc tac atg agc tgg atc acg cag      1341
Gln Gln Leu Glu Glu Asp Leu Arg Gly Tyr Met Ser Trp Ile Thr Gln
            360                 365                 370 ggc gag gtc atg gac gtg gag gac ctg aga gaa gga aag ctg tcc ttg      1389
Gly Glu Val Met Asp Val Glu Asp Leu Arg Glu Gly Lys Leu Ser Leu
            375                 380                 385 gaa gag gga ggc tcc gac acg gaa agc ctg tac gaa atc gag ggc ttg      1437
Glu Glu Gly Gly Ser Asp Thr Glu Ser Leu Tyr Glu Ile Glu Gly Leu
390                 395                 400 aac aaa atc atc cag ttc atc cga cac tgg agg cag tgg aac cgt gtc      1485
Asn Lys Ile Ile Gln Phe Ile Arg His Trp Arg Gln Trp Asn Arg Val
405                 410                 415                 420 ttt cgc tgg aag tgc cat gac ctg gtg aag tcg aga gtc ttc tac tgg      1533
Phe Arg Trp Lys Cys His Asp Leu Val Lys Ser Arg Val Phe Tyr Trp
                425                 430                 435 ctg gtc atc ctg atc gtg gcc ctc aac acc ctg tcc atc gcc tcg gag      1581
Leu Val Ile Leu Ile Val Ala Leu Asn Thr Leu Ser Ile Ala Ser Glu
            440                 445                 450 cac cac aac cag ccg ctc tgg ctg acc cac ttg caa gac atc gcc aat      1629
His His Asn Gln Pro Leu Trp Leu Thr His Leu Gln Asp Ile Ala Asn
            455                 460                 465 cga gtg ctg ctg tca ctc ttc acc atc gag atg ctg ctg aag atg tac      1677
Arg Val Leu Leu Ser Leu Phe Thr Ile Glu Met Leu Leu Lys Met Tyr
470                 475                 480
```

-continued

| | |
|---|---|
| ggg ctg ggc ctg cgc cag tac ttc atg tcc atc ttc aac cgc ttc gac<br>Gly Leu Gly Leu Arg Gln Tyr Phe Met Ser Ile Phe Asn Arg Phe Asp<br>485                      490                      495                      500 | 1725 |
| tgc ttc gtg gtg tgc agc ggc atc ctg gag ctg ctg gtg gag tcg<br>Cys Phe Val Val Cys Ser Gly Ile Leu Glu Leu Leu Val Glu Ser<br>                      505                      510                      515 | 1773 |
| ggc gcc atg acg ccg ctg ggc atc tcc gtg ttg cgc tgc atc cgc ctc<br>Gly Ala Met Thr Pro Leu Gly Ile Ser Val Leu Arg Cys Ile Arg Leu<br>            520                      525                      530 | 1821 |
| ctg agg ctc ttc aag atc acc aag tac tgg acg tcg ctc agc aac ctg<br>Leu Arg Leu Phe Lys Ile Thr Lys Tyr Trp Thr Ser Leu Ser Asn Leu<br>              535                      540                      545 | 1869 |
| gtg gcc tcc ctg ctc aac tcc atc cgc tcc atc gcc tcg ctg ctg ctg<br>Val Ala Ser Leu Leu Asn Ser Ile Arg Ser Ile Ala Ser Leu Leu Leu<br>550                      555                      560 | 1917 |
| ctg ctc ttc ctc ttc atc atc atc ttc gcc ctg ctg ggc atg cag ctc<br>Leu Leu Phe Leu Phe Ile Ile Ile Phe Ala Leu Leu Gly Met Gln Leu<br>565                      570                      575                      580 | 1965 |
| ttc ggg ggc cgg tac gac ttc gag gac acg gaa gtg cga cgc agc aac<br>Phe Gly Gly Arg Tyr Asp Phe Glu Asp Thr Glu Val Arg Arg Ser Asn<br>                      585                      590                      595 | 2013 |
| ttc gac aac ttc ccc cag gcc ctc atc agc gtc ttc cag gtg ctg acg<br>Phe Asp Asn Phe Pro Gln Ala Leu Ile Ser Val Phe Gln Val Leu Thr<br>            600                      605                      610 | 2061 |
| ggt gag gac tgg aac tcc gtg atg tac aac ggg atc atg gcc tac gga<br>Gly Glu Asp Trp Asn Ser Val Met Tyr Asn Gly Ile Met Ala Tyr Gly<br>              615                      620                      625 | 2109 |
| ggc ccg tcc tac ccg ggc gtt ctc gtg tgc atc tat ttc atc atc ctt<br>Gly Pro Ser Tyr Pro Gly Val Leu Val Cys Ile Tyr Phe Ile Ile Leu<br>630                      635                      640 | 2157 |
| ttt gtc tgc ggc aac tat atc ctg ctg aat gtc ttc ctg gcc atc gcc<br>Phe Val Cys Gly Asn Tyr Ile Leu Leu Asn Val Phe Leu Ala Ile Ala<br>645                      650                      655                      660 | 2205 |
| gtg gac aac ctg gcc gag gcg gag agc ctg act tcc gcg caa aag gcc<br>Val Asp Asn Leu Ala Glu Ala Glu Ser Leu Thr Ser Ala Gln Lys Ala<br>              665                      670                      675 | 2253 |
| aag gcc gag gag agg aaa cgc agg aag atg tcc agg ggt ctc cct gac<br>Lys Ala Glu Glu Arg Lys Arg Arg Lys Met Ser Arg Gly Leu Pro Asp<br>            680                      685                      690 | 2301 |
| aag aca gag gag gag aag tct gtg atg gcc aag aag ctg gag cag aag<br>Lys Thr Glu Glu Glu Lys Ser Val Met Ala Lys Lys Leu Glu Gln Lys<br>              695                      700                      705 | 2349 |
| ccc aag ggg gag ggc atc ccc acc act gcc aag ctc aag gtc gat gag<br>Pro Lys Gly Glu Gly Ile Pro Thr Thr Ala Lys Leu Lys Val Asp Glu<br>710                      715                      720 | 2397 |
| ttc gaa tct aac gtc aac gag gtg aag gac ccc tac cct tca gct gac<br>Phe Glu Ser Asn Val Asn Glu Val Lys Asp Pro Tyr Pro Ser Ala Asp<br>725                      730                      735                      740 | 2445 |
| ttc cca ggg gat gat gag gag gac gag cct gag atc cca gtg agc ccc<br>Phe Pro Gly Asp Asp Glu Glu Asp Glu Pro Glu Ile Pro Val Ser Pro<br>              745                      750                      755 | 2493 |
| cga ccg cgc ccg ctg gcc gag ctg cag ctc aaa gag aag gca gtg ccc<br>Arg Pro Arg Pro Leu Ala Glu Leu Gln Leu Lys Glu Lys Ala Val Pro<br>            760                      765                      770 | 2541 |
| atc ccg gaa gcc agc tcc ttc ttc atc ttc agt ccc acc aat aag gtc<br>Ile Pro Glu Ala Ser Ser Phe Phe Ile Phe Ser Pro Thr Asn Lys Val<br>              775                      780                      785 | 2589 |
| cgt gtc ctg tgt cac cgc atc gtc aac gcc acc tgg ttc acc aac ttc<br>Arg Val Leu Cys His Arg Ile Val Asn Ala Thr Trp Phe Thr Asn Phe | 2637 |

-continued

|  |  |  |  |  |
|---|---|---|---|---|
| 790 | 795 | 800 | | |

| | | |
|---|---|---|
| atc ctg ctc ttc atc ctg ctc agc agt gct gcg ctg gcc gcc gag gac<br>Ile Leu Leu Phe Ile Leu Leu Ser Ser Ala Ala Leu Ala Ala Glu Asp<br>805            810            815            820 | 2685 |
| ccc atc cgg gcg gag tcc gtg agg aat cag atc ctt gga tat ttt gat<br>Pro Ile Arg Ala Glu Ser Val Arg Asn Gln Ile Leu Gly Tyr Phe Asp<br>            825            830            835 | 2733 |
| att gcc ttc acc tct gtc ttc act gtg gag att gtc ctc aag atg acg<br>Ile Ala Phe Thr Ser Val Phe Thr Val Glu Ile Val Leu Lys Met Thr<br>840            845            850 | 2781 |
| acc tac ggc gcc ttc ctg cac aag ggc tcc ttc tgc cgc aac tac ttc<br>Thr Tyr Gly Ala Phe Leu His Lys Gly Ser Phe Cys Arg Asn Tyr Phe<br>            855            860            865 | 2829 |
| aac atc ctg gac ctg ctg gtg gtg gct gtg tct ctc atc tcc atg ggt<br>Asn Ile Leu Asp Leu Leu Val Val Ala Val Ser Leu Ile Ser Met Gly<br>870            875            880 | 2877 |
| ctc gag tcc agc acc atc tcc gtg gta aag atc ctg aga gtc cta agg<br>Leu Glu Ser Ser Thr Ile Ser Val Val Lys Ile Leu Arg Val Leu Arg<br>885            890            895            900 | 2925 |
| gtg ctc cgg ccc ctg cga gcc atc aac aga gcc aaa ggg ttg aag cac<br>Val Leu Arg Pro Leu Arg Ala Ile Asn Arg Ala Lys Gly Leu Lys His<br>            905            910            915 | 2973 |
| gtg gtc cag tgc gtg ttc gtg gcc atc cgc acc atc ggg aac atc gtc<br>Val Val Gln Cys Val Phe Val Ala Ile Arg Thr Ile Gly Asn Ile Val<br>920            925            930 | 3021 |
| ctg gtc acc acg ctc ctg cag ttc atg ttc gcc tgc att ggt gtc cag<br>Leu Val Thr Thr Leu Leu Gln Phe Met Phe Ala Cys Ile Gly Val Gln<br>            935            940            945 | 3069 |
| ctc ttc aag ggc aag ttc ttc agc tgc aac gac cta tcc aag atg aca<br>Leu Phe Lys Gly Lys Phe Phe Ser Cys Asn Asp Leu Ser Lys Met Thr<br>950            955            960 | 3117 |
| gaa gag gag tgc agg ggc tac tac tat gtg tac aag gac ggg gac ccc<br>Glu Glu Glu Cys Arg Gly Tyr Tyr Tyr Val Tyr Lys Asp Gly Asp Pro<br>965            970            975            980 | 3165 |
| acg cag atg gag ctg cgc ccc gcg cag tgg ata cac aat gac ttc cac<br>Thr Gln Met Glu Leu Arg Pro Arg Gln Trp Ile His Asn Asp Phe His<br>            985            990            995 | 3213 |
| ttt gac aac gtg  ctg tcg gcc atg atg  tcg ctc ttc acg gtg  tcc<br>Phe Asp Asn Val  Leu Ser Ala Met Met  Ser Leu Phe Thr Val  Ser<br>1000                  1005                1010 | 3258 |
| acc ttc gag gga  tgg ccc cag ctg ctg  tac agg gcc ata gac  tcc<br>Thr Phe Glu Gly  Trp Pro Gln Leu Leu  Tyr Arg Ala Ile Asp  Ser<br>1015                  1020                1025 | 3303 |
| aac gag gag gac  atg ggc ccc gtt tac  aac aac cga gtg gag  atg<br>Asn Glu Glu Asp  Met Gly Pro Val Tyr  Asn Asn Arg Val Glu  Met<br>1030                  1035                1040 | 3348 |
| gcc atc ttc ttc  atc atc tac atc atc  ctc att gcc ttc ttc  atg<br>Ala Ile Phe Phe  Ile Ile Tyr Ile Ile  Leu Ile Ala Phe Phe  Met<br>1045                  1050                1055 | 3393 |
| atg aac atc ttt  gtg ggc ttt gtc atc  gtc acc ttc cag gag  cag<br>Met Asn Ile Phe  Val Gly Phe Val Ile  Val Thr Phe Gln Glu  Gln<br>1060                  1065                1070 | 3438 |
| ggg gag aca gag  tac aag aac tgc gag  ctg gac aag aac cag  cgc<br>Gly Glu Thr Glu  Tyr Lys Asn Cys Glu  Leu Asp Lys Asn Gln  Arg<br>1075                  1080                1085 | 3483 |
| cag tgt gtg cag  tat gcc ctg aag gcc  cgc cca ctt cgg tgc  tac<br>Gln Cys Val Gln  Tyr Ala Leu Lys Ala  Arg Pro Leu Arg Cys  Tyr<br>1090                  1095                1100 | 3528 |
| atc ccc aag aac  cca tac cag tac cag  gtg tgg tac gtc gtc  acc | 3573 |

```
                                                -continued

Ile Pro Lys Asn Pro Tyr Gln Tyr Gln Val Trp Tyr Val Thr
            1105                1110                1115 tcc tcc tac ttt gaa tac ctg atg ttc gcc ctc atc atg ctc aac    3618
Ser Ser Tyr Phe Glu Tyr Leu Met Phe Ala Leu Ile Met Leu Asn
            1120                1125                1130 acc atc tgc ctg ggc atg cag cac tac cac cag tcg gag gag atg    3663
Thr Ile Cys Leu Gly Met Gln His Tyr His Gln Ser Glu Glu Met
            1135                1140                1145 aac cac atc tcg gac atc ctc aac gtg gcc ttc acc atc atc ttc    3708
Asn His Ile Ser Asp Ile Leu Asn Val Ala Phe Thr Ile Ile Phe
            1150                1155                1160 aca ctg gag atg atc ctc aag ctc ttg gcg ttc aag gcc agg ggc    3753
Thr Leu Glu Met Ile Leu Lys Leu Leu Ala Phe Lys Ala Arg Gly
            1165                1170                1175 tat ttc gga gac ccc tgg aat gtg ttc gac ttc ctg atc gtc atc    3798
Tyr Phe Gly Asp Pro Trp Asn Val Phe Asp Phe Leu Ile Val Ile
            1180                1185                1190 ggc agc atc att gac gtc atc ctc agc gag atc gac act ttc ctg    3843
Gly Ser Ile Ile Asp Val Ile Leu Ser Glu Ile Asp Thr Phe Leu
            1195                1200                1205 gcc tcc agc ggg gga ctg tat tgc ctg ggt ggc ggc tgc ggg aac    3888
Ala Ser Ser Gly Gly Leu Tyr Cys Leu Gly Gly Gly Cys Gly Asn
            1210                1215                1220 gtt gac cca gac gag agc gcc cgc atc tcc agt gcc ttc ttc cgc    3933
Val Asp Pro Asp Glu Ser Ala Arg Ile Ser Ser Ala Phe Phe Arg
            1225                1230                1235 ctg ttc cgg gtc atg agg ctg atc aag ctg ctg agt cgg gcc gag    3978
Leu Phe Arg Val Met Arg Leu Ile Lys Leu Leu Ser Arg Ala Glu
            1240                1245                1250 ggc gtg cgc acg ctg ctg tgg acg ttc atc aag tcc ttc cag gcc    4023
Gly Val Arg Thr Leu Leu Trp Thr Phe Ile Lys Ser Phe Gln Ala
            1255                1260                1265 ctg ccc tac gtg gcc ctg ctc atc gtc atg ctg ttc ttc atc tac    4068
Leu Pro Tyr Val Ala Leu Leu Ile Val Met Leu Phe Phe Ile Tyr
            1270                1275                1280 gcc gtc atc ggc atg cag atg ttt gga aag atc gcc ctg gtg gac    4113
Ala Val Ile Gly Met Gln Met Phe Gly Lys Ile Ala Leu Val Asp
            1285                1290                1295 ggg acc cag atc aac cgc aac aac aac ttc cag acc ttc ccg cag    4158
Gly Thr Gln Ile Asn Arg Asn Asn Asn Phe Gln Thr Phe Pro Gln
            1300                1305                1310 gcc gtg ctg ctg ctc ttc agg tgt gcg aca ggg gag gcg tgg caa    4203
Ala Val Leu Leu Leu Phe Arg Cys Ala Thr Gly Glu Ala Trp Gln
            1315                1320                1325 gag atc ctg ctg gcc tgc agc tac ggg aag ttg tgc gac cca gag    4248
Glu Ile Leu Leu Ala Cys Ser Tyr Gly Lys Leu Cys Asp Pro Glu
            1330                1335                1340 tca gac tac gcc ccg ggc gag gag tac acg tgt ggc acc aac ttc    4293
Ser Asp Tyr Ala Pro Gly Glu Glu Tyr Thr Cys Gly Thr Asn Phe
            1345                1350                1355 gcc tac tac tac ttc atc agc ttc tac atg ctc tgc gcc ttc ctg    4338
Ala Tyr Tyr Tyr Phe Ile Ser Phe Tyr Met Leu Cys Ala Phe Leu
            1360                1365                1370 atc atc aac ctc ttc gtg gct gtc atc atg gac aac ttt gac tac    4383
Ile Ile Asn Leu Phe Val Ala Val Ile Met Asp Asn Phe Asp Tyr
            1375                1380                1385 ctg aca cgc gac tgg tcc atc ctg ggc cct cac cac ctg gac gag    4428
Leu Thr Arg Asp Trp Ser Ile Leu Gly Pro His His Leu Asp Glu
            1390                1395                1400
```

```
                             -continued ttc aag gct atc tgg gca gag tat gac cca gag gcc aag ggg cga      4473
Phe Lys Ala Ile Trp Ala Glu Tyr Asp Pro Glu Ala Lys Gly Arg
         1405                1410                1415 atc aag cac ctg gac gtg gtg acc ctg ctg aga agg atc cag ccc      4518
Ile Lys His Leu Asp Val Val Thr Leu Leu Arg Arg Ile Gln Pro
         1420                1425                1430 cct ctg ggc ttc ggg aag ttc tgt cca cac cgg gtg gcc tgt aag      4563
Pro Leu Gly Phe Gly Lys Phe Cys Pro His Arg Val Ala Cys Lys
         1435                1440                1445 cgc ctg gtg ggc atg aac atg ccc ctg aac agt gac ggc acg gtc      4608
Arg Leu Val Gly Met Asn Met Pro Leu Asn Ser Asp Gly Thr Val
         1450                1455                1460 acc ttc aat gcc acg ctc ttt gcc ctg gtg cgc acg gcc ctc aag      4653
Thr Phe Asn Ala Thr Leu Phe Ala Leu Val Arg Thr Ala Leu Lys
         1465                1470                1475 atc aag aca gaa ggt aac ttt gag cag gcc aac gag gag ctg agg      4698
Ile Lys Thr Glu Gly Asn Phe Glu Gln Ala Asn Glu Glu Leu Arg
         1480                1485                1490 gcc atc atc aag aag atc tgg aag aga acc agc atg aag ctg ctg      4743
Ala Ile Ile Lys Lys Ile Trp Lys Arg Thr Ser Met Lys Leu Leu
         1495                1500                1505 gac cag gtc atc cct ccc ata gga gat gac gag gtg acc gtg ggg      4788
Asp Gln Val Ile Pro Pro Ile Gly Asp Asp Glu Val Thr Val Gly
         1510                1515                1520 aag ttc tac gcc aca ttc ctc atc cag gag cac ttc cgg aag ttc      4833
Lys Phe Tyr Ala Thr Phe Leu Ile Gln Glu His Phe Arg Lys Phe
         1525                1530                1535 atg aag cgc cag gag gaa tat tat ggg tat cgg ccc aag aag gac      4878
Met Lys Arg Gln Glu Glu Tyr Tyr Gly Tyr Arg Pro Lys Lys Asp
         1540                1545                1550 acc gtg cag atc cag gct ggg ctg cgg acc ata gag gag gag gcg      4923
Thr Val Gln Ile Gln Ala Gly Leu Arg Thr Ile Glu Glu Glu Ala
         1555                1560                1565 gcc cct gag atc cgc cgc acc atc tca gga gac ctg acc gcc gag      4968
Ala Pro Glu Ile Arg Arg Thr Ile Ser Gly Asp Leu Thr Ala Glu
         1570                1575                1580 gag gag ctg gag aga gcc atg gtg gag gct gcg atg gag gag agg      5013
Glu Glu Leu Glu Arg Ala Met Val Glu Ala Ala Met Glu Glu Arg
         1585                1590                1595 atc ttc cgg agg acg gga ggc ctg ttt ggc cag gtg gac acc ttc      5058
Ile Phe Arg Arg Thr Gly Gly Leu Phe Gly Gln Val Asp Thr Phe
         1600                1605                1610 ctg gaa agg acc aac tcc ctg ccc ccg gtg atg gcc aac caa aga      5103
Leu Glu Arg Thr Asn Ser Leu Pro Pro Val Met Ala Asn Gln Arg
         1615                1620                1625 ccg ctc cag ttt gct gag ata gaa atg gaa gag ctt gag tcg cct      5148
Pro Leu Gln Phe Ala Glu Ile Glu Met Glu Glu Leu Glu Ser Pro
         1630                1635                1640 gtc ttc ttg gag gac ttc cct caa gat gca aga acc aac cct ctc      5193
Val Phe Leu Glu Asp Phe Pro Gln Asp Ala Arg Thr Asn Pro Leu
         1645                1650                1655 gct cgt gcc aat acc aac aac gcc aat gcc aat gtt gcc tat ggc      5238
Ala Arg Ala Asn Thr Asn Asn Ala Asn Ala Asn Val Ala Tyr Gly
         1660                1665                1670 aac agc aac cat agc aac aac cag atg ttt tcc agc gtc cac tgt      5283
Asn Ser Asn His Ser Asn Asn Gln Met Phe Ser Ser Val His Cys
         1675                1680                1685 gaa agg gag ttc ccg gga gag gcg gag aca ccg gct gcc gga cga      5328
Glu Arg Glu Phe Pro Gly Glu Ala Glu Thr Pro Ala Ala Gly Arg
         1690                1695                1700
```

-continued

```
gga gcc ctc agc cac tcc cac agg gcc ctg gga cct cac agc aag       5373
Gly Ala Leu Ser His Ser His Arg Ala Leu Gly Pro His Ser Lys
        1705                1710                1715 ccc tgt gct gga aaa ctg aat ggg cag ctg gtc cag ccg ggg atg       5418
Pro Cys Ala Gly Lys Leu Asn Gly Gln Leu Val Gln Pro Gly Met
    1720                1725                1730 ccc atc aac cag gca cct cct gcc ccc tgc cag cag cct agc acg       5463
Pro Ile Asn Gln Ala Pro Pro Ala Pro Cys Gln Gln Pro Ser Thr
        1735                1740                1745 gat ccc cca gag cgc ggg cag agg agg acc tcc ctg aca ggg tct       5508
Asp Pro Pro Glu Arg Gly Gln Arg Arg Thr Ser Leu Thr Gly Ser
    1750                1755                1760 ctg caa gac gaa gca ccc cag agg agg agc tcc gag ggg agc acc       5553
Leu Gln Asp Glu Ala Pro Gln Arg Arg Ser Ser Glu Gly Ser Thr
        1765                1770                1775 ccc agg cgc ccg gct cct gct aca gct ctg ctg atc caa gag gct       5598
Pro Arg Arg Pro Ala Pro Ala Thr Ala Leu Leu Ile Gln Glu Ala
    1780                1785                1790 ctg gtt cga ggg ggc ctg gac acc ttg gca gct gat gct ggc ttc       5643
Leu Val Arg Gly Gly Leu Asp Thr Leu Ala Ala Asp Ala Gly Phe
        1795                1800                1805 gtc acg gca aca agc cag gcc ctg gca gac gcc tgt cag atg gaa       5688
Val Thr Ala Thr Ser Gln Ala Leu Ala Asp Ala Cys Gln Met Glu
    1810                1815                1820 ccg gag gaa gta gag gtc gca gcc aca gag cta ctg aaa gcg cga       5733
Pro Glu Glu Val Glu Val Ala Ala Thr Glu Leu Leu Lys Ala Arg
        1825                1830                1835 gag tct gtc cag ggc atg gcc agt gtc ccg gga agc ctg agc cgc       5778
Glu Ser Val Gln Gly Met Ala Ser Val Pro Gly Ser Leu Ser Arg
    1840                1845                1850 agg tcc tcc ctg ggc agc ctt gac cag gtc cag ggc tcc cag gaa       5823
Arg Ser Ser Leu Gly Ser Leu Asp Gln Val Gln Gly Ser Gln Glu
        1855                1860                1865 acc ctt att cct ccc agg ccg tga tggctgtggt gtccacatga ccaaggcgag  5877
Thr Leu Ile Pro Pro Arg Pro
                1870 agggacagtg cgtgcagaag ctcagccctg catggcagcc tccctctgtc tcagccctcc  5937 tgctgagctg gggcggtctg gaaccgcacc aggaagccag gagcctcccc tggccagcaa  5997 gaggcatgat tctaaagcca tccagaaagg cctggtcagt gccactcccc agcaggacat  6057 taaagtctct aggtctgtgg cactgg                                       6083

<210> SEQ ID NO 22
<211> LENGTH: 1873
<212> TYPE: PRT
<213> ORGANISM: Oryctolagus cuniculus

<400> SEQUENCE: 22

Met Glu Pro Ser Ser Pro Gln Asp Glu Gly Leu Arg Lys Lys Gln Pro
1               5                   10                  15

Lys Lys Pro Leu Pro Glu Val Leu Pro Arg Pro Pro Arg Ala Leu Phe
            20                  25                  30

Cys Leu Thr Leu Gln Asn Pro Leu Arg Lys Ala Cys Ile Ser Ile Val
        35                  40                  45

Glu Trp Lys Pro Phe Glu Thr Ile Ile Leu Leu Thr Ile Phe Ala Asn
    50                  55                  60

Cys Val Ala Leu Ala Val Tyr Leu Pro Met Pro Glu Asp Asp Asn Asn
65                  70                  75                  80
```

-continued

```
Ser Leu Asn Leu Gly Leu Glu Lys Leu Glu Tyr Phe Phe Leu Thr Val
                85                  90                  95
Phe Ser Ile Glu Ala Ala Met Lys Ile Ile Ala Tyr Gly Phe Leu Phe
            100                 105                 110
His Gln Asp Ala Tyr Leu Arg Ser Gly Trp Asn Val Leu Asp Phe Ile
        115                 120                 125
Ile Val Phe Leu Gly Val Phe Thr Ala Ile Leu Glu Gln Val Asn Val
    130                 135                 140
Ile Gln Ser Asn Thr Ala Pro Met Ser Ser Lys Gly Ala Gly Leu Asp
145                 150                 155                 160
Val Lys Ala Leu Arg Ala Phe Arg Val Leu Arg Pro Leu Arg Leu Val
                165                 170                 175
Ser Gly Val Pro Ser Leu Gln Val Val Leu Asn Ser Ile Phe Lys Ala
            180                 185                 190
Met Leu Pro Leu Phe His Ile Ala Leu Leu Val Leu Phe Met Val Ile
        195                 200                 205
Ile Tyr Ala Ile Ile Gly Leu Glu Leu Phe Lys Gly Lys Met His Lys
    210                 215                 220
Thr Cys Tyr Tyr Ile Gly Thr Asp Ile Val Ala Thr Val Glu Asn Glu
225                 230                 235                 240
Lys Pro Ser Pro Cys Ala Arg Thr Gly Ser Gly Arg Pro Cys Thr Ile
                245                 250                 255
Asn Gly Ser Glu Cys Arg Gly Gly Trp Pro Gly Pro Asn His Gly Ile
            260                 265                 270
Thr His Phe Asp Asn Phe Gly Phe Ser Met Leu Thr Val Tyr Gln Cys
        275                 280                 285
Ile Thr Met Glu Gly Trp Thr Asp Val Leu Tyr Trp Val Asn Asp Ala
    290                 295                 300
Ile Gly Asn Glu Trp Pro Trp Ile Tyr Phe Val Thr Leu Ile Leu Leu
305                 310                 315                 320
Gly Ser Phe Phe Ile Leu Asn Leu Val Leu Gly Val Leu Ser Gly Glu
                325                 330                 335
Phe Thr Lys Glu Arg Glu Lys Ala Lys Ser Arg Gly Thr Phe Gln Lys
            340                 345                 350
Leu Arg Glu Lys Gln Gln Leu Glu Glu Asp Leu Arg Gly Tyr Met Ser
        355                 360                 365
Trp Ile Thr Gln Gly Glu Val Met Asp Val Glu Asp Leu Arg Glu Gly
    370                 375                 380
Lys Leu Ser Leu Glu Glu Gly Ser Asp Thr Glu Ser Leu Tyr Glu
385                 390                 395                 400
Ile Glu Gly Leu Asn Lys Ile Ile Gln Phe Ile Arg His Trp Arg Gln
                405                 410                 415
Trp Asn Arg Val Phe Arg Trp Lys Cys His Asp Leu Val Lys Ser Arg
            420                 425                 430
Val Phe Tyr Trp Leu Val Ile Leu Ile Val Ala Leu Asn Thr Leu Ser
        435                 440                 445
Ile Ala Ser Glu His His Asn Gln Pro Leu Trp Leu Thr His Leu Gln
    450                 455                 460
Asp Ile Ala Asn Arg Val Leu Leu Ser Leu Phe Thr Ile Glu Met Leu
465                 470                 475                 480
Leu Lys Met Tyr Gly Leu Gly Leu Arg Gln Tyr Phe Met Ser Ile Phe
                485                 490                 495
```

-continued

```
Asn Arg Phe Asp Cys Phe Val Val Cys Ser Gly Ile Leu Glu Leu Leu
                500                 505                 510
Leu Val Glu Ser Gly Ala Met Thr Pro Leu Gly Ile Ser Val Leu Arg
            515                 520                 525
Cys Ile Arg Leu Leu Arg Leu Phe Lys Ile Thr Lys Tyr Trp Thr Ser
        530                 535                 540
Leu Ser Asn Leu Val Ala Ser Leu Leu Asn Ser Ile Arg Ser Ile Ala
545                 550                 555                 560
Ser Leu Leu Leu Leu Leu Phe Leu Phe Ile Ile Ile Phe Ala Leu Leu
                565                 570                 575
Gly Met Gln Leu Phe Gly Gly Arg Tyr Asp Phe Glu Asp Thr Glu Val
            580                 585                 590
Arg Arg Ser Asn Phe Asp Asn Phe Pro Gln Ala Leu Ile Ser Val Phe
        595                 600                 605
Gln Val Leu Thr Gly Glu Asp Trp Asn Ser Val Met Tyr Asn Gly Ile
    610                 615                 620
Met Ala Tyr Gly Gly Pro Ser Tyr Pro Gly Val Leu Val Cys Ile Tyr
625                 630                 635                 640
Phe Ile Ile Leu Phe Val Cys Gly Asn Tyr Ile Leu Leu Asn Val Phe
                645                 650                 655
Leu Ala Ile Ala Val Asp Asn Leu Ala Glu Ala Glu Ser Leu Thr Ser
            660                 665                 670
Ala Gln Lys Ala Lys Ala Glu Glu Arg Lys Arg Arg Lys Met Ser Arg
        675                 680                 685
Gly Leu Pro Asp Lys Thr Glu Glu Lys Ser Val Met Ala Lys Lys
    690                 695                 700
Leu Glu Gln Lys Pro Lys Gly Glu Gly Ile Pro Thr Thr Ala Lys Leu
705                 710                 715                 720
Lys Val Asp Glu Phe Glu Ser Asn Val Asn Glu Val Lys Asp Pro Tyr
                725                 730                 735
Pro Ser Ala Asp Phe Pro Gly Asp Asp Glu Glu Asp Glu Pro Glu Ile
            740                 745                 750
Pro Val Ser Pro Arg Pro Arg Pro Leu Ala Glu Leu Gln Leu Lys Glu
        755                 760                 765
Lys Ala Val Pro Ile Pro Glu Ala Ser Ser Phe Phe Ile Phe Ser Pro
    770                 775                 780
Thr Asn Lys Val Arg Val Leu Cys His Arg Ile Val Asn Ala Thr Trp
785                 790                 795                 800
Phe Thr Asn Phe Ile Leu Leu Phe Ile Leu Leu Ser Ser Ala Ala Leu
                805                 810                 815
Ala Ala Glu Asp Pro Ile Arg Ala Glu Ser Val Arg Asn Gln Ile Leu
            820                 825                 830
Gly Tyr Phe Asp Ile Ala Phe Thr Ser Val Phe Thr Val Glu Ile Val
        835                 840                 845
Leu Lys Met Thr Thr Tyr Gly Ala Phe Leu His Lys Gly Ser Phe Cys
    850                 855                 860
Arg Asn Tyr Phe Asn Ile Leu Asp Leu Leu Val Val Ala Val Ser Leu
865                 870                 875                 880
Ile Ser Met Gly Leu Glu Ser Ser Thr Ile Ser Val Val Lys Ile Leu
                885                 890                 895
Arg Val Leu Arg Val Leu Arg Pro Leu Arg Ala Ile Asn Arg Ala Lys
            900                 905                 910
Gly Leu Lys His Val Val Gln Cys Val Phe Val Ala Ile Arg Thr Ile
```

-continued

```
                915                 920                 925
Gly Asn Ile Val Leu Val Thr Thr Leu Leu Gln Phe Met Phe Ala Cys
            930                 935                 940
Ile Gly Val Gln Leu Phe Lys Gly Lys Phe Phe Ser Cys Asn Asp Leu
945                 950                 955                 960
Ser Lys Met Thr Glu Glu Cys Arg Gly Tyr Tyr Val Tyr Lys
            965                 970                 975
Asp Gly Asp Pro Thr Gln Met Glu Leu Arg Pro Arg Gln Trp Ile His
            980                 985                 990
Asn Asp Phe His Phe Asp Asn Val Leu Ser Ala Met Met Ser Leu Phe
            995                 1000                1005
Thr Val Ser Thr Phe Glu Gly Trp Pro Gln Leu Leu Tyr Arg Ala
        1010                1015                1020
Ile Asp Ser Asn Glu Glu Asp Met Gly Pro Val Tyr Asn Asn Arg
        1025                1030                1035
Val Glu Met Ala Ile Phe Phe Ile Ile Tyr Ile Ile Leu Ile Ala
        1040                1045                1050
Phe Phe Met Met Asn Ile Phe Val Gly Phe Val Ile Val Thr Phe
        1055                1060                1065
Gln Glu Gln Gly Glu Thr Glu Tyr Lys Asn Cys Glu Leu Asp Lys
        1070                1075                1080
Asn Gln Arg Gln Cys Val Gln Tyr Ala Leu Lys Ala Arg Pro Leu
        1085                1090                1095
Arg Cys Tyr Ile Pro Lys Asn Pro Tyr Gln Tyr Gln Val Trp Tyr
        1100                1105                1110
Val Val Thr Ser Ser Tyr Phe Glu Tyr Leu Met Phe Ala Leu Ile
        1115                1120                1125
Met Leu Asn Thr Ile Cys Leu Gly Met Gln His Tyr His Gln Ser
        1130                1135                1140
Glu Glu Met Asn His Ile Ser Asp Ile Leu Asn Val Ala Phe Thr
        1145                1150                1155
Ile Ile Phe Thr Leu Glu Met Ile Leu Lys Leu Leu Ala Phe Lys
        1160                1165                1170
Ala Arg Gly Tyr Phe Gly Asp Pro Trp Asn Val Phe Asp Phe Leu
        1175                1180                1185
Ile Val Ile Gly Ser Ile Ile Asp Val Ile Leu Ser Glu Ile Asp
        1190                1195                1200
Thr Phe Leu Ala Ser Ser Gly Gly Leu Tyr Cys Leu Gly Gly Gly
        1205                1210                1215
Cys Gly Asn Val Asp Pro Asp Glu Ser Ala Arg Ile Ser Ser Ala
        1220                1225                1230
Phe Phe Arg Leu Phe Arg Val Met Arg Leu Ile Lys Leu Leu Ser
        1235                1240                1245
Arg Ala Glu Gly Val Arg Thr Leu Leu Trp Thr Phe Ile Lys Ser
        1250                1255                1260
Phe Gln Ala Leu Pro Tyr Val Ala Leu Leu Ile Val Met Leu Phe
        1265                1270                1275
Phe Ile Tyr Ala Val Ile Gly Met Gln Met Phe Gly Lys Ile Ala
        1280                1285                1290
Leu Val Asp Gly Thr Gln Ile Asn Arg Asn Asn Asn Phe Gln Thr
        1295                1300                1305
Phe Pro Gln Ala Val Leu Leu Leu Phe Arg Cys Ala Thr Gly Glu
        1310                1315                1320
```

```
Ala Trp Gln Glu Ile Leu Leu Ala Cys Ser Tyr Gly Lys Leu Cys
1325                1330                1335

Asp Pro Glu Ser Asp Tyr Ala Pro Gly Glu Tyr Thr Cys Gly
1340                1345                1350

Thr Asn Phe Ala Tyr Tyr Phe Ile Ser Phe Tyr Met Leu Cys
1355                1360                1365

Ala Phe Leu Ile Ile Asn Leu Phe Val Ala Val Ile Met Asp Asn
1370                1375                1380

Phe Asp Tyr Leu Thr Arg Asp Trp Ser Ile Leu Gly Pro His His
1385                1390                1395

Leu Asp Glu Phe Lys Ala Ile Trp Ala Glu Tyr Asp Pro Glu Ala
1400                1405                1410

Lys Gly Arg Ile Lys His Leu Asp Val Val Thr Leu Leu Arg Arg
1415                1420                1425

Ile Gln Pro Pro Leu Gly Phe Gly Lys Phe Cys Pro His Arg Val
1430                1435                1440

Ala Cys Lys Arg Leu Val Gly Met Asn Met Pro Leu Asn Ser Asp
1445                1450                1455

Gly Thr Val Thr Phe Asn Ala Thr Leu Phe Ala Leu Val Arg Thr
1460                1465                1470

Ala Leu Lys Ile Lys Thr Glu Gly Asn Phe Glu Gln Ala Asn Glu
1475                1480                1485

Glu Leu Arg Ala Ile Ile Lys Lys Ile Trp Lys Arg Thr Ser Met
1490                1495                1500

Lys Leu Leu Asp Gln Val Ile Pro Pro Ile Gly Asp Asp Glu Val
1505                1510                1515

Thr Val Gly Lys Phe Tyr Ala Thr Phe Leu Ile Gln Glu His Phe
1520                1525                1530

Arg Lys Phe Met Lys Arg Gln Glu Glu Tyr Tyr Gly Tyr Arg Pro
1535                1540                1545

Lys Lys Asp Thr Val Gln Ile Gln Ala Gly Leu Arg Thr Ile Glu
1550                1555                1560

Glu Glu Ala Ala Pro Glu Ile Arg Arg Thr Ile Ser Gly Asp Leu
1565                1570                1575

Thr Ala Glu Glu Glu Leu Glu Arg Ala Met Val Glu Ala Ala Met
1580                1585                1590

Glu Glu Arg Ile Phe Arg Arg Thr Gly Gly Leu Phe Gly Gln Val
1595                1600                1605

Asp Thr Phe Leu Glu Arg Thr Asn Ser Leu Pro Pro Val Met Ala
1610                1615                1620

Asn Gln Arg Pro Leu Gln Phe Ala Glu Ile Glu Met Glu Glu Leu
1625                1630                1635

Glu Ser Pro Val Phe Leu Glu Asp Phe Pro Gln Asp Ala Arg Thr
1640                1645                1650

Asn Pro Leu Ala Arg Ala Asn Thr Asn Asn Ala Asn Ala Asn Val
1655                1660                1665

Ala Tyr Gly Asn Ser Asn His Ser Asn Asn Gln Met Phe Ser Ser
1670                1675                1680

Val His Cys Glu Arg Glu Phe Pro Gly Glu Ala Glu Thr Pro Ala
1685                1690                1695

Ala Gly Arg Gly Ala Leu Ser His Ser His Arg Ala Leu Gly Pro
1700                1705                1710
```

```
His Ser Lys Pro Cys Ala Gly Lys Leu Asn Gly Gln Leu Val Gln
    1715                1720                1725

Pro Gly Met Pro Ile Asn Gln Ala Pro Ala Pro Cys Gln Gln
    1730                1735                1740

Pro Ser Thr Asp Pro Pro Glu Arg Gly Gln Arg Thr Ser Leu
    1745                1750                1755

Thr Gly Ser Leu Gln Asp Glu Ala Pro Gln Arg Ser Ser Glu
    1760                1765                1770

Gly Ser Thr Pro Arg Arg Pro Ala Pro Ala Thr Ala Leu Leu Ile
    1775                1780                1785

Gln Glu Ala Leu Val Arg Gly Gly Leu Asp Thr Leu Ala Ala Asp
    1790                1795                1800

Ala Gly Phe Val Thr Ala Thr Ser Gln Ala Leu Ala Asp Ala Cys
    1805                1810                1815

Gln Met Glu Pro Glu Glu Val Glu Val Ala Ala Thr Glu Leu Leu
    1820                1825                1830

Lys Ala Arg Glu Ser Val Gln Gly Met Ala Ser Val Pro Gly Ser
    1835                1840                1845

Leu Ser Arg Arg Ser Ser Leu Gly Ser Leu Asp Gln Val Gln Gly
    1850                1855                1860

Ser Gln Glu Thr Leu Ile Pro Pro Arg Pro
    1865                1870

<210> SEQ ID NO 23
<211> LENGTH: 57
<212> TYPE: DNA
<213> ORGANISM: Homo sapiens
<220> FEATURE:
<221> NAME/KEY: partial_cDNA
<222> LOCATION: (1)..(57)

<400> SEQUENCE: 23
actttcctgg cctccagcgg gggactgtat tgcctgggtg gaggctgcgg gaacgtt      57

<210> SEQ ID NO 24
<211> LENGTH: 19
<212> TYPE: PRT
<213> ORGANISM: Homo sapiens
<220> FEATURE:
<221> NAME/KEY: DOMAIN
<222> LOCATION: (1)..(19)

<400> SEQUENCE: 24

Thr Phe Leu Ala Ser Ser Gly Gly Leu Tyr Cys Leu Gly Gly Gly Cys
1               5                   10                  15

Gly Asn Val

<210> SEQ ID NO 25
<211> LENGTH: 45
<212> TYPE: DNA
<213> ORGANISM: Homo sapiens
<220> FEATURE:
<221> NAME/KEY: partial_cDNA
<222> LOCATION: (1)..(45)

<400> SEQUENCE: 25
ccaactgaaa gtgaaaatgt ccctgtccca actgctacac ctggg                45

<210> SEQ ID NO 26
<211> LENGTH: 15
<212> TYPE: PRT
```

```
-continued

<213> ORGANISM: Homo sapiens
<220> FEATURE:
<221> NAME/KEY: DOMAIN
<222> LOCATION: (1)..(15)

<400> SEQUENCE: 26

Pro Thr Glu Ser Glu Asn Val Pro Val Pro Thr Ala Thr Pro Gly
1               5                   10                  15

<210> SEQ ID NO 27
<211> LENGTH: 20
<212> TYPE: PRT
<213> ORGANISM: Homo sapiens

<400> SEQUENCE: 27

Asn Glu Glu Leu Arg Ala Ile Ile Lys Lys Ile Trp Lys Arg Thr Ser
1               5                   10                  15

Met Lys Leu Leu
            20

<210> SEQ ID NO 28
<211> LENGTH: 35
<212> TYPE: DNA
<213> ORGANISM: Homo sapiens

<400> SEQUENCE: 28
ggccctcagc gaagcggaca actctgaaga gagca                             35

<210> SEQ ID NO 29
<211> LENGTH: 35
<212> TYPE: DNA
<213> ORGANISM: Homo sapiens

<400> SEQUENCE: 29
atcctcagtg agatcgacga cccagatgag agtgc                             35
```

PURIFIED AND ISOLATED PLATELET CALCIUM CHANNEL NUCLEIC ACIDS AND POLYPEPTIDES AND THERAPEUTIC AND SCREENING METHODS USING SAME

CROSS REFERENCE TO RELATED APPLICATIONS

This application is a continuation-in-part of U.S. patent application Ser. No. 10/029,413, filed Dec. 20, 2001, now U.S. Pat. No. 7,041,475 which itself is based on and claims priority to U.S. Provisional Patent Application Ser. No. 60/258,169 filed Dec. 22, 2000, the entire contents of both of which are herein incorporated by reference.

GRANT STATEMENT

This work was supported by NIH grants I-P20-DE123474 and I-P60-DE 13079. Thus, the U.S. Government has certain rights in the presently claimed subject matter.

TECHNICAL FIELD

The presently claimed subject matter relates generally to isolated and purified proteins and nucleic acids. In one embodiment, the presently claimed subject matter relates to modulating phosphatidylserine exposure on the surface of a cell.

Table of Abbreviations

| | |
|---|---|
| 2D | two-dimensional |
| $^{32}P_i$ | radioactive inorganic phosphate |
| ACD | acid-citrate-dextrose |
| ADP | adenosine diphosphate |
| ASO | allele-specific oligonucleotide |
| A-T | ataxia-telangiectasia |
| ATP | adenosine triphosphate |
| b.i.d. | bis in die; twice a day |
| bp | basepair (s) |
| BSA | bovine serum albumin |
| $[Ca^{2+}]_i$ | $Ca^{2+}$ concentration (intracellular) |
| cAMP | cyclic adenosine monophosphate |
| CDR | complementarity-determining region |
| cmRNA | complementary mRNA |
| DHP | dihydropyridine |
| ECL | electrochemiluminescence |
| ELISA | enzyme-linked immunosorbent assay |
| EM | electron microscope/microscopy |
| EST | expressed sequence tag |
| FACS | fluorescence activated cell sorting |
| FISH | fluorescence in situ hybridization |
| FITC | fluorescein isothiocyanate |
| fl | full length |
| $h\alpha_1 D$ | human platelet VDCC $\alpha_1 D$ subunit |
| $h\alpha_1 S$ | human platelet VDCC $\alpha_1 S$ subunit |
| HAT | cell culture media comprising hypoxanthine, aminopterin, and thymidine |
| IMAGE | integrated molecular analysis of genomes and their expression |
| kDa | kilodalton (s) |
| KLH | keyhole limpet hemocyanin |
| kV | kilovolt (s) |
| L | liter (s) |
| LAT | ligation-activated translation |
| LCR | ligase chain reaction |
| MAb | monoclonal antibody |
| MAb 1A | Monoclonal Antibody 1A |
| MCF | mean cell fluorescence |
| µg | microgram (s) |
| mL | milliliter (s) |
| MTD | maximally tolerated dose |
| NASBA™ | nucleic acid sequence-based amplification |

-continued

Table of Abbreviations

| | |
|---|---|
| nm | nanometer (s) |
| nt | nucleotide (s) |
| OCS | open canalicular system |
| OLAs | oligonucleotide ligation assays |
| ORF | open reading frame |
| $P_{2x}$ | an adenosine diphosphate receptor |
| $p\alpha_1 D$ | porcine platelet VDCC $\alpha_1 D$ subunit |
| $p\alpha_1 S$ | porcine platelet VDCC $\alpha_1 S$ subunit |
| PADGEM | platelet activation-dependent granule-external membrane protein; P-selectin |
| PAGE | polyacrylamide gel electrophoresis |
| PBS | phosphate buffered saline |
| PCR | polymerase chain reaction |
| $PGI_2$ | prostaglandin $I_2$ |
| PLSCR1 | phospholipid scramblase 1 |
| PRP | platelet-rich plasma |
| PS | phosphatidylserine |
| PVD | polyvinyl derivative |
| RACE | rapid amplification of conserved ends |
| RCR | repair chain reaction |
| RFLP | restriction fragment length polymorphism |
| r.t. | room temperature |
| RT-PCR | reverse transcription polymerase chain reaction |
| SDA | strand displacement activation |
| SDS | sodium dodecyl sulfate |
| SDS-PAGE | sodium dodecyl sulfate polyacrylamide gel electrophoresis |
| SNPs | single nucleotide polymorphisms |
| SR | sarcoplasmic reticulum |
| SSC | standard saline citrate; 150 mM NaCl/15 mM sodium citrate, pH 7.0 |
| SSCP | single strand conformation polymorphism |
| SV40 | Simian Virus 40 |
| TLC | thin layer chromatography |
| VDCC(s) | voltage dependent calcium channel (s) |
| vWf | von Willebrand factor |
| wt | wild type |

BACKGROUND ART

Calcium influx into the platelet controls important processes during platelet activation. Sage, 1997; Mills, 1996. The pathway for this calcium entry is not well understood. Recently, gating of an ADP receptor ($P_{2x}$) has been suggested to be responsible for rapid calcium ($Ca^{2+}$) influx into the platelet. Mackenzie et al., 1996; Sun et al., 1998. Indeed, several ions, including $Ca^{2+}$, $Mg^{2+}$, and $Na^+$, enter when this receptor is activated. However, calcium entry via this receptor is believed not to be sufficient for the processes that take place during platelet activation. Jin & Kanapuli 1998; Kanapuli, 1998. $P_{2x}$ is an ionotropic channel, and its gating in other cell types, such as skeletal muscle cells, has an excitatory depolarizing effect that activates voltage dependent calcium channels (VDCCs). Bean, 1993; Surprenant et al., 1995; Abbrachio et al., 1994. It is the activation of these calcium selective VDCCs that triggers calcium dependent events inside these cells, such as secretion and contraction. Ashcroft, 2000; Boyd, 1992; Hille 1992; Armstrong & Hille, 1998; Berridge, 1997.

The presence of VDCCs in platelets is controversial (Sage, 1997), and heretofore their expression has not been investigated at the molecular level. Thus, in view of the role of calcium influx in controlling processes during platelet activation, the identification of a VDCC polypeptide in platelets represents a long-felt and continuing need in the art.

SUMMARY

This Summary lists several embodiments of the presently claimed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

The presently claimed subject matter provides a method of screening candidate substances for an ability to modulate phosphatidylserine exposure on the surface of a cell. In one embodiment, the method comprises (a) establishing a test sample comprising a platelet voltage dependent calcium channel (VDCC) $\alpha_1$ subunit polypeptide; (b) administering a candidate substance to the test sample; and (c) measuring the interaction, effect, or combination thereof, of the candidate substance on the test sample to thereby determine the ability of the candidate substance to modulate phosphatidylserine exposure on the surface of the cell. In one embodiment, the candidate substance is a candidate polypeptide, in another embodiment an antibody, in another embodiment a nucleic acid, and in yet another embodiment a chemical compound.

In another embodiment of the present method, the method further comprises isolating a gene encoding the candidate polypeptide. In one embodiment, the test sample comprises a nucleic acid molecule encoding a platelet voltage dependent calcium channel (VDCC) $\alpha_1$ subunit polypeptide. In one embodiment, the platelet voltage dependent calcium channel (VDCC) $\alpha_1$ subunit polypeptide is contained within a cell in cell culture. In one embodiment, the measuring comprises (a) determining a first level of phosphatidylserine exposure on a surface of the test sample before the administering step (b); (b) determining a second level of phosphatidylserine exposure on the surface of the test sample after the administering step (b); and (c) comparing the first level and the second level, wherein a difference between the first level and the second level is indicative of the ability of the candidate substance to modulate phosphatidylserine exposure on the surface of the cell. In one embodiment, the determining comprises (a) contacting the test sample with an antibody comprising a detectable moiety, wherein the antibody binds to phosphatidylserine; and (b) quantitating an amount of the antibody bound to the test sample, wherein the amount of the antibody bound to the test sample is indicative of an amount of phosphatidylserine on the surface of the test sample. In one embodiment, the detectable moiety is selected from the group consisting of a radiolabel, a fluorescent label, a chemiluminescent label, and an enzyme. In one embodiment, the quantitating is by a method selected from the group consisting of radioactive detection, fluorescence detection, chemiluminescent detection, calorimetric detection, Western blotting, immunoprecipitation, and fluorescence-activating cell sorting (FACS).

In one embodiment of the present method, the interaction, effect, or combination thereof, of the candidate substance on the test sample results in an increase in phosphatidylserine exposure on the surface of the cell. In another embodiment, the interaction, effect, or combination thereof, of the candidate substance on the test sample results in a decrease in phosphatidylserine exposure on the surface of the cell.

The presently claimed subject matter also provides a method of screening candidate substances for an ability to modulate phosphatidylserine exposure on a surface of a cell comprising (a) establishing a test sample comprising a modulatable transcriptional regulatory sequence of a platelet voltage dependent calcium channel (VDCC) $\alpha_1$ subunit polypeptide-encoding gene and a reporter gene which is capable of producing a detectable signal; (b) administering a candidate substance to the test sample; and (c) measuring the detectable signal produced as a result of an interaction between the candidate substance and the test sample, wherein a candidate substance as a modulator of phosphatidylserine exposure on a surface of a cell is based on the amount of signal produced in relation to a control sample. In one embodiment, the reporter gene encodes a platelet voltage dependent calcium channel (VDCC) $\alpha_1$ subunit polypeptide.

The presently claimed subject matter also provides a method of screening candidate substances for an ability to modulate platelet voltage dependent calcium channel (VDCC) $\alpha_1$ subunit biological activity. In one embodiment, the method comprises (a) establishing a test sample comprising a platelet voltage dependent calcium channel (VDCC) $\alpha_1$ subunit polypeptide; (b) administering a candidate substance to the test sample; and (c) measuring the interaction, effect, or combination thereof, of the candidate substance on the test sample to thereby determine the ability of the candidate substance to modulate platelet voltage dependent calcium channel (VDCC) $\alpha_1$ subunit biological activity. The candidate substance is in one embodiment a candidate polypeptide, in another embodiment an antibody, in another embodiment a nucleic acid, and in still another embodiment a chemical compound. In one embodiment, the method further comprises the step of purifying and isolating a gene encoding the candidate polypeptide.

In one embodiment of the present method, the test sample comprises a nucleic acid molecule encoding a platelet voltage dependent calcium channel (VDCC) $\alpha_1$ subunit polypeptide. In one embodiment, the platelet voltage dependent calcium channel (VDCC) $\alpha_1$ subunit polypeptide is contained within cells in cell culture. In another embodiment of the present method, the measuring comprises (a) determining a first level of phosphatidylserine exposure in the test sample before the administering step (b); (b) determining a second level of phosphatidylserine exposure in the test sample after the administering step (b); and (c) comparing the first level and the second level, wherein a difference between the first level and the second level is indicative of the ability of the candidate substance to modulate platelet voltage dependent calcium channel (VDCC) $\alpha_1$ subunit biological activity.

In still another embodiment of the present method, the determining comprises (a) contacting the test sample with an antibody comprising a detectable moiety, wherein the antibody binds to phosphatidylserine; and (b) quantitating an amount of the antibody bound to the test sample, wherein the amount of the antibody bound to the test sample is indicative of the ability of the candidate substance to modulate platelet voltage dependent calcium channel (VDCC) $\alpha_1$ subunit biological activity. In one embodiment, the detectable moiety is selected from the group consisting of a radiolabel, a fluorescent label, a chemiluminescent label, and an enzyme. In still another embodiment of the present method, the quantitating is by a method chosen from the group consisting of radioactive detection, fluorescence detection, chemiluminescent detection, calorimetric detection, Western blotting, immunoprecipitation, and fluorescence-activating cell sorting (FACS).

The presently claimed subject matter also provides a method of screening candidate substances for an ability to modulate platelet voltage dependent calcium channel (VDCC) $\alpha_1$ subunit biological activity. In one embodiment, the method comprises (a) establishing a test sample comprising a modulatable transcriptional regulatory sequence of a platelet voltage dependent calcium channel (VDCC) $\alpha_1$ subunit polypeptide-encoding gene and a reporter gene which is capable of producing a detectable signal; (b) administering a candidate substance to the test sample; and (c) measuring the detectable signal produced as a result of an interaction between the candidate substance and the test sample, wherein a candidate substance as a modulator of platelet voltage dependent calcium channel (VDCC) $\alpha_1$ subunit biological activity is based on the amount of signal produced in relation to a control sample. In one embodiment, the reporter gene encodes a platelet voltage dependent calcium channel (VDCC) $\alpha_1$ subunit polypeptide. The presently claimed subject matter also provides a method of modulating platelet voltage dependent calcium channel (VDCC) $\alpha_1$ subunit polypeptide biological activity in a cell, the method comprising administering to the cell an effective amount of a substance capable of modulating activity of a platelet voltage dependent calcium channel (VDCC) $\alpha_1$ subunit polypeptide in the cell to thereby modulate platelet voltage dependent calcium channel (VDCC) $\alpha_1$ subunit polypeptide biological activity in the cell. In one embodiment, the cell is a platelet or a megakaryocyte. In another embodiment, the cell comprises a cell in a vertebrate subject. In one embodiment, the vertebrate subject is a mammal.

In one embodiment of the presently claimed subject matter, the administering further comprises administering an effective amount of a substance that modulates expression of a platelet voltage dependent calcium channel (VDCC) $\alpha_1$ subunit polypeptide-encoding nucleic acid molecule in the cell. The substance that modulates the platelet voltage dependent calcium channel (VDCC) $\alpha_1$ subunit biological activity comprises in one embodiment an anti-platelet voltage dependent calcium channel (VDCC) $\alpha_1$ subunit polypeptide antibody, in another embodiment a polypeptide, in another embodiment a chemical compound, and in still another embodiment a nucleic acid. In one embodiment, the nucleic acid comprises an antisense oligonucleotide. In one embodiment, the polypeptide or chemical compound comprises a ligand for a modulatable transcriptional regulatory sequence of a platelet voltage dependent calcium channel (VDCC) $\alpha_1$ subunit polypeptide-encoding nucleic acid molecule.

The presently claimed subject matter also provides a method of modulating phosphatidylserine exposure on a surface of a cell, the method comprising administering to the cell an effective amount of a substance capable of modulating the activity of a platelet voltage dependent calcium channel (VDCC) $\alpha_1$ subunit polypeptide in the cell to thereby modulate phosphatidylserine exposure on the surface of the cell. In one embodiment, the cell is a platelet, and in another embodiment the cell is a megakaryocyte. In one embodiment, the cell comprises a cell in a vertebrate subject. In one embodiment, the vertebrate subject is a mammal. In one embodiment of the present method, the administering further comprises administering an effective amount of a substance that modulates expression of a platelet voltage dependent calcium channel (VDCC) $\alpha_1$ subunit polypeptide-encoding nucleic acid molecule in the cell.

In one embodiment of the present method, the substance capable of modulating the activity of a platelet voltage dependent calcium channel (VDCC) $\alpha_1$ subunit polypeptide in the cell comprises an anti-platelet voltage dependent calcium channel (VDCC) $\alpha_1$ subunit polypeptide antibody, in another embodiment a polypeptide, in another embodiment a chemical compound, and in still another embodiment a nucleic acid.

In one embodiment, the nucleic acid comprises an antisense oligonucleotide. In one embodiment, the polypeptide or chemical compound comprises a ligand for a modulatable transcriptional regulatory sequence of a platelet voltage dependent calcium channel (VDCC) $\alpha_1$ subunit polypeptide-encoding nucleic acid molecule.

The presently claimed subject matter also provides a method for modulating phosphatidylserine exposure on a surface of a cell comprising introducing to the cell a construct comprising a nucleic acid sequence encoding a platelet voltage dependent calcium channel (VDCC) $\alpha_1$ subunit polypeptide operatively linked to a promoter, wherein production of the platelet voltage dependent calcium channel (VDCC) $\alpha_1$ subunit polypeptide in the cell results in modulation of phosphatidylserine exposure on a surface of the cell. In one embodiment, the construct further comprises a vector selected from the group consisting of a plasmid vector and a viral vector. In another embodiment, the construct further comprises a liposome complex. In one embodiment, the cell is a platelet or a megakaryocyte. In another embodiment, the cell comprises a cell in a vertebrate subject. In one embodiment, the vertebrate subject is a mammal.

The presently claimed subject matter also provides a method for modulating thrombosis in a subject, the method comprising administering to the subject an effective amount of a substance capable of modulating the activity of a platelet voltage dependent calcium channel (VDCC) $\alpha_1$ subunit polypeptide in the cell, wherein thrombosis in the subject is modulated. In one embodiment, the subject is a mammal. In one embodiment, the mammal is a human.

In one embodiment of the present method, the administering further comprises administering an effective amount of a substance that modulates expression of a platelet voltage dependent calcium channel (VDCC) $\alpha_1$ subunit polypeptide-encoding nucleic acid molecule in the cell. The substance that modulates expression of a platelet voltage dependent calcium channel (VDCC) $\alpha_1$ subunit polypeptide-encoding nucleic acid molecule in the cell comprises in one embodiment an anti-platelet voltage dependent calcium channel (VDCC) $\alpha_1$ subunit polypeptide antibody, in another embodiment a polypeptide, in another embodiment a chemical compound, and in still another embodiment a nucleic acid. In one embodiment, the nucleic acid comprises an antisense oligonucleotide. In one embodiment, the polypeptide or chemical compound comprises a ligand for a modulatable transcriptional regulatory sequence of a platelet voltage dependent calcium channel (VDCC) $\alpha_1$ subunit polypeptide-encoding nucleic acid molecule.

The presently claimed subject matter also provides a method for modulating thrombosis in a subject, the method comprising introducing into a cell present within the subject a construct comprising a nucleic acid sequence encoding a platelet voltage dependent calcium channel (VDCC) $\alpha_1$ subunit polypeptide operatively linked to a promoter, wherein production of the platelet voltage dependent calcium channel (VDCC) $\alpha_1$ subunit polypeptide in the cell results in modulation of thrombosis in the subject. In one embodiment, the construct further comprises a vector selected from the group consisting of a plasmid vector and a viral vector. In another embodiment, the construct further comprises a liposome complex. In one embodiment, the cell is a platelet or a megakaryocyte. In one embodiment, the subject is a mammal. In one embodiment, the mammal is a human.

The presently claimed subject matter also provides a method for modulating calcium transport in a cell, the method comprising introducing to the cell a construct comprising a nucleic acid sequence encoding a platelet voltage dependent calcium channel (VDCC) $\alpha_1$ subunit polypeptide operatively linked to a promoter, wherein production of the platelet voltage dependent calcium channel (VDCC) $\alpha_1$ subunit polypeptide in the cell results in modulation of calcium transport. In one embodiment, the construct further comprises a vector selected from the group consisting of a plasmid vector or a viral vector. In another embodiment, the construct further comprises a liposome complex. In one embodiment, the cell is a platelet and in another embodiment the cells is a megakaryocyte. In still another embodiment, the cell comprises a cell in a vertebrate subject. In one embodiment, the vertebrate subject is a mammal.

The presently claimed subject matter also provides a method of modulating apoptosis in a cell selected from the group consisting of a platelet and a megakaryocyte and comprising a voltage dependent calcium channel (VDCC) $\alpha_1$ subunit polypeptide. In one embodiment, the method comprises (a) identifying a candidate substance that modulates the exposure of phosphatidylserine on a surface of the platelet or megakaryocyte; and (b) contacting the cell with the candidate substance identified in step (a), whereby apoptosis in the cell is modulated. In one embodiment, the exposure of phosphatidylserine on a surface of the cell is increased, thereby enhancing apoptosis in the cell. In another embodiment, the exposure of phosphatidylserine on a surface of the cell is decreased, thereby inhibiting apoptosis in the cell. In one embodiment, the cell is a platelet.

The presently claimed subject matter also provides pharmaceutical compositions of the modulators identified by the disclosed screening methods. In one embodiment, a pharmaceutical composition comprises a therapeutically effective amount of a modulator of phosphatidylserine exposure on a surface of a cell and a pharmaceutically acceptable diluent or vehicle. In one embodiment, the modulator of phosphatidylserine exposure on a surface of a cell binds a platelet voltage dependent calcium channel (VDCC) $\alpha_1$ subunit polypeptide, or a fragment or derivative thereof. In another embodiment, a pharmaceutical composition comprises a therapeutically effective amount of a modulator of thrombosis and a pharmaceutically acceptable diluent or vehicle, wherein the modulator of thrombosis binds a platelet voltage dependent calcium channel (VDCC) $\alpha_1$ subunit polypeptide, or a fragment or derivative thereof. In still another embodiment, a pharmaceutical composition comprises a therapeutically effective amount of a modulator of a biological activity of a platelet voltage dependent calcium channel (VDCC) $\alpha_1$ subunit polypeptide and a pharmaceutically acceptable diluent or vehicle. In one embodiment, the modulator binds a platelet voltage dependent calcium channel (VDCC) $\alpha_1$ subunit polypeptide, or a fragment or derivative thereof.

The presently claimed subject matter also provides a method of increasing a storage life of a cell selected from the group consisting of a platelet and a megakaryocyte. In one embodiment, the method comprises (a) identifying a candidate substance that decreases the exposure of phosphatidylserine on the surface of the cell; and (b) contacting the cell with the candidate substance identified in step (a), whereby the storage life of the cell is increased. In one embodiment, the cell is a platelet.

The presently claimed subject matter also provides recombinant cell lines suitable for use in the claimed methods.

An object of the presently claimed subject matter having been stated herein above, other objects will become evident as the description proceeds when taken in connection with the accompanying Figures and Examples as best described herein below.

BRIEF DESCRIPTION OF THE DRAWINGS

FIGS. 3A-3F depicts a nucleotide sequence alignment of a human platelet VDCC $\alpha_1$S subunit gene fragment of SEQ ID NO: 5 and three closely related sequences: GENBANK® Accession No. XM_001910 (SEQ ID NO: 9; FIGS. 3A-3B), GENBANK® Accession No. NM_000069 (SEQ ID NO: 11; FIGS. 3C-3D), and GENBANK® Accession No. L33798 (SEQ ID NO: 13; FIGS. 3E-3F).

FIG. 4 depicts a nucleotide sequence alignment of a porcine platelet VDCC $\alpha_1$S subunit gene fragment of SEQ ID NO: 7 and a human VDCC $\alpha_1$S subunit fragment sequence: GENBANK® Accession No. XM_001910 (SEQ ID NO: 9).

FIGS. 5A-5F depict a nucleotide sequence alignment of a human platelet VDCC $\alpha_1$D subunit fragment of SEQ ID NO: 6 and three closely related sequences: GENBANK® Accession No. XM_003238 (SEQ ID NO: 15; FIGS. 5A and 5B), GENBANK® Accession No. NM_000720 (SEQ ID NO: 17; FIGS. 5C and 5D), and GENBANK® Accession No. M83566 (SEQ ID NO: 19; FIGS. 5E and 5F).

BRIEF DESCRIPTION OF THE SEQUENCE LISTING

Figure 1A:
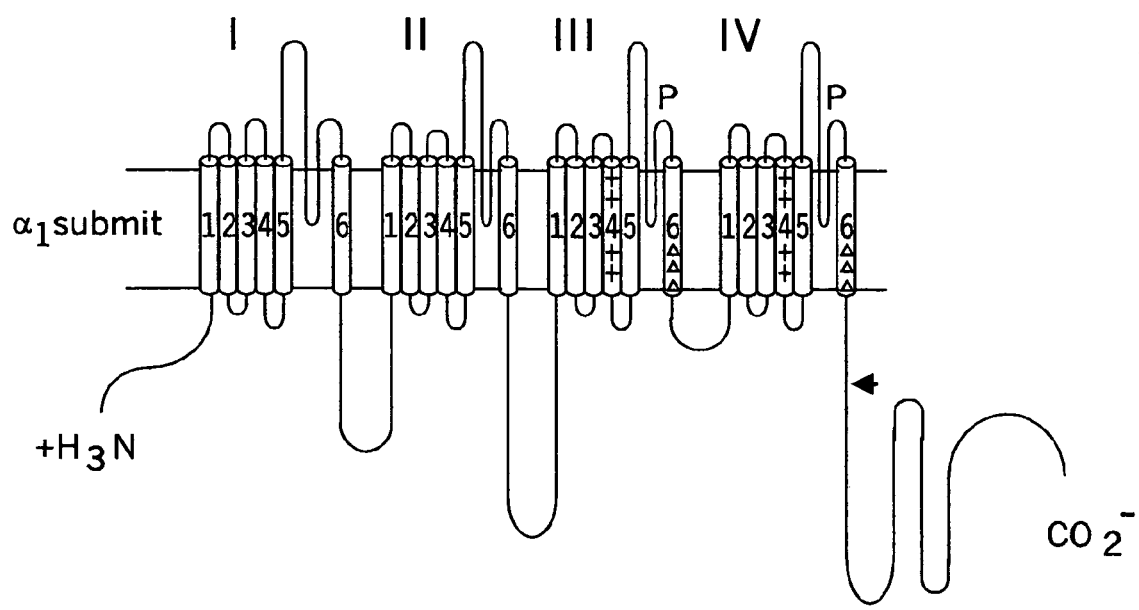
FIG. 1A is a schematic presentation of platelet VDCC $\alpha_1$ subunit polypeptides cloned from human megakaryocytes and porcine platelets. A human platelet VDCC $\alpha_1$S subunit clone (h$\alpha_1$S, 3130 bp) from human megakaryocytes encodes a polypeptide between III $S_4$ and the $CO_2^-$ end of the human $\alpha_1$S. A 400 bp platelet VDCC $\alpha_1$ subunit clone encodes the intra-cytoplasmic loop between motifs II-III. A human platelet VDCC $\alpha_1$D subunit (h$\alpha_1$D, 2682 bp) clone from human megakaryocytes encodes a polypeptide between IIIP and $CO_2^-$ end of the human $\alpha_1$D subunit. A porcine platelet VDCC $\alpha_1$S subunit polypeptide (p$\alpha_1$S, 1031 bp) clone from porcine platelets encodes a polypeptide region between IV $S_3$ and amino acid 1531 of $\alpha_1$S. A porcine platelet VDCC $\alpha_1$D subunit polypeptide (p$\alpha_1$D, 210 bp) clone from porcine platelets encodes a polypeptide between II $S_3$ and II S5. ●=glutamate residue in cloned regions; +=positively charged residue in cloned regions; P=pore in cloned regions; Δ=residues that contribute to dihydropyridine (DHP) binding.

SEQ ID NOs: 1 and 2 are nucleic acid and deduced amino acid sequences, respectively, of a human platelet VDCC family member (ha1S).

SEQ ID NOs: 3 and 4 are nucleic acid and deduced amino acid sequences, respectively, of a human platelet VDCC family member (ha1D).

SEQ ID NO: 5 is a nucleic acid sequence of a partial cDNA for a human platelet VDCC family member (clone 990312Ca50ha1S1181-1392).

SEQ ID NO: 6 is a nucleic acid sequence of a partial cDNA for a human platelet VDCC family member (clone 990303Ca61ha1D1294-1490).

SEQ ID NO: 7 is a nucleic acid sequence of a partial cDNA for a porcine platelet VDCC family member (clone 990208Cb18pa1S1172-1365).

SEQ ID NO: 8 is a nucleic acid sequence of a partial cDNA for a porcine platelet VDCC family member (clone 990210Db29pa1S1511-1325).

SEQ ID NOs: 9 and 10 are the nucleic acid and deduced amino acid sequences, respectively for CACNA1S, a human calcium channel, voltage-dependent, L type, alpha 1S subunit (GENBANK™ Accession No. XM_001910).

SEQ ID NOs: 11 and 12 are the nucleic acid and deduced amino acid sequences, respectively for CACNA1S, a human calcium channel, voltage-dependent, L type, alpha 1S subunit (GENBANK™ Accession No. NM_000069).

SEQ ID NOs: 13 and 14 are the nucleic acid and deduced amino acid sequences, respectively for CACNL1A3, a human dihydropyridine-sensitive L-type calcium channel alpha-1 subunit (GENBANK™ Accession No. L33798).

SEQ ID NOs: 15 and 16 are the nucleic acid and deduced amino acid sequences, respectively for CACNA1D, a human calcium channel, voltage-dependent, L type, alpha 1D subunit (GENBANK™ Accession No. XM_003238).

SEQ ID NOs: 17 and 18 are the nucleic acid and deduced amino acid sequences, respectively, for CACNA1D, a human calcium channel, voltage-dependent, L type, alpha 1 D subunit (GENBANK™ Accession No. NM_000720).

SEQ ID NOs: 19 and 20 are the nucleic acid and deduced amino acid sequences, respectively, for HUMCACH1A, a human neuroendocrine/beta-cell-type calcium channel alpha-1 subunit (GENBANK™ Accession No. M83566).

SEQ ID NOs: 21 and 22 are the nucleic acid and deduced amino acid sequences, respectively, for OCDHPR, a rabbit skeletal muscle dihydropyridine (DHP) receptor (GENBANK™ Accession No. X05921).

SEQ ID NO: 23 is the 57 nucleotide sequence that is missing in the human platelet VDCC family member (ha1S; SEQ ID NO: 1) when compared to the human calcium channel, voltage-dependent, L type, alpha 1S subunit (SEQ ID NO: 11).

SEQ ID NO: 24 is the amino acid sequence deduced from SEQ ID NO: 23.

SEQ ID NO: 25 is the 45 nucleotide sequence that is missing in the human platelet VDCC family member (ha1D; SEQ ID NO: 3) when compared to the human calcium channel, voltage-dependent, L type, alpha 1D subunit (SEQ ID NO: 15).

SEQ ID NO: 26 is the amino acid sequence deduced from SEQ ID NO: 25.

SEQ ID NO: 27 is the amino acid sequence of a peptide antigen (NEELRAIIKKIWKRTSMKLL), which corresponds to the sequence of amino acids 1487-1506 (arrow in FIG. 1A) in the putative intracytoplasmic carboxyl-terminal region of adult rabbit and human calcium channel, voltage-dependent, L type, alpha 1S subunit polypeptide as disclosed in Tanabe et al., 1987 and Hogan et al., 1994.

SEQ ID NO: 28 is the nucleic acid sequence of the platelet ha1D junction.

SEQ ID NO: 29 is the nucleic acid sequence of the platelet ha1S junction.

DETAILED DESCRIPTION

Disclosed herein is the first evidence for the expression of VDCC $\alpha_1$ subunits in platelets. The presently claimed subject matter teaches novel members of the VDCC gene family that are expressed in platelets. Representative embodiments are set forth in SEQ ID NOs: 1-8, 28, and 29.

Thus, the presently claimed subject matter pertains to isolated and purified nucleic acids encoding platelet VDCC $\alpha_1$ subunit polypeptides, to isolated and purified platelet VDCC $\alpha_1$ subunit polypeptides, to the characterization of the role played by the platelet VDCC $\alpha_1$ subunit polypeptides in modulating calcium levels within and outside cells, and to the characterization of upstream or downstream processes affected by such modulation (e.g., inside-out and/or outside-in signaling and phosphatidylserine exposure on the surface of a cell).

Summarily, the identification of sequences that encode platelet VDCC $\alpha_1$ subunit polypeptides, the cloning of the corresponding cDNAs, and the expression of the corresponding proteins affords the molecular tools required for modulating calcium homeostasis in platelets, and has application in the development of diagnostic, pharmacological, and/or therapeutic applications, including treatments for various bleeding, thrombotic, and related disorders in human and animal subjects.

Following long-standing patent law convention, the terms "a" and "an" mean "one or more" when used in this application, including the claims.

A. General Considerations

Diversity among VDCCs, expressed in their biophysical and pharmacological properties, has led to their classification into several categories (Birnbaumer et al., 1994). The long-activating (L-type) dihydropyridine (DHP)-sensitive VDCC is such a channel. cDNA cloning of its major, pore forming $\alpha_1$ subunit from skeletal muscle, $\alpha_1 S$, has led to a proposed structural model for all $\alpha_1$ subunits. Tanabe et al., 1987; see also FIG. 1. This model predicts that the encoded polypeptide contains four homologous but not identical tandem motifs (I-IV) which are made up of six transmembrane regions ($S_1$-$S_6$) each. This $\alpha_1$ subunit contains sequences that convey to the channel calcium selectivity, voltage and pharmacological sensitivities, gating properties, and susceptibility to bind with other subunits and neighboring proteins. Hille, 1992; Peres-Reyes & Schneider, 1995. While $\alpha_1 S$ is the major subunit from L-type VDCC in skeletal muscle, $\alpha_1 D$ is that from neuroendocrine cells. Birnbaumer et al., 1994; Seino et al., 1992.

The expression and ultrastructural localization of the VDCCs in platelets and their progenitor cell, the megakaryocyte, has been investigated. The novel polypeptides and polynucleotides disclosed herein represent the first identification of a VDCC in platelets and megakaryocytes.

The gene structure of platelet VDCC $\alpha_1$ subunits derived from human megakaryocytes and porcine platelets is depicted in FIG. 1. The characteristic feature of platelet VDCC $\alpha_1$ subunits as compared with known VDCC $\alpha_1$ subunits is indicated as a missing sequence in the IV $S_3$-$S_4$ linker. FIG. 2 demonstrates that platelet VDCC $\alpha_1 S$ and $\alpha_1 D$ subunit polypeptides are expressed in platelets and megakaryocytes.

In accordance with the presently disclosed subject matter, the functionality of recently described L-type voltage dependent calcium channels (VDCC) in platelets has also been characterized. There are many agonists and antagonists of the DHP-sensitive VDCC that have been developed for skeletal and cardiac muscle. As discussed in more detail herein below, several of these modulators were selected to investigate the role of VDCCs in thrombin activated human platelets. These modulators included a monoclonal antibody to the alpha 1 subunit of the DHP receptor (MA3-920), nitrendipine, and two stereoisomers of Bay K8644 (Bay K(−) and Bay K(+)).

B. Polypeptides and Polynucleotides

As used in the following detailed description and in the claims, the term "platelet VDCC" includes nucleic acids and polypeptides encoding calcium channels in platelets and megakaryocytes. Platelet VDCC $\alpha_1 S$ subunit nucleic acid sequences are expressed in platelets and megakaryocytes, and optionally in other tissues. The term "platelet VDCC" specifically refers to a VDCC $\alpha_1$ subunit characterized by the IV $S_3$-$S_4$ linker. Particularly, a platelet VDCC $\alpha_1 S$ subunit polypeptide and a platelet VDCC $\alpha_1 D$ subunit polypeptide are disclosed herein. Representative platelet VDCC $\alpha_1 S$ subunits from human and porcine sources are disclosed in SEQ ID NOs: 1, 2, 5, and 28 and SEQ ID NOs: 7-8, respectively. Representative human platelet VDCC $\alpha_1 D$ subunits are disclosed in SEQ ID NOs: 3, 4, 6, and 29.

The term "platelet VDCC" further comprises vertebrate homologues of platelet calcium channel family members including, but not limited to mammalian and avian homologues. Representative mammalian homologues of platelet calcium channel family members include, but are not limited to porcine and human homologues. VDCC $\alpha_1$ subunit homologues are characterized by missing sequences that encode the IV $S_3$-$S_4$ linker region of VDCC $\alpha_1 S$ polypeptides, as disclosed herein for human VDCC $\alpha_1 S$ subunit, porcine VDCC $\alpha_1 S$ subunit, and human VDCC $\alpha_1 D$ subunit.

As used herein, the term "polypeptide" means any polymer comprising any of the 20 protein amino acids, regardless of its size. Although "protein" is often used in reference to relatively large polypeptides, and "peptide" is often used in reference to small polypeptides, usage of these terms in the art overlaps and varies. The term "polypeptide" as used herein refers to peptides, polypeptides, and proteins, unless otherwise noted. As used herein, the terms "protein", "polypeptide", and "peptide" are used interchangeably herein when referring to a gene product.

The terms "platelet VDCC $\alpha_1$ subunit gene product", "platelet VDCC $\alpha_1$ subunit protein", and "platelet VDCC $\alpha_1$ subunit polypeptide" refer to peptides having amino acid sequences which are substantially identical to native amino acid sequences from the organism of interest and which are biologically active in that they comprise the amino acid sequence of a platelet VDCC $\alpha_1$ subunit polypeptide, or cross-react with antibodies that specifically bind a platelet VDCC $\alpha_1$ subunit polypeptide, or retain all or some of the biological activity of the native amino acid sequence or protein. Such biological activity can include immunogenicity. As disclosed herein below, an important feature of platelet VDCC $\alpha_1$ subunits is the absence of sequences encoding a portion of the IV $S_3$-$S_4$ linker of VDCC $\alpha_1$ subunit polypeptides.

The terms "platelet VDCC $\alpha_1$ subunit gene product", "platelet VDCC $\alpha_1$ subunit protein", and "platelet VDCC $\alpha_1$ subunit polypeptide" are meant to encompass a platelet VDCC $\alpha_1 S$ subunit polypeptide or a platelet VDCC $\alpha_1 D$ subunit polypeptide including, but not limited to those disclosed herein as SEQ ID NOs: 2 and 4. Indeed, the definitions and descriptions of "platelet VDCC $\alpha_1$ subunit gene product", "platelet VDCC $\alpha_1$ subunit protein", and "platelet VDCC $\alpha_1$ subunit polypeptide" presented herein are also meant to be applied to a platelet VDCC $\alpha_1 S$ subunit polypeptide or a platelet VDCC $\alpha_1 D$ subunit polypeptide.

The terms "platelet VDCC $\alpha_1$ subunit gene product", "platelet VDCC $\alpha_1$ subunit protein", and "platelet VDCC $\alpha_1$ subunit polypeptide" also include analogs of a platelet VDCC $\alpha_1$ subunit polypeptide. By "analog" it is intended that a DNA or peptide sequence can contain alterations relative to the sequences disclosed herein, yet retain all or some of the biological activity of those sequences. Analogs can be derived from nucleotide sequences as are disclosed herein or from other organisms, or can be created synthetically. Those skilled in the art will appreciate that other analogs, as yet undisclosed or undiscovered, can be used to design and/or construct calcium channel analogs. There is no need for a "platelet VDCC $\alpha_1$ subunit gene product", "platelet VDCC $\alpha_1$ subunit protein", and "platelet VDCC $\alpha_1$ subunit polypeptide" to comprise all or substantially all of the amino acid sequence of a native platelet VDCC $\alpha_1$ subunit polypeptide gene product. Shorter or longer sequences are anticipated to be of use in the presently claimed subject matter; shorter sequences are herein referred to as "segments". Thus, the terms "platelet VDCC $\alpha_1$ subunit gene product", "platelet VDCC $\alpha_1$ subunit protein", and "platelet VDCC $\alpha_1$ subunit polypeptide" also include fusion or recombinant platelet VDCC $\alpha_1$ subunit polypeptides and proteins comprising sequences of the presently claimed subject matter. Methods of preparing such proteins are known in the art.

The terms "platelet VDCC $\alpha_1$ subunit gene", "platelet VDCC $\alpha_1$ subunit gene segment", "platelet VDCC $\alpha_1$ subunit gene sequence", "platelet VDCC $\alpha_1$ subunit polynucleotide", "platelet VDCC $\alpha_1$ subunit nucleic acid molecule", and "platelet VDCC $\alpha_1$ subunit nucleic acid sequence" refer to any nucleic acid sequence (e.g., a DNA sequence) that is substantially identical to a polynucleotide sequence encoding a platelet VDCC $\alpha_1$ subunit gene product, platelet VDCC $\alpha_1$ subunit protein, or platelet VDCC $\alpha_1$ subunit polypeptide as defined above, and can also comprise any combination of associated control sequences. The terms also refer to RNA, or antisense sequences, complementary to such DNA sequences. As used herein, the term "DNA segment" refers to a DNA molecule that has been isolated free of total genomic DNA of a particular species. Furthermore, a DNA segment encoding a platelet VDCC $\alpha_1$ subunit polypeptide refers to a DNA segment that contains platelet VDCC $\alpha_1$ subunit coding sequences, yet is isolated away from, or purified free from, total genomic DNA of a source species, such as *Homo sapiens*. Included within the term "DNA segment" are DNA segments and smaller fragments of such segments, and also recombinant vectors, including, for example, plasmids, cosmids, phages, viruses, and the like.

The terms "platelet VDCC $\alpha_1$ subunit gene", "platelet VDCC $\alpha_1$ subunit gene segment", "platelet VDCC $\alpha_1$ subunit gene sequence", "platelet VDCC $\alpha_1$ subunit polynucleotide", "platelet VDCC $\alpha_1$ subunit nucleic acid molecule", and "platelet VDCC $\alpha_1$ subunit nucleic acid sequence" are meant to encompass a polynucleotide encoding a platelet VDCC $\alpha_1$S subunit polypeptide or a platelet VDCC $\alpha_1$D subunit polypeptide, including but not limited to those disclosed herein as SEQ ID NOs: 1, 3, 5-8, 28, and 29. Indeed, the definitions and explanations of the terms "platelet VDCC $\alpha_1$ subunit gene", "platelet VDCC $\alpha_1$ subunit gene segment", "platelet VDCC $\alpha_1$ subunit gene sequence", "platelet VDCC $\alpha_1$ subunit polynucleotide", "platelet VDCC $\alpha_1$ subunit nucleic acid molecule", and "platelet VDCC $\alpha_1$ subunit nucleic acid sequence" presented herein are also meant to be applied to a platelet VDCC $\alpha_1$S subunit polypeptide or a platelet VDCC $\alpha_1$D subunit polypeptide.

A characteristic feature of the platelet VDCC $\alpha_1$S subunits of the presently claimed subject matter is the absence of sequences that encode a portion of the IV $S_3$-$S_4$ linker of known VDCC $\alpha_1$S subunits. The sequences that are lacking in the disclosed platelet VDCC $\alpha_1$S subunits are set forth as SEQ ID NOs: 23-24 ($\alpha_1$S) and SEQ ID NOs: 25-26 ($\alpha_1$D). The absence of these sequences from the platelet VDCC $\alpha_1$S subunits of the presently claimed subject matter is depicted in FIGS. 1A, 1B, and 3-5.

Figure 1B:
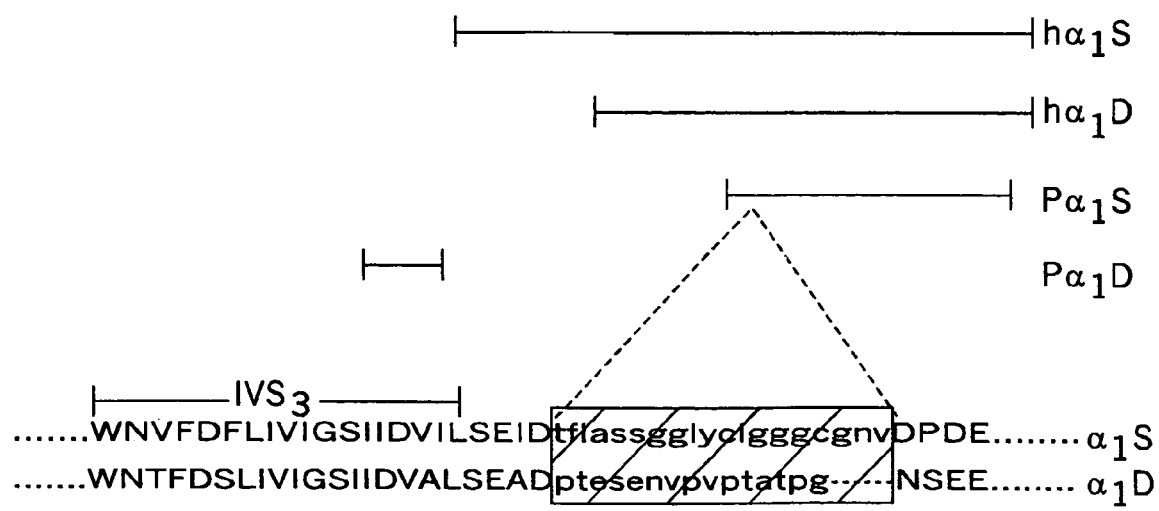
FIG. 1B is a schematic depicting sequences absent from human $\alpha_1$S and $\alpha_1$D and porcine $\alpha_1$S in cloned regions (shaded areas).
Figure 1C:
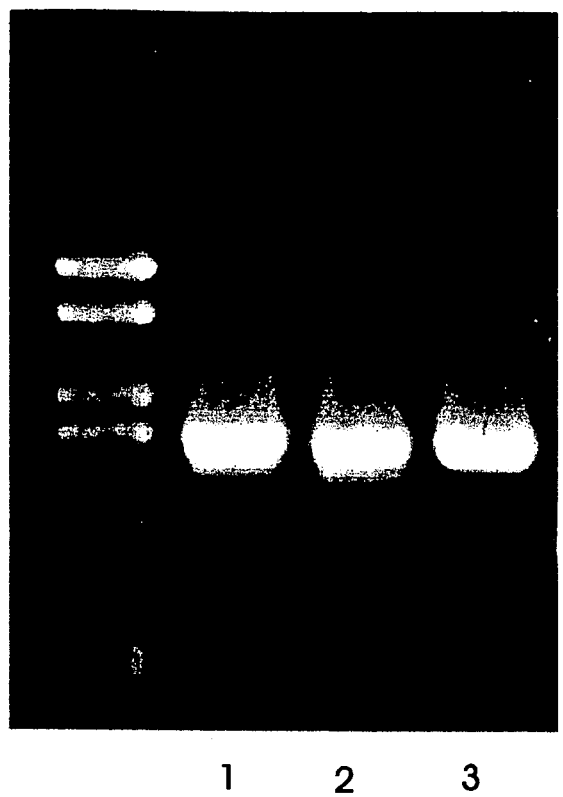
FIG. 1C depicts a photograph of gel electrophoresis of a 1033 basepair (bp) polymerase chain reaction (PCR) product from human megakaryocytes that was producing using oligonucleotides 1 and 2 (Table 3) as primers to amplify cDNA regions. The cDNA clones obtained in this reaction had two different sequences. Clones 1 and 2 (lanes 1 and 2) were $\alpha_1$S, clone 3 (lane 3) was $\alpha_1$D. Left lane, DNA low molecular weight markers VI (2.1-0.5 kb, Boehringer Mannheim, Indianapolis, Ind., United States of America)
Figure 2B:
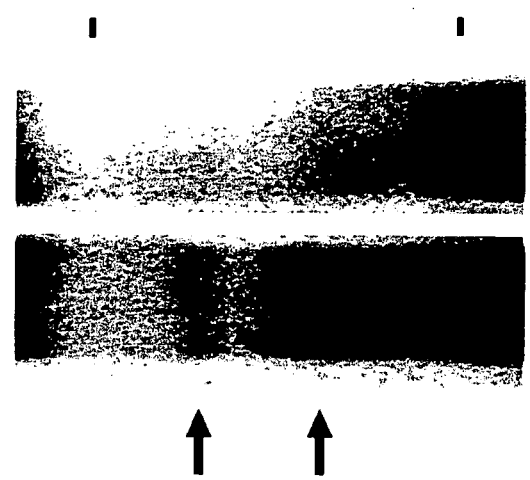
FIG. 2B depicts an autoradiograph of an immunoblot of immunoprecipitations on porcine platelets. The anti-peptide antibody precipitated determinants in polypeptides with electrophoretic mobilities of 208 kDa and 170 kDa (lane a, arrows). The primary antibody was replaced with non-immune rabbit IgG in the immunoprecipitation control condition (lane b). Bars on right depict the positions of 218 kDa and 125 kDa molecular weight standards.

FIGS. 1A and 1B show a schematic representation of the sequences that are absent from human and porcine platelet VDCC $\alpha_1$ subunits in the region of the IV $S_3$-$S_4$ linker.

FIG. 3 depicts a nucleotide sequence alignment of a human platelet VDCC $\alpha_1$S subunit fragment of SEQ ID NO: 5 and three closely related sequences, GENBANK®) Accession No. XM_001910 (SEQ ID NO: 9), GENBANK® Accession No. NM_00069 (SEQ ID NO: 11), and GENBANK® Accession No. L33798 (SEQ ID NO: 13). The nucleotide sequence of SEQ ID NO: 5 represents an individual sequence read of a cloned human platelet VDCC $\alpha_1$S subunit fragment. When using this fragment as a query sequence, BLAST analysis indicated the three above-mentioned GENBANK® sequences as having the highest level of sequence identity with platelet VDCC $\alpha_1$S subunit sequences of the presently claimed subject matter. The alignment further reveals the absence of an about 57 base pair sequence (SEQ ID NO: 23) in the human platelet VDCC $\alpha_1$S subunit fragment of SEQ ID NO: 5 compared to known VDCC $\alpha_1$S subunit sequences. The deleted sequence is revealed by disruption of each alignment between contiguous base pairs 48 and 49 of the query sequence, and substantial sequence conservation is observed over the remainder of the query sequence.

FIG. 4 depicts a nucleotide sequence alignment of a porcine platelet VDCC $\alpha_1$S subunit gene fragment of SEQ ID NO: 7 and a human VDCC $\alpha_1$S subunit fragment sequence, GENBANK®) Accession No. XM_001910 (SEQ ID NO: 9). The nucleotide sequence of SEQ ID NO: 7 represents an individual sequence read of a cloned porcine platelet VDCC $\alpha_1$S subunit fragment. When using this fragment as a query sequence, BLAST analysis indicated human VDCC $\alpha_1$S subunit gene (GENBANK® Accession No. XM_001910, SEQ ID NO: 9) and rabbit dihydropyridine receptor (GENBANK® Accession No. X05921, SEQ ID NO: 21) as being the most closely related sequences (Table 1). The alignment further reveals the absence of an about 57 base pair sequence (SEQ ID NO: 23) in the porcine platelet VDCC $\alpha_1$S subunit fragment of SEQ ID NO: 7, as the alignment is disrupted between base pairs 60 and 67 base pairs of the query sequence, but substantial sequence conservation is observed over the remainder of the query sequence.

TABLE 1

| SEQ ID NO. | Applicants' Reference | Best BLAST hit | Score | E value | Identities |
|---|---|---|---|---|---|
| 7 | 990210Db29 pa1S1511 | XM 001910 | 761 | 0.0 | 516/599 92% |
| 8 | 990208Cb18 pa1S1172 | X05921 | 563 | 0.0 | 395/432 91% |

A comparison of the predicted amino acid sequences encoded by the human and porcine platelet VDCC $\alpha_1$S subunit fragments demonstrates that the deleted sequence, relative to known VDCC $\alpha_1$S subunit sequences, is similarly positioned in human and porcine platelet VDCC $\alpha_1$S subunit sequences (FIGS. 1A and 1B).

FIG. 5 depicts a nucleotide sequence alignment of a human platelet VDCC $\alpha_1$D subunit gene fragment of SEQ ID NO: 6 and three closely related sequences: GENBANK® Accession No. XM_003238 (SEQ ID NO: 15), GENBANK® Accession No. NM_000720 (SEQ ID NO: 17), and GENBANK®) Accession No. M83566 (SEQ ID NO: 19). The nucleotide sequence of SEQ ID NO: 6 represents an individual sequence read of a cloned human platelet VDCC $\alpha_1$D subunit fragment. When using this fragment as a query sequence, BLAST analysis indicated the three above-mentioned GENBANK® sequences as having the highest level of sequence identity with platelet VDCC $\alpha_1$D subunit sequences of the presently claimed subject matter. The alignment further reveals the absence of an about 48 basepair sequence (SEQ ID NO: 25) in the human platelet VDCC $\alpha_1$D subunit fragment of SEQ ID NO: 6 as compared to known sequences. The deleted sequence is revealed by disruption of each alignment between contiguous base pairs 44 and 49 of the query sequence. Substantial sequence conservation is observed over the remainder of the query sequence.

B.1. Sequence Similarity and Identity

As used herein, the term "substantially similar" means that a particular sequence varies from a platelet VDCC $\alpha_1$ subunit nucleic acid sequence, or a platelet VDCC $\alpha_1$ subunit amino acid sequence, by one or more deletions, substitutions, or additions, the net effect of which is to retain at least some of biological activity of the natural gene, gene product, or sequence. For example, a "substantially similar" polypeptide can exhibit decreased or increased biological activity, as in a pathological or disease- or dysfunction-causing condition. Such sequences include "mutant" or "polymorphic"

sequences, or sequences in which the biological activity is altered to some degree but retains at least some of the original biological activity. A critical measure of substantial identity of a platelet VDCC $\alpha_1$ subunit is the absence of nucleotide sequences encoding and amino acid sequences comprising (SEQ ID NOs: 23-26) a region of the IV $S_3$-$S_4$ linker of VDCC $\alpha_1$ subunit polypeptides.

Nucleic acids that are substantially identical to SEQ ID NOs: 1, 3, 5-8, 28, and 29 are representative platelet VDCC $\alpha_1$ subunit sequences; e.g., allelic variants, genetically altered versions of the gene, etc., bind to the provided platelet VDCC $\alpha_1$ subunit sequences under stringent hybridization conditions. By using probes, particularly labeled probes of DNA sequences, one can isolate homologous or related genes. The source of homologous genes can be any species, e.g., primate species, rodents (such as rats and mice), canines, felines, bovines, equines, etc.

Between mammalian species, for example human and pig, homologues have substantial sequence similarity; in one embodiment at least 75% sequence identity between nucleotide sequences and in another embodiment at least 90% sequence identity. Sequence similarity is calculated based on a reference sequence, which can be a subset of a larger sequence, such as a conserved motif, coding region, flanking region, etc. A reference sequence will usually be at least about 18 nucleotides (nt) long, more usually at least about 30 nt long, and can extend to the complete sequence that is being compared. Algorithms for sequence analysis are known in the art, such as BLAST, described in Altschul et al., 1990. In determining nucleic acid sequences, all subject nucleic acid sequences capable of encoding substantially similar amino acid sequences are considered to be substantially similar to a reference nucleic acid sequence, regardless of differences in codon sequences or substitution of equivalent amino acids to create biologically functional equivalents.

Percent identity or percent similarity of a DNA or peptide sequence can be determined, for example, by comparing sequence information using the GAP computer program, available from the Accelrys, Inc. (San Diego, Calif., United States of America). The GAP program utilizes the alignment method of Needleman et al., 1970, as revised by Smith et al., 1981. Briefly, the GAP program defines similarity as the number of aligned symbols (i.e., nucleotides or amino acids) which are similar, divided by the total number of symbols in the shorter of the two sequences. Representative parameters for the GAP program are the default parameters, which do not impose a penalty for end gaps. See Schwartz et al., 1979; Gribskov et al., 1986.

The term "similarity" is contrasted with the term "identity". Similarity is defined as above; "identity", however, means a nucleic acid or amino acid sequence having the same amino acid at the same relative position in a given family member of a gene family. Homology and similarity are generally viewed as broader terms than the term identity. Biochemically similar amino acids, for example leucine and isoleucine or glutamate and aspartate, can be present at the same position—these are not identical per se, but are biochemically "similar." As disclosed herein, these are referred to as conservative differences or conservative substitutions. This differs from a conservative mutation at the DNA level, which changes the nucleotide sequence without making a change in the encoded amino acid, e.g., TCC to TCA, both of which encode serine.

As used herein, DNA analog sequences are "substantially identical" to specific DNA sequences disclosed herein if: (a) the DNA analog sequence is derived from coding regions of the nucleic acid sequence shown in any of SEQ ID NOs: 1, 3, 5-8, 28, and 29 and lacks sequences of SEQ ID NOs: 23 and 25; or (b) the DNA analog sequence is capable of hybridization to any of SEQ ID NOs: 1, 3, 5-8, 28, and 29 under stringent conditions, lacks sequences of SEQ ID NOs: 23 and 25, and encodes a biologically active gene product of the nucleic acid sequence shown in any of SEQ ID NOs: 1, 3, 5-8, 28, and 29; or (c) the DNA sequences are degenerate as a result of alternative genetic code to the DNA analog sequences defined in (a) and/or (b). Substantially identical analog proteins will be greater than about 60% identical to the corresponding sequence of the native protein. Sequences having lesser degrees of identity but comparable biological activity are considered to be equivalents.

As used herein, "stringent conditions" means conditions of high stringency, for example 6× standard saline citrate (SSC), 0.2% polyvinylpyrrolidone, 0.2% Ficoll, 0.2% bovine serum albumin, 0.1% sodium dodecyl sulfate, 100 g/mL salmon sperm DNA and 15% formamide at 68° C. For the purposes of specifying additional conditions of high stringency, exemplary conditions are salt concentration of about 200 mM and temperature of about 45° C. One example of such stringent conditions is hybridization at 4×SSC at 65° C., followed by a washing in 0.1×SSC at 65° C. for one hour. Another exemplary stringent hybridization scheme uses 50% formamide, 4×SSC at 42° C. Stringent features are understood to be able to detect a remoter address.

In contrast, nucleic acids having sequence similarity are detected by hybridization under lower stringency conditions. Thus, sequence identity can be determined by hybridization under lower stringency conditions, for example, at 50° C. or higher and 0.1×SSC (15 mM NaCl/1.5 mM sodium citrate) and the sequences will remain bound when subjected to washing at 55° C. in 1×SSC.

Thus, in certain embodiments, the presently claimed subject matter concerns the use of platelet VDCC $\alpha_1$ subunit genes and gene products that include within their respective sequences a sequence which is essentially that of a platelet VDCC $\alpha_1$ subunit gene, or the corresponding protein. The term "a sequence essentially as that of a platelet VDCC $\alpha_1$ subunit gene", means that the sequence is substantially identical to a portion of a platelet VDCC $\alpha_1$ subunit gene and contain a minority of bases or amino acids (whether DNA or protein) which are not identical to those of a platelet VDCC $\alpha_1$ subunit protein or a platelet VDCC $\alpha_1$ subunit gene, or which are not a biologically functional equivalent. The term "biologically functional equivalent" is well understood in the art and is further defined in detail herein.

Nucleotide sequences are "substantially identical" where they have in one embodiment between about 70% and about 80%, in another embodiment between about 81% and about 90%, and in still another embodiment between about 91% and about 99%, sequence identity for nucleic acid residues which are identical to the nucleotide sequence of a platelet VDCC $\alpha_1$ subunit gene. Gene structure is also a useful measure of substantially identical sequences. In this case, the omission of sequences encoding a region of the IV $S_3$-$S_4$ linker of VDCC $\alpha_1$ subunit polypeptides is a critical feature of the disclosed sequences.

Peptide sequences which have in one embodiment from 35% to 45%, in another embodiment from 45 to 55%, in another embodiment from 55 to 65%, or in yet another embodiment 65% or greater, amino acids which are identical or functionally equivalent or biologically functionally equivalent to the amino acids of a platelet VDCC $\alpha_1$ subunit polypeptide will be sequences which are "substantially similar". Peptide structure is also a useful indicator of substantially identical sequences. The presently claimed subject matter discloses sequences that have a shorter IV $S_3$-$S_4$ linker compared to known VDCC $\alpha_1$ subunit polypeptides. Thus, this is an important feature when considering substantial similarity among VDCC $\alpha_1$ subunit sequences.

Platelet VDCC $\alpha_1$ subunit gene products and platelet VDCC $\alpha_1$ subunit-encoding nucleic acid sequences which have functionally equivalent codons are also covered by the presently claimed subject matter. The term "functionally equivalent codon" is used herein to refer to codons that encode the same amino acid, such as the ACG and AGU codons for serine (Table 2). Thus, when referring to the sequence examples presented in SEQ ID NOs: 1, 3, 5-8, 28, and 29 applicants contemplate substitution of functionally equivalent codons of Table 2 into the sequence examples of SEQ ID NOs: 1, 3, 5-8, 28, and 29. Thus, applicants are in possession of amino acid and nucleic acids sequences which include such substitutions but which are not set forth herein in their entirety for convenience.

TABLE 2

| Functionally Equivalent Codons | | | |
|---|---|---|---|
| Amino Acid | 3-Letter | 1-Letter | mRNA Codons |
| Alanine | Ala | A | GCA GCC GCG GCU |
| Arginine | Arg | R | AGA AGG CGA CGC CGG CGU |
| Asparagine | Asn | N | AAC AAU |
| Aspartic Acid | Asp | D | GAC GAU |
| Cysteine | Cys | C | UGC UGU |
| Glutamic Acid | Glu | E | GAA GAG |
| Glutamine | Gln | Q | CAA CAG |
| Glycine | Gly | G | GGA GGC GGG GGU |
| Histidine | His | H | CAC CAU |
| Isoleucine | lie | I | AUA AUC AUU |
| Leucine | Leu | L | UUA UUG CUA CUC CUG CUU |
| Lysine | Lys | K | AAA AAG |
| Methionine | Met | M | AUG |
| Proline | Pro | P | CCA CCC CCG CCU |
| Phenylalanine | Phe | F | UUC UUU |
| Serine | Ser | S | ACG AGU UCA UCC UCG UCU |
| Threonine | Thr | T | ACA ACC ACG ACU |
| Tryptophan | Trp | W | UGG |
| Tyrosine | Tyr | Y | UAC UAU |
| Valine | Val | V | GUA GUC GUG GUU |

It will also be understood by those of skill in the art that amino acid and nucleic acid sequences can include additional residues, such as additional N- or C-terminal amino acids or 5' or 3' nucleic acid sequences, and yet still be essentially as set forth in one of the sequences disclosed herein, so long as the sequence retains biological protein activity where protein expression is concerned. The addition of terminal sequences particularly applies to nucleic acid sequences which can, for example, include various non-coding sequences flanking either of the 5' or 3' portions of the coding region or can include various internal sequences such as introns, which are known to occur within genes.

The presently claimed subject matter also encompasses the use of nucleotide segments that are complementary to the sequences of the presently claimed subject matter. Nucleic acid sequences which are "complementary" are those which are base-paired according to the standard Watson-Crick complementarity rules. As used herein, the term "complementary sequences" means nucleic acid sequences which are substantially complementary, as can be assessed by the same nucleotide comparison set forth above, or is defined as being capable of hybridizing to the nucleic acid segment in question under moderately stringent conditions such as those described herein. A particular example of a provided complementary nucleic acid segment is an antisense oligonucleotide. In this case, complementary is defined by both cross-hybridization and the lack of coding sequences of SEQ ID NOs: 23 and 25.

Hybridization can be used to assess complementary sequences and/or to isolate complementary nucleotide sequences. Nucleic acid hybridization will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in one embodiment in excess of about 30° C., in another embodiment in excess of about 37° C., and in still another embodiment in excess of about 45° C. Stringent salt conditions will in one embodiment be less than about 1,000 mM, in another embodiment less than about 500 mM, and in still another embodiment less than about 200 mM. However, the combination of parameters is much more important than the measure of any single parameter. (See e.g., Wetmur & Davidson, 1968). Determining appropriate hybridization conditions to identify and/or isolate sequences containing high levels of identity is well known in the art. (See e.g., Sambrook et al., 1989).

Representative moderate stringency conditions comprise, for example, hybridization at 50° C. and in 10×SSC (1.5 M NaCl/0.15 M sodium citrate), wherein the hybridized nucleic acid molecules remain bound when subjected to washing at 55° C. in 1×SSC. Sequence identity can be further determined by hybridization under more stringent conditions, for example, at 50° C. or higher and 0.1×SSC (15 mM NaCl/1.5 mM sodium citrate), as described below. Typically, under "stringent conditions" a probe will hybridize specifically to its target sequence, but to no other sequences.

For the purposes of specifying conditions of high stringency, exemplary conditions are salt concentration of about 200 mM and temperature of about 45° C. One example of such stringent conditions is hybridization at 4×SSC, at 65° C., followed by a washing in 0.1×SSC at 65° C. for one hour. Another representative stringent hybridization scheme uses 50% formamide, 4×SSC at 42° C. As used herein, "stringent conditions" can also mean conditions of high stringency, for example 6×SSC, 0.2% polyvinylpyrrolidone, 0.2% Ficoll, 0.2% bovine serum albumin, 0.1% sodium dodecyl sulfate, 100 μg/mL salmon sperm DNA and 15% formamide at 60° C.

Nucleic acids that are substantially identical to the provided platelet VDCC $\alpha_1$ subunit sequences, e.g., allelic variants, genetically altered versions of the gene, polymorphic sequences, etc., bind to the provided platelet VDCC $\alpha_1$ subunit sequences under stringent hybridization conditions. By using probes, particularly labeled probes of DNA sequences, one can isolate homologous or related genes. The source of homologous genes can be any species, for example, primate species, rodents (such as rats and mice), canines, felines, bovines, ovines, equines, etc.

Between mammalian species, (for example, human and pig), homologues display similar gene structure, have substantial sequence similarity: in one embodiment at least 75% sequence identity between nucleotide sequences and in another embodiment greater than 90% sequence similarity, and specifically lack nucleotide sequences set forth as SEQ ID NOs: 23 and 25. Sequence similarity is calculated based on a reference sequence, which can be a subset of a larger sequence, such as a conserved motif, coding region, flanking region, etc. A reference sequence is in one embodiment at least about 18 nt long and in another embodiment at least about 30 nt long, and can extend to the complete sequence that is being compared. Algorithms for sequence analysis are known in the art, such as BLAST, described in Altschul et al., 1990. Another commonly used alignment program is entitled CLUSTAL W and is described in Thompson et al., 1994, among other places. The sequences provided herein are useful for recognizing platelet VDCC $\alpha_1$ subunit related and homologous proteins in database searches.

At a biological level, identity is just that, i.e. the same amino acid at the same relative position in a given family member of a gene family. Homology and similarity are generally viewed as broader terms. For example, biochemically similar amino acids, for example leucine and isoleucine or glutamate/aspartate, can be present at the same position— these are not identical per se, but are biochemically "similar". As disclosed herein, these are referred to as conservative differences or conservative substitutions. This differs from a conservative mutation at the DNA level, which changes the nucleotide sequence without making a change in the encoded amino acid, e.g., TCC to TCA, both of which encode serine.

The platelet VDCC $\alpha_1$ subunit genes disclosed herein are thus homologous proteins, but when percentages are referred to herein, it is meant to refer to percent identity.

Probe sequences can also hybridize specifically to duplex DNA under certain conditions to form triplex or other higher order DNA complexes. The preparation of such probes and suitable hybridization conditions are disclosed herein and are known in the art.

As used herein and in the claims, the term "gene" refers to both genomic sequences and cDNA sequences. "Isolated substantially away from other coding sequences" means that the gene of interest, in this case, a platelet VDCC $\alpha_1$ subunit gene, forms the significant part of the coding region of the DNA segment, and that the DNA segment does not contain large portions of naturally-occurring coding DNA, such as large chromosomal fragments or other functional genes or cDNA coding regions. Of course, this refers to the DNA segment as originally isolated, and does not exclude genes or coding regions later added to the segment by the hand of man.

Thus, in particular embodiments, the presently claimed subject matter concerns isolated DNA segments and recombinant vectors incorporating DNA sequences which encode a platelet VDCC $\alpha_1$ subunit polypeptide that includes within its amino acid sequence an amino acid sequence of the presently claimed subject matter. In other particular embodiments, the presently claimed subject matter concerns recombinant vectors incorporating DNA segments which encode a protein comprising the amino acid sequence of a human platelet VDCC $\alpha_1$ subunit polypeptide protein.

B.2. Biologically Functional Equivalents

As mentioned above, modifications and changes can be made in the structure of the platelet VDCC $\alpha_1$ subunit polypeptide proteins and peptides described herein and still constitute a molecule having like or otherwise desirable characteristics. For example, certain amino acids can be substituted for other amino acids in a protein structure without appreciable loss of interactive capacity with, for example, structures in the nucleus of a cell. Since it is the interactive capacity and nature of a protein that defines that protein's biological functional activity, certain amino acid sequence substitutions can be made in a protein sequence (or the nucleic acid sequence encoding it) to obtain a protein with the same, enhanced, or antagonistic properties. Such properties can be achieved by interaction with the normal targets of the native protein, but this need not be the case, and the biological activity of the presently claimed subject matter is not limited to a particular mechanism of action. It is thus provided in accordance with the presently claimed subject matter that various changes can be made in the sequence of the platelet VDCC $\alpha_1$ subunit polypeptide proteins and peptides or underlying nucleic acid sequence without appreciable loss of their biological utility or activity.

Biologically functional equivalent peptides, as used herein, are peptides in which certain, but not most or all, of the amino acids can be substituted. Thus, when referring to the sequence examples presented in SEQ ID NOs: 1, 3, 5-8, 28, and 29, applicants envision substitution of codons that encode biologically equivalent amino acids as described herein into the sequence examples of SEQ ID NOs: 1, 3, 5-8, 28, and 29. Thus, applicants are in possession of amino acid and nucleic acids sequences which include such substitutions but which are not set forth herein in their entirety for convenience.

Alternatively, functionally equivalent proteins or peptides can be created via the application of recombinant DNA technology, in which changes in the protein structure can be engineered, based on considerations of the properties of the amino acids being exchanged, e.g., substitution of Ile for Leu. Changes designed by man can be introduced through the application of site-directed mutagenesis techniques, e.g., to introduce improvements to the antigenicity of the protein or to test platelet VDCC $\alpha_1$ subunit mutants in order to examine platelet VDCC $\alpha_1$ subunit calcium transport activity, or other activity at the molecular level.

Amino acid substitutions, such as those which might be employed in modifying the platelet VDCC $\alpha_1$ subunit polypeptide proteins and peptides described herein, are generally based on the relative similarity of the amino acid side-chain substituents, for example, their hydrophobicity, hydrophilicity, charge, size, and the like. An analysis of the size, shape, and type of the amino acid side-chain substituents reveals that arginine, lysine, and histidine are all positively charged residues; that alanine, glycine, and serine are all of similar size; and that phenylalanine, tryptophan, and tyrosine all have a generally similar shape. Therefore, based upon these considerations, arginine, lysine, and histidine; alanine, glycine, and serine; and phenylalanine, tryptophan, and tyrosine; are defined herein as biologically functional equivalents. Other biologically functionally equivalent changes will be appreciated by those of skill in the art.

In making biologically functional equivalent amino acid substitutions, the hydropathic index of amino acids can be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte & Doolittle, 1982, incorporated herein by reference). It is known that certain amino acids can be substituted for other amino acids having a similar hydropathic index or score and still retain a similar biological activity. In one embodiment, amino acids for which the hydropathic indices are within ±2 of the original value are chosen, in another embodiment those for which the hydropathic indices are within ±1 of the original value are chosen, and in still another embodiment those for which the hydropathic indices are within ±0.5 of the original value are chosen when making amino acid substitutions based on hydropathic indices.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with a biological property of the protein. It is understood that an amino acid can be substituted for another having a similar hydrophilicity value and still obtain a biologically equivalent protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±2 of the original value are chosen in one embodiment, those that are within ±1 of the original value are chosen in another embodiment, and those within ±0.5 of the original value are chosen in still another embodiment.

While discussion has focused on functionally equivalent polypeptides arising from amino acid changes, it will be appreciated that these changes can be effected by alteration of the encoding DNA, taking into consideration also that the genetic code is degenerate and that two or more codons can code for the same amino acid.

Thus, it will also be understood that this presently claimed subject matter is not limited to the particular nucleic acid and amino acid sequences of SEQ ID NOs: 1-8, 28, and 29. Recombinant vectors and isolated DNA segments can therefore variously include the platelet VDCC $\alpha_1$ subunit polypeptide-encoding region itself, coding regions bearing selected alterations or modifications in the basic coding region, or larger polypeptides which nevertheless comprise platelet VDCC $\alpha_1$ subunit polypeptide-encoding regions or can encode biologically functional equivalent proteins or peptides. Biological activity of a platelet VDCC $\alpha_1$ subunit polypeptide can be determined, for example, by any of the assays disclosed herein below in Section G.2.

In particular embodiments, the presently claimed subject matter concerns gene therapy methods that use isolated DNA segments and recombinant vectors incorporating DNA sequences which encode a protein comprising an amino acid sequence of SEQ ID NO: 2 or 4. In other particular embodiments, the presently claimed subject matter concerns isolated DNA sequences and recombinant DNA vectors incorporating DNA sequences which encode a protein comprising an amino acid sequence of a platelet VDCC $\alpha_1$ subunit polypeptide protein from human or pig. In certain other embodiments, the presently claimed subject matter concerns isolated DNA segments and recombinant vectors that comprise a nucleic acid sequence essentially as set forth in any of SEQ ID NOs: 1, 3, 5-8, 28, and 29.

The nucleic acid segments of the presently claimed subject matter, regardless of the length of the coding sequence itself, can be combined with other DNA sequences, such as promoters, enhancers, polyadenylation signals, additional restriction enzyme sites, multiple cloning sites, other coding segments, and the like, such that their overall length can vary considerably. Thus, a nucleic acid fragment of almost any length can be employed, with the total length being limited in one embodiment by the ease of preparation and use in the intended recombinant DNA protocol. For example, nucleic acid fragments can be prepared which include a short stretch complementary to a nucleic acid sequence set forth in any of SEQ ID NOs: 1, 3, 5-8, 28, and 29, in one embodiment about 10 nucleotides, and which are up to 10,000 or 5,000 base pairs in length, with segments of 3,000 being an exemplary embodiment. DNA segments with total lengths of about 4,000, 3,000, 2,000, 1,000, 500, 200, 100, and about 50 base pairs in length are also useful.

The DNA segments of the presently claimed subject matter encompass biologically functional equivalent platelet VDCC $\alpha_1$ subunit polypeptides. Such sequences can rise as a consequence of codon redundancy and functional equivalency that are known to occur naturally within nucleic acid sequences and the proteins thus encoded. Alternatively, functionally equivalent proteins or peptides can be created via the application of recombinant DNA technology, in which changes in the protein structure can be engineered, based on considerations of the properties of the amino acids being exchanged. Changes can be introduced through the application of site-directed mutagenesis techniques, e.g., to introduce improvements to the antigenicity of the protein or to test platelet VDCC $\alpha_1$ subunit mutants in order to examine activity in the modulation of calcium transport, or other activity at the molecular level. Site-directed mutagenesis techniques are known to those of skill in the art and are disclosed herein.

The presently claimed subject matter further encompasses fusion proteins and peptides wherein the platelet VDCC $\alpha_1$ subunit polypeptide coding region is aligned within the same expression unit with other proteins or peptides having desired functions, such as for purification or immunodetection purposes.

Recombinant vectors form important further aspects of the presently claimed subject matter. Particularly useful vectors are those in which the coding portion of the DNA segment is positioned under the control of a promoter. The promoter can be that naturally associated with the platelet VDCC $\alpha_1$ subunit polypeptide gene, as can be obtained by isolating the 5' non-coding sequences located upstream of the coding segment or exon, for example, using recombinant cloning and/or PCR technology and/or other methods known in the art, in conjunction with the compositions disclosed herein.

In other embodiments, certain advantages will be gained by positioning the coding DNA segment under the control of a recombinant, or heterologous, promoter. As used herein, a recombinant or heterologous promoter is a promoter that is not normally associated with a platelet VDCC $\alpha_1$ subunit polypeptide gene in its natural environment. Such promoters can include promoters isolated from bacterial, viral, eukaryotic, or mammalian cells. Representative heterologous promoters can thus comprise PF4, $\alpha_{IIb/\beta_3}$ (GPIIb/IIIa), P-selectin, or GPIb promoter, which have been disclosed in the art. Naturally, it will be important to employ a promoter that effectively directs the expression of the DNA segment in the cell type chosen for expression. The use of promoter and cell type combinations for protein expression is generally known to those of skill in the art of molecular biology (for example, see Sambrook et al., 1989, specifically incorporated herein by reference). The promoters employed can be constitutive or inducible and can be used under the appropriate conditions to direct high level expression of the introduced DNA segment, such as is advantageous in the large-scale production of recombinant proteins or peptides. Appropriate promoter systems provided for use in high-level expression include, but are not limited to, the vaccinia virus promoter and the baculovirus promoter.

In an alternative embodiment, the presently claimed subject matter provides an expression vector comprising a polynucleotide that encodes a biologically active platelet VDCC $\alpha_1$ subunit polypeptide in accordance with the presently claimed subject matter. In one embodiment, an expression vector of the presently claimed subject matter comprises a polynucleotide that encodes human or pig platelet VDCC $\alpha_1$ subunit polypeptide gene product. In another embodiment, an expression vector of the presently claimed subject matter comprises a polynucleotide that encodes a polypeptide comprising an amino acid residue sequence of SEQ ID NO: 2 or 4. In another embodiment, an expression vector of the presently claimed subject matter comprises a polynucleotide comprising the nucleotide sequence of any of SEQ ID NOs: 1, 3, 5-8, 28, and 29. In another embodiment, an expression vector of the presently claimed subject matter comprises a polynucleotide operatively linked to an enhancer-promoter. In still another embodiment, an expression vector of the presently claimed subject matter comprises a polynucleotide operatively linked to a prokaryotic promoter. Alternatively, an expression vector of the presently claimed subject matter can comprise a polynucleotide operatively linked to an enhancer-promoter that is a eukaryotic promoter and the expression vector further comprises a polyadenylation signal that is positioned 3' of the carboxy-terminal amino acid and within a transcriptional unit of the encoded polypeptide. The expression vector can further comprise an intronic sequence from a platelet VDCC $\alpha_1$ subunit gene, another platelet or megakaryocytic intronic sequence, or any other intronic sequence, as it has been shown that the inclusion of an intronic sequence into an expression vector can increase levels of expression.

In yet another embodiment, the presently claimed subject matter provides a recombinant host cell transfected, infected, or adsorbed with a polynucleotide that encodes a biologically active platelet VDCC $\alpha_1$ subunit polypeptide in accordance with the presently claimed subject matter. SEQ ID NOs: 1-8, 28, and 29 set forth nucleotide and amino acid sequences from representative vertebrates, human and pig. Also provided by the presently claimed subject matter are homologous or biologically functionally equivalent polynucleotides and platelet VDCC $\alpha_1$ subunit polypeptides found in other vertebrates, including particularly dog and bovine homologues. In one embodiment, a recombinant host cell of the presently claimed subject matter is transfected with the polynucleotide that encodes human or pig platelet VDCC $\alpha_1$ subunit polypeptide. In another embodiment, a recombinant host cell of the presently claimed subject matter is transfected with the polynucleotide sequence encoding or set forth in any of SEQ ID NOs: 1-8, 28, and 29. In another embodiment, a recombinant host cell is a mammalian cell. In still another embodiment, a recombinant host cell is a platelet or a megakaryocyte.

In another aspect, a recombinant host cell of the presently claimed subject matter is a prokaryotic host cell, including parasitic and bacterial cells. In one embodiment, a recombinant host cell of the presently claimed subject matter is a bacterial cell, in one embodiment a strain of *Escherichia coli*. In another embodiment, a recombinant host cell comprises a polynucleotide under the transcriptional control of regulatory signals functional in the recombinant host cell, wherein the regulatory signals appropriately control expression of the platelet VDCC $\alpha_1$ subunit polypeptide in a manner to enable all necessary transcriptional and post-transcriptional modification.

In yet another embodiment, the presently claimed subject matter provides a method of preparing a platelet VDCC $\alpha_1$ subunit polypeptide comprising transfecting a cell with polynucleotide that encodes a biologically active platelet VDCC $\alpha_1$ subunit polypeptide in accordance with the presently claimed subject matter, to produce a transformed host cell, and maintaining the transformed host cell under biological conditions sufficient for expression of the polypeptide. The polypeptide can be isolated if desired, using any suitable technique. The host cell can be a prokaryotic or eukaryotic cell. In one embodiment, the prokaryotic cell is a bacterial cell of *Escherichia coli*. In one embodiment, a polynucleotide transfected into the transformed cell comprises the nucleotide base sequence of any of SEQ ID NOs: 1, 3, 5-8, 28, and 29. SEQ ID NOs: 1-8, 28, and 29 set forth nucleotide and amino acid sequences for representative vertebrates, human and pig. Also provided by the presently claimed subject matter are homologues or biologically equivalent platelet VDCC $\alpha_1$ subunit polypeptide polynucleotides and polypeptides found in other vertebrates, particularly warm-blooded vertebrates, more particularly mammals, and even more particularly bovine and rat homologues.

As mentioned above, in connection with expression embodiments to prepare recombinant platelet VDCC $\alpha_1$ subunit polypeptide proteins and peptides, it is contemplated that longer DNA segments will most often be used, with DNA segments encoding the entire platelet VDCC $\alpha_1$ subunit polypeptide protein, functional domains, or cleavage products thereof being representative examples. However, it will be appreciated that the use of shorter DNA segments to direct the expression of platelet VDCC $\alpha_1$ subunit polypeptides or core regions, such as can be used to generate anti-platelet VDCC $\alpha_1$ subunit polypeptide antibodies, also falls within the scope of the presently claimed subject matter.

DNA segments which encode peptide antigens in one embodiment from about 15 to about 50 amino acids in length and in another embodiment from about 15 to about 30 amino acids in length are contemplated to be particularly useful. DNA segments encoding peptides will generally have a minimum coding length in the order of about 45 to about 150, or to about 90 nucleotides. DNA segments encoding full length proteins can have a minimum coding length on the order of about 4,000 or 5,000 nucleotides for a protein in accordance with any of SEQ ID NOs: 1, 3, 5-8, 28, and 29. DNA segments of the presently claimed subject matter can contain 300, 400, 500, 1,000, 1,500, 2,000, 2,500, 3,000, 3,500, 4,000, 4,500, or up to 5,000 nucleotides. Peptides of the presently claimed subject matter can contain 10, 20, 50, 100, 200, 300, 400, 500, 750, 1,000, or up to 1,500 amino acids.

B.3. Sequence Modification Techniques

Modifications to the platelet VDCC $\alpha_1$ subunit proteins and peptides described herein can be carried out using techniques known in the art, including site directed mutagenesis. Site-specific mutagenesis is a technique useful in the preparation of individual peptides, or biologically functional equivalent proteins or peptides, through specific mutagenesis of the underlying DNA. The technique further provides a ready ability to prepare and test sequence variants; for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. In one embodiment, a primer of about 17 to 30 nucleotides in length is employed, with about 5 to 10 residues on both sides of the junction of the sequence being altered.

In general, the technique of site-specific mutagenesis is well known in the art as exemplified by publications (see e.g., Adelman et al., 1983; Sambrook et al., 1989) and can be achieved in a variety of ways generally known to those of skill in the art.

B.4. Other Structural Equivalents

The knowledge of the structure of the platelet VDCC $\alpha_1$ subunit polypeptide of the presently claimed subject matter provides a tool for investigating the mechanism of action of these proteins in a subject. For example, binding of these proteins to various substrate molecules can be predicted by various computer models. Upon discovering that such binding in fact takes place, knowledge of the protein structure then allows design and synthesis of small molecules which mimic the functional binding of the platelet VDCC $\alpha_1$ subunit polypeptide to the substrate. This is the method of "rational" drug design, also described below.

Use of the isolated and purified platelet VDCC $\alpha_1$ subunit polypeptide of the presently claimed subject matter in rational drug design is thus provided in accordance with the presently claimed subject matter. Additional rational drug design techniques are described in U.S. Pat. Nos. 5,834,228 and 5,872,011, herein incorporated in their entirety.

Thus, in addition to the peptidyl compounds described herein, other sterically similar compounds can be formulated to mimic the key portions of the peptide structure. Such compounds can be used in the same manner as the peptides of the presently claimed subject matter and hence are also functional equivalents. The generation of a structural functional equivalent can be achieved by the techniques of modeling and chemical design known to those of skill in the art. It will be understood that all such sterically similar constructs fall within the scope of the presently claimed subject matter.

C. Introduction of Gene Products

In accordance with the presently claimed subject matter, where a platelet VDCC $\alpha_1$ subunit gene itself is employed to introduce a platelet VDCC $\alpha_1$ subunit gene product, a convenient method of introduction will be through the use of a recombinant vector that incorporates the desired gene, together with its associated control sequences. The preparation of recombinant vectors is well known to those of skill in the art and described in many references, such as, for example, Sambrook et al., 1989, incorporated herein by reference in its entirety.

C.1. Vector Construction

It is understood that the DNA coding sequences to be expressed, in this case those encoding the platelet VDCC $\alpha_1$ subunit gene products, are positioned in a vector adjacent to and under the control of a promoter. It is understood in the art that to bring a coding sequence under the control of such a promoter, one generally positions the 5' end of the transcription initiation site of the transcriptional reading frame of the gene product to be expressed between about 1 and about 50 nucleotides "downstream" of (i.e., 3' of) the chosen promoter. One can also desire to incorporate into the transcriptional unit of the vector an appropriate polyadenylation site (e.g., 5'-AATAAA-3'), if one was not contained within the original inserted DNA. Typically, these poly-A addition sites are placed about 30 to 2000 nucleotides "downstream" of the coding sequence at a position prior to transcription termination.

While in one embodiment the control sequences of the specific gene is employed, other control sequences can be employed, so long as they are compatible with the genotype of the cell being treated. Thus, one can mention other useful promoters by way of example, including, e.g., a Simian Virus 40 (SV40) early promoter, a long terminal repeat promoter from retrovirus, an actin promoter, a heat shock promoter, a metallothionein promoter, and the like. Representative platelet specific promoters include but are not limited to PF4, $\alpha_{IIb}$ (GPIIb), P-selectin or GPIb.

As is known in the art, a promoter is a region of a DNA molecule typically within about 100 nucleotide pairs upstream of (i.e., 5' to) the point at which transcription begins (i.e., a transcription start site). That region typically contains several types of DNA sequence elements that are located in similar relative positions in different genes.

Another type of discrete transcription regulatory sequence element is an enhancer. An enhancer imposes specificity of time, location and expression level on a particular coding region or gene. A major function of an enhancer is to increase the level of transcription of a coding sequence in a cell that contains one or more transcription factors that bind to that enhancer. An enhancer can function when located at variable distances from transcription start sites so long as a promoter is present.

As used herein, the phrase "enhancer-promoter" means a composite unit that contains both enhancer and promoter elements. An enhancer-promoter is operatively linked to a coding sequence that encodes at least one gene product. As used herein, the phrase "operatively linked" means that an enhancer-promoter is connected to a coding sequence in such a way that the transcription of that coding sequence is controlled and regulated by that enhancer-promoter. Means for operatively linking an enhancer-promoter to a coding sequence are well known in the art; the precise orientation and location relative to a coding sequence of interest is dependent, inter alia, upon the specific nature of the enhancer-promoter.

An enhancer-promoter used in a vector construct of the presently claimed subject matter can be any enhancer-promoter that drives expression in a cell to be transfected. By employing an enhancer-promoter with well-known properties, the level and pattern of gene product expression can be optimized. The vector can further comprise an intronic sequence from a platelet VDCC $\alpha_1$ subunit gene, another platelet or megakaryocytic intronic sequence, or any other intronic sequence, as it has been shown that the inclusion of an intronic sequence into an vector can increase levels of expression, particularly in the case of a gene therapy vector.

For introduction of, for example, a human platelet VDCC $\alpha_1$ subunit gene, a vector construct that will deliver the gene to the affected cells is desired. Viral vectors can be used. In exemplary embodiments, these vectors can be an adenoviral, a retroviral, a vaccinia viral vector, adeno-associated virus or Lentivirus; these vectors have been successfully used to deliver desired sequences to cells and tend to have a high infection efficiency. Suitable vector-platelet VDCC $\alpha_1$ subunit gene constructs are adapted for administration as pharmaceutical compositions, as described herein below. Viral promoters can also be of use in vectors of the presently claimed subject matter, and are known in the art.

Commonly used viral promoters for expression vectors are derived from polyoma, cytomegalovirus, Adenovirus 2, and Simian Virus 40 (SV40). The early and late promoters of SV40 virus are particularly useful because both are obtained easily from the virus as a fragment that also contains the SV40 viral origin of replication. Smaller or larger SV40 fragments can also be used, provided there is included the approximately 250 bp sequence extending from the Hind III site toward the Bgl I site located in the viral origin of replication. Further, it is also possible, and often desirable, to utilize promoter or control sequences normally associated with the desired gene sequence, provided such control sequences are compatible with the host cell systems.

The origin of replication can be provided either by construction of the vector to include an exogenous origin, such as can be derived from SV40 or other viral source, or can be provided by the host cell chromosomal replication mechanism. If the vector is integrated into the host cell chromosome, the latter is often sufficient.

Where a platelet VDCC $\alpha_1$ subunit gene itself is employed it will be most convenient to simply use a wild type platelet VDCC $\alpha_1$ subunit gene directly. However, certain regions of a platelet VDCC $\alpha_1$ subunit gene can be employed exclusively without employing an entire wild type platelet VDCC $\alpha_1$ subunit gene. It is proposed that it will ultimately be advantageous to employ the smallest region needed to modulate biological activity so that one is not introducing unnecessary DNA into cells which receive a platelet VDCC $\alpha_1$ subunit gene construct. The biological activity of these regions can easily be determined by the assays reported herein.

C.2. Genetically Modified Cell Lines and Animals

It is also within the scope of the presently claimed subject matter to prepare a genetically modified cell line (e.g., platelet or megakaryocyte) and/or a genetically modified animal (e.g., a transgenic non-human animal) that expresses a platelet VDCC $\alpha_1$ subunit gene of the presently claimed subject matter, that does not express a platelet VDCC $\alpha_1$ subunit gene, or that has a modified expression of a platelet VDCC $\alpha_1$ subunit gene of the presently claimed subject matter. Representative transgenic animals include, but are not limited to mice, pigs, and dogs.

Techniques for the preparation of genetically modified cell lines are disclosed herein above, and are generally known in the art. Modified megakaryocyte and platelet cell lines have utility in the study of the biological activity and in the preparation and development of laboratory and medical applications for platelets, including enhanced ability to store or otherwise manipulate platelets.

Techniques for the preparation of transgenic animals are known in the art. Exemplary techniques are described in U.S. Pat. No. 5,489,742 (transgenic rats); U.S. Pat. Nos. 4,736,866, 5,550,316, 5,614,396, 5,625,125 and 5,648,061 (transgenic mice); U.S. Pat. No. 5,573,933 (transgenic pigs); U.S. Pat. No. 5,162,215 (transgenic avian species) and U.S. Pat. No. 5,741,957 (transgenic bovine species), the entire contents of each of which are herein incorporated by reference.

With respect to a representative method for the preparation of a transgenic pig, cloned recombinant or synthetic DNA sequences or DNA segments encoding a platelet VDCC $\alpha_1$ subunit polypeptide gene product are injected into fertilized eggs. The injected eggs are implanted in pseudo pregnant females and are grown to term to provide transgenic pigs whose cells express a platelet VDCC $\alpha_1$ subunit polypeptide gene product.

Additionally, a genetically modified animal of the presently claimed subject matter can comprise a pig with targeted modification of the platelet VDCC $\alpha_1$ subunit polypeptide gene. Pig strains with complete or partial functional inactivation of a platelet VDCC $\alpha_1$ subunit polypeptide gene in megakaryocytes and/or in platelets are generated using standard techniques of site-specific recombination in embryonic stem cells. Capecchi, 1989; Thomas & Capecchi, 1990; Delpire, 1999. Procedures analogous to those employed in the generation of a "knock-out" animal can be applied in the generation of a "knock-out" cell line.

Alternatives include the use of anti-sense or ribozyme VDCC constructs, driven by a universal or tissue-specific promoter, to reduce levels of a platelet VDCC $\alpha_1$ subunit polypeptide in platelets or megakaryocytes, thus achieving a "knock-down" of individual isoforms (Luyckx et al., 1999). The presently claimed subject matter also provides the generation of animal strains with conditional or inducible inactivation of individual or multiple VDCC genes (Sauer, 1998). For example, pigs are created which lack expression of any platelet VDCC $\alpha_1$ subunit polypeptide in platelets or megakaryocytes through the sequential mating of pig strains with lox-P-flanked VDCC genes with a transgenic line expressing Cre-recombinase in platelets or megakaryocytes, using a platelet specific promoter, such as PF4, $\alpha_{IIb}$ (GPIIb), P-selectin, or GPIb (Ding et al., 1997).

The presently claimed subject matter also provides animal strains with specific "knocked-in" modifications in a platelet VDCC $\alpha_1$ subunit polypeptide gene. This includes animals with genetically (Forlino et al., 1999) and functionally (Kissel et al., 2000) relevant point mutations in the VDCC genes, in addition to manipulations such as the insertion of disease-specific repeat expansions (White et al., 1997).

D. Generation of Antibodies

In still another embodiment, the presently claimed subject matter provides an antibody that specifically binds a polypeptide of the presently claimed subject matter. In one embodiment, an antibody of the presently claimed subject matter is a monoclonal antibody. Techniques for preparing and characterizing antibodies are well known in the art (See e.g., Harlow & Lane, 1988).

The phrase "specifically (or selectively) binds to an antibody", or "specifically (or selectively) immunoreactive with", when referring to a protein or peptide, refers to a binding reaction which is determinative of the presence of the protein in a heterogeneous population of proteins and other biological materials. Thus, under designated immunoassay conditions, the specified antibodies bind to a particular protein and do not show significant binding to other proteins present in the sample. Specific binding to an antibody under such conditions can require an antibody that is selected for its specificity for a particular protein. For example, antibodies raised to a protein with an amino acid sequence encoded by any of the nucleic acid sequences of the presently claimed subject matter can be selected to obtain antibodies specifically immunoreactive with that protein and not with other proteins.

Briefly, a polyclonal antibody is prepared by immunizing an animal with an immunogen comprising a polypeptide or polynucleotide of the presently claimed subject matter, and collecting antisera from that immunized animal. A wide range of animal species can be used for the production of antisera. Because of the relatively large blood volume of rabbits, a rabbit is a representative choice for production of polyclonal antibodies.

As is well known in the art, a given polypeptide or polynucleotide can vary in its immunogenicity. It is often necessary therefore to couple the immunogen (e.g., a polypeptide or polynucleotide) of the presently claimed subject matter) with a carrier. Exemplary carriers are keyhole limpet hemocyanin (KLH) and bovine serum albumin (BSA). Other albumins such as ovalbumin, mouse serum albumin or rabbit serum albumin can also be used as carriers.

Reagents for conjugating a polypeptide or a polynucleotide to a carrier protein are well known in the art and include glutaraldehyde, N-maleimidobenzoyl-N-hydroxysuccinimide ester, carbodiimide, and bis-diazotized benzidine.

As is also well known in the art, immunogenicity to a particular immunogen can be enhanced by the use of non-specific stimulators of the immune response known as adjuvants. Exemplary adjuvants include complete Freund's adjuvant, incomplete Freund's adjuvants, and aluminum hydroxide adjuvant.

The amount of immunogen used of the production of polyclonal antibodies varies, inter alia, upon the nature of the immunogen as well as the animal used for immunization. A variety of routes can be used to administer the immunogen, e.g., subcutaneous, intramuscular, intradermal, intravenous, and intraperitoneal. The production of polyclonal antibodies is monitored by sampling blood of the immunized animal at various points following immunization. When a desired level of immunogenicity is obtained, the immunized animal can be bled and the serum isolated and stored.

In another aspect, the presently claimed subject matter provides a method of producing an antibody that specifically binds a platelet VDCC $\alpha_1$ subunit polypeptide, the method comprising: (a) transfecting recombinant host cells with a polynucleotide that encodes that polypeptide; (b) culturing the host cells under conditions sufficient for expression of the polypeptide; (c) recovering the polypeptide; and (d) preparing antibodies to the polypeptide. In one embodiment, the platelet VDCC $\alpha_1$ subunit polypeptide is capable of modulating calcium levels within or outside of cells in accordance with the presently claimed subject matter.

A monoclonal antibody of the presently claimed subject matter can be readily prepared through use of well-known techniques such as the hybridoma techniques exemplified in U.S. Pat. No. 4,196,265 and the phage-displayed techniques disclosed in U.S. Pat. No. 5,260,203, the contents of which are herein incorporated by reference.

A typical technique involves first immunizing a suitable animal with a selected antigen (e.g., a polypeptide or polynucleotide of the presently claimed subject matter) in a manner sufficient to provide an immune response. Rodents such as mice and rats are representative animals. Spleen cells from the immunized animal are then fused with cells of an immortal myeloma cell. Where the immunized animal is a mouse, an exemplary myeloma cell is a murine NS-1 myeloma cell.

The fused spleen/myeloma cells are cultured in a selective medium to select fused spleen/myeloma cells from the parental cells. Fused cells are separated from the mixture of non-fused parental cells, for example, by the addition of agents that block the de novo synthesis of nucleotides in the tissue culture media. This culturing provides a population of hybridomas from which specific hybridomas are selected. Typically, selection of hybridomas is performed by culturing the cells by single-clone dilution in microtiter plates, followed by testing the individual clonal supernatants for reactivity with an antigen-polypeptides. The selected clones can then be propagated indefinitely to provide the monoclonal antibody.

By way of specific example, to produce an antibody of the presently claimed subject matter, mice are injected intraperitoneally with between about 1-200 μg of an antigen comprising a polypeptide of the presently claimed subject matter. B lymphocyte cells are stimulated to grow by injecting the antigen in association with an adjuvant such as complete Freund's adjuvant (a non-specific stimulator of the immune response containing killed *Mycobacterium tuberculosis*). At some time (e.g., at least two weeks) after the first injection, mice are boosted by injection with a second dose of the antigen mixed with incomplete Freund's adjuvant.

A few weeks after the second injection, mice are tail bled and the sera titered by immunoprecipitation against radiolabeled antigen. In one embodiment, the method of boosting and titering is repeated until a suitable titer is achieved. The spleen of the mouse with the highest titer is removed and the spleen lymphocytes are obtained by homogenizing the spleen with a syringe.

Mutant lymphocyte cells known as myeloma cells are obtained from laboratory animals in which such cells have been induced to grow by a variety of well-known methods. Myeloma cells lack the salvage pathway of nucleotide biosynthesis. Because myeloma cells are tumor cells, they can be propagated indefinitely in tissue culture, and are thus "immortal". Numerous cultured cell lines of myeloma cells from mice and rats, such as murine NS-1 myeloma cells, have been established.

Myeloma cells are combined under conditions appropriate to foster fusion with the normal antibody-producing cells from the spleen of the mouse or rat injected with the antigen/polypeptide of the presently claimed subject matter. Fusion conditions include, for example, the presence of polyethylene glycol. The resulting fused cells are hybridoma cells. Like myeloma cells, hybridoma cells grow indefinitely in culture.

Hybridoma cells are separated from unfused myeloma cells by culturing in a selection medium such as HAT media (hypoxanthine, aminopterin, and thymidine). Unfused myeloma cells lack the enzymes necessary to synthesize nucleotides from the salvage pathway because they are killed in the presence of aminopterin, methotrexate, or azaserine. Unfused lymphocytes also do not continue to grow in tissue culture. Thus, only cells that have successfully fused (hybridoma cells) can grow in the selection media.

Each of the surviving hybridoma cells produces a single antibody. These cells are then screened for the production of the specific antibody that specifically binds an antigen/polypeptide of the presently claimed subject matter. Single cell hybridomas are isolated by limiting dilutions of the hybridomas. The hybridomas are serially diluted many times and, after the dilutions are allowed to grow, the supernatant is tested for the presence of the monoclonal antibody. The clones producing that antibody are then cultured in large amounts to produce an antibody of the presently claimed subject matter in convenient quantity.

By use of a monoclonal antibody of the presently claimed subject matter, specific polypeptides and polynucleotide of the presently claimed subject matter can be recognized as antigens, and thus identified. Once identified, those polypeptides and polynucleotide can be isolated and purified by techniques such as antibody-affinity chromatography. In antibody-affinity chromatography, a monoclonal antibody is bound to a solid substrate and exposed to a solution containing the desired antigen. The antigen is removed from the solution through an immunospecific reaction with the bound antibody. The polypeptide or polynucleotide is then easily removed from the substrate and purified.

E. Detecting a Polynucleotide or a Polypeptide

Alternatively, the presently claimed subject matter provides a method of detecting a polypeptide of the presently claimed subject matter, wherein the method comprises immunoreacting the polypeptides with antibodies prepared according to the method described above to form antibody-polypeptide conjugates, and detecting the conjugates.

In yet another embodiment, the presently claimed subject matter provides a method of detecting messenger RNA transcripts that encode a polypeptide of the presently claimed subject matter, wherein the method comprises hybridizing the messenger RNA transcripts with polynucleotide sequences that encode the polypeptide to form duplexes; and detecting the duplex. Alternatively, the presently claimed subject matter provides a method of detecting DNA molecules that encode a polypeptide of the presently claimed subject matter, wherein the method comprises hybridizing DNA molecules with a polynucleotide that encodes that polypeptide to form duplexes; and detecting the duplexes.

The detection and screening assays disclosed herein can optionally be used as a prognosis tool and/or diagnostic aid. Platelet VDCC $\alpha_1$ subunit polypeptides and nucleic acids can be readily used in clinical setting as a prognostic and/or diagnostic indicator for screening for levels of expression of platelet VDCC $\alpha_1$ subunit polypeptides, or alterations in native sequences. The nucleotide sequences of the subject presently claimed subject matter can be used to detect differences in gene or gene product sequences between normal, carrier, or affected individuals. As discussed herein above, such differences can consist of single-nucleotide changes or multiple changes, deletions, or additions in the native sequence which result in altered transcription, translation, or activity or biological activity or properties of the gene or gene product. These differences can be readily detected using the compositions of the presently claimed subject matter and techniques known in the art, including but not limited to single strand conformation polymorphism (SSCP) analysis, restriction fragment length polymorphism (RFLP) analysis, or other PCR- or nucleotide-based analyses.

DNA segments of the presently claimed subject matter or RNA having the sequence of, or a sequence complementary to, SEQ ID NOs: 1, 3, 5-8, 28, and 29 can be used. Such polynucleic acids can comprise 10, 20, 40, 50, 70, 100, 250, 300, 400, 500, or 1,000 nucleotides or up to the full length of SEQ ID NOs: 1, 3, 5-8, 28, and 29. Such polynucleic acids can, but need not, encode polypeptides which retain some or all of the biological activity of the native gene or gene product.

The presently claimed subject matter provides a method of screening a biological sample for the presence of a platelet VDCC $\alpha_1$ subunit polypeptide. A biological sample to be screened can be a biological fluid such as extracellular or intracellular fluid, or a cell or tissue extract or homogenate. A biological sample can also be an isolated cell (e.g., in culture) or a collection of cells such as in a tissue sample or histology sample. A tissue sample can be suspended in a liquid medium or fixed onto a solid support such as a microscope slide.

In accordance with a screening assay method, a biological sample is exposed to an antibody that specifically binds the polypeptide whose presence is being assayed. Typically, exposure is accomplished by forming an admixture in a liquid medium that contains both the antibody and the candidate polypeptide. Either the antibody or the sample with the polypeptide can be affixed to a solid support (e.g., a column or a microtiter plate). Additional details of methods for such assays are known in the art. The presence of polypeptide in the sample is detected by evaluating the formation and presence of antibody-polypeptide conjugates. Techniques for detecting such antibody-antigen conjugates or complexes are well known in the art and include but are not limited to centrifugation, affinity chromatography and the like, and binding of a secondary antibody to the antibody-candidate receptor complex.

In one embodiment, detection is accomplished by detecting an indicator affixed to the antibody. Exemplary and well-known indicators include radioactive labels (e.g., $^{32}$P, $^{125}$I, $^{14}$C), a second antibody, or an enzyme such as horseradish peroxidase. Techniques for affixing indicators to antibodies are known in the art.

In another aspect, the presently claimed subject matter provides a method of screening a biological sample for the presence of antibodies that specifically bind a platelet VDCC $\alpha_1$ subunit polypeptide. In one embodiment, the antibody so identified has activity in the modulation of platelet VDCC $\alpha_1$ subunit polypeptide biological activity in accordance with the presently claimed subject matter. In accordance with such a method, a biological sample is exposed to a platelet VDCC $\alpha_1$ subunit polypeptide under biological conditions and for a period of time sufficient for antibody-polypeptide conjugate formation and the formed conjugates are detected.

A DNA or RNA molecule and particularly a DNA segment or polynucleotide can be used for hybridization to a DNA or RNA source or sample suspected of encoding a platelet VDCC $\alpha_1$ subunit polypeptide of the presently claimed subject matter; such molecules are referred to as "probes", and such hybridization is "probing". Such probes can be made synthetically. The probing is usually accomplished by hybridizing the oligonucleotide to a DNA source suspected of possessing a platelet VDCC $\alpha_1$ subunit polypeptide gene. In some cases, the probes constitute only a single probe, and in others, the probes constitute a collection of probes based on a certain amino acid sequence or sequences of the polypeptide and account in their diversity for the redundancy inherent in the genetic code.

Other molecules which are neither DNA nor RNA but are capable of hybridizing in a similar manner and which are designed structurally to mimic the DNA or RNA sequence of a platelet VDCC $\alpha_1$ subunit polypeptide gene are also provided. Here, a suitable source to examine is capable of expressing a polypeptide of the presently claimed subject matter and can be a genomic library of a cell line of interest. Alternatively, a source of DNA or RNA can include total DNA or RNA from the cell line of interest. Once the hybridization method of the presently claimed subject matter has identified a candidate DNA segment, a positive clone can be confirmed by further hybridization, restriction enzyme mapping, sequencing and/or expression and testing.

Alternatively, such DNA molecules can be used in a number of techniques including their use as: (1) diagnostic tools to detect normal and abnormal DNA sequences in DNA derived from patient's cells; (2) reagents for detecting and isolating other members of the polypeptide family and related polypeptides from a DNA library potentially containing such sequences; (3) primers for hybridizing to related sequences for the purpose of amplifying those sequences; (4) primers for altering native platelet VDCC $\alpha_1$ subunit DNA sequences; as well as (5) other techniques which rely on the similarity of the sequences of interest to those of the sequences herein disclosed.

As set forth above, in certain aspects, DNA sequence information provided by the presently claimed subject matter allows for the preparation of probes that specifically hybridize to encoding sequences of a selected platelet VDCC $\alpha_1$ subunit gene. In these aspects, probes of an appropriate length are prepared based on a consideration of the encoding sequence for a polypeptide of this presently claimed subject matter. The ability of such probes to specifically hybridize to other encoding sequences lends them particular utility in a variety of embodiments. Most importantly, the probes can be used in a variety of assays for detecting the presence of complementary sequences in a given sample. However, other uses are envisioned, including the use of the sequence information for the preparation of mutant species primers, or primers for use in preparing other genetic constructions.

To provide certain of the advantages in accordance with the presently claimed subject matter, an exemplary nucleic acid sequence employed for hybridization studies or assays includes probe sequences that are complementary to or mimic at least a 14 to 40 or so long nucleotide stretch of a nucleic acid sequence of the presently claimed subject matter, such as a sequence shown in any of SEQ ID NOs: 1, 3, 5-8, 28, and 29. A size of at least 14 nucleotides in length helps to ensure that the fragment is of sufficient length to form a duplex molecule that is both stable and selective. Molecules having complementary sequences over stretches greater than 14 bases in length are generally employed, though, to increase stability and selectivity of the hybrid, and thereby improve the quality and degree of specific hybrid molecules obtained. One will generally design nucleic acid molecules having gene-complementary stretches of 14 to 20 nucleotides, or even longer where desired, such as 30, 40, 50, 60, 100, 200, 300, or 500 nucleotides or up to the full length of any of SEQ ID NOs: 1, 3, 5-8, 28, and 29. Such fragments can be readily prepared by, for example, directly synthesizing the fragment by chemical synthesis, by application of nucleic acid amplification technology, such as the PCR technology of U.S. Pat. No. 4,683,202, herein incorporated by reference, or by introducing selected sequences into recombinant vectors for recombinant production.

Accordingly, a nucleotide sequence of the presently claimed subject matter can be used for its ability to selectively form duplex molecules with complementary stretches of the gene. Depending on the application envisioned, one employs varying conditions of hybridization to achieve varying degrees of selectivity of the probe toward the target sequence. For applications requiring a high degree of selectivity, one typically employs relatively stringent conditions to form the hybrids. For example, one selects relatively low salt and/or high temperature conditions, such as provided by 15 to 300 mM salt (e.g., NaCl), in one embodiment 200 mM salt, at temperatures of 50° C. to 70° C., in one embodiment a temperature of about 55° C., in another embodiment about 60° C. and in still another embodiment about 65° C. Such conditions are particularly selective, and tolerate little, if any, mismatch between the probe and the template or target strand.

Of course, for some applications, less stringent hybridization conditions are typically needed to allow formation of the heteroduplex; one of skill in the art will know how to adjust the hybridization conditions for optimizing particular procedures. For example, it is generally appreciated that conditions can be rendered more stringent by the addition of increasing amounts of formamide, which serves to destabilize the hybrid duplex in the same manner as increased temperature. Thus, hybridization conditions can be readily manipulated by one of skill in the art using known methods to carry out the desired function or experiment, without undue experimentation.

In another aspect, the presently claimed subject matter provides assay kits for detecting the presence of a polypeptide of the presently claimed subject matter in biological samples, where the kits comprise a first antibody capable of immunoreacting with the polypeptide. In one embodiment, the assay kits of the presently claimed subject matter further comprise a second container containing a second antibody that immunoreacts with the first antibody. In another embodiment, the antibodies used in the assay kits of the presently claimed subject matter are monoclonal antibodies. In another embodiment, the first antibody is affixed to a solid support. In still another embodiment, the first and second antibodies comprise an indicator, and, in one embodiment, the indicator is a radioactive label or an enzyme.

The presently claimed subject matter also provides an assay kit for screening agents. Such a kit can contain a polypeptide of the presently claimed subject matter. The kit can additionally contain reagents for detecting an interaction between an agent and a polypeptide of the presently claimed subject matter.

In an alternative aspect, the presently claimed subject matter provides assay kits for detecting the presence, in biological samples, of a polynucleotide that encodes a polypeptide of the presently claimed subject matter, the kits comprising a first container that contains a second polynucleotide identical or complementary to a segment of at least 10 contiguous nucleotide bases of, as representative examples, any of SEQ ID NOs: 1, 3, 5-8, 28, and 29. In another embodiment, the presently claimed subject matter provides assay kits for detecting the presence, in a biological sample, of antibodies that specifically binds a polypeptide of the presently claimed subject matter, the kits comprising a platelet VDCC $\alpha_1$ subunit polypeptide that immunoreacts with the antibodies.

F. Mapping and Polynucleotide and Polypeptide Screening

In another embodiment of the presently claimed subject matter, the nucleic acid sequences which encode a platelet VDCC $\alpha_1$ subunit polypeptide can also be used to generate hybridization probes which are useful for mapping naturally occurring genomic sequences and/or disease loci. The sequences can be mapped to a particular chromosome or to a specific region of the chromosome using well-known techniques. Such techniques include, but are not limited to fluorescence in situ hybridization (FISH), fluorescence activated cell sorting (FACS), or artificial chromosome constructions, such as yeast artificial chromosomes, bacterial artificial chromosomes, bacterial P1 constructions or single chromosome cDNA libraries as reviewed in Price, 1993 and Trask, 1991.

F.1. Mapping

FISH (as described in Verma et al., 1988) can be correlated with other physical chromosome mapping techniques and genetic map data. Examples of genetic map data can be found in the 1994 Genome Issue of Science (volume 265, page 1981f). Correlation between the location of the gene encoding a platelet VDCC $\alpha_1$ subunit polypeptide on a physical chromosomal map and a specific disease, or predisposition to a specific disease, can help delimit the region of DNA associated with that genetic disease. The nucleotide sequences of the subject presently claimed subject matter can be used to detect differences in gene sequences between normal, carrier, or affected individuals.

In situ hybridization of chromosomal preparations and physical mapping techniques such as linkage analysis using established chromosomal markers can be used for extending genetic maps. Often the placement of a gene on the chromosome of another mammalian species, such as mouse, reveals associated markers also found in other mammals such as humans even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, ataxia-telangiectasia (A-T) to 11q22-23 (Gatti et al., 1988), any sequences mapping to that area can represent associated or regulatory genes for further investigation. The nucleotide sequences of the presently claimed subject matter can thus also be used to detect differences in the chromosomal location due to translocation, inversion, etc. among normal, carrier, or affected individuals.

The mapping methods of the presently claimed subject matter also employ genomic clones of the exons of a platelet VDCC $\alpha_1$ subunit gene. Sequences for a human platelet VDCC $\alpha_1$ subunit polypeptide gene are set forth in SEQ ID NOs: 1-6, 28, and 29. Thus, the presently claimed subject matter also provides genetic assays based on the genomic sequence of the human platelet VDCC $\alpha_1$ subunit polypeptide genes. An intronic sequence flanking an individual exon encoding a platelet VDCC $\alpha_1$ subunit polypeptide is employed in the design of oligonucleotide primers suitable for the mutation analysis of human genomic DNA. Thus, intronic primers can be used to screen for genetic variants by a number of PCR-based techniques, including single-strand conformation polymorphism (SSCP) analysis (Orita et al., 1989), SSCP/heteroduplex analysis, enzyme mismatch cleavage, and direct sequence analysis of amplified exons (Kestila et al., 1998; Yuan et al., 1999). Similar techniques can be applied to putative 5'-regulatory regions, e.g., the putative promoters 5' of a platelet VDCC $\alpha_1$ subunit gene.

F.2. Polynucleotide Screening

Automated methods can also be applied the large-scale characterization of single nucleotide polymorphisms (SNPs; Brookes, 1999; Wang et al., 1998) within and near a platelet VDCC $\alpha_1$ subunit gene. Once genetic variants have been detected in specific patient populations, the presently claimed subject matter provides assays to detect the mutation by methods such as allele-specific hybridization (Stoneking et al., 1991), or restriction analysis of amplified genomic DNA containing the specific mutation. Again, these detection methods can be automated using existing technology (Wang et al., 1998). In the case of genetic disease or human phenotypes caused by repeat expansion (Lafreniere et al., 1997; Timchenko & Caskey, 1996), the presently claimed subject matter provides an assay based on PCR of genomic DNA with oligonucleotide primers flanking the involved repeat.

As used herein and in the claims, the term "polymorphism" refers to the occurrence of two or more genetically determined alternative sequences or alleles in a population. A polymorphic marker is the locus at which divergence occurs. Representative markers have at least two alleles, each occurring at frequency of greater than 1%. A polymorphic locus can be as small as one base pair.

The provided nucleic acid molecules can be labeled according to any technique known in the art, such as with radiolabels, fluorescent labels, enzymatic labels, sequence tags, etc. Such molecules can be used as allele-specific oligonucleotide probes. Body samples can be tested to determine whether a platelet VDCC $\alpha_1$ subunit gene contains a polymorphism. Suitable body samples for testing include those comprising DNA, RNA, or protein obtained from biopsies, including bone marrow biopsies; or from blood.

In one embodiment of the presently claimed subject matter two pairs of isolated oligonucleotide primers are provided. These sets of primers are optionally derived from a platelet VDCC $\alpha_1$ subunit exon. The oligonucleotide primers are useful, for example, in detecting a polymorphism of a platelet VDCC $\alpha_1$ subunit gene. The primers direct amplification of a target polynucleotide prior to sequencing. In another embodiment of the presently claimed subject matter isolated allele specific oligonucleotides (ASO) are provided. The allele specific oligonucleotides are also useful in detecting a polymorphism of a platelet VDCC $\alpha_1$ subunit gene.

The terms "substantially complementary to" or "substantially the sequence of" refer to sequences which hybridize to the sequences provided (e.g., SEQ ID NOs: 1, 3, 5-8, 28, and 29) under stringent conditions as disclosed herein and/or sequences having sufficient identity with any of SEQ ID NOs: 1, 3, 5-8, 28, and 29, such that the allele specific oligonucleotides of the presently claimed subject matter hybridize to the sequence. The term "isolated" as used herein includes oligonucleotides substantially free of other nucleic acids, proteins, lipids, carbohydrates or other materials with which they can be associated, such association being either in cellular material or in a synthesis medium. A "target polynucleotide" or "target nucleic acid" refers to the nucleic acid sequence of interest e.g., a platelet VDCC $\alpha_1$ subunit-encoding polynucleotide. Other primers which can be used for primer hybridization are readily ascertainable to those of skill in the art based upon the disclosure herein.

The primers of the presently claimed subject matter embrace oligonucleotides of sufficient length and appropriate sequence so as to provide initiation of polymerization on a significant number of nucleic acids in the polymorphic locus. Specifically, the term "primer" as used herein refers to a sequence comprising in one embodiment two or more deoxyribonucleotides or ribonucleotides, in another embodiment more than three, in another embodiment more than eight, and in still another embodiment at least about 20 nucleotides of a platelet VDCC $\alpha_1$ subunit exonic or intronic region as are disclosed herein. Such oligonucleotides can be between ten and thirty bases in length. Such oligonucleotides can optionally further comprises a detectable label.

Environmental conditions conducive to synthesis include the presence of nucleoside triphosphates and an agent for polymerization, such as DNA polymerase, and a suitable temperature and pH. The primer can be single stranded for maximum efficiency in amplification, but can be double stranded. If double stranded, the primer is first treated to separate its strands before being used to prepare extension products. The primer must be sufficiently long to prime the synthesis of extension products in the presence of the inducing agent for polymerization. The exact length of primer will depend on many factors, including temperature, buffer, and nucleotide composition. The oligonucleotide primer typically contains 12-20 or more nucleotides, although it can contain fewer nucleotides.

Primers of the presently claimed subject matter are designed to be "substantially" complementary to each strand of the genomic locus to be amplified. This means that the primers must be sufficiently complementary to hybridize with their respective strands under conditions which allow the agent for polymerization to perform. In other words, the primers should have sufficient complementarity with the 5' and 3' sequences flanking the transition to hybridize therewith and permit amplification of the genomic locus.

Oligonucleotide primers of the presently claimed subject matter are employed in the amplification method which is an enzymatic chain reaction that produces exponential quantities of polymorphic locus relative to the number of reaction steps involved. Typically, one primer is complementary to the negative (−) strand of the polymorphic locus and the other is complementary to the positive (+) strand. Annealing the primers to denatured nucleic acid followed by extension with an enzyme, such as the large fragment of DNA polymerase I (Klenow) and nucleotides, results in newly synthesized + and − strands containing the target polymorphic locus sequence. Because these newly synthesized sequences are also templates, repeated cycles of denaturing, primer annealing, and extension results in exponential production of the region (i.e., the target polymorphic locus sequence) defined by the primers. The product of the chain reaction is a discreet nucleic acid duplex with termini corresponding to the ends of the specific primers employed.

The oligonucleotide primers of the presently claimed subject matter can be prepared using any suitable method, such as conventional phosphotriester and phosphodiester methods or automated embodiments thereof. In one such automated embodiment, diethylphosphoramidites are used as starting materials and can be synthesized as described in Beaucage et al., 1981. One method for synthesizing oligonucleotides on a modified solid support is described in U.S. Pat. No. 4,458,066.

Any nucleic acid specimen, in purified or non-purified form, can be utilized as the starting nucleic acid or acids, providing it contains, or is suspected of containing, a nucleic acid sequence containing the polymorphic locus. Thus, the method can amplify, for example, DNA or RNA, including messenger RNA, wherein DNA or RNA can be single stranded or double stranded. In the event that RNA is to be used as a template, enzymes, and/or conditions optimal for reverse transcribing the template to DNA would be utilized. In addition, a DNA-RNA hybrid which contains one strand of each can be utilized. A mixture of nucleic acids can also be employed, or the nucleic acids produced in a previous amplification reaction herein, using the same or different primers can be so utilized. The specific nucleic acid sequence to be amplified, i.e., the polymorphic locus, can be a fraction of a larger molecule or can be present initially as a discrete molecule, so that the specific sequence constitutes the entire nucleic acid. It is not necessary that the sequence to be amplified be present initially in a pure form; it can be a minor fraction of a complex mixture, such as contained in whole human DNA.

DNA utilized herein can be extracted from a body sample, such as blood, tissue material (e.g., bone marrow tissue), and the like by a variety of techniques such as that described by Maniatis et al., 1982. If the extracted sample is impure, it can be treated before amplification with an amount of a reagent effective to open the cells, or animal cell membranes of the sample, and to expose and/or separate the strand(s) of the nucleic acid(s). This lysing and nucleic acid denaturing step to expose and separate the strands will allow amplification to occur much more readily.

The deoxyribonucleotide triphosphates dATP, dCTP, dGTP, and dTTP are added to the synthesis mixture, either separately or together with the primers, in adequate amounts and the resulting solution is heated to about 90-100° C. from in one embodiment about 1 to 10 minutes and in another embodiment from 1 to 4 minutes. After this heating period, the solution is allowed to cool, which allows for the primer to hybridize. To the cooled mixture is added an appropriate agent for effecting the primer extension reaction (called herein "agent for polymerization"), and the reaction is allowed to occur under conditions known in the art. The agent for polymerization can also be added together with the other reagents if it is heat stable. This synthesis (or amplification) reaction can occur at room temperature up to a temperature above which the agent for polymerization no longer functions. Thus, for example, if DNA polymerase is used as the agent, the temperature is generally no greater than about 40° C. Most conveniently the reaction occurs at room temperature.

The agent for polymerization can be any compound or system which will function to accomplish the synthesis of primer extension products, including enzymes. Suitable enzymes for this purpose include, for example, E. coli DNA polymerase I, Klenow fragment of E. coli DNA polymerase, polymerase muteins, reverse transcriptase, other enzymes, including heat-stable enzymes (i.e., those enzymes which perform primer extension after being subjected to temperatures sufficiently elevated to cause denaturation), such as Taq polymerase. Suitable enzyme will facilitate combination of the nucleotides in the proper manner to form the primer extension products which are complementary to each polymorphic locus nucleic acid strand. Generally, the synthesis will be initiated at the 3' end of each primer and proceed in the 5' direction along the template strand, until synthesis terminates, producing molecules of different lengths.

The newly synthesized strand and its complementary nucleic acid strand will form a double-stranded molecule under hybridizing conditions described herein and this hybrid is used in subsequent steps of the method. In the next step, the newly synthesized double-stranded molecule is subjected to denaturing conditions using any of the procedures described above to provide single-stranded molecules.

The steps of denaturing, annealing, and extension product synthesis can be repeated as often as needed to amplify the target polymorphic locus nucleic acid sequence to the extent necessary for detection. The amount of the specific nucleic acid sequence produced will accumulate in an exponential fashion. McPherson et al., 1991.

The amplification products can be detected by Southern blot analysis with or without using radioactive probes. In one such method, for example, a small sample of DNA containing a very low level of the nucleic acid sequence of the polymorphic locus is amplified, and analyzed via a Southern blotting technique or similarly, using dot blot analysis. The use of non-radioactive probes or labels is facilitated by the high level of the amplified signal. Alternatively, probes used to detect the amplified products can be directly or indirectly detectably labeled, for example, with a radioisotope, a fluorescent compound, a bioluminescent compound, a chemiluminescent compound, a metal chelator or an enzyme. Those of ordinary skill in the art will know of other suitable labels for binding to the probe, or will be able to ascertain such, using routine experimentation.

Sequences amplified by the methods of the presently claimed subject matter can be further evaluated, detected, cloned, sequenced, and the like, either in solution or after binding to a solid support, by any method usually applied to the detection of a specific DNA sequence such as dideoxy sequencing, PCR, oligomer restriction (Saiki et al., 1985), allele-specific oligonucleotide (ASO) probe analysis (Conner et al., 1983), oligonucleotide ligation assays (OLAs; Landgren et al., 1988a), and the like. Molecular techniques for DNA analysis have been reviewed (Landgren et al., 1988b).

In one embodiment, the method of amplifying is by PCR, as described herein and in U.S. Pat. Nos. 4,683,195; 4,683,202; and 4,965,188 each of which is hereby incorporated by reference; and as is commonly used by those of ordinary skill in the art. Alternative methods of amplification have been described and can also be employed as long as a VDCC locus amplified by PCR using primers of the presently claimed subject matter is similarly amplified by the alternative means. Such alternative amplification systems include but are not limited to self-sustained sequence replication, which begins with a short sequence of RNA of interest and a T7 promoter. Reverse transcriptase copies the RNA into cDNA and degrades the RNA, followed by reverse transcriptase polymerizing a second strand of DNA.

Another nucleic acid amplification technique is nucleic acid sequence-based amplification (NASBA™) which uses reverse transcription and T7 RNA polymerase and incorporates two primers to target its cycling scheme. NASBA™ amplification can begin with either DNA or RNA and finish with either, and amplifies to about 108 copies within 60 to 90 minutes.

Alternatively, nucleic acid can be amplified by ligation-activated transcription (LAT). LAT works from a single-stranded template with a single primer that is partially single-stranded and partially double-stranded. Amplification is initiated by ligating a cDNA to the promoter oligonucleotide and within a few hours, amplification is about $10^8$- to about $10^9$-fold. The QB replicase system can be utilized by attaching an RNA sequence called MDV-1 to RNA complementary to a DNA sequence of interest. Upon mixing with a sample, the hybrid RNA finds its complement among the specimen's mRNAs and binds, activating the replicase to copy the tag-along sequence of interest.

Another nucleic acid amplification technique, ligase chain reaction (LCR), works by using two differently labeled halves of a sequence of interest which are covalently bonded by ligase in the presence of the contiguous sequence in a sample, forming a new target. The repair chain reaction (RCR) nucleic acid amplification technique uses two complementary and target-specific oligonucleotide probe pairs, thermostable polymerase and ligase, and DNA nucleotides to geometrically amplify targeted sequences. A 2-base gap separates the oligo probe pairs, and the RCR fills and joins the gap, mimicking normal DNA repair.

Nucleic acid amplification by strand displacement activation (SDA) utilizes a short primer containing a recognition site for Hinc II with short overhang on the 5' end which binds to target DNA. A DNA polymerase fills in the part of the primer opposite the overhang with sulfur-containing adenine analogs. Hinc II is added but only cuts the unmodified DNA strand. A DNA polymerase that lacks 5' exonuclease activity enters at the site of the nick and begins to polymerize, displacing the initial primer strand downstream and building a new one which serves as more primer.

SDA produces greater than about a $10^7$-fold amplification in 2 hours at 37° C. Unlike PCR and LCR, SDA does not require instrumented temperature cycling. Another amplification system useful in the method of the presently claimed subject matter is the QB Replicase System. Although PCR is a representative method of amplification of the presently claimed subject matter, these other methods can also be used to amplify a platelet VDCC $\alpha_1$ subunit locus as described herein. Thus, the term "amplification technique" as used herein and in the claims is meant to encompass all the foregoing methods.

In another embodiment of the presently claimed subject matter a method is provided for identifying a subject having a polymorphism of a platelet VDCC $\alpha_1$ subunit gene, comprising sequencing a target nucleic acid of a sample from a subject by dideoxy sequencing, in one embodiment following amplification of the target nucleic acid.

In another embodiment of the presently claimed subject matter a method is provided for identifying a subject having a polymorphism of a platelet VDCC $\alpha_1$ subunit gene, comprising contacting a target nucleic acid of a sample from a subject with a reagent that detects the presence of a platelet VDCC $\alpha_1$ subunit polymorphism and detecting the reagent. A number of hybridization methods and conditions are well known to those skilled in the art and are disclosed herein. Many of them are useful in carrying out the presently claimed subject matter.

Accordingly, a nucleotide sequence of the presently claimed subject matter can be used for its ability to selectively form duplex molecules with complementary stretches of a platelet VDCC $\alpha_1$ subunit gene. Depending on the application envisioned, one employs varying conditions of hybridization to achieve varying degrees of selectivity of the probe toward the target sequence. For applications requiring a high degree of selectivity, one typically employs relatively stringent conditions to form the hybrids. For example, one selects relatively low salt and/or high temperature conditions, such as provided by 15-300 mM salt at temperatures of about 50° C. to about 70° C. including in one embodiment a temperature of about 55° C., in another embodiment about 60° C., and in still another embodiment of about 65° C. Such conditions are particularly selective, and tolerate little, if any, mismatch between the probe and the template or target strand.

Of course, for some applications, for example, where one desires to prepare mutants employing a mutant primer strand hybridized to an underlying template or where one seeks to isolate polypeptide coding sequences from related species, functional equivalents, or the like, less stringent hybridization conditions are typically needed to allow formation of the heteroduplex. Under such circumstances, one employs conditions such as 0.15 M-0.9 M salt, at temperatures ranging from about 20° C. to about 55° C., including in one embodiment a temperature of about 25° C., in another embodiment of about 37° C., in another embodiment of about 45° C., and in yet another embodiment of about 50° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it is advantageous to employ a nucleic acid sequence of the presently claimed subject matter in combination with an appropriate means, such as a label, for determining hybridization. A wide variety of appropriate indicator reagents are known in the art, including radioactive, enzymatic or other ligands, such as avidin/biotin, which are capable of giving a detectable signal. In exemplary embodiments, one likely employs an enzyme tag such a urease, alkaline phosphatase, or peroxidase instead of radioactive or other environmentally undesirable reagents. In the case of enzyme tags, calorimetric indicator substrates are known which can be employed to provide a reagent visible to the human eye or spectrophotometrically, to identify specific hybridization with complementary nucleic acid-containing samples.

In general, it is envisioned that the hybridization probes described herein are useful both as reagents in solution hybridization as well as in embodiments employing a solid phase. In embodiments involving a solid phase, the sample containing test DNA (or RNA) is adsorbed or otherwise affixed to a selected matrix or surface. This fixed, single-stranded nucleic acid is then subjected to specific hybridization with selected probes under desired conditions. The selected conditions depend inter alia on the particular circumstances based on the particular criteria required (depending, for example, on the G+C contents, type of target nucleic acid, source of nucleic acid, size of hybridization probe, etc.). Following washing of the hybridized surface so as to remove nonspecifically bound probe molecules, specific hybridization is detected, or even quantified, by means of the label.

The materials for use in the method of the presently claimed subject matter are ideally suited for the preparation of a screening kit. Such a kit can comprise a carrier having compartments to receive in close confinement one or more containers such as vials, tubes, and the like, each of the containers comprising one of the separate elements to be used in the method. For example, one of the containers can comprise an amplifying reagent for amplifying a platelet VDCC $\alpha_1$ subunit DNA, such as the necessary enzyme(s) and oligonucleotide primers for amplifying target DNA from the subject.

The oligonucleotide primers include primers having a sequence derived from the group including, but not limited to: SEQ ID NOs: 1, 3, 5-8, 28, and 29, or primer sequences substantially complementary or substantially homologous thereto. Oligonucleotide primers comprising target flanking 5' and 3' polynucleotide sequence have substantially the sequence set forth in the flanking 5' and 3' portions of any of SEQ ID NOs: 1, 3, 5-8, 28, and 29, and sequences substantially complementary or homologous thereto. Other oligonucleotide primers for amplifying a platelet VDCC $\alpha_1$ subunit will be known or readily ascertainable to those of skill in the art given the disclosure of the presently claimed subject matter presented herein.

A kit in accordance with the presently claimed subject matter can further comprise solutions, buffers, or other reagents for extracting a nucleic acid sample from a biological sample obtained from a subject. Any such reagents as would be readily apparent to one of ordinary skill in the art fall within the scope of the presently claimed subject matter. By way of particular example, a suitable lysis buffer for the tissue or cells along with a suspension of glass beads for capturing the nucleic acid sample and an elution buffer for eluting the nucleic acid sample off of the glass beads comprise a reagent for extracting a nucleic acid sample from a biological sample obtained from a subject.

Other examples include commercially available extraction kits, such as the GENOMIC ISOLATION KIT A.S.A.P.™ (Boehringer Mannheim, Indianapolis, Ind., United States of America), Genomic DNA Isolation System (GIBCO BRL, Gaithersburg, Md., United States of America), ELU-QUIK™ DNA Purification Kit (Schleicher & Schuell, Keene, N.H., United States of America), DNA Extraction Kit (Stratagene, La Jolla, Calif., United States of America), TURBOGEN™ Isolation Kit (Invitrogen, San Diego, Calif., United States of America), and the like. Use of these kits according to the manufacturer's instructions is generally acceptable for purification of DNA prior to practicing the methods of the presently claimed subject matter.

F.3. Polypeptide Screening

A method of screening for a disorder affecting calcium homeostasis in platelets is also provided. The method comprises: (a) obtaining a biological sample from a subject; (b) determining an amount of a platelet VDCC $\alpha_1$ subunit polypeptide present in the biological sample; (c) determining the activity of a platelet VDCC $\alpha_1$ subunit polypeptide present in the biological sample; and (d) detecting variations in calcium transport activity between a wild type platelet VDCC $\alpha_1$ subunit polypeptide and an isolated platelet VDCC $\alpha_1$ subunit polypeptide, any calcium transport activity variations between the wild type platelet VDCC $\alpha_1$ subunit polypeptide and the isolated platelet VDCC $\alpha_1$ subunit indicating the possibility of a disorder affecting calcium homeostasis in platelets. Detecting an amount of a platelet VDCC $\alpha_1$ subunit polypeptide present in the biological sample can also be carried out in assessing a response to medication in a subject.

The nucleic acid sequences shown in SEQ ID NOs: 1, 3, 5-8, 28, and 29 comprise platelet VDCC $\alpha_1$ subunit polypeptide encoding sequences that are isolated from wild type cells. The sequence represents the platelet VDCC $\alpha_1$ subunit nucleic acid sequence occurring in nature and existing without mutation. Therefore, wild type cells, as referred to herein, are those cells occurring in nature that contain non-mutated platelet VDCC $\alpha_1$ subunit nucleic acid sequences. The wild type sequence is the native nucleic acid sequence and is the sequence against which assessments of polymorphism and mutation are made.

In another embodiment, the presently claimed subject matter provides an antibody that specifically binds a platelet VDCC $\alpha_1$ subunit polypeptide. In one embodiment, an antibody of the presently claimed subject matter is a monoclonal antibody. In one embodiment, an antibody distinguishes between a wild type form and a mutant or polymorphic form of a platelet VDCC $\alpha_1$ subunit polypeptide. Techniques for preparing such antibodies are disclosed herein. The antibodies can be used to screen for the presence of a mutant or polymorphic form of a platelet VDCC $\alpha_1$ subunit polypeptide in a manner analogous to that set forth above with respect to polynucleotide screening G. Screening for Modulators of VDCC Biological Activity In yet another aspect, the presently claimed subject matter provides a method of screening substances for their ability to affect or modulate the biological activity of platelet VDCC $\alpha_1$ subunit gene products, and for their ability to affect or modulate in vivo platelet VDCC $\alpha_1$ subunit levels. This modulation can affect platelet activation and other biological functions of platelets. Compounds identified via the screening methods of the presently claimed subject matter have application as anti-thrombotic agents or as agents for modulation of other biological events mediated by platelets.

Utilizing the methods and compositions of the presently claimed subject matter, screening assays for the testing of candidate substances are performed. A candidate substance is a substance which potentially can promote or inhibit the biological activity of gene product by binding or other intermolecular interaction with a platelet VDCC $\alpha_1$ subunit gene or gene product or control sequence.

G.1. Method of Screening for Modulators of Platelet VDCC $\alpha_1$ Subunit Biological Activity A representative method of screening candidate substances for their ability to modulate platelet VDCC $\alpha_1$ subunit biological activity comprises: (a) establishing replicate test and control samples that comprise a biologically active platelet VDCC $\alpha_1$ subunit polypeptide; (b) administering a candidate substance to test samples; (c) measuring the biological activity of the platelet VDCC $\alpha_1$ subunit polypeptide in the test and the control samples; and (d) determining whether the candidate substance modulates platelet VDCC $\alpha_1$ subunit biological activity relative to an appropriate control. By "modulate" it is intended an increase, decrease, preservation, maintenance, or other effect of any or all biological activities or properties of a platelet VDCC. By way of additional example, a candidate substance identified according to the screening assay described herein has an ability to facilitate preservation of stored platelets. Thus, a candidate substance identified according to the screening assay described herein has an ability to modulate platelet VDCC $\alpha_1$ subunit biological activity.

Such a candidate compound has utility in the treatment of disorders and conditions associated with the biological activity of a platelet VDCC $\alpha_1$ subunit. Candidate compounds are typically about 500-1,000 daltons, and can be hydrophobic, polycyclic, or both, molecules. Such compounds should be considered as candidates for therapeutic intervention in accordance with the methods described herein below. Thus, compounds identified via the screening methods of the presently claimed subject matter have application as anti-thrombotic agents or as agents for modulation of other biological events mediated by platelets. Dosages of test agents can be determined by deriving dose-response curves, such as those disclosed in U.S. Pat. No. 5,849,578, herein incorporated by reference.

In a cell-free system, the method comprises establishing a control system comprising a platelet VDCC $\alpha_1$ subunit polypeptide and a ligand to which the platelet VDCC $\alpha_1$ subunit polypeptide is capable of binding, establishing a test system comprising the platelet VDCC $\alpha_1$ subunit polypeptide, the ligand, and a candidate compound, and determining whether the candidate compound modulates platelet VDCC $\alpha_1$ subunit activity in a cell-free system. A representative ligand comprises a monoclonal antibody, and in this embodiment, the biological activity or property screened includes binding affinity. Additionally, the platelet VDCC $\alpha_1$ subunit polypeptide can be provided in a lipid bi-layer in accordance with techniques disclosed by Malouf et al., 1987 to facilitate the simulation of in vivo conditions in a cell-free setting.

In another embodiment of the presently claimed subject matter, a platelet VDCC $\alpha_1$ subunit polypeptide (e.g., platelet VDCC $\alpha_1$S subunit or platelet VDCC $\alpha_1$D subunit) or catalytic or immunogenic fragment or oligopeptide thereof, can be used for screening libraries of compounds in any of a variety of drug screening techniques. The fragment employed in such screening can be free in solution, affixed to a solid support, borne on a cell surface, or located intracellularly. The formation of binding complexes, between the platelet VDCC $\alpha_1$ subunit polypeptide and the agent being tested, can be measured.

Another technique for drug screening which can be used provides for high throughput screening of compounds having suitable binding affinity to the protein of interest as described in published PCT application WO 84/03564, herein incorporated by reference. In this method, as applied to a platelet VDCC $\alpha_1$ subunit polypeptide, large numbers of different small test compounds are synthesized on a solid substrate, such as plastic pins or some other surface. The test compounds are reacted with a platelet VDCC $\alpha_1$ subunit polypeptide, or fragments thereof, and washed. Bound platelet VDCC $\alpha_1$ subunit polypeptide is then detected by methods well known in the art. Purified platelet VDCC $\alpha_1$ subunit polypeptide can also be coated directly onto plates for use in the aforementioned drug screening techniques. Alternatively, non-neutralizing antibodies can be used to capture the peptide and immobilize it on a solid support.

As is well known in the art, a screening assay can provide a cell under conditions suitable for testing the modulation of VDCC biological activity and/or levels of calcium channels. These conditions include but are not limited to pH, temperature, tonicity, the presence of relevant metabolic factors (e.g., metal ions such as for example $Ca^{2+}$, growth factor, interleukins, or colony stimulating factors), and relevant modifications to the polypeptide such as glycosylation or prenylation. A polypeptide of the presently claimed subject matter can be expressed and utilized in a prokaryotic or eukaryotic cell. The host cell can also be fractionated into sub-cellular fractions where the receptor can be found. For example, cells expressing the polypeptide can be fractionated into the nuclei, the endoplasmic reticulum, vesicles, or the membrane surfaces of the cell. U.S. Pat. Nos. 5,837,479; 5,645,999; 5,786,152; 5,739,278; and 5,352,660 also describe exemplary screening assays, and the entire contents of each are herein incorporated by reference.

In one embodiment, a screening assay is designed to be capable of discriminating candidate substances having selective ability to interact with or modulate one or more of the genes or gene products of the presently claimed subject matter but which substances are without a substantially overlapping activity with another gene or gene product. For example, a substance can modulate the biological activity of a platelet VDCC $\alpha_1$S subunit but have no effect, or a diminished effect, on a platelet VDCC $\alpha_1$D subunit. Such selective effect can comprise in one embodiment a 30% greater effect on one test sample versus another, or in another embodiment 100% or greater effect.

A method of identifying modulators of a platelet calcium channel polypeptide by rational drug design is provided in accordance with the presently claimed subject matter. The method comprises the steps of designing a potential modulator for a platelet calcium channel polypeptide that will form non-covalent bonds with amino acids in the substrate binding site based upon the structure of a platelet VDCC $\alpha_1$ subunit polypeptide; synthesizing the modulator; and determining whether the potential modulator modulates the activity of a calcium channel. Modulators can be synthesized using techniques known in the art. The determination of whether the modulator modulates the biological activity of a calcium channel is made in accordance with the screening methods disclosed herein, or by other screening methods known in the art.

A screening assay of the presently claimed subject matter can also involve determining the ability of a candidate substance to modulate, i.e. preserve, inhibit, or promote platelet VDCC $\alpha_1$ subunit biological activity and in one embodiment to thereby modulate the biological activity of calcium channels in target cells. Target cells can be either naturally occurring cells known to contain a polypeptide of the presently claimed subject matter or transformed cells produced in accordance with a method of transformation set forth herein above. The test samples can further comprise a cell or cell line that expresses a platelet VDCC $\alpha_1$ subunit polypeptide; the presently claimed subject matter also provides a recombinant cell line suitable for use in the exemplary method. Such cell lines can be mammalian, or human, or they can from another organism, including but not limited to yeast. Exemplary assays include, but are not limited to genetic screening assays and molecular biology screens such as a yeast two-hybrid screen that will effectively identify platelet VDCC $\alpha_1$ subunit-interacting genes important for calcium transport or other platelet VDCC $\alpha_1$ subunit-mediated cellular method. One version of the yeast two-hybrid system has been described (Chien et al., 1991) and is commercially available from Clontech (Palo Alto, Calif., United States of America).

G.2. Assays for Biological Activity

Biological activity of a platelet VDCC $\alpha_1$ subunit polypeptide can be determined, for example, by an assay disclosed immediately below. Indeed, the biological activity of a platelet VDCC $\alpha_1$ subunit polypeptide of the presently claimed subject matter can also be monitored as an indicator of drug therapy, such anti-thrombotic therapy or other therapy directed at platelet activity.

G.2.a. Measurement of Cytoplasmic Calcium Signal

The conduction of calcium by the VDCC is measured in vitro by measuring changes in cytoplasmic free (ionized) calcium concentrations. Cytoplasmic calcium concentrations are measured by performing flow cytometric analysis with the calcium indicators fluo-3 and fura red as detailed by Novak & Rabinovitch, 1994. Briefly, platelets in whole blood, platelet rich plasma or biological buffers are incubated with esters of fluo-3 and fura red, and then aspirated into the flow cytometric instrument for measurement of calcium-dependent fluorescent changes. Cytoplasmic calcium concentrations are calculated from the ratio or fluo-3 and fura red relative fluorescence intensities. Experiments are performed with increasing doses of VDCC inhibitors with platelets that are in the resting state and subjected to different concentrations of activation agonists and VDCC antagonists and agonists.

G.2.b. Platelet Activation Reactions

The following methods are used to analyze the effect of VDCC channel inhibition, potentiation, and/or structural manipulation on platelet function.

1. Activation time courses. Platelets are incubated at 37° C. with [$^3$H]serotonin and $^{32}PO_4$ for one hour to respectively load dense granules with a secretion marker and label the cytoplasmic ATP pool for protein phosphorylation studies. During this time period, some samples are incubated with increasing concentrations of prostaglandin $I_2$ ($PGI_2$) to elevate intracellular cyclic AMP (cAMP). The cells are exposed with agitation to different concentrations of thrombin, ADP, epinephrine, collagen, phorbol ester, and A23187. Samples are withdrawn, quenched, and analyzed to characterize the time course of aggregation, secretion, morphological changes, and clot retraction.

2. Aggregation. Aggregation is followed with flow cytometry by analyzing forward and side scatter patterns. Samples are be examined with light microscopy and scored morphometrically and subjected to optical aggrenometry.

3. Secretion. Platelets are diluted and centrifuged during the activation time course to obtain a supernatant with granule contents. Dense, alpha and lysozomal granule secretion are analyzed respectively by measuring [$^3$H]serotonin, thrombospondin, and beta-N-acetylglucose aminadase levels in the supernatants. P-selectin expression on the surface membrane is quantified with flow cytometry after incubation of the cells with FITC-labeled monoclonal antibody to P-selectin (e.g., anti-P-selectin, Sigma Chemical Corp, St. Louis, Mo., United States of America).

4. Ultrastructural analysis. Platelet samples are subjected to scanning and transmission electron microscopy to study shape change, pseudopodia extension, granule centralization, microfilament organization, and microtubule structure.

5. Clot retraction. Microscale clot retraction analysis is performed in platelet-free plasma in siliconized glass capillary tubes with 10 μL samples. Time courses are initiated by adding thrombin for 1 unit/mL and calcium to 10 mM. The time course of retraction is followed by photographing the capillary sample every 10 seconds, and then the size of the clots are measured morphometrically.

6. Intracellular stimulus response coupling. Protein kinase activities are followed by performing two-dimensional (2D) isoelectric focusing, sodium dodecyl sulfate polyacrylamide gel electrophoresis (SDS-PAGE), and autoradiography as has been detailed elsewhere (Fischer et al., 2000; White et al., 1990). The identity of tyrosine, threonine and serine protein kinase substrates is confirmed with Western analysis.

7. Analysis of cytoplasmic nucleotide pool. Platelets are incubated with radioactive inorganic phosphate ($^{32}P_i$) to incorporate a radiolabel into cytoplasmic nucleotides. Cytoplasmic levels of ATP and ADP are measured with polyethyleneimine thin layer chromatography (TLC) and autoradiography as has been detailed elsewhere (Fischer et al., 2000). Ethanol solubility is used to determine the ratio of free versus protein bound nucleotides (Holmsen, 1972). The intracellular nucleotide pool are examined before cross-linking, after cross-linking, and after lyophilization and rehydration. TLC analysis and sample preparation follow the procedure of Crabtree & Henderson, 1971. Briefly, TLC plates are developed with 2 M sodium formate, pH=3.4, and then subjected to autoradiography. ATP, ADP, and monophosphate spots are scraped and subjected to liquid scintillation counting to measure cytoplasmic levels of the nucleotides.

8. GPIIb-IIIa function: fibrinogen binding and trafficking. The density of unligated GPIIb-IIIa on the platelet surface is determined by measuring RGD-inhabitable $^{125}$I-fibrinogen binding as detailed by Sanders et al., 1996. Also, the amount of fibrinogen that is present on the surface of platelets from alpha-granule secretion is measured by quantifying fluorescein isothiocyanate (FITC)-conjugated anti-fibrinogen monoclonal antibody binding with fluorescence. The $^{125}$I-fibrinogen and anti-fibrinogen monoclonal antibody-FITC binding studies are conducted with standards so as to respectively yield the number of unoccupied and fibrinogen-ligated GPIIb-IIIa receptor per cell. The functionality of clathrin-dependent trafficking of surface bound fibrinogen to alpha-granules and clathrin-independent internalization to lyosos-omes (see e.g., Benke, 1992) is followed with confocal microscopy as described by Merricks et al., 1998.

9. GPIb-IX function: von Willebrand binding The function of the von Willebrand receptor complex is analyzed by performing binding studies with $^{125}$I-labeled von Willebrand factor (vWf) as detailed elsewhere (Khandelwal et al., 1997). Briefly, platelets are incubated with the radio labeled ligand, washed and then subjected to liquid scintillation counting. Binding studies are performed in the presence and absence of an inhibitory anti-GPIb monoclonal antibody (GPIb-mAb, Immunotech, Inc., Westbrook, Me., United States of America) and/or ristocetin.

G.3. Method of Screening for Modulators of In Vivo Platelet VDCC $\alpha_1$ Subunit Levels In accordance with the presently claimed subject matter there are also provided methods for screening candidate compounds for the ability to modulate in vivo platelet VDCC $\alpha_1$ subunit levels and/or activity. Representative modulators of platelet VDCC $\alpha_1$ subunit levels can comprise modulators of platelet VDCC $\alpha_1$ subunit transcription or expression. Pharmaceuticals that increase or decrease the transcription or expression of platelet VDCC $\alpha_1$ subunit encoding genes have important clinical application for the modulation of the biological activity of calcium channels. This modulation can affect calcium homeostasis in platelets.

This presently claimed subject matter thus includes a method for discovery of compounds that modulate the expression levels of platelet VDCC $\alpha_1$ subunit encoding genes, including not only the platelet VDCC $\alpha_1$ subunit genes of the presently claimed subject matter but also other calcium channel polypeptide-encoding genes, and describes the use of such compounds. The general approach is to screen compound libraries for substances which increase or decrease expression of platelet VDCC $\alpha_1$ subunit-encoding genes. Exemplary techniques are described in U.S. Pat. Nos. 5,846, 720 and 5,580,722, the entire contents of each of which are herein incorporated by reference.

While the following terms are believed to be well understood by one of skill in the art, the following definitions are set forth to facilitate explanation of the presently claimed subject matter.

"Transcription" means a cellular method involving the interaction of an RNA polymerase with a gene that directs the expression as RNA of the structural information present in the coding sequences of the gene. The method includes, but is not limited to the following steps: (a) the transcription initiation, (b) transcript elongation, (c) transcript splicing, (d) transcript capping, (e) transcript termination, (f) transcript polyadenylation, (g) nuclear export of the transcript, (h) transcript editing, and (i) stabilizing the transcript. "Expression" generally refers to the cellular methods by which a biologically active polypeptide is produced from RNA.

"Transcription factor" means a cytoplasmic or nuclear protein which binds to such gene, or binds to an RNA transcript of such gene, or binds to another protein which binds to such gene or such RNA transcript or another protein which in turn binds to such gene or such RNA transcript, so as to thereby modulate expression of the gene. Such modulation can additionally be achieved by other mechanisms; the essence of "transcription factor for a gene" is that the level of transcription of the gene is altered in some way.

In accordance with the presently claimed subject matter there is provided a method of identifying a candidate compound or molecule that is capable of modulating the transcription level of a gene encoding a platelet VDCC $\alpha_1$ subunit polypeptide and thus is capable of acting as a therapeutic agent in the modulation of platelet VDCC $\alpha_1$ subunit polypeptide effects. This modulation can affect calcium homeostasis in platelets, platelet activation, and other biological functions of platelets, and can also affect platelet storage or production of platelet products. Such modulation can be direct, i.e., through binding of a candidate molecule directly to the nucleotide sequence, whether DNA or RNA transcript, or such modulation can be achieved via one or more intermediaries, such as proteins other than a platelet VDCC $\alpha_1$ subunit polypeptide which are affected by the candidate compound and ultimately modulate platelet VDCC $\alpha_1$ subunit polypeptide transcription by any mechanism, including direct binding, phosphorylation or dephosphorylation, etc.

This method comprises contacting a cell or nucleic acid sample with a candidate compound or molecule to be tested. These samples contain nucleic acids which can contain elements that modulate transcription and/or translation of a platelet VDCC $\alpha_1$ subunit gene, such as a platelet VDCC $\alpha_1$ subunit promoter or putative upstream regulatory region, or other VDCC $\alpha_1$ subunit promoter or putative upstream regulatory region, and a DNA sequence encoding a polypeptide which can be detected in some way. Thus, the polypeptide can be described as a "reporter" or "marker". In one embodiment, the candidate compound directly and specifically transcriptionally modulates expression of the platelet VDCC $\alpha_1$ subunit polypeptide-encoding gene. Such have therapeutic or pharmaceutical uses in treating platelet VDCC $\alpha_1$ subunit polypeptide-related diseases and/or disorders, in platelet-based medicine and laboratory efforts, and in preserving and transporting platelets.

The DNA sequence is coupled to and under the control of the promoter, under conditions such that the candidate compound or molecule, if capable of acting as a transcriptional modulator of a gene encoding platelet VDCC $\alpha_1$ subunit polypeptide, causes the polypeptide to be expressed and so produces a detectable signal, which can be assayed quantitatively and compared to an appropriate control. Candidate compounds or molecules of interest can include those that increase or decrease, i.e., modulate, transcription from a platelet VDCC $\alpha_1$ subunit promoters. The reporter gene can encode a reporter known in the art, such as luciferase, or it can encode a platelet VDCC $\alpha_1$ subunit.

In certain embodiments of the presently claimed subject matter the polypeptide so produced is capable of complexing with an antibody or is capable of complexing with biotin. In this case the resulting complexes can be detected by methods known in the art. The detectable signal of this assay can also be provided by messenger RNA produced by transcription of said reporter gene. Exactly how the signal is produced and detected can vary and is not the subject of the presently claimed subject matter; rather, the presently claimed subject matter provides the nucleotide sequences and/or putative regulatory regions of a platelet VDCC $\alpha_1$ subunit for use in such an assay. The molecule to be tested in these methods can be a purified molecule, a homogenous sample, or a mixture of molecules or compounds. Further, in the method of the presently claimed subject matter, the DNA in the cell can comprise more than one modulatable transcriptional regulatory sequence.

In accordance with the presently claimed subject matter there is also provided a rapid and high throughput screening method that relies on the methods described above. This screening method comprises separately contacting each of a plurality of substantially identical samples. In such a screening method, the plurality of samples comprises in one embodiment more than about $10^4$ samples and in another embodiment comprises more than about $5\times10^4$ samples.

G.4. Method of Screening for Modulators of Phosphatidylserine Exposure on the Surface of a Cell In accordance with the presently claimed subject matter there are also provided methods for screening candidate compounds for the ability to modulate phosphatidylserine exposure on the surface of a cell. In one embodiment, the method comprises (a) establishing a test sample comprising a platelet voltage dependent calcium channel (VDCC) $\alpha_1$ subunit polypeptide; (b) administering a candidate substance to the test sample; and (c) measuring the interaction, effect, or combination thereof, of the candidate substance on the test sample to thereby determine the ability of the candidate substance to modulate phosphatidylserine exposure on the surface of the cell.

In one embodiment, a candidate compound can be a polypeptide, in another embodiment an antibody, in another embodiment a nucleic acid, and in still another embodiment a chemical compound (for example, a small molecule). In one embodiment, a candidate modulator can be a polypeptide encoded by a gene present in an organism: for example, a human gene. In this embodiment, the gene encoding the polypeptide might be known (i.e. the sequence of the gene has been published or is present in a publicly available database) or might be novel. In one embodiment, the present method further comprises isolating the gene encoding the candidate polypeptide. The cloning of nucleic acid sequences encoding polypeptides is known in the art, and can include the use of degenerate primers in the polymerase chain reaction (PCR). Briefly, degenerate primers are synthesized, the sequences of which are based upon the amino acid sequence of the candidate polypeptide. These degenerate primers can then be used in a PCR reaction to amplify a region of the genome of an appropriate organism (for example, the human genome) or a cDNA library from the organism (for example, a cDNA library made from mRNA isolated from a tissue of the organism believed to express the candidate polypeptide). After an amplified nucleic acid fragment is isolated, the full length gene or a full length cDNA can be isolated using the amplified nucleic acid fragment (if necessary). Techniques for the generation of amplified nucleic acid fragments by PCR and the isolation of full length genes and sequences using amplified nucleic acid fragments are known in the art. For an example of the use of degenerate primers to clone the human erythropoietin gene, see U.S. Pat. No. 4,703,008.

In one embodiment of the present method, the test sample can comprise a nucleic acid molecule encoding a platelet voltage dependent calcium channel (VDCC) $\alpha_1$ subunit polypeptide. In one embodiment, the platelet voltage dependent calcium channel (VDCC) $\alpha_1$ subunit polypeptide is contained within a cell in cell culture.

Representative modulators of phosphatidylserine exposure can also comprise modulators of platelet VDCC $\alpha_1$ subunit gene transcription and/or expression, or can comprise modulators of platelet VDCC $\alpha_1$ subunit polypeptide activity. Pharmaceuticals that increase or decrease the transcription, expression, or activity of platelet VDCC $\alpha_1$ subunit encoding genes and/or polypeptides can have clinical application for the modulation of the biological activity of calcium channels. This modulation can affect calcium homeostasis in platelets.

As disclosed herein, the concentration of intracellular calcium ($[Ca^{2+}]_i$) has been found to correlate with the level of exposure of phosphatidylserine on the surface of the platelets. As $[Ca^{2+}]_i$ increases, the level of phosphatidylserine exposed on the surface of the platelet increases. Similarly, as $[Ca^{2+}]_i$ decreases, phosphatidylserine exposure also decreases. As phosphatidylserine exposure has been associated with such processes as apoptosis (Fadok et al., 1992; Kunzelmann-Marche et al., 2000; Zhou et al., 2002) and platelet activation (Thiagarajan & Tait, 1990; Kunzelmann-Marche et al., 2000; Zhou et al., 2002), the modulation of phosphatidylserine exposure on the surface of platelets can be used to modulate the biological activities of platelets (for example, apoptosis and thrombosis).

This presently claimed subject matter thus includes a method for discovery of compounds that modulate the exposure of phosphatidylserine on the surface of a cell (for example, a platelet), and describes the use of such compounds. The general approach is to screen compound libraries for substances that increase or decrease the exposure of phosphatidylserine on the surface of a cell.

Differences phosphatidylserine exposure on the surface of a cell can be measured using any standard technique. In one embodiment, the measuring comprises (a) determining a first level of phosphatidylserine exposure on a surface of the test sample before the administering of the test substance; (b) determining a second level of phosphatidylserine exposure on the surface of the test sample after the administering the test substance; and (c) comparing the first level and the second level, wherein a difference between the first level and the second level is indicative of the ability of the candidate substance to modulate phosphatidylserine exposure on the surface of the cell.

The levels of exposure of phosphatidylserine on the surface of a cell can be measured, for example, using antibodies that are specific for phosphatidylserine. The antibodies can be employed in techniques that are known in the art including, but not limited to Western blotting, immunoprecipitation, and fluorescence-activated cell sorting (FACS). The level of exposure of phosphatidylserine on the surface of the cell can be determined, for example, by employing an antibody comprising a detectable label (for example, a radiolabel, a fluorescent label, a chemiluminescent label, or a calorimetric label such as an enzyme). The level of exposure of phosphatidylserine on the surface of the cell can be determined before and after exposure to a candidate substance, and a comparison of the before and after levels can indicate whether or not the candidate substance has modulated the level of phosphatidylserine exposure. In one embodiment, the determining comprises (a) contacting the test sample with an antibody comprising a detectable moiety, wherein the antibody binds to phosphatidylserine; and (b) quantitating an amount of the antibody bound to the test sample, wherein the amount of the antibody bound to the test sample is indicative of an amount of phosphatidylserine on the surface of the test sample.

The presently disclosed subject matter also provides a method of screening candidate substances for an ability to modulate phosphatidylserine exposure on a surface of a cell comprising (a) establishing a test sample comprising a modulatable transcriptional regulatory sequence of a platelet voltage dependent calcium channel (VDCC) $\alpha_1$ subunit polypeptide-encoding gene and a reporter gene which is capable of producing a detectable signal; (b) administering a candidate substance to the test sample; and (c) measuring the detectable signal produced as a result of an interaction between the candidate substance and the test sample, wherein a candidate substance as a modulator of phosphatidylserine exposure on a surface of a cell is based on the amount of signal produced in relation to a control sample. In one embodiment, the reporter gene encodes a platelet voltage dependent calcium channel (VDCC) $\alpha_1$ subunit polypeptide, although any reporter gene that produces a detectable signal can be employed. Other exemplary reporter genes include, but are not limited to genes encoding fluorescent proteins (for example, genes encoding green fluorescent protein (GFP), enhanced green fluorescent protein, or red fluorescent protein), chloramphenicol acetyl transferase, β-galactosidase, luciferase, and aquorlin secretory alkaline phosphatase (SEAP).

G.5. Animal Models

In addition, animal-based systems can be used to identify compounds capable of modulating platelet VDCC $\alpha_1$ subunit biological activity. Such animal models can be used for the identification of drugs, pharmaceuticals, therapies, and interventions that can be effective in modulating platelet VDCC $\alpha_1$ subunit polypeptide biological activity. For example, animal models can be exposed to a compound that is suspected of exhibiting an ability to modulate platelet VDCC $\alpha_1$ subunit polypeptide biological activity at a sufficient concentration and for a time sufficient to elicit such modulation of platelet VDCC $\alpha_1$ subunit polypeptide biological activity in the exposed animals. The response of the animals to the exposure can be monitored by assessing in vivo platelet VDCC $\alpha_1$ subunit polypeptide expression levels and activity, or by testing biological samples from the animal. As in the methods described above, the mechanism by which a compound modulates a platelet VDCC $\alpha_1$ subunit polypeptide activity or achieves therapeutic effects can vary; the utility of the presently claimed subject matter does not depend on the precise mechanism by which an effect is achieved.

For example, an animal model of the presently claimed subject matter can comprise a pig with targeted modification of a pig platelet VDCC $\alpha_1$ subunit polypeptide gene, as described herein above.

H. Modulation of Platelet VDCC $\alpha_1$ Subunit Biological Activity in a Laboratory or Clinical Setting An aspect of the presently claimed subject matter encompasses any treatments that alter any aspect of platelet VDCC $\alpha_1$ subunit polypeptide biological activity. Such methods of modulating the biological activity of a platelet calcium channel polypeptide are applicable in the laboratory and/or clinical setting to enhance the capability to store, freeze dry, dehydrate, or otherwise manipulate platelets or platelet products, as well as being applicable in therapeutic intervention in a subject. Therapeutic intervention in a subject can encompass, for example, anti-thrombotic therapy or therapy via modulation of other biological events mediated by platelets. Representative anti-thrombotic therapy comprises treatment or prevention of arterial thromboses, e.g., the blood clots that cause heart attacks and strokes. Another representative therapeutic application comprises increasing platelet function in bleeding disorders (e.g., hemophilia), whether acquired or inherited.

As used herein, the terms "activity" and "biological activity" are meant to be synonymous and are meant to refer to any biological activity of a platelet VDCC $\alpha_1$ subunit polypeptide (e.g., platelet VDCC $\alpha_1$S subunit or platelet VDCC $\alpha_1$D subunit). Representative biological activities of a platelet VDCC $\alpha_1$ subunit include calcium transport or other biological activity in accordance with the presently claimed subject matter.

With respect to the therapeutic methods of the presently claimed subject matter, an exemplary subject is a vertebrate subject. A representative vertebrate is warm-blooded; a representative warm-blooded vertebrate is a mammal. A representative mammal is a pig or, in one embodiment a human. As used herein and in the claims, the term "patient" is contemplated to include both human and animal patients. Thus, veterinary diagnostic and therapeutic uses are provided in accordance with the presently claimed subject matter and comprise an exemplary embodiment of the presently claimed subject matter.

Contemplated is the treatment of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also contemplated is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, contemplated is the treatment of livestock, including, but not limited to, domesticated swine, ruminants, ungulates, horses, poultry, and the like.

H.1. Modulation of Platelet VDCC $\alpha_1$ Subunit Polypeptide Biological Activity In one embodiment, the present inventive method comprises administering to a cell a substance that modulates, i.e., inhibits or promotes a biological activity of a platelet VDCC $\alpha_1$ subunit polypeptide or modulates the level of phosphatidylserine exposure on the surface of a cell. Such a substance can be identified according to any of the screening assays set forth above, either in vitro or in vivo. Representative cells include platelets and megakaryocytes. The cell can be in an in vitro setting or can be in a subject to be treated, such as a warm-blooded vertebrate as described herein above.

The method comprises treating a vertebrate subject suffering from a disorder associated with or mediated by platelet VDCC $\alpha_1$ subunit polypeptide biological activity (for example, thrombosis) by administering to the subject an effective amount of a substance identified according to a screening assay described above. By the term "modulating", it is meant that the substance can either promote or inhibit a biological activity of a platelet VDCC $\alpha_1$ subunit, depending on the disorder to be treated, and can affect one or several of the platelet VDCC $\alpha_1$ subunit polypeptides, including the platelet VDCC $\alpha_1$D subunit polypeptide or the platelet VDCC $\alpha_1$S subunit polypeptide, as well as other ion transporters, or other unrelated genes or gene products. The modulation of the biological activity of the platelet VDCC $\alpha_1$ subunit can result in a modulation of the exposure of phosphatidylserine on the surface of a cell (for example, a platelet), thereby modulating the biological activity of the cell (for example, thrombosis).

Therapeutic treatment can comprise the administration of antibodies against a chosen region of a platelet VDCC $\alpha_1$ subunit polypeptide, the administration of a protein that enhances activity, or the administration of a protein that inhibits the transcription of the platelet VDCC $\alpha_1$ subunit polypeptide. Such administration can provide treatment of disorders which can be caused or exacerbated by platelet VDCC $\alpha_1$ subunit polypeptide-mediated mechanisms (for example, thrombosis).

Insofar as a modulator of platelet VDCC $\alpha_1$ subunit polypeptide activity can take the form of a polypeptide or of an anti-platelet VDCC $\alpha_1$ subunit polypeptide monoclonal antibody or fragment thereof, it is to be appreciated that the potency can vary, and therefore a "therapeutically effective" amount can vary. However, as shown by the present assay methods, one skilled in the art can readily assess the potency and efficacy of a candidate platelet VDCC $\alpha_1$ subunit polypeptide biological activity modulator of the presently claimed subject matter and adjust the therapeutic regimen accordingly. A modulator of platelet VDCC $\alpha_1$ subunit biological activity can be evaluated by a variety of techniques, including through the use of a responsive reporter, which drives expression of a reporter gene; interaction of platelet VDCC $\alpha_1$ subunit polypeptides with a monoclonal antibody as described herein; and other assays known in the art and described herein.

The monoclonal antibodies or polypeptides of the presently claimed subject matter can be administered parenterally by injection or by gradual infusion over time. Although the tissue to be treated can typically be accessed in the body by systemic administration and therefore most often treated by intravenous administration of therapeutic compositions, other tissues and delivery means are contemplated where there is a likelihood that the tissue targeted contains the target molecule and are known to those of skill in the art. The compositions are formulated in an appropriate manner and administered in a manner compatible with the dosage formulation.

H.2. Monoclonal Antibodies

The presently claimed subject matter describes, in one embodiment, platelet VDCC $\alpha_1$ subunit polypeptide modulators in the form of monoclonal antibodies which were elicited in response to platelet VDCC $\alpha_1$ subunit but which can immunoreact with any platelet VDCC $\alpha_1$ subunit polypeptide, or with a specific isoform of a platelet VDCC $\alpha_1$ subunit polypeptide, and bind the platelet VDCC $\alpha_1$ subunit polypeptide to modulate biological activity. The presently claimed subject matter also describes cell lines that produce the antibodies, methods for producing the cell lines, and methods for producing the monoclonal antibodies.

The term "antibody" or "antibody molecule" refers collectively to a population of immunoglobulin molecules and/or immunologically active portions of immunoglobulin molecules, i.e., molecules that contain a paratope. A paratope is the portion or portions of an antibody(ies) that is or are responsible for that antibody binding to an antigenic determinant, or epitope.

Representative antibodies for use in the presently claimed subject matter are intact immunoglobulin molecules, substantially intact immunoglobulin molecules, single chain immunoglobulins or antibodies, those portions of an immunoglobulin molecule that contain the paratope, including antibody fragments. Indeed, it is within the scope of the presently claimed subject matter that a monovalent modulator can optionally be used. Thus, the terms "modulate", "modulating", and "modulator" are intended to encompass such a mechanism.

The term "monoclonal antibody" refers to a population of antibody molecules that contain only one species of paratope and thus typically display a single binding affinity for any particular epitope with which it immunoreacts; a monoclonal antibody can have a plurality of antibody combining sites, each immunospecific for a different epitope, e.g., a bispecific monoclonal antibody. Methods of producing a monoclonal antibody, a hybridoma cell, or a hybridoma cell culture are described above.

It is also possible to determine, without undue experimentation, if a monoclonal antibody has the same or equivalent specificity or immunoreaction characteristics as a monoclonal antibody of this presently claimed subject matter by ascertaining whether the former prevents the latter from binding to a preselected target molecule. If the monoclonal antibody being tested competes with the monoclonal antibody of the presently claimed subject matter, as shown by a decrease in binding by the monoclonal antibody of the presently claimed subject matter in standard competition assays for binding to the target molecule when present in the solid phase, then it is likely that the two monoclonal antibodies bind to the same, or a closely related, epitope.

Still another way to determine whether a monoclonal antibody has the specificity of a monoclonal antibody of the presently claimed subject matter is to pre-incubate the monoclonal antibody of the presently claimed subject matter with the target molecule with which it is normally reactive, and then add the monoclonal antibody being tested to determine if the monoclonal antibody being tested is inhibited in its ability to bind the target molecule. If the monoclonal antibody being tested is inhibited then, in all likelihood, it has the same, or functionally equivalent, epitopic specificity as the monoclonal antibody of the presently claimed subject matter.

An additional way to determine whether a monoclonal antibody has the specificity of a monoclonal antibody of the presently claimed subject matter is to determine the amino acid residue sequence of the complementarity-determining regions (CDRs) regions of the antibodies in question. "CDRs" mean the three subregions of the light or heavy chain variable regions which have hypervariable sequences and form loop structures that are primarily responsible for making direct contact with antigen. Antibody molecules having identical, or functionally equivalent, amino acid residue sequences in their CDR regions have the same binding specificity. Methods for sequencing polypeptides are well known in the art. Further, other ways of determining whether antibodies have similar immunospecificities are known in the art and can be useful in practicing the presently claimed subject matter.

The immunospecificity of an antibody, its target molecule binding capacity, and the attendant affinity the antibody exhibits for the epitope are defined by the epitope with which the antibody immunoreacts. The epitope specificity is defined at least in part by the amino acid residue sequence of the variable region of the heavy chain of the immunoglobulin that comprises the antibody, and in part by the light-chain-variable-region amino acid residue sequence. Use of the terms "having the binding specificity of" or "having the binding preference of" indicates that equivalent monoclonal antibodies exhibit the same or similar immunoreaction (binding) characteristics and compete for binding to a preselected target molecule.

Humanized monoclonal antibodies offer particular advantages over monoclonal antibodies derived from other mammals, particularly insofar as they can be used therapeutically in humans. Specifically, human antibodies are not cleared from the circulation as rapidly as "foreign" antigens, and do not activate the immune system in the same manner as foreign antigens and foreign antibodies. Methods of preparing "humanized" antibodies are generally well known in the art, and can readily be applied to the antibodies of the presently claimed subject matter.

The use of a molecular cloning approach to generate antibodies, particularly monoclonal antibodies, and more particularly single chain monoclonal antibodies, is also provided. The production of single chain antibodies has been described in the art, see e.g., U.S. Pat. No. 5,260,203, the contents of which are herein incorporated by reference. For this approach, combinatorial immunoglobulin phagemid libraries are prepared from RNA isolated from the spleen of the immunized animal, and phagemids expressing appropriate antibodies are selected by panning on endothelial tissue. The advantages of this approach over conventional hybridoma techniques are that approximately 104 times as many antibodies can be produced and screened in a single round, and that new specificities are generated by H and L chain combination in a single chain, which further increases the chance of finding appropriate antibodies. Thus, an antibody of the presently claimed subject matter, or a "derivative" of an antibody of the presently claimed subject matter, pertains to a single polypeptide chain binding molecule which has binding specificity and affinity substantially similar to the binding specificity and affinity of the light and heavy chain aggregate variable region of an antibody described herein.

H.3. Other Modulators

Given the disclosure of the platelet VDCC $\alpha_1$ subunit polypeptide activity in tissues herein, chemical compounds (e.g., small molecule mimetics) can be used to modulate platelet VDCC $\alpha_1$ subunit polypeptide activity in tissues in accordance with the methods of the presently claimed subject matter. The identification of such compounds is facilitated by the description of screening assays directed to platelet VDCC $\alpha_1$ subunit polypeptide activity in tissues presented above. Such compounds are typically about 500-1,000 daltons, and can be hydrophobic, polycyclic, or both, molecules.

H.4. Gene Therapy

Platelet VDCC $\alpha_1$ subunit polypeptide genes can be used for gene therapy in accordance with the presently claimed subject matter. Exemplary gene therapy methods, including liposomal transfection of nucleic acids into host cells, are described in U.S. Pat. Nos. 5,279,833; 5,286,634; 5,399,346; 5,646,008; 5,651,964; 5,641,484; and 5,643,567, the contents of each of which are herein incorporated by reference.

Briefly, gene therapy directed toward modulation of platelet VDCC $\alpha_1$ subunit polypeptide levels, to thereby affect or modulate the biological activity of platelet VDCC $\alpha_1$ subunit polypeptide in a target cell is described. This modulation can affect calcium transport, to thereby affect platelet activation (i.e. thrombosis) or other biological effect (for example, apoptosis). In one embodiment, a therapeutic method of the presently claimed subject matter provides a method for modulation of platelet VDCC $\alpha_1$ subunit polypeptide levels comprising the steps of: (a) delivering to the cell an effective amount of a DNA molecule comprising a polynucleotide that encodes a polypeptide that modulates the biological activity of one or more than one platelet VDCC $\alpha_1$ subunit polypeptide; and (b) maintaining the cell under conditions sufficient for expression of said polypeptide.

In one embodiment, the delivered polypeptide comprises the sequence of SEQ ID NO: 2 or 4. Delivery can be accomplished by injecting the DNA molecule into the cell. Where the cell is in a subject, administering comprises: (a) providing a vehicle that contains the DNA molecule; and (b) administering the vehicle to the subject.

A vehicle is in one embodiment a cell transformed or transfected with the DNA molecule or a transfected cell derived from such a transformed or transfected cell. An exemplary transformed or transfected cell is a lymphocyte or a tumor cell from the tumor being treated. Methods for transforming or transfecting a cell with a DNA molecule of the presently claimed subject matter are set forth above.

Alternatively, the vehicle is a virus or an antibody that specifically infects or immunoreacts with an antigen of the target tissue or tumor. An advantage of a viral infection system is that it allows for a very high level of infection into the appropriate recipient cell. Also, antibodies have been used to target and deliver DNA molecules.

It is also envisioned that this embodiment of the presently claimed subject matter can be practiced using alternative viral or phage vectors, including retroviral vectors, adenoviral vectors and vaccinia viruses whose genome has been manipulated in alternative ways so as to render the virus non-pathogenic. Methods for creating such a viral mutation are set forth in detail in U.S. Pat. No. 4,769,331, incorporated herein by reference.

In one embodiment, the vector is a recombinant vector comprising: (a) a sequence of genomic viral DNA showing affinity for host cells; (b) a DNA sequence encoding a platelet VDCC $\alpha_1$ subunit polypeptide and operatively linked to said sequence of genomic viral DNA; and (c) a selectable marker.

H.5. Method of Modulating Phosphatidylserine Exposure on a Surface of a Cell

In one embodiment, the presently claimed subject matter provides a method of modulating phosphatidylserine exposure on a surface of a cell, the method comprising administering to the cell an effective amount of a substance capable of modulating the activity of a platelet voltage dependent calcium channel (VDCC) $\alpha_1$ subunit polypeptide in the cell to thereby modulate phosphatidylserine exposure on the surface of the cell. In one embodiment, the cell comprises a cell in a vertebrate subject. In one embodiment, the vertebrate subject is a mammal, for example, a human. In one embodiment, the cell is a platelet or a megakaryocyte.

In one embodiment of the present method, the administering further comprises administering an effective amount of a substance that modulates expression of a platelet voltage dependent calcium channel (VDCC) $\alpha_1$ subunit polypeptide-encoding nucleic acid molecule in the cell. In one embodiment, the substance capable of modulating the activity of a platelet voltage dependent calcium channel (VDCC) $\alpha_1$ subunit polypeptide in the cell comprises an anti-platelet voltage dependent calcium channel (VDCC) $\alpha_1$ subunit polypeptide antibody, a polypeptide, a chemical compound, or a nucleic acid. In one embodiment, the nucleic acid comprises an antisense oligonucleotide. In one embodiment, the polypeptide or chemical compound comprises a ligand for a modulatable transcriptional regulatory sequence of a platelet voltage dependent calcium channel (VDCC) $\alpha_1$ subunit polypeptide-encoding nucleic acid molecule. In one embodiment, the substance capable of modulating the activity of a platelet is supplied in the form of a pharmaceutical composition of the presently claimed subject matter, as discussed in more detail herein below.

In another embodiment, the presently claimed subject matter provides a method for modulating phosphatidylserine exposure on a surface of a cell, the method comprising introducing to the cell a construct comprising a nucleic acid sequence encoding a platelet voltage dependent calcium channel (VDCC) $\alpha_1$ subunit polypeptide operatively linked to a promoter, wherein production of the platelet voltage dependent calcium channel (VDCC) $\alpha_1$ subunit polypeptide in the cell results in modulation of phosphatidylserine exposure on a surface of the cell. In one embodiment, the construct further comprises a vector selected from the group consisting of a plasmid vector and a viral vector. In another embodiment, the construct further comprises a liposome complex. In one embodiment, the cell comprises a cell in a vertebrate subject. In one embodiment, the vertebrate subject is a mammal. In another embodiment, the cell is a platelet or a megakaryocyte.

H.6. Method of Modulating In Vivo Platelet VDCC $\alpha_1$ Subunit Polypeptide Levels in the Treatment of Related Diseases and Disorders A method for transcriptionally modulating in a cell or in a multicellular organism the expression of a gene encoding a platelet VDCC $\alpha_1$ subunit polypeptide to modulate platelet VDCC $\alpha_1$ subunit polypeptide biological activity in the cell or organism is also provided in accordance with the presently claimed subject matter. This method comprises administering to cell or to the organism a compound at a concentration effective to transcriptionally modulate expression of platelet VDCC $\alpha_1$ subunit polypeptide or co-transporters. Representative cells include platelets and megakaryocytes. The cell can be in an in vitro setting or can be in an organism to be treated, such as a warm-blooded vertebrate as described herein above.

In accordance with the presently claimed subject matter, the provided compound can optionally comprise an antibody or polypeptide prepared as described above and which transcriptionally modulates expression of platelet VDCC $\alpha_1$ subunit polypeptides. Optionally, the antibody or polypeptide directly binds to DNA or RNA, or directly binds to a protein involved in transcription.

Particular chemical entities (e.g., small molecule mimetics) for use in accordance with the presently claimed subject matter do not naturally occur in any cell, whether of a multicellular or a unicellular organism. Even more particularly, the chemical entity is not a naturally occurring molecule, e.g., it is a chemically synthesized entity. Optionally, the compound can bind a modulatable transcription sequence of the gene. For example, the compound can bind a promoter region upstream of a nucleic acid sequence encoding a platelet VDCC $\alpha_1$ subunit polypeptide.

In the methods above, modulation of transcription results in either upregulation or downregulation of expression of the gene encoding the protein of interest, depending on the identity of the molecule that contacts the cell.

H.7. Modulation of Thrombosis

The presently claimed subject matter also provides a method for modulating thrombosis in a subject, the method comprising administering to the subject an effective amount of a substance capable of modulating the activity of a platelet voltage dependent calcium channel (VDCC) $\alpha_1$ subunit polypeptide in the cell, wherein thrombosis in the subject is modulated. In one embodiment, the subject is a mammal. In one embodiment, the mammal is a human.

In one embodiment of the present method, the administering further comprises administering an effective amount of a substance that modulates expression of a platelet voltage dependent calcium channel (VDCC) $\alpha_1$ subunit polypeptide-encoding nucleic acid molecule in the cell. In one embodiment, the substance that modulates expression of a platelet voltage dependent calcium channel (VDCC) $\alpha_1$ subunit polypeptide-encoding nucleic acid molecule in the cell comprises an anti-platelet voltage dependent calcium channel (VDCC) $\alpha_1$ subunit polypeptide antibody, a polypeptide, a chemical compound, or a nucleic acid. In another embodiment, the substance that modulates expression of a platelet voltage dependent calcium channel (VDCC) $\alpha_1$ subunit polypeptide-encoding nucleic acid molecule in the cell comprises a nucleic acid comprising an antisense oligonucleotide.

In still another embodiment, the substance that modulates expression of a platelet voltage dependent calcium channel (VDCC) $\alpha_1$ subunit polypeptide-encoding nucleic acid molecule in the cell comprises a polypeptide or chemical compound comprising a ligand for a modulatable transcriptional regulatory sequence of a platelet voltage dependent calcium channel (VDCC) $\alpha_1$ subunit polypeptide-encoding nucleic acid molecule.

The presently claimed subject matter also provides a method for modulating thrombosis in a subject, the method comprising introducing into a cell present within the subject a construct comprising a nucleic acid sequence encoding a platelet voltage dependent calcium channel (VDCC) $\alpha_1$ subunit polypeptide operatively linked to a promoter, wherein production of the platelet voltage dependent calcium channel (VDCC) $\alpha_1$ subunit polypeptide in the cell results in modulation of thrombosis in the subject. In one embodiment, the construct further comprises a vector selected from the group consisting of a plasmid vector and a viral vector. In another embodiment, the construct further comprises a liposome complex. In one embodiment, the cell is a platelet or a megakaryocyte. In one embodiment, the subject is a mammal, and in one embodiment the mammal is a human.

H.8. Modulation of Apoptosis

The presently claimed subject matter also provides a method of modulating apoptosis in a cell selected from the group consisting of a platelet and a megakaryocyte and comprising a voltage dependent calcium channel (VDCC) $\alpha_1$ subunit polypeptide comprising (a) identifying a candidate substance that modulates the exposure of phosphatidylserine on a surface of the platelet or megakaryocyte; and (b) contacting the cell with the candidate substance identified in step (a), whereby apoptosis in the cell is modulated. In one embodiment of the present method, the exposure of phosphatidylserine on a surface of the cell is increased, thereby enhancing apoptosis in the cell. In another embodiment, the exposure of phosphatidylserine on a surface of the cell is decreased, thereby inhibiting apoptosis in the cell. In one embodiment, the cell is a platelet.

H.9. Increasing the Storage Life of a Cell

The presently claimed subject matter also provides a method of increasing a storage life of a cell (for example, a platelet or a megakaryocyte) comprising (a) identifying a candidate substance that decreases the exposure of phosphatidylserine on the surface of the cell; and (b) contacting the cell with the candidate substance identified in step (a), whereby the storage life of the cell is increased. For example, a candidate substance identified by any one of the disclosed methods can be added to a platelet preparation (for example, as a component of a preservative) in an amount sufficient to decrease the rate of platelet cell death that occurs during storage of the cells.

H.10. Antisense Oligonucleotide Therapy

It is also provided according to the presently claimed subject matter that expression of a platelet VDCC $\alpha_1$ subunit polypeptide can be modulated in a vertebrate subject through the administration of an antisense oligonucleotide derived from a nucleic acid molecule encoding a platelet VDCC $\alpha_1$ subunit polypeptide, such as those described in SEQ ID NO: 2 and 4. Therapeutic methods utilizing antisense oligonucleotides have been described in the art, for example, in U.S. Pat. Nos. 5,627,158 and 5,734,033, the contents of each of which are herein incorporated by reference.

H.11. Pharmaceutical Compositions

The presently disclosed subject matter also provides a pharmaceutical composition comprising a therapeutically effective amount of a modulator of thrombosis and a pharmaceutically acceptable diluent or vehicle, wherein the modulator of thrombosis binds a platelet voltage dependent calcium channel (VDCC) $\alpha_1$ subunit polypeptide, or a fragment or derivative thereof.

H.12. Dosages

As used herein, an "effective" dose refers to one that is administered in doses tailored to a particular application in which calcium transport modulation or other modulation of platelet VDCC $\alpha_1$ subunit biological activity is sought. For example, after review of the disclosure herein of the presently claimed subject matter, one of ordinary skill in the art can tailor the dosages to an individual patient, taking into account the particular formulation and method of administration to be used with the composition as well as patient height, weight, severity of symptoms, and stage of the disorder to be treated.

An effective dose and a therapeutically effective dose are generally synonymous. However, compounds can be administered to patients having reduced symptoms or even administered to patients as a preventative measure. Hence, the composition can be effective in therapeutic treatment even in the absence of symptoms of the disorder.

A unit dose can be administered, for example, 1 to 4 times per day. In one embodiment, the unit dose is administered twice a day (b.i.d.). The dose depends on the route of administration and the formulation of a composition containing the compound or compounds. Further, it will be appreciated by one of ordinary skill in the art after receiving the disclosure of the presently claimed subject matter that it can be necessary to make routine adjustments or variations to the dosage depending on the combination of agents employed, on the age and weight of the patient, and on the severity of the condition to be treated.

Such adjustments or variations, as well as evaluation of when and how to make such adjustments or variations, are well known to those of ordinary skill in the art of medicine. Evaluation parameters and techniques can vary with the patient and the severity of the disease. Particularly useful evaluative techniques are disclosed in the Examples.

H12.a Gene Therapy Vector Construct Dosing

Maximally tolerated dose (MTD) of vector construct when administered directly into the affected tissue is determined. Primary endpoints are: 1) the rate of transduction in abnormal and/or normal cells, 2) the presence and stability of this vector in the systemic circulation and in affected cells, and 3) the nature of the systemic (fever, myalgia) and local (infections, pain) toxicities induced by the vector. A secondary endpoint is the clinical efficacy of the vector construct.

For example, a 4 mL serum-free volume of viral (e.g., adenoviral, retroviral, etc.) vector construct (containing up to $5 \times 10^7$ viral particles in AIM V media) is administered daily per session. During each session, 1 mL of medium containing the appropriate titer of vector construct is injected into 4 regions of the affected tissue for a total of 4 mL per session in a clinical examination room. This is repeated daily for 4 days (4 sessions). This 16 mL total inoculum volume over 4 days is proportionally well below the one safely tolerated by nude mice (0.5 mL/20 g body weight).

Patient evaluation includes history and physical examination prior to initiation of therapy and daily during the 4-day period of vector construct injection. Toxicity grading is done using the ECOG Common Toxicity Criteria. CBC, SMA-20, urinalysis, and conventional studies are performed daily during this period.

H.12.b. Dose Escalation and MTD

Patients are treated with $3 \times 10^6$ viral particles×4. Once they have all recovered from all grade 2 or less toxicities (except alopecia), and as long as grade 3-4 toxicity is not encountered, a subsequent dose level is initiated in patients. As one grade 3 or 4 toxicity occurs at a given dose level, a minimum of 6 patients are enrolled at that level. As only 1 of 6 patients has grade 3 or 4 toxicity, dose escalation continues. The MTD of vector construct is defined as the dose where 2 of 6 patients experience grade 3 or 4 toxicity. If 2 of 3, or if 3 of 6 patients experience grade 3 or 4 toxicity, the MTD is defined as the immediately lower dose level.

The following escalation schema is followed: 1) level 1, $3\times10^6$ viral particles; 2) level 2, $1\times10^7$; 3) level 3, $3\times10^7$; 4) level 4, $5\times10^7$. Patients with measurable disease are evaluated for a clinical response to vector construct. Histology and local symptoms are followed.

H.13. Formulation of Therapeutic Compositions

The platelet VDCC $\alpha_1$ subunit polypeptide biological activity modulating substances, gene therapy vectors, substances that inhibit or promote expression of a platelet VDCC $\alpha_1$ subunit polypeptide encoding nucleic acid segment, and substances that modulate the expression of phosphatidylserine on the surface of a cell described above are adapted for administration as a pharmaceutical compositions as described above. Additional formulation and dose preparation techniques have been described in the art, see for example, those described in U.S. Pat. No. 5,326,902 issued to Seipp et al. on Jul. 5, 1994, U.S. Pat. No. 5,234,933 issued to Marnett et al. on Aug. 10, 1993, and PCT Publication WO 93/25521 of Johnson et al. published Dec. 23, 1993, the entire contents of each of which are herein incorporated by reference.

For the purposes described above, the identified substances can normally be administered systemically or partially, usually by oral or parenteral administration. The doses to be administered are determined depending upon age, body weight, symptom, the desired therapeutic effect, the route of administration, and the duration of the treatment, etc.; one of skill in the art of therapeutic treatment will recognize appropriate procedures and techniques for determining the appropriate dosage regimen for effective therapy. Various compositions and forms of administration are provided and are generally known in the art. Other compositions for administration include liquids for external use, and endermic liniments (ointment, etc.), suppositories, and pessaries which comprise one or more of the active substances and can be prepared by known methods.

Thus, the presently claimed subject matter provides pharmaceutical compositions comprising a polypeptide, polynucleotide, or molecule or compound of the presently claimed subject matter and a physiologically acceptable carrier. In one embodiment, a pharmaceutical composition comprises a compound discovered via the screening methods described herein below.

A composition of the presently claimed subject matter is typically administered parenterally in dosage unit formulations containing standard, well-known nontoxic physiologically acceptable carriers, adjuvants, and vehicles as desired. The term "parenteral" as used herein includes intravenous, intramuscular, intra-arterial injection, or infusion techniques.

Injectable preparations, for example sterile injectable aqueous or oleaginous suspensions, are formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol.

Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid find use in the preparation of injectables.

Representative carriers include neutral saline solutions buffered with phosphate, lactate, Tris, and the like. Of course, one purifies the vector sufficiently to render it essentially free of undesirable contaminants, such as defective interfering adenovirus particles or endotoxins and other pyrogens such that it does not cause any untoward reactions in the individual receiving the vector construct. An exemplary means of purifying the vector involves the use of buoyant density gradients, such as cesium chloride gradient centrifugation or column chromatography.

A transfected cell can also serve as a carrier. By way of example, a liver cell can be removed from an organism, transfected with a polynucleotide of the presently claimed subject matter using methods set forth above and then the transfected cell returned to the organism (e.g., injected intra-vascularly).

EXAMPLES

The following Examples have been included to illustrate modes of the presently claimed subject matter. Certain aspects of the following Examples are described in terms of techniques and procedures found or contemplated by the present inventors to work well in the practice of the presently claimed subject matter. These Examples are exemplified through the use of standard laboratory practices of the inventors. In light of the present disclosure and the general level of skill in the art, those of skill will appreciate that the following Examples are intended to be exemplary only and that numerous changes, modifications and alterations can be employed without departing from the spirit and scope of the presently claimed subject matter.

Example 1

Isolation of Fresh Platelets and Cultured Megakaryocytes

Due to the paucity of undegraded mRNA in stored human platelets, mRNA was isolated from platelet precursor cells, megakaryocytes, in culture. The findings disclosed herein were confirmed in freshly isolated porcine platelets. Freshly isolated human platelets were used for the ultrastructural studies.

Blood was collected in sodium citrate (9:1 v/v) from informed and consenting healthy volunteers and from pigs according to the National Institute of Health (NIH) human and animal utilization guidelines and approved by University of North Carolina-Chapel Hill (UNC-CH) committees. Platelet-rich plasma (PRP) was obtained by centrifugation of the blood at 800 g for 5 minutes at room temperature (r. t.), and platelets were isolated at 2000 g centrifugation for 15 minutes at r. t. The platelets were immediately used for mRNA or protein isolations.

Meg 01 cells (a human megakaryocytic cell line available from the American Type Culture Collection (ATCC) in Manassas, Va., United States of America) were grown in RPMI (GIBCO BRL, Gaithersburg, Md., United States of America) supplemented with 10% fetal calf serum in 10% $CO_2$ at 37° C. Cells were harvested by pelleting. Human megakaryocytes were obtained from discarded bone marrow smears with permission from the (UNC—CH) Internal Review Board (IRB) committee.

Example 2

Preparation of mRNA for Northern Blots and RT-PCR

Platelets or megakaryocytes were lysed in a reagent sold under the registered trademark TRIPURE® by Boehringer Manheim (Indianapolis, Ind., United States of America) via repetitive pipeting. Total RNA was isolated according to the specifications supplied by the vendor. The total RNA was treated with 20 units of RNase-free DNAse per 100 μg of total RNA. mRNA was enriched using a mRNA kit sold under the registered trademark OLIGOTEX® (Qiagen, Inc. Valencia, Calif., United States of America). Approximately 10 μg of mRNA was size fractionated on gels (Ambion Inc., Austin, Tex., United States of America) in formaldehyde denaturing conditions for Northern blots. See FIG. 4. mRNA was transferred onto a membrane by capillary action for Northern blots.

Antisense riboprobes of 1033 nucleotides (nt) were synthesized to correspond to the region between IV $S_3$ and amino acid 1531 (aa1531) for $\alpha_1 S$ and between IV $S_3$ and amino acid 1663 (aa1663) for $\alpha_1 D$ (Seino et al., 1992). These probes were obtained from the PCR reaction using oligonucleotides 1 and 2 (Table 3). The probes were transcribed as the antisense strand from the linearized PCR-TOPO® cloning vector (Invitrogen Corporation Carlsbad, Calif., United States of America) that contained the PCR product as an insert.

First strand cDNA was synthesized from 0.2 μg mRNA with Oligo (dT) or random hexamers as primers. A reverse transcriptase enzyme sold under the trademark SUPERSCRIPT II™ by Life Technologies, Inc. (Rockville, Md., United States of America) was used, and the reaction was carried out according to specifications provided by the vendor. Following the synthesis of the first strand, the mRNA template was removed with RNase treatment. The cDNA obtained was ethanol precipitated and then used for PCR amplification. PCR primers were designed based upon regions of VDCC $\alpha_1 S$ (Hogan et al., 1994) and $\alpha_1 D$ (Seino et al., 1992) subunits, such that isoform specific intervening sequences containing regions previously reported to have functional importance would be amplified. Primers (Table 3) were used at a concentration of 100 picomoles per reaction.

PCR was carried out according to standard techniques. The PCR products were examined by agarose gel electrophoresis and cloned into a vector sold under the registered trademark PCR II-TOPO® by Invitrogen Corporation (Carlsbad, Calif., United States of America). The clones were screened by PCR, and the desired cDNA was prepared using a DNA Miniprep kit (Qiagen, Inc. Valencia, Calif., United States of America) for sequencing by the UNC-CH Automated DNA Sequencing Facility.

TABLE 3

| Oligonucleotide No. | 5' position | 3' position | Oligonucleotide Combination for PCR Amplification | ref. | Predicted Polypeptide Region Amplified |
|---|---|---|---|---|---|
| 1 | 3763 | 3785 | 1 × 2 (see FIG. 1) | $\alpha_1 S$ | IV $S_3$-aa1531 |
| 2 | 4796 | 4760 | 1 × 2 (see FIG. 1) | $\alpha_1 D$ | IV S3-aa1633 |
| 3 | 4684 | 4705 | 3 × 4 | $\alpha_1 S$ | aa1483-end of the polypeptide |
| 4 | 5845 | 5824 | | | |
| 5 | 6661 | 6633 | 3 × 5 | $\alpha_1 D$ | aa1586-end of the polypeptide |
| 6 | 3240 | 3265 | 6 × 7 | $\alpha_1 D$ | III P–IV P |
| 7 | 4220 | 4194 | | | |
| 8 | 2221 | 2243 | 8 × 9 | $\alpha_1 S$ | Intracytoplasmic loop II–III |
| 9 | 2622 | 2601 | | | |
| 10 | 2949 | 2972 | 10 × 11 | $\alpha_1 S$ | III $S_4$–IV $S_3$ |

Oligonucleotide primers were used in PCR reactions to amplify regions of $\alpha_1 S$ and $\alpha_1 D$ from platelets and megakaryocytes. The 5' and 3' positions are numbered according to the cDNAs accessed in GENBANK® under Accession Nos. L33798 (Hogan et al., 1994) and M83566 (Seino et al., 1992) for the human $\alpha_1 S$ and $\alpha_1 D$ cDNAs, respectively. The predicted polypeptide position of the encoded protein is designated. P=pore.

Example 3

Antibodies and Immunoprecipitation

A rabbit antibody was generated against the synthetic peptide NEELRAIIKKIWKRTSMKLL (SEQ ID NO: 27) which corresponds to the sequence amino acids 1487-1506 (arrow in FIG. 1A) in the putative intracytoplasmic carboxyl-terminal region of adult rabbit and human $\alpha_1 S$ (Tanabe et al., 1987; Hogan et al., 1994). This sequence is common to many L-type calcium channel $\alpha_1$ subunits from various species. A tetravalent multiple antigenic peptide was synthesized by the protein chemistry laboratories of UNC—CH and was used for immunization at a concentration of 500 μg for the initial dose. A boosting dose of 100 μg of peptide was administered twice at 3 week intervals. Antibody response was detected with ELISA using the synthetic peptide as antigen and on Western blots using megakaryocytes solubilized with Laemmli sample buffer and fractionated by SDS-PAGE electrophoresis.

Pig platelets were used at a concentration of $1.5 \times 10^{11}$/mL. They were isolated from 1 L of fresh whole blood, pelleted, and washed twice in RPMI supplemented with a cocktail of protease inhibitors. Washed platelets were then lysed in a lysis buffer (Boehringer Manheim, Indianapolis, Ind., United States of America) which contained 50 mM Tris-HCl, pH 7.5, 150 mM NaCl, 1% Nonidet P40, 0.5% sodium deoxycholate, and a cocktail of protease inhibitors (supplied by Boehringer Manheim, Indianapolis, Ind., United States of America). The platelet lysate was transferred to a pre-chilled Dounce homogenizer and homogenized by approximately 10-15 repeated strokes using a type B pestle. After clearing with centrifugation at 12,000 g, the supernatant was pre-absorbed onto protein A-agarose suspension overnight at 4° C. The beads were discarded, and the supernatant was incubated overnight at 4° C. with the purified rabbit anti-peptide IgG at a concentration of 200 μg/mL. Controls were incubated with a non-immune rabbit IgG at the same concentration (Dako Corp., Carpinteria, Calif., United States of America).

The immune-complexes were captured with 100 μg of protein A-agarose beads overnight, at 4° C. After extensive washings, the immunoprecipitated proteins were separated on SDS-PAGE after eluting the immune complex with Laemmli sample buffer at 100° C. for 3-4 minutes. Western blots were performed after transfer of proteins onto nitrocellulose or polyvinyl derivative (PVD) membranes. The anti-peptide antiserum was used as a primary antibody on western blots at a dilution of 1:500. A goat anti-rabbit antibody labeled with alkaline phosphatase was used as a secondary antibody. The substrate for the immunoprecipitation reactions was provided in the electrochemiluminescence (ECL) reaction (Amersham Biosciences Corp., Piscataway, N.J., United States of America).

To confirm that the anti-peptide antibody recognized $\alpha_1 S$ and $\alpha_1 D$ in human bone marrow megakaryocytes, it was incubated for 60 minutes at r. t. on human bone marrow smears. The antiserum was used in 1:1000 dilution. A fluorescent-labeled goat anti-rabbit antibody (Jackson ImmunoResearch Laboratories, Inc., West Grove, Pa., United States of America) was used as a secondary antibody.

To preserve the antigenicity of the determinant recognized by our antipeptide antibody, human platelets were processed using the post-embedding method described by Madden, 1998. Fresh human platelets were allowed to settle and adhere on glass coverslips for ten minutes at r. t. Following gentle rinsing with PBS, the platelets were fixed in 2% paraformaldehyde, 0.5% glutaraldehyde in 0.1 M sodium cacodylate, pH 7.4, and irradiated using a laboratory microwave oven (Ted Pella, Inc., Redding, Calif., United States of America). The cells were postfixed in 1% buffered osmium tetroxide for 10 minutes at r. t. They were dehydrated in acetone and infiltrated with L.R. White resin (London Resin Co., Ltd., Reading, England) using microwave irradiation. After polymerization with ultraviolet light (365 nm wavelength), the monolayers were sectioned en face at a thickness of 80 nm and mounted on 300 mesh nickel grids.

For immunocytochemical labeling, all steps were carried out at r. t. The anti-peptide antibody was diluted in 0.1 M phosphate-buffered saline with globulin-free 0.1% bovine serum albumin, pH 7.4, and the secondary immunogold labeled antibody (Amersham Life Science Inc., Arlington Heights, Ill., United States of America) was diluted in 0.1 M Tris-buffered saline with 0.1% bovine serum albumin, pH 8.2. Grid-mounted sections were etched in 5% aqueous sodium metaperiodate for 30 minutes, then incubated in 0.2 M glycine in PBS/BSA for 5 minutes. The sections were blocked in 5% normal goat serum in PBS/BSA for 10 minutes before incubation in the anti-peptide antibody (1:5 dilution) for 2 hours. After rinsing with PBS/BSA, the sections were incubated for 1 hour in goat anti-rabbit IgG 10 nm colloidal gold (1:25 dilution). Negative controls were performed concurrently by deleting primary antiserum and/or incubating in normal rabbit IgG at 1:5 dilution (Dako Corp. of Carpinteria, Calif., United States of America).

The immunogold-labeled sections were post-fixed in 1% glutaraldehyde in phosphate-buffered saline (PBS) followed by uranyl acetate and lead citrate treatment. The grids were observed and photographed using a LEO EM-910 transmission electron microscope (LEO Electron Microscopy, Thornwood, N.Y., United States of America) at 80 kilovolts (kV). Platelets were also prepared by conventional electron microscopy using 0.1% tannic acid in the fixative so as to obtain the optimal ultrastructural morphology of the surface-connected membranous open canalicular system.

Example 4

Two L-type VDCC $\alpha_1$ Subunit cDNAs are Expressed in Platelets and Megakaryocytes Reverse transcription-polymerase chain reaction (RT-PCR) was used to amplify, clone, and sequence flanking regions of VDCC $\alpha_1$ subunit cDNA from cultured human megakaryocytes (Meg 01, ATCC) and from fresh porcine platelets. Two different isoforms were found to be expressed in human megakaryocytes. One exhibits sequence identity to the L-type VDCC $\alpha_1$ subunit sequence from human skeletal muscle $\alpha_1 S$ (Hogan et al., 1994), and is presented herein as SEQ ID NOs: 1, 2, 5, and 28. The other exhibits sequence identity to the human neuroendocrine cells $\alpha_1 D$ sequence (Seino et al., 1992; see also FIGS. 1A and 1B), and is presented herein as SEQ ID NOs: 3, 4, 6, and 29. These partial cDNAs encode regions between III $S_4$ and the carboxyl-end of $\alpha_1 S$, and between III $S_5$ and the carboxyl-end of $\alpha_1 D$, respectively (FIGS. 1A and 1B). Both cDNAs are missing nucleotides that encode a peptide in the putative extracellular linker between IV $S_3$ and IV $S_4$ (FIG. 1B). The intracytoplasmic loop between motifs II-III of the human $\alpha_1 S$ was also sequenced (FIGS. 1A and 1B).

Similarly, a cDNA was obtained from circulating porcine platelets that corresponds to an encoded peptide in the region between IV $S_3$ and the amino acid 1531 of $\alpha_1 S$ (FIGS. 1A and 1B). This platelet cDNA has 91% sequence identity with the rabbit $\alpha_1 S$ skeletal muscle subunit (Tanabe et al., 1987), is presented herein as SEQ ID NOs: 7 and 8 and demonstrates the same missing sequence as the above human sequence in the putative IV $S_3$ and IV $S_4$ linker (FIGS. 1A and 1B). Another porcine platelet cDNA which encodes the region between II $S_3$ and II $S_6$ of the $\alpha_1$ subunit was sequenced. This partial porcine cDNA has 88% sequence identity to the human neuroendocrine $\alpha_1 D$ cDNA.

The cloned cDNAs indicate that two different $\alpha_1$ subunits of L-type voltage dependent calcium channels are expressed in the platelet and their megakaryocytic precursors and that they encode polypeptides having sequence identity with the $\alpha_1$ subunits of VDCCs from human skeletal muscle and neuroendocrine cells. Importantly, the encoded polypeptides have regions of known active roles in the VDCC functions.

The cloned cDNAs predict the following structural and functional regions:

(a) pore lining segments in III $S_5$-$S_6$ and IV $S_5$-$S_6$ linkers (FIGS. 1A and 1B): VDCCs pores are lined by the amphipathic loops in the $S_5$-$S_6$ linkers in each of the four motifs, where a glutamate residue in equivalent positions conveys calcium selectivity to the ion-conducting channel;

(b) voltage sensing segments in transmembrane regions III $S_4$ and IV $S_4$ where the positively charged residues in every third or fourth position sense depolarization and induce conformational changes responsible for channel gating;

(c) dihydropyridine binding sites in III S$_6$ and IV S$_6$ characteristic of L-type calcium channels (Striessnig et al., 1998); and (d) an intracytoplasmic loop between II S$_6$ and III S$_1$ that is unique to α$_1$S and believed to be specific for the type of excitation-contraction coupling in skeletal muscle.

Figure 1D:
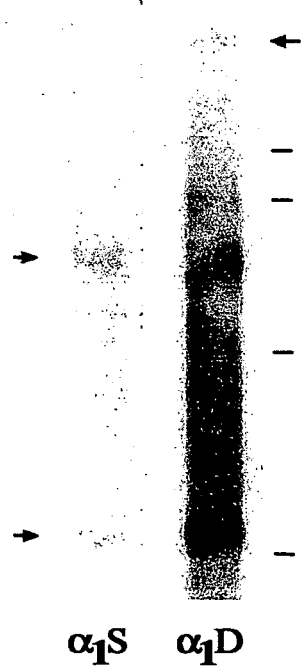
FIG. 1D depicts an autoradiograph of a Northern blot of mRNA from human megakaryocytes. 10 µg of mRNA was loaded per lane and probed with riboprobes synthesized from the PCR products described for FIG. 1C. An antisense mRNA (hereinafter "complementary mRNA" or "cmRNA") synthesized from clone 1 ($\alpha_1$S) was used to probe the mRNA on the left lane and cmRNA from clone 3 ($\alpha_1$D) was synthesized and used to probe the mRNA on the right lane. Arrows point to a 6.5 kilobase (kb) transcript in $\alpha_1$S and a 10.8 kb transcript in $\alpha_1$D. In addition, a 2.5 kb band hybridized with both probes, which are homologous but not identical. Bars on right are 9.4 kb, 7.46 kb, 4.4 kb, and 2.37 kb molecular weight standards.

The missing sequence in the IV S$_3$-S$_4$ linker in every cDNA cloned is envisioned to be a characteristic for the VDCC function in the platelets. A skipped exon has been detected in the same region in other L-type VDCCs. Peres-Reyes & Schneider, 1995; Snutch et al., 1991; Diebold et al., 1992. Isoform specific riboprobes that correspond to the nucleotides between 3763 and 4796 of the human α$_1$S and the corresponding sequence from α$_1$D (FIG. 1C) were synthesized as cmRNA and used to probe separate mRNA blots from human megakaryocytes. A 6.5 kb transcript hybridized with the α$_1$S specific cmRNA, and a 10.8 kb transcript hybridized with the α$_1$D specific cmRNA on Northern blots (FIG. 1D). The sizes of these transcripts are consistent with those published for α$_1$S and α$_1$D from skeletal muscle and neuroendocrine mRNA respectively. Tanabe et al., 1987; Seino et al., 1992.

Figure 2A:
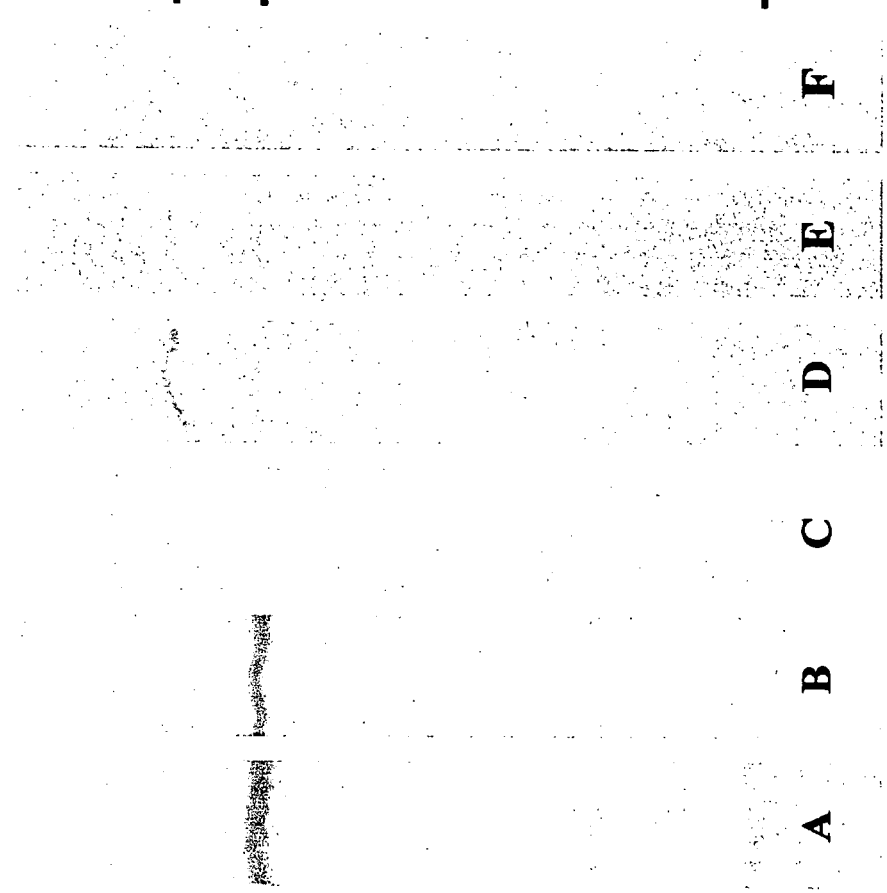
FIG. 2A depicts an autoradiograph of a Western blot on cultured megakaryocytes, which depicts that $\alpha_1$S and $\alpha_1$D subunits are expressed at the protein level in platelets and megakaryocytes. Lane a: the antiserum generated in rabbit against the peptide NEELRAIIKKIWKRTSMKLL (SEQ ID NO: 27) located in the putative carboxyl end of $\alpha_1$ subunits (arrow in FIG. 1) recognized its determinant in a 170 kilodalton (kDa) polypeptide. Lane b: a monoclonal antibody, Mab 1A, previously described to recognize its determinant in $\alpha_1$S from skeletal muscle, was used to confirm that the 170 kDa polypeptide is $\alpha_1$S. Lane c: normal rabbit IgG. Lane d: β cells from pancreas confirmed that the anti-peptide antibody recognized its determinant in $\alpha_1$D (208 kDa) in β cells. Lane e: the monoclonal antibody Mab 1A did not recognize a determinant in $\alpha_1$D. Lane f: normal non-immune rabbit serum. Bars on the right depict the positions of 218 kDa and 125 kDa molecular weight standards.

Example 5

α$_1$S and α$_1$D VDCC Subunits are Expressed at the Protein Level in Platelets and Megakaryocytes An anti-peptide antibody was generated in a rabbit against the peptide sequence amino acids 1486-1506 (Tanabe et al., 1987; see also FIG. 1 arrow). This sequence is conserved in all published L-type VDCC α$_1$ subunits. This antibody recognizes its antigenic determinant in a 170 kDa polypeptide on Western blots from human megakaryocytes resolved by SDS-PAGE (FIG. 2A). This electrophoretic mobility is consistent with that of α$_1$S on SDS-PAGE previously described from skeletal muscle by Tanabe et al., 1987. That the 170 kDa polypeptide is indeed α$_1$S was confirmed with a monoclonal antibody (Mab 1A) previously published to recognize its determinant in α$_1$S from skeletal muscle (FIG. 2A), kindly provided by Dr. S. Froehner, Department of Cell Physiology, UNC-CH and described by Morton & Froehner, 1987.

Suspecting that α$_1$D is expressed at a level below the detection threshold on direct Western blots, the subunits were enriched by immuno-precipitation using the anti-peptide antibody described in Example 3 above. Polypeptides with 208 kDa and 170 kDa electrophoretic mobilities were immunoprecipitated from porcine platelets. When the primary antibody in the immunoprecipitation reaction was replaced with non-immune IgG, these polypeptides were not present. See FIG. 2B.

That the anti-peptide antibody recognizes the 208 kDa as α$_1$D was confirmed by Western blots on pancreatic β cells in culture resolved by SDS-PAGE, as shown in FIG. 2A. Pancreatic β cells in culture were kindly provided by Dr. Michael Freemark, Duke University Department of Pediatrics. The antibody recognized a determinant in a polypeptide with electrophoretic mobility of 208 kDa in the pancreatic β cells. Mab 1A did not recognize a determinant in these cells. The determinant recognized by Mab 1A has not been mapped and thus, might be specific to α$_1$S.

The expression of the α$_1$ subunits in in vivo megakaryocytes was demonstrated on human bone marrow smears with the anti-peptide antibody as a primary antibody and an FITC labeled anti-rabbit secondary antibody. A discrete speckled pattern was detected on the megakaryocytes and was interpreted to be α$_1$ subunits. Thus, the anti-peptide antibody recognized its determinant in a speckled pattern. The anti-peptide antibody was also replaced with non-immune rabbit IgG as a negative control. In the analysis, original magnification was 60×.

Thus, the polypeptide that has an electrophoretic mobility of 170 kDa corresponds to the 6.5 kb transcript identified on Northern blots and represents the α$_1$S subunit from human megakaryocytes and porcine platelets (SEQ ID NOs: 1, 2, and 7-8, respectively). In contrast, the 208 kDa polypeptide corresponds to the 10.8 kb transcript on Northern blots and represents the α$_1$D subunit from human megakaryocytes and porcine platelets.

Example 6

The Platelet VDCC α$_1$ Subunit Polypeptide α$_1$ Subunit is Localized in a Tight Membranous Network of the Open Canalicular System The site of probable function of the VDCC in the platelet was investigated at the ultrastructural level using the anti-peptide antibody to localize the antigenic determinant in unstimulated human platelets. An anti-rabbit secondary antibody labeled with 10 nm gold particles showed that the epitope recognized by the anti-peptide antibody was present in a tightly branching membranous network inside the platelets. This network forms a tortuous cribriform vesicular membranous system previously described by conventional electron microscopy to be continuous with the surface-connected open canalicular system (White, 1970; White, 1972).

In the examination of localization of VDCC, human platelets were post-embedded and incubated with the anti-peptide antibody as primary antibody. Ten nm gold particle labeled goat anti-rabbit antibody was the secondary antibody. Electron dense gold particles represented antigenic sites recognized by the anti-peptide antibody. This determinant was present in a membranous network continuous with the surface-connected open canalicular system. This network forms tightly branching vacuoles that extend deep inside the platelet. A sample was prepared by conventional electron microscopy (EM) to maintain the morphological integrity of the surface-connected open canalicular system. No gold particles were present when the anti-peptide antibody was replaced with normal rabbit IgG in a control experiment. In the analysis, original magnification was 16,000× and 500×.

Discussion of Examples 1-6

L-type VDCCs are generally co-localized with specialized intracellular organelles of which the function is calcium concentration dependent (Berridge, 1997; Bokvist et al., 1995; López-López et al., 1995; Shirokova et al., 1998). Activation of the VDCC in the cell membrane generates highly localized signals in the inner microenvironment that trigger responses strictly from the underlying organelles. Indeed, the L-type VDCC in striated muscle is preferentially localized in the t-tubule membrane, a sequestered surface membrane that invaginates from the cell membrane deep into the muscle cell. There, the VDCC is in close proximity with the calcium storing sarcoplasmic reticulum (SR) of muscle. Activation of the L-type VDCC in the t-tubule triggers the primary signal that causes release of Ca$^{2+}$ from the SR lumen (Hille, 1992; López-López et al., 1995; Shirokova et al., 1998). This then generates the global Ca$^{2+}$ signal that results in muscle contraction (Berridge, 1997).

Similarly, the L-type VDCC is clustered in the cell membrane of insulin secreting β cells in a domain that is adjacent to the highest density of secretory granules inside the cell (Bokvist et al., 1995). Activation of the L-type VDCCs in the cell membrane results in a localized intracellular Ca burst that initiates exocytosis and release of insulin from these granules.

These morphological relationships in muscle and endocrine cells between the VDCC in surface membrane domains and specialized intracellular organelles appear structurally homologous to those observed in the platelet, as discussed herein above. The surface-connected open canalicular system allows the platelet cell membrane to extend deeply into the platelet. There, some of its components are juxtaposed with the dense tubular system, the calcium storing compartment of the platelet (White, 1970). Others act as a conduit in the platelet secretory pathway (White, 1972). The finding of a preferential localization of the VDCC $\alpha_1$ subunit in this membranous network implicates the VDCC at these sites in specific functions of the platelet, such as contraction and secretion.

That the L-type voltage dependent calcium channel is physiologically active in platelets is supported by a study on the effects of the dihydropyridine antagonists on platelet aggregation (Palés et al., 1991). When used in a nanomolar range, these L-type calcium channel blockers inhibit platelet aggregation in a dose-dependent manner. Inhibition of $Ca^{2+}$ channels at these submicromolar concentrations is believed to be selective for the L-type voltage dependent calcium channel (Lee et al., 1983). Also, and of interest, is the unexplained finding that platelet aggregation time is prolonged in hypertensive patients receiving an L-type dihydropyridine calcium channel blocker for control of their hypertension (Sinzinger et al., 1992; Gebara et al., 1996; Tison et al., 1994).

Other studies, namely electrophysiological patch experiments, have not supported the role of VDCC in $Ca^{2+}$ entry in the platelets (Mahaut-Smith et al., 1992) while other electrophysiologic studies have confirmed in phospholipid bilayers the presence of a calcium selective channel in platelet vesicles (Zschauer et al., 1998). The preferential localization of the VDCC, as disclosed herein for the first time, in membranes deep inside the platelets could have masked these channels from patch experiments. Furthermore, the binding and antagonistic effects of dihydropyridines on the L-type VDCC are known to depend on the gated state of the channel. In the resting state this channel has a low affinity for these pharmacological agents (Bean, 1984). This gated dependent property could complicate the interpretation of results from experiments that use channel blockers on platelet aggregation and could explain some of the discrepancies reported on their effects on platelet function in different assays.

Tissue-specific expression of VDCC $\alpha_1$ subunits confers a unique function to that tissue or organ. The expression of $\alpha_1 D$ in neuroendocrine cells reflects the characteristics of the VDCC in excitation-secretion coupling in these cells. Similarly, the expression of $\alpha_1 S$ in skeletal muscle (Birnbaumer et al., 1994; Tanabe et al., 1987) or $\alpha_1 C$ in cardiac muscle (Birnbaumer et al., 1994; Mikami et al., 1989) reflects the characteristics of the corresponding VDCC in excitation-contraction coupling in skeletal (Shirokova et al., 1998) and cardiac (López-López et al., 1995) muscles respectively. Extrapolating the expression of $\alpha_1 D$ and $\alpha_1 S$ subunits to the function of the platelet, the corresponding channels are implicated in excitation-secretion and excitation-contraction couplings in platelets.

Summary of Examples 7-9

An inhibitory monoclonal antibody to the alpha 1 subunit of the DHP receptor (MA3-920), two antagonists (nitrendipine and Bay K(+)), and one agonist (Bay K(-)), were used to characterize the functionality of VDCCs in thrombin-activated platelets. Using these reagents, it was possible to show that intracellular calcium concentrations can be modulated in thrombin-activated platelets. MA3-920 was the most potent inhibitor of $[Ca^{2+}]_i$, reducing PS exposure by 21%. Nitrendipine reduced $[Ca^{2+}]_i$ under certain conditions and also decreased annexin V binding by 22%.

A striking observation was consistently observed: alterations in $[Ca^{2+}]_i$ occurred concomitantly with platelet surface PS exposure. Bay K(-) caused a trend towards increased $[Ca^{2+}]_i$ and a 56% increase in annexin V binding. Considered together, these observations suggest one function of the platelet VDCC is control of platelet surface PS exposure.

Upon activation, there is exposure of phosphatidylserine on the surface of platelets. Also, other negatively charged phospholipids migrate to the outer membrane leaflet as well (See Sims & Wiedmer, 2001; Zhou et al., 2002). This not only forms a pro-coagulant surface, but also might depolarize the membrane enough to activate VDCCs. It is possible that the VDCC is involved with platelet surface phospholipid scrambling during activation. Interestingly, a recently reported knockout mouse for phospholipid scramblase 1 (PLSCR1) showed normal platelet function as measured by normal bleeding time and factor V binding reflecting PS exposure (Zhou et al., 2002). The authors suggest that this apparent discrepancy might be due to redundancy of function among the four known PLSCR genes. Likewise, redundancy of function between platelet $\alpha_1 D$ and $\alpha_1 S$ VDCC might account for normal platelet aggregation with ablated $[Ca^{2+}]_i$ seen in these Examples.

The absence or varied results in platelet aggregation suggest that VDCCs might have little or no role in platelet aggregation under these experimental conditions. Little or no change was seen in the expression of activated GPIIb/IIIa on the platelet surface (Table 4). The binding of fibrinogen to the activated GPIIb/IIIa receptor is required for platelet aggregation. Alternatively, the activity of VDCCs in platelet aggregation might be slightly delayed and have more of an influence on platelet secretion of granular contents. Furthermore, since VDCCs are encrypted or deep in the OCS, initial activation might cause depolarization of the membrane which leads to opening of VDCCs, causing release of calcium from the dense tubular system and further activation of the platelet.

Example 7

MA3-920 Blocks Calcium Influx

Figure 6:
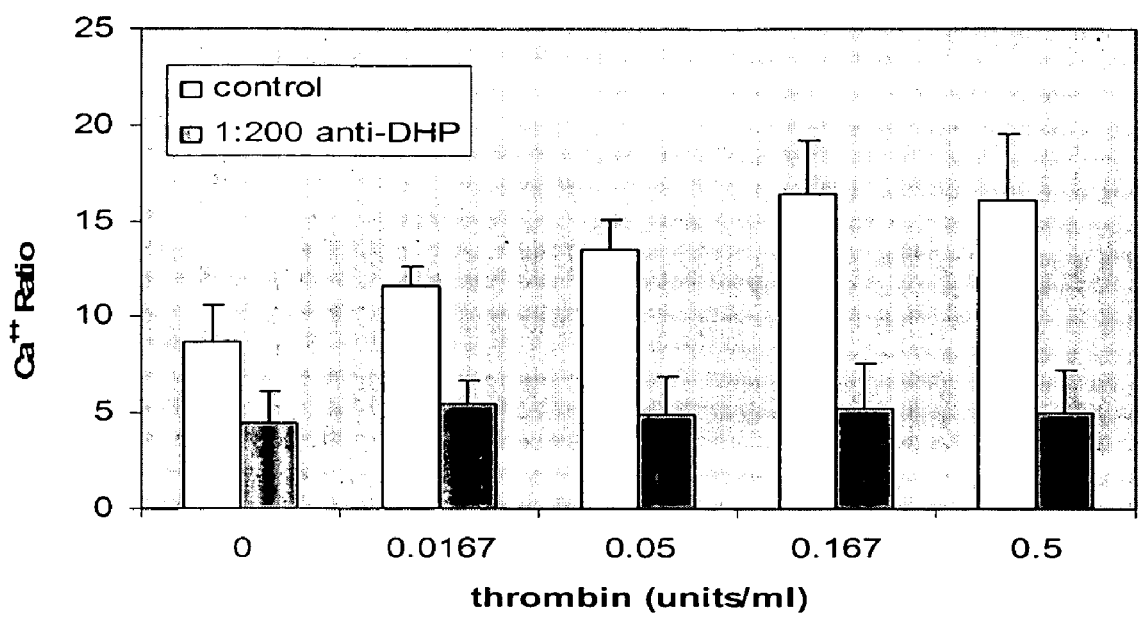
FIG. 6 depicts the effects of monoclonal antibody MA3-920 on intracellular platelet calcium concentration ([$Ca^{2+}$]$_i$) at various thrombin concentrations (p<0.003; student's t test).

As shown in FIG. 6, a 1:200 dilution of MA3-920 completely blocked the rise of $[Ca^{2+}]_i$ over the entire range of thrombin. MA3-920-treated platelets exhibited a 21% reduction in annexin V binding consistent with decreased phosphatidylserine exposure (see Table 4). As shown in Table 4, this antibody increased PAC1 and CD62 surface expression by 12% and 16%, respectively. Its effects on the rate of platelet aggregation varied, giving anywhere from a 27% increase to a 70% decrease. The rise in platelet aggregation receptors and α-granule release could account for the variability seen in aggregation experiments.

TABLE 4

Effect of VDCC Blockers on Platelet Activation Markers Following Thrombin Stimulation[a]

|  | Annexin V | PAC1 | CD62 |
| --- | --- | --- | --- |
| Bay K (−) | 56% ↑ | 9% ↓ | 4% ↓ |
| MA3-920 | 21% ↓ | 12% ↑ | 16% ↑ |
| Nitrendipine | 22% ↓ | — | 2% ↓ |
| Bay K (+) | 4% ↓ | 7% ↓ | 5% ↓ |

[a]Platelets were analyzed by flow cytometry to detect changes in the following cell surface markers of activation: Annexin-V (phosphatidylserine); PAC1 (activated GPIIb/IIIa); CD62 (PADGEM; P-selectin).

Example 8

Effects of Nitrendipine Treatment on Calcium Influx and Annexin V Binding

Figure 7:
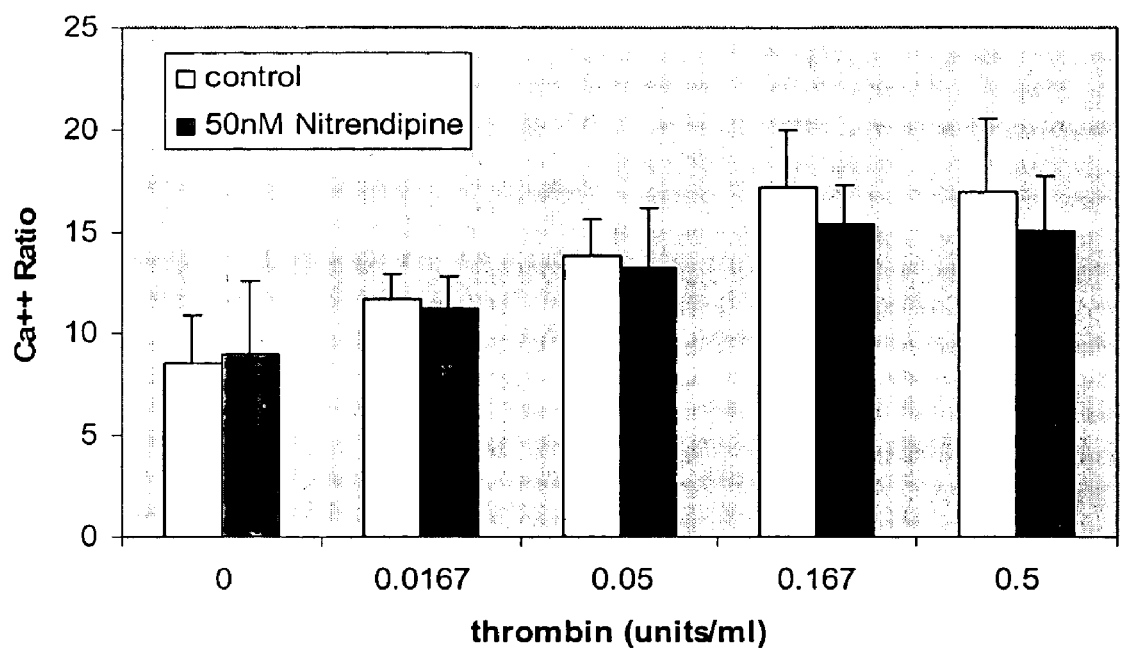
FIG. 7 depicts the effects of the antagonist nitrendipine on platelet [$Ca^{2+}$]$_i$ at various thrombin concentrations.

As shown in FIG. 7, 50 nM nitrendipine (a DHP antagonist) showed a decrease in $[Ca^{2+}]_i$ ratio at the two highest concentrations of thrombin: 0.167 and 0.5 units/ml. Additionally, nitrendipine caused a 22% decrease in annexin V binding. It had minimal effect on the surface expression of PAC1 and CD62 (Table 4). It had no effect on the rate of platelet aggregation.

Example 9

Effects of Bay K8644 Stereoisomers

Figure 8:
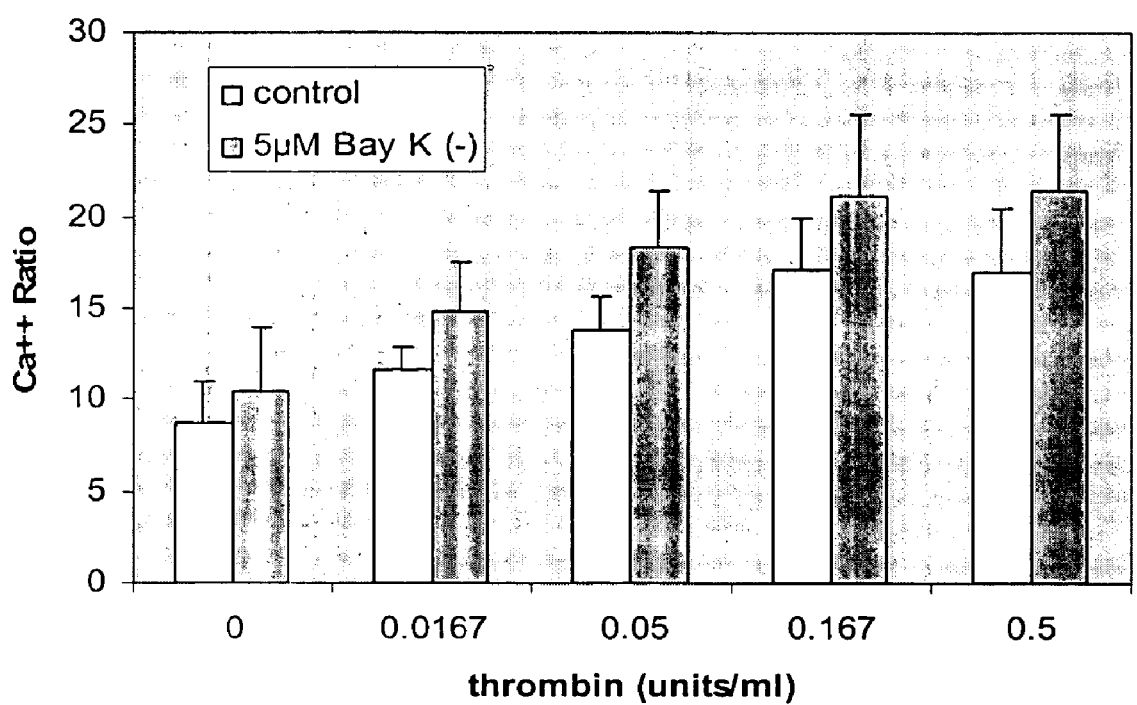
FIG. 8 depicts the effects of the agonist Bay K(−) on platelet [$Ca^{2+}$]$_i$ at various thrombin concentrations.

5 μM Bay K(−) caused an increase in $[Ca^{2+}]_i$ at one minute with thrombin concentrations ranging from 0.0167 to 0.5 units/ml (FIG. 8). Bay K(−) produced a 56% increase in annexin V binding consistent with a significant increase in platelet surface phosphatidylserine (PS) exposure (Table 4). In contrast, Bay K(−) produced a 9% decrease in PAC1 and a 4% decrease in CD62, suggesting that the reduction in GPIIb/IIIa receptors and platelet alpha granule release was much less pronounced than platelet surface PS exposure. Bay K(+), on the other hand, showed no significant effect on $[Ca^{2+}]_i$, platelet surface activation markers, or platelet aggregation.

Discussion of Example 9

Bay K(+) has been shown to be an agonist of VDCC activity in the following tissues: frog skeletal muscle, guinea pig smooth muscle cells and papillary muscle, rat aorta and heart, pituitary cells, canine ventricular muscle, mice brain, and rabbit aorta and heart (Franckowiak et al., 1985; Kass, 1987; O'Neill & Bolger, 1988; Ferrante et al., 1989; Saha et al., 1989; van Amsterdam et al., 1989; Enyeart et al., 1990; O'Neill et al., 1990; Ravens & Schopper, 1990; Gil-Longo et al., 1992; Usowicz et al., 1995; Oz et al., 2000). Although one might infer that the stereoisomer Bay K(−) would produce an opposite effect, this has not been the case in the literature cited or in the instant findings in platelets. In platelets, Bay K(−) produced variable results as seen in the other tissues described in the references disclosed hereinabove. The reason for these apparent discrepancies is unknown, but might relate to differences in the extent of membrane depolarization, ion concentration, pH, or other unknown variables.

Materials and Methods for Examples 7-9

A. Calcium Channel Modulators and Platelet Activation Markers

Monoclonal antibody MA3-920 was obtained from Affinity Bioreagents, Inc. (Golden, Colo., United States of America). Nitrendipine and stereoisomers of Bay K8644, termed BK(+) and BK(−) were obtained from Sigma-RBI (St. Louis, Mo., United States of America). Fura 2-AM and Fluo 3-AM were from Molecular Probes, inc. (Eugene, Oreg., United States of America). Thrombin was purchased from Chrono-log Corp. (Havertown, Pa., United States of America) and CaCl$_2$ from Diagnostica Stago, Inc. (Parsippany, N.J., United States of America). Annexin-V-Fluos staining kit was from Roche Diagnostics Corp., Roche Applied Science (Indianapolis, Ind., United States of America) and PAC-1 FITC, CD61 PerCP, and CD62 PE were from BD Biosciences (San Jose, Calif., United States of America).

B. Fresh Platelets

Human blood was collected in acid-citrate-dextrose (ACD, 85 mM trisodium citrate, 70 mM citric acid, 111 mM dextrose). Platelet rich plasma (PRP) was prepared by centrifugation of anticoagulated blood at 25° C. for 8 minutes at 200×g. Platelets were separated from plasma via gel filtration by applying the PRP to a 2.7×10 cm SEPHAROSE™ CL4B column (Amersham Biosciences Corp., Piscataway, N.J., United States of America) equilibrated with modified Tyrode's buffer (145 mM NaCl, 4 mM KCl, 1 mM MgSO$_4$, 6 mM glucose, 10 mM Na-HEPES). Gel filtered platelets were collected and adjusted to a concentration of about 200×10$^6$ platelets/ml.

C. Flow Cytometric Analysis of $[Ca^{2+}]_i$

PRP (prepared as above) was incubated with 5 μM Fura 2-AM and 5 μM Fluo 3-AM for 20 minutes at 37° C. Gel filtration followed, as above, and platelets were adjusted to a concentration of about 200×10$^6$ platelets/ml. Gel filtered platelets were then incubated for 2 hours with 1:200, 500, and 1000 MA3-920, 50, 20, and 10 nM nitrendipine, or 5, 1, and 0.5 μM Bay K(+) or Bay K(−). Platelets were then diluted 1:20 in modified Tyrode's and CaCl$_2$ was added to a final concentration of 1 μM. Thrombin was then added to a final concentration of 0.0167, 0.05, 0.167 or 0.5 units/ml and mean cell fluorescence (MCF) of Fura 2 and Fluo 3 was measured at 1 minute on a FACSCAN™ (BD Biosciences, San Jose, Calif., United States of America) flow cytometer as per Novak & Rabinovitch, 1994. The ratio of fluo 3 to fura 2 MCF was calculated and compared to controls for each experimental condition.

D. Cell Surface Markers of Platelet Activation

Platelets were stained for cell surface activation markers according to "Flow Cytometric Analysis of Platelets". *Monoclonal Antibodies Source Book*. Vol. Section 2.19 (Becton, Dickinson And Co., Franklin Lakes, N.J., United States of America). Briefly, after treatment with agonists or antagonists as above, cells were activated with 0.167 units/ml thrombin (concentration chosen based on $[Ca^{2+}]_i$ studies) for 1 minute in the presence of 1 μM CaCl$_2$, and then stained with the combination of CD61 PerCP and Annexin V FITC, or PAC-1 FITC, CD61 PerCP, and CD62 PE for 15 minutes at room temperature in the dark. The reaction was then quenched with cold 1% paraformaldehyde in PBS. Cells were analyzed on a FACSCAN™ flow cytometer. Mean cell fluorescence (MCF) was compared to control platelets (thrombin only) for each experimental condition. CD61 PerCP was used as the platelet marker for gating purposes. CD61 recognizes the GPIIIa (the β subunit of the GPIIb/IIIa complex) and the vitronectin receptor. It is found on all normal resting and activated platelets. Annexin V has a high binding affinity for phosphatidylserine. PAC-1 recognizes an epitope of GPIIb/IIIa on activated platelets at or near the fibrinogen receptor. CD62 is a marker of platelet a granule release (PADGEM: platelet activation-dependent granule-external membrane protein; also called P-selectin).

E. Platelet Aggregation

Gel-filtered platelets at about 200×10$^6$/ml were incubated for 2 hours with 1:200 MA3-920, 50 nM nitrendipine, 5 μM Bay K(−), or 5 μM Bay K(+). These concentrations exhibited the greatest effect on $[Ca^{2+}]_i$ by flow cytometry. CaCl$_2$ was added to a final concentration of 1 μM and aggregation was observed at 37° C. with various concentrations of thrombin on a Chrono-log aggregometer. Results were analyzed with the AGGROLINK® software (Chrono-log Corp.).

REFERENCES

The publications and other materials listed below and/or set forth by author and date in the text above to illuminate the background of the presently claimed subject matter, and in particular cases, to provide additional details respecting the practice, are incorporated herein by reference. Materials used herein include but are not limited to the following listed references.

Abbrachio et al. (1994) *Pharmacol Ther.* 64:445-475.
Adelman et al. (1983) *DNA* 2:183.
Altschul et al. (1990) *J. Mol. Biol.* 215: 403-10
Armstrong, C. M. and Hille, B. (1998) *Neuron* 20:371-380.
Ashcroft, F. M. (2000) *Ion channels and disease.* Academic Press, San Diego, Calif., United States of America.
Bean, B. P. (1984) *Proc Natl Acad Sci USA* 81:6388-6392.
Bean, B. P. (1993) *Trends Phys Sci.* 13:87-90.
Beaucage et al. (1981) *Tetrahedron Letters* 22:1859-1862.
Berridge, M. J. (1997) *J Physiol (Lond)* 499.2:291-306.
Bhenke, O. (1992) *J. Submicroscopic Cytology and Pathology* 24:169-178.
Birnbaumer et al. (1994) *Neuron* 1994) 13:505-506.
Bokvist et al. (1995) *EMBO J* 14:50-57.
Boyd, A. E. (1992) *J Cell Biochem.* 48:234-261.
Brookes, A. J. (1999) *Gene* 234(2):177-186.
Capecchi, M. R. (1989) *Science* 244(4910):1288-92.
Chien et al. (1991) *Proc. Natl. Acad. Sci. USA*, 88:9578-9582.
Conner et al. (1983) *Proc. Natl. Acad. Sci. U.S.A.* 80:278.
Crabtree, G. and Henderson, J. (1971) *Cancer Res.* 31:985-991.
Delpire et al. (1999) *Nat Genet* 22(2):192-5.
Diebold et al. (1992) *Proc Natl Acad Sci USA.* 89:1497-1501.
Ding et al. (1997) *J Biol Chem* 272(44):28142-8.
Enyeart J J, Biagi B & Day R N (1990) Opposing actions of Bay K 8644 enantiomers on calcium current, prolactin secretion, and synthesis in pituitary cells. *Mol Endocrinol* 4:727-35.
Fadok et al. (1992) *J Immunol* 148:2207-2216.
Ferrante J, Luchowski E, Rutledge A & Triggle D J (1989) Binding of A 1,4-dihydropyridine calcium channel activator, (−) S Bay K 8644, to cardiac preparations. *Biochem Biophys Res Commun* 158:149-54.
Fischer et al. (2000) *Brit J Haematol* 111(1): 167-74.
Forlino et al. (1999) *J Biol Chem* 274(53):37923-31.
Franckowiak G, Bechem M, Schramm M & Thomas G (1985) The optical isomers of the 1,4-dihydropyridine BAY K 8644 show opposite effects on Ca channels. *Eur J Pharmacol* 114:223-6.
Gatti et al. (1988) *Nature* 336:577-580.
Gebara et al. (1996) *Clin Cardiol.* 19:205-211.
Gil-Longo J, Orallo F, Verde I, Campos M & Calleja J M (1992) Role of the endothelial system in Bay K 8644 enantiomer and nifedipine vasomodulator action in rat aorta. *Eur J Pharmacol* 221:1-8.
Gribskov et al. (1986) *Nucl. Acids. Res.* 14:6745.
Harlow, E. & Lane, D. (1988) *Antibodies: A Laboratory Manual*, Cold Spring Harbor Laboratory Press, Cold Spring Harbor, N.Y., United States of America.
Hille, B. (1992) *Ionic channels of excitable membranes*, Sinauer Associate, Inc. Publishers, Sunderland, Mass., United States of America.
Hogan et al. (1994) *Genomics* 24:608-609.
Holmsen, H. (1972) *Ann. N.Y. Acad. Sci* 201:109-115.
Jin, J. and Kanapuli S. (1998) *Proc Natl Acad Sci USA.* 95:8070-8074.
Kanapuli, S. (1998) *Trends Pharmacol Sci.* 19:391-394.
Kass R S (1987) Voltage-dependent modulation of cardiac calcium channel current by optical isomers of Bay K 8644: implications for channel gating. *Circ Res* 61:11-5.
Kestila et al. (1998) *Mol Cell* 1 (4), 575-82.
Khandelwal et al. (1997) *FASEB J.* 11:1812.
Kissel et al. (2000) *EMBO J* 19(6):1312-1326.
Kunzelmann-Marche et al. (2000) *J Biol Chem* 276:5134-5139.
Kyte et al. (1982) *J. Mol. Biol.* 157:105.
Lafreniere et al. (1997) *Nat Genet* 15(3):298-302.
Landgren et al. (1988a) *Science* 241:1007.
Landgren et al., (1988b) *Science* 242:229-237.
Lee et al., (1983) *Nature* 302:790-794.
López-López et al., (1995) *Science* 268:1042-1045.
Luyckx et al. (1999) *Proc Natl Acad Sci USA* 96(21):12174-9.
Mackenzie et al. (1996) *J Biol Chem.* 271:2879-2881.
Madden, V. J. (1998) *Microscp. Microanal.* 4 (Suppl2: proceedings), 854-855.
Mahaut-Smith et al. (1992) *J Biol Chem.* 267:3060-3065.
Malouf et al. (1987) *Proc. Natl. Acad. Sci. USA* 84:5019-5023.
Maniatis et al. (1982) in *Molecular Cloning: A Laboratory Manual*, Cold Spring Harbor Laboratory Press, Cold Spring Harbor, N.Y., United States of America, pp. 280-281.
McPherson et al. (eds.) (1991) *PCR: A Practical Approach*, ILR Press at Oxford University Press, New York, N.Y., United States of America.
Merricks et al. (1998) *Blood* 10(S1-2):71 b.
Mikami et al., (1989) *Nature* 340:230-233.
Mills, D. C. (1996) *Thromb Haemost.* 76:835-856.
Morton M. E. and Froehner S. C. (1987) *J Biol Chem.* 262: 11904-11907.
Needleman et al. (1970) *J. Mol. Biol.* 48:443.
Novak, E. and Rabinovitch, P. (1994) *Cytometry* 17:135-141.
O'Neill S K & Bolger G T (1988) Enantiomer selectivity and the development of tolerance to the behavioral effects of the calcium channel activator BAY K 8644. *Brain Res Bull* 21:865-72.
O'Neill S K, McKay D W, Campbell N, Triggle C R, Crowley M & Bolger G T (1990) Comparative behavioral, neurochemical and pharmacological activities of dihydropyridine calcium channel activating drugs. *J Pharmacol Exp Ther* 253:905-12.
Orita et al. (1989) *Proc Natl Acad Sci USA* 86(8):2766-70.
Oz M, Tchugunova Y & Dinc M (2000) Effects of (+) and (−) enantiomers of calcium channel agonist, Bay K 8644, on mechanical and electrical responses of frog skeletal muscle. *Can J Physiol Pharmacol* 78:649-55.
Palés et al., (1991) *Biochem. et Biophys. Acta* 1064:169-174.
PCT International Publication WO 84/03564
PCT International Publication WO 93/25521
Peres-Reyes, E. and Schneider, T., (1995) *Kidney Int.* 48:1111-1124.
Price, C. M. (1993) *Blood Rev.* 7:127-134.
Ravens U & Schopper H P (1990) Opposite cardiac actions of the enantiomers of Bay K 8644 at different membrane potentials in guinea-pig papillary muscles. *Naunyn Schmiedebergs Arch Pharmacol* 341:232-9.
Sage, S. O., (1997) *Exp Physiol.* 82:807-823.
Saha J K, Hryshko L V, Bouchard R A, Chau T & Bose D (1989) Analysis of the effects of (−) and (+) isomers of the 1,4-dihydropyridine calcium channel agonist BAY k 8644 on postrest potentiation in the canine ventricular muscle. *Can J Physiol Pharmacol* 67:788-94.
Saiki et al. (1985) *Bio/Technology* 3:1008-1012.
Sambrook et al. (1989) *Molecular Cloning: A Laboratory Manual*, Cold Spring Harbor Laboratory Press, Cold Spring Harbor, N.Y., United States of America.
Sanders et al. (1996) *Blood* 88:S107.
Sauer, B. (1998) *Methods* 14(4):381-92.

Schwartz et al., (eds.) (1979) *Atlas of Protein Sequence and Structure*, National Biomedical Research Foundation, Washington, D.C., United States of America, pp. 357-358.
Seino et al., (1992) *Proc Natl Acad Sci USA*. 89:584-588.
Shirokova et al., (1998) *J Physiol* (Lond). 512 (Pt. 2):377-384.
Sims P. J. & Wiedmer T. (2001) *Thromb Haemost.* 86:266-275.
Sinzinger et al., (1992) *Eur J Clin Pharmacol.* 42:43-46.
Smith et al., (1981) *Adv. Appl. Math.* 2:482.
Snutch et a. (1991) *Neuron* 7:45-57.
Stoneking et al. (1991) *Am J Hum Genet* 48(2):370-82.
Striessnig et al., (1998) *Trends Pharmacol Sci.* 19:108-115.
Sun et al. (1998) *J Biol Chem.* 273:11544-11547.
Surprenant et al., (1995) *Trends Neurosci.* 18:224-229.
Tanabe et al., (1987) *Nature* 328:313-318.
Thiagarajan P and Tait J. F. (1990) *J Biol Chem* 265:17420-17423.
Thomas, K. R., and Capecchi, M. R. (1990) *Nature* 346 (6287):847-50.
Thompson et a. (1994) *Nucleic Acids Res* 22:4673-80 Timchenko, L. T., and Caskey, C. T. (1996) *FASEB J* 10(14): 1589-97.
Tison et al., (1994) *Am J Hypertens.* 7:465-495.
Trask, B. J. (1991) *Trends Genet.* 7:149-154.
Usowicz M M, Gigg M, Jones L M, Cheung C W & Hartley S A (1995) Allosteric interactions at L-type calcium channels between FPL 64176 and the enantiomers of the dihydropyridine Bay K 8644. *J Pharmacol Exp Ther* 275:638-45.
U.S. Pat. No. 4,196,265
U.S. Pat. No. 4,458,066
U.S. Pat. No. 4,554,101
U.S. Pat. No. 4,683,195
U.S. Pat. No. 4,683,202
U.S. Pat. No. 4,703,008
U.S. Pat. No. 4,769,331
U.S. Pat. No. 4,736,866
U.S. Pat. No. 4,965,188
U.S. Pat. No. 5,162,215
U.S. Pat. No. 5,234,933
U.S. Pat. No. 5,260,203
U.S. Pat. No. 5,279,833
U.S. Pat. No. 5,286,634
U.S. Pat. No. 5,326,902
U.S. Pat. No. 5,352,660
U.S. Pat. No. 5,399,346
U.S. Pat. No. 5,489,742
U.S. Pat. No. 5,550,316
U.S. Pat. No. 5,573,933
U.S. Pat. No. 5,580,722
U.S. Pat. No. 5,614,396
U.S. Pat. No. 5,625,125
U.S. Pat. No. 5,627,158
U.S. Pat. No. 5,641,484
U.S. Pat. No. 5,643,567
U.S. Pat. No. 5,645,999
U.S. Pat. No. 5,646,008
U.S. Pat. No. 5,648,061
U.S. Pat. No. 5,651,964
U.S. Pat. No. 5,734,033
U.S. Pat. No. 5,739,278
U.S. Pat. No. 5,741,957
U.S. Pat. No. 5,786,152
U.S. Pat. No. 5,834,228
U.S. Pat. No. 5,837,479
U.S. Pat. No. 5,846,720
U.S. Pat. No. 5,849,578
U.S. Pat. No. 5,872,011
van Amsterdam F T, Punt N C, Haas M, van Amsterdam-Magnoni M S & Zaagsma J (1989) Stereoisomers of BAY K 8644 show opposite activities in the normal and ischaemic rat heart. A comparison with nifedipine. *Naunyn Schmiedebergs Arch Pharmacol* 339:647-52.
Verma et al. (1988) *Human Chromosomes: A Manual of Basic Techniques*, Pergamon Press, New York, N.Y., United States of America.
Wang et al. (1998) *Science* 280(5366):1077-82.
Wetmur & Davidson (1968) *J. Mol. Biol.* 31:349-370.
White, J. G. (1970) *Am J Pathol.* 58:31-49.
White, J. G. (1972) *Am J Pathol.* 66:295-305.
White et al. (1997) *Nat Genet* 17(4):404-10.
White et al. (1990) *Proc. Natl. Acad. Sci.* 87:758-762.
Yuan et al. (1999) *Hum Mutat* 14(5):440-6
Zhou et al. (2002) *Blood.* 99:4030-4038
Zschauer et al., (1998) *Nature* 334:703-705.

It will be understood that various details of the presently claimed subject matter can be changed without departing from the scope of the presently claimed subject matter. Furthermore, the foregoing description is for the purpose of illustration only, and not for the purpose of limitation—the presently claimed subject matter being defined by the claims.

What is claimed is:

1. A method of screening candidate substances for an ability to modulate phosphatidylserine exposure on the surface of a platelet, the method comprising:

(a) providing a test sample comprising a platelet voltage dependent calcium channel (VDCC) comprising a VDCCα1 subunit polypeptide on the surface of a platelet, wherein said VDCCα1 subunit polypeptide is selected from the group consisting of SEQ ID NO: 2 or SEQ ID NO: 4, (b) administering a candidate substance to the test sample, and (c) measuring the effect of said candidate substance on phosphatidylserine exposure on the surface of the platelet by determining a first level of phosphatidylserine exposure on the surface of the platelet before the administering step (b); determining a second level of phosphatidylserine exposure on the surface of the platelet after the administering step (b); and comparing the first level and the second level, wherein a difference between the first level and the second level indicates the ability of the candidate substance to modulate phosphatidylserine exposure on the surface of a platelet.

2. The method of claim 1, wherein the candidate substance is a polypeptide, an antibody, a nucleic acid, or a chemical compound.

3. The method of claim 1, wherein the platelet expresses a nucleic acid molecule encoding the platelet VDCCα1 subunit.

4. The method of claim 3 wherein the nucleic acid molecule encoding the platelet VDCCα1 subunit polypeptide is selected from the group consisting of SEQ ID NO: 1 or SEQ ID NO: 3.

5. The method of claim 1, wherein said determining of phosphatidylserine exposure comprises contacting the platelet with an antibody comprising a detectable moiety, wherein the antibody binds to phosphatidylserine; and quantitating an amount of the antibody bound to the platelet, wherein the amount of the antibody bound to the platelet is indicates the amount of phosphatidylserine on the surface of the platelet.

6. The method of claim 5, wherein the detectable moiety is selected from the group consisting of a radiolabel, a fluorescent label, a chemiluminescent label, and an enzyme.

7. The method of claim 5, wherein the quantitating is by a method selected from the group consisting of radioactive detection, fluorescence detection, chemiluminescent detection, calorimetric detection, Western blotting, immunoprecipitation, and fluorescence-activating cell sorting (FACS).

8. The method of claim 1 wherein the platelets are human platelets.

9. The method of claim 1 wherein the platelets are porcine platelets.

* * * * *